(12) United States Patent
Zhang et al.

(10) Patent No.: US 11,332,719 B2
(45) Date of Patent: May 17, 2022

(54) RECOMBINANT VIRUS AND PREPARATIONS THEREOF

(71) Applicants: THE BROAD INSTITUTE, INC., Cambridge, MA (US); THE PRESIDENT AND FELLOWS OF HARVARD COLLEGE, Cambridge, MA (US); MASSACHUSETTS INSTITUTE OF TECHNOLOGY, Cambridge, MA (US)

(72) Inventors: Feng Zhang, Cambridge, MA (US); Mark D. Brigham, Somerville, MA (US); Le Cong, Cambridge, MA (US); Silvana Konermann, Zurich (CH)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 0 days.

(21) Appl. No.: 14/213,991

(22) Filed: Mar. 14, 2014

(65) Prior Publication Data
US 2014/0287938 A1 Sep. 25, 2014

Related U.S. Application Data

(60) Provisional application No. 61/799,800, filed on Mar. 15, 2013.

(51) Int. Cl.
| | |
|---|---|
| *C12N 7/00* | (2006.01) |
| *C12N 15/86* | (2006.01) |
| *C12P 19/34* | (2006.01) |
| *C12Q 1/686* | (2018.01) |
| *C12Q 1/70* | (2006.01) |

(52) U.S. Cl.
CPC .............. *C12N 7/00* (2013.01); *C12N 15/86* (2013.01); *C12P 19/34* (2013.01); *C12Q 1/686* (2013.01); *C12Q 1/701* (2013.01); *C12N 2750/14043* (2013.01); *C12N 2750/14121* (2013.01); *C12N 2750/14151* (2013.01); *C12N 2750/14152* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,566,118 B1 | 5/2003 | Atkinson et al. | |
| 6,593,123 B1 | 7/2003 | Wright et al. | |
| 2002/0146691 A1* | 10/2002 | Case | C12N 15/1079 435/6.1 |
| 2003/0198627 A1* | 10/2003 | Arts | C12N 9/22 424/93.21 |
| 2006/0040391 A1* | 2/2006 | Bailey et al. | 435/455 |
| 2011/0183912 A1* | 7/2011 | Okano | A01K 67/027 514/17.8 |
| 2011/0301073 A1* | 12/2011 | Gregory et al. | 514/1.1 |
| 2012/0232133 A1 | 9/2012 | Balazs et al. | |
| 2012/0237966 A1* | 9/2012 | Dolmetsch et al. | 435/29 |
| 2013/0253040 A1* | 9/2013 | Miller et al. | 514/44 R |
| 2014/0010797 A1* | 1/2014 | Jantz | C12N 9/22 424/94.3 |
| 2015/0024467 A1 | 1/2015 | Sheldon et al. | |
| 2015/0119327 A1 | 4/2015 | Muotri et al. | |
| 2016/0369268 A1 | 12/2016 | Bleris et al. | |
| 2017/0107536 A1* | 4/2017 | Zhang | C12N 15/86 |

OTHER PUBLICATIONS

Blouin et al., J. Gene Med., 6:S223-S228, 2004.*
Lock et al., Human Gene Therapy 21:1259-1271, 2010.*
J. Amer. Cehm. Soc. 134:16480-16483, 2012.*
Drittanti et al., Gene Therapy 7:924-929, 2000.*
Xiao et al., J. Virology, 72(3):2224-2232, 1998.*
Kennedy et al., Nature Methd. 7:973, 2010 (Year: 2010).*
Liu et al., Science 322:1535-1539, (Year: 2008).*
Horvath et al., Science 327:167-179, (Year: 2010).*
Rolling et al., "AAV as a Viral Vector for Human Gene Therapy" 3 Molecular Biotechnology 9-15 (Year: 1995).*
Martha C. Bohn, Overview of Gene Therapy and Viral Vectors for CNS Applications (2005) p. 9-21; Retrieved from the internet Sep. 10, 2014: URL:http://diyhpl.us/~bryan/papers2/gene-therapv/Overview%20of%20gene%20therapv%20and%20viral$20vectors%20for%20CNS%20applications%20-%20Martha%20Bohn%202005.pdf.
Konermann et al., "Optical control of mammalian endogenous transcription and epigenetic states", Nature, Jul. 23, 2013, pp. 1-17.
U.S. Appl. No. 14/855,046, filed Sep. 15, 2015, Treptow, Nancy Ann.

* cited by examiner

Primary Examiner — Nancy J Leith
(74) Attorney, Agent, or Firm — Foley & Lardner LLP; Sunit Talapatra

(57) ABSTRACT

The present invention generally relates to methods and compositions used delivery of gene editing compositions including transcriptional effectors with parvovirus and preferred methods for making same.

16 Claims, 57 Drawing Sheets

Specification includes a Sequence Listing.

FIG. 1
Spatial control
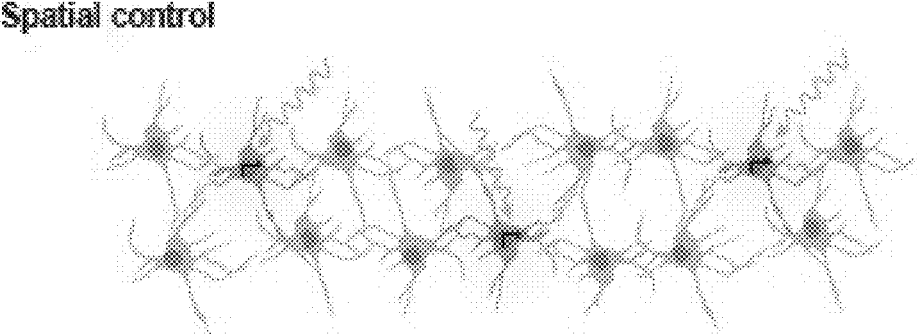
Temporal control
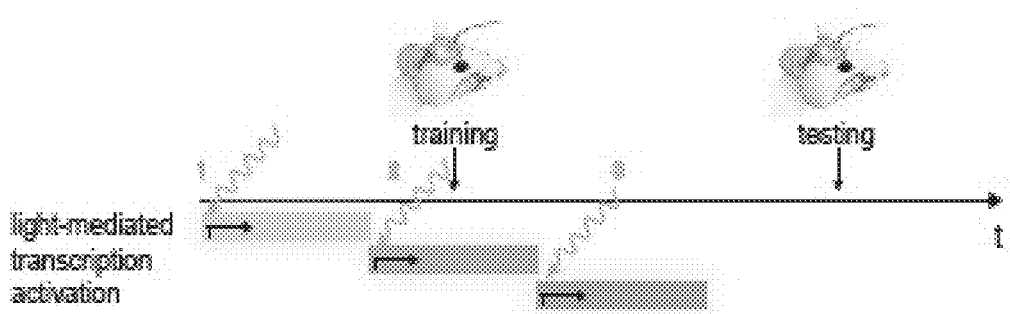

FIG. 3
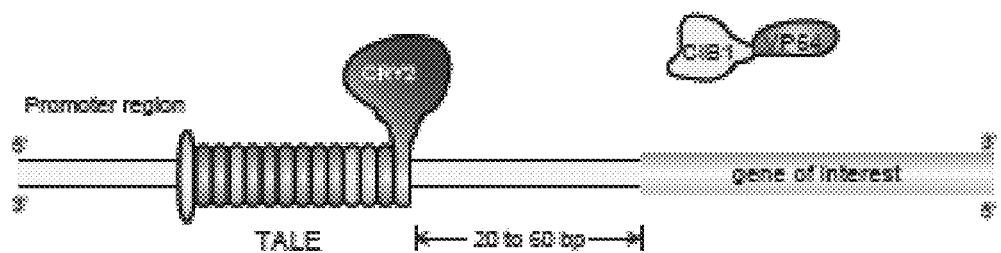
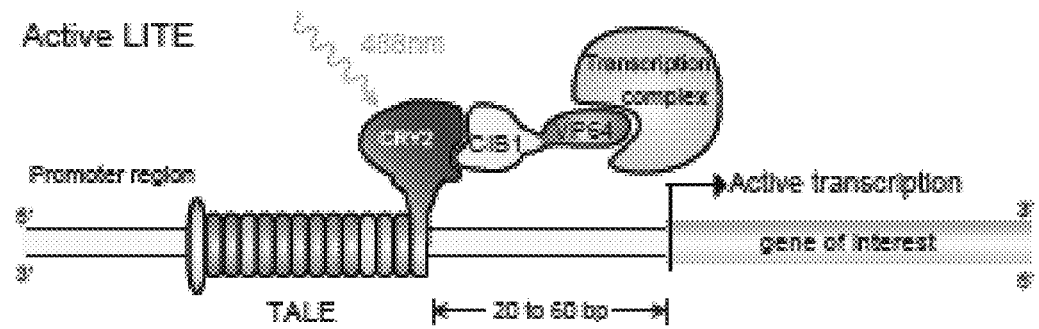

FIG. 6
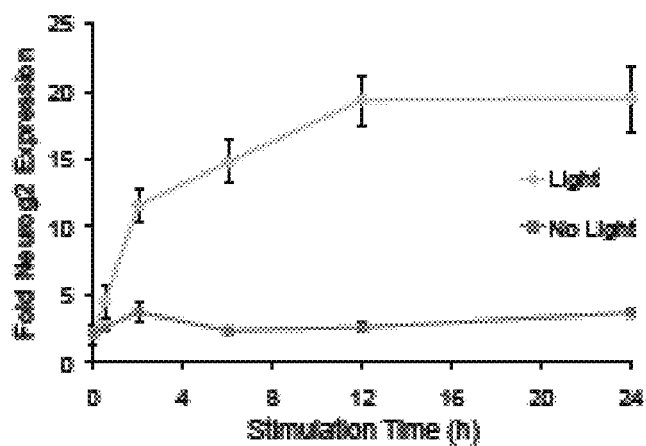
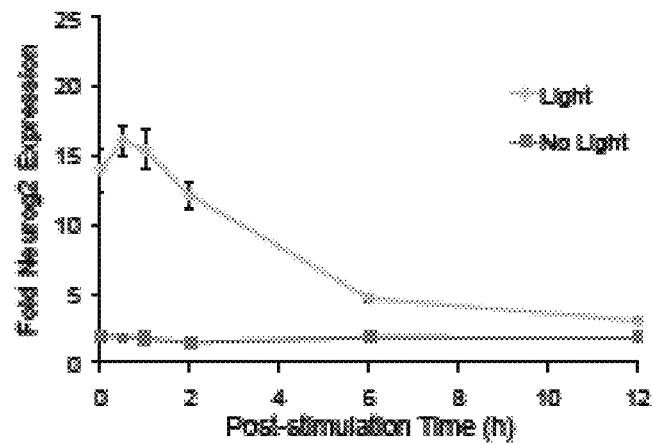

FIG. 7A

FIGS. 8A-D
a
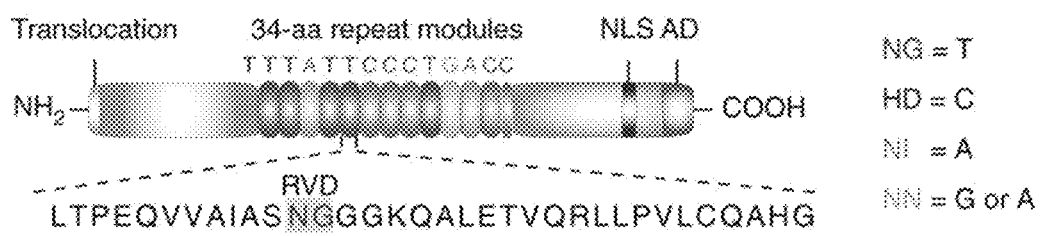
b
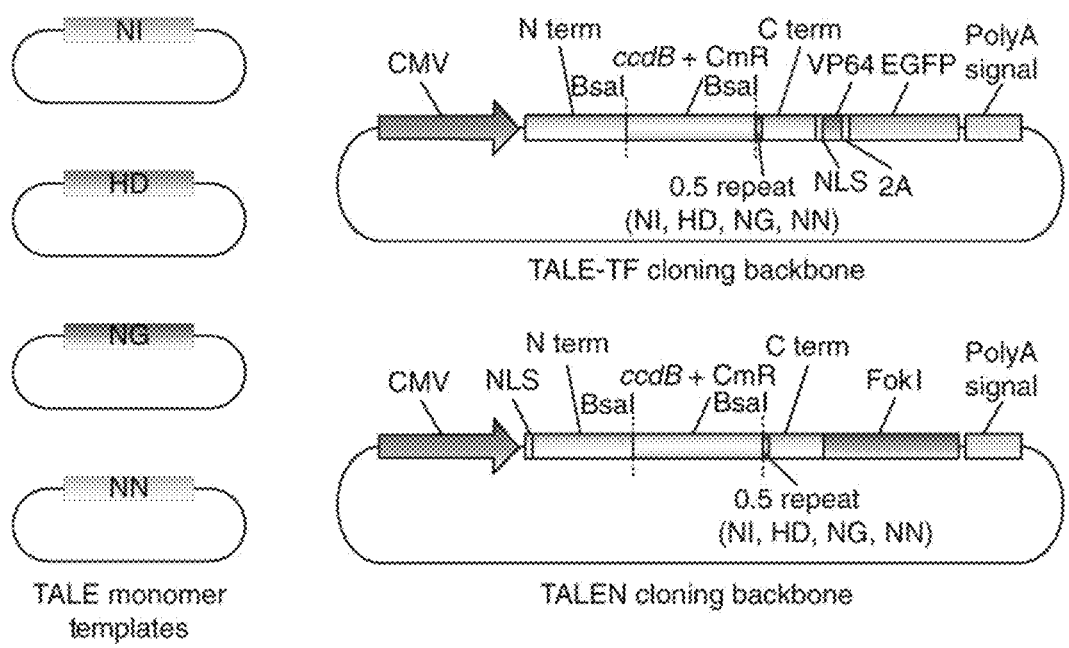
c
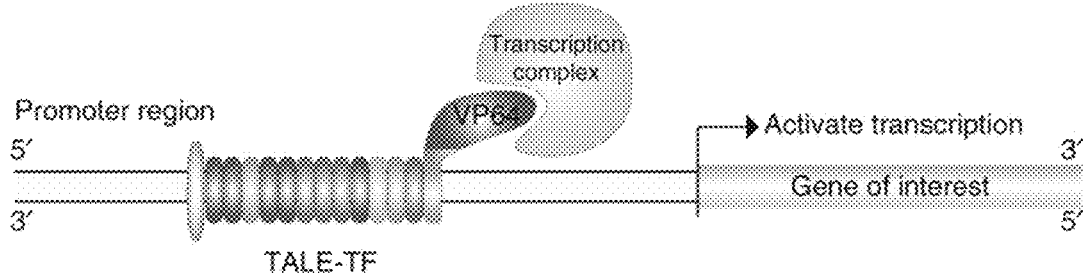
d
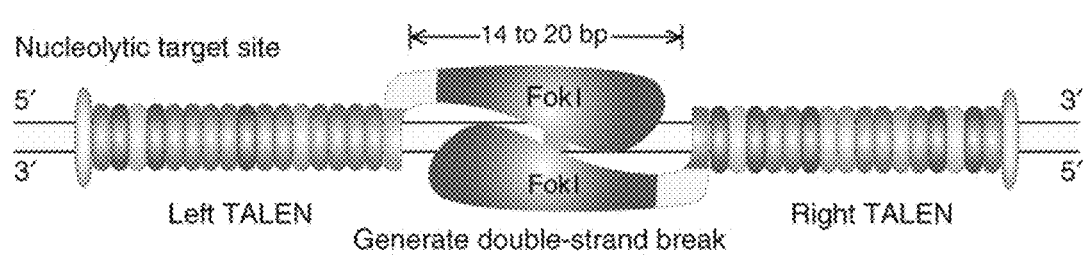

FIG. 9A

| SEQ ID NO.s | Monomers (RVD removed) | Frequency |
|---|---|---|
| | LTPDQVVAIASGGKQALETVQRLLPVLCQDHG | 754 |
| | LTPEQVVAIASGGKQALETVQRLLPVLCQAHG | 278 |
| | LTPDQVVAIASGGKQALETVQRLLPVLCQAHG | 254 |
| | LTPAQVVAIASGGKQALETVQRLLPVLCQAHG | 147 |
| | LTPAQVVAIASGGKQALETVQRLLPVLCQDHG | 143 |
| | LTPDQVVAIASGGKQALETVQRLLPVLCEQHG | 107 |
| | LTPDQVVAIANGGKQALETVQRLLPVLCQDHG | 72 |
| | LTLDQVVAIASGGKQALETVQRLLPVLCQDHG | 47 |
| | LTPQQVVAIASGGKQALETVQRLLPVLCQAHG | 47 |
| | LTPDQVVAIANGGKQALETVQRLLPVLCQAHG | 40 |
| | LTPNQVVAIASGGKQALETVQRLLPVLCQDHG | 35 |
| | LTLDQVVAIASGGKQALETVQRLLPVLCQAHG | 27 |
| | LTPAQVVAIANGGKQALETVQRLLPVLCQDHG | 20 |
| | LTPEQVVAIASGGKQALETVQALLPVLCQAHG | 19 |
| | LTLDQVVAIASGSKQALETVQRLLPVLCQDHG | 19 |
| | LTQDQVVAIASGGKQALETVQRLLPVLCQDHG | 18 |
| | LSPDQVVAIASGGKQALETVQRLLPVLCQDHG | 13 |
| | LTPDQVVAIANGGKQALETLQRLLPVLCQDHG | 13 |
| | LTPDQVVAIASGGKQALETLQRLLPVLCQDHG | 11 |
| | LTPDQVVAIASGGKQALETVQRLLPVLRQAHG | 11 |
| | LTPDQVVAIASGGNQALETVQRLLPVLCQAHG | 11 |
| | LTPDQVVAIASGGKQALATVQRLLPVLCQAHG | 10 |
| | LTPAQVVAIANGGKQALETVQRLLPVLCQAHG | 9 |
| | LTLAQVVAIASGGKQALETVQRLLPVLCQAHG | 9 |
| | LTPEQVVAIACGGKQALETVQRLLPVLCQAHG | 9 |
| | LTPAQVVAIASGGKQALETVQQLLPVLCEQHG | 9 |
| | LTPQQVVAIASGGRPALETVQRLLPVLCQAHG | 9 |
| | LTPDQVVAIASGSKQALETVQRLLPVLCQDHG | 8 |
| | LTPNQVVAIASGGKQALETVQRLLPVLCQAHG | 8 |
| | LTPDQVVAIASGGKQALGTVQRLLPVLCQDHG | 8 |
| | LTLAQVVAIASGGKQALETVQRLLPVLCQDHG | 8 |
| | LTPAQAVAIASGGKQALETVQRLLPVLCQDHG | 7 |
| | LTPAQVVAIASGGNQALETVQRLLPVLCQDHG | 7 |
| | LTPDQVVAIASGGKQALETLQRLLPVLCQAHG | 7 |
| | LTPDQVVAIANGGKQALETLQRLLPVLCQAHG | 7 |
| | LTPDQVVTIASGGKQALETVQRLLPVLCQDHG | 7 |
| | LTPAQVVAIANGGKQALETVRRLLPVLCQDHG | 7 |
| | LTPDQVVAIASGGNQALETVQRLLPVLCQDHG | 6 |
| | LTPDQVVAIASGGKQALETVQRLLPVLCQTHG | 6 |
| | LPPDQVVAIASGGKQALETVQRLLPVLCQDHG | 6 |

FIG. 9B

| SEQ ID NO.s | Monomers (RVD removed) | Frequency |
|---|---|---|
| | LTSDQVVAIASGGKQALETVQRLLPVLCQDHG | 6 |
| | LTPAQVVAIASGGKQALETVQRLLPVLCEQHG | 6 |
| | LIPAQVVAIASGGKQALETVQRLLPVLCQDHG | 5 |
| | LTPAQVVAIASGGKQALETMQRLLPVLCQAHG | 5 |
| | LTRDQVVAIASGGKQALETVQRLLPVLCQDHG | 5 |
| | LTPDQVVATASGGKQALETVQRLLPVLCQDHG | 5 |
| | LIPDQVVAIANGGKQALETVQRLLPVLCQAHG | 5 |
| | LTPDQVVAIASGGKQALETVQRLLPVLCQNHG | 5 |
| | LTLDQVVAIASGGKKALETVQRLLPVLCQDHG | 4 |
| | LTPDQLVAIANGGKQALETVQRLLPVLCQDHG | 4 |
| | LTPDQVVAIASGGKQALETVQRLLPVLCQGHG | 4 |
| | LTPDQVVAIASGGKQALETVQRLLPVLCQEHG | 4 |
| | LTLDKVVAIASGGKQALETVQRLLPVLCQDHG | 4 |
| | LTPAQVVAIASGSKQALETVQRLLPVLCQAHG | 4 |
| | LTPDKVVAIASGGKQALETVQRLLPVLCQAHG | 4 |
| | LTQDQVVAIASGGKQALETVQRLLPVLYQDHG | 4 |
| | LTPAQVVAIVSGGKQALETVQRLLPVLCQAHG | 4 |
| | LTPDKVVAIANGGKQALETVQRLLPVLCQDHG | 4 |
| | LTQDQVVAIASGGKQALETVQRLLPVLCQAHG | 4 |
| | LTPDQVMAIANGGKQALETVQRLLPVLCQDHG | 4 |
| | LTTDQVVAIASGGKQALETVQRLLPVLCQAHG | 4 |
| | LTPDQVVAIASGSKQALETVQRLLPVLCQAHG | 3 |
| | LTPDQVVAIANGGKQALETVQRLLLVLCQAHG | 3 |
| | LTQEQVVAIASGGKQALETVQRLLPVLCQAHG | 3 |
| | LTPDQVVTIANGGKQALETVQRLLPVLCQAHG | 3 |
| | LSPAQVVAIASGGKQALETVQRLLPVLCHDHG | 3 |
| | LTPDQVVAIASGGKQALEMVQRLLPVLCQAHG | 3 |
| | LIPDQVVAIASGGKQALETVQRLLPVLCQDHG | 3 |
| | LTPVQVVAIASGGKQALETVQRLLPVLCQDHG | 3 |
| | LTPDQVVAIASGGKQALKTVQRLLPVLCQDHG | 3 |
| | LTPDQVVAIASGGKQALETMQRLLPVLCQAHG | 3 |
| | LTPAQVVAIASGGKQALETVQRLFPVLCQDHG | 3 |
| | LTPAQVVAIASGGKQALETVQQLLPVLCQAHG | 3 |
| | LTPAQVVALSGGKQALETVQRLLPVLCQDHG | 3 |
| | LTPDQVVAIASGGRPALETVQRLLPVLCEQHG | 3 |
| | LTPDQVVAIASGGKQALATVQRLLPVLCQDHG | 3 |
| | LTQVQVVAIASGGKQALETVQRLLPVLCQAHG | 3 |
| | LTPDQVVAIARGGKQALETVQRLLPVLCQAHG | 3 |
| | LPPDQVVAIASGGKQALETVQRLLPVLCQAHG | 3 |
| | LTLDQVVAIASGSKQALETVQRLLPVLCQAHG | 3 |

FIG. 9C

| SEQ ID NO.s | Monomers (RVD removed) | Frequency |
|---|---|---|
| | LSPDQVVAIANGGKQALETLQRLLPVLCQTHA | 3 |
| | LNPDQVVAIASGGKQALETVQRLLPVLCQDHG | 3 |
| | LTPDQVMAIASGGKQALETVQRLLPVLCQDHG | 3 |
| | LTPAQVVAIASGGKQALETVRRLLPVLCQAHG | 3 |
| | LTPDQVVAIASGGKQTLETVQRLLPVLCQDHG | 3 |
| | LTPDQVMTIASGGKQALETVQRLLPVLCQDHG | 3 |
| | LTPAQVVTIASGGKQALETVQRLLPVLCQDHG | 3 |
| | LTPAQVVAIASGGKQALETVQRLLPVLCRAHG | 3 |
| | LSPDQVVAIASGGKQALETVQRLLPVLCQAHG | 3 |
| | LTPDQVVGIASGGKQALETVQRLLPVLCQDHG | 2 |
| | LTPDQVVAIASGGKQALETVQRLLPVLCQANG | 2 |
| | LTPAQVVAIASGGKQALETVQRLLPVLCQTHG | 2 |
| | LTPDQVVAIASGGKQALEMVQRLLPVLCQDHG | 2 |
| | LTPDQVVAIASGGKQALETMQRLLPVLCQDHG | 2 |
| | LTPDQVVAIANGGKQALATVQRLLPVLCQDHG | 2 |
| | LTPDQVVTIASGGKQALETVQRLLPVLCQAHG | 2 |
| | LTPDQVVAIASGGKQALETVQRLLTVLCQDHG | 2 |
| | MTPDQVVAIASGGKQALETVQRLLPVLCQDHG | 2 |
| | LAPDQVVAVASGGKQALETVQRLLPVLCQDHG | 2 |
| | LTPAQVVAIASGGKQALKTVQQLLPVLCEQHG | 2 |
| | LTPDQVVAIARGGKQALETVQRLLPVLCQDHG | 2 |
| | LTPDQVVAIASGGKQALETVQQLLPVLCQAHG | 2 |
| | LTPDQVLAIASGGKQALETLQRLLPVLCQDHG | 2 |
| | LTPEQVVAIARGGKQALETVQRLLPVLCQAHG | 2 |
| | LTPAQVVAIASGGKQALETMQRLLPVLCRAHG | 2 |
| | LTPDQVVAIANGGKQALEMVQRLLPVLCQDHG | 2 |
| | LTTDQVVTIASGGKQALETVQRLLPVLCQDHG | 2 |
| | LTPTQVMAIANGGKQALETVQRLLPVLCQDHG | 2 |
| | LTPQQVVAIASGGKQALETVQALLPVLCQAHG | 2 |
| | LTPDQVVAIASGGKQALETVQRLLPMLCQDHG | 2 |
| | LTSAQVVAIANGGKQALETVQRLLPVLCQDHG | 2 |
| | LTPDQVVAIASGGKQALETVQQLLPVLCQDHG | 2 |
| | LTPDQVVAIANGGKQALATVQRLLPVLCQAHG | 2 |
| | LTPAQVVAIASGGKQALETVQRLLPMLCQAHG | 2 |
| | LTLDQVVAIASGGKQALETVQRLLPVLCQARG | 2 |
| | LTPAQVVAIASGGKQALETLQRLLPVLCQDHG | 2 |
| | LTPDQVVAIANGGKQALETVQRLLPVLCQNHG | 2 |
| | LTPDQVVTIASGGKQALEMVQRLLPVLCQDHG | 2 |
| | LTPDQVVAIASGGKQALERVQRLLPVLCEQHG | 1 |
| | LTPEQVVAICGGKQALETVQALLPVLRQAHG | 1 |

FIG. 9D

| SEQ ID NO.s | Monomers (RVD removed) | Frequency |
|---|---|---|
| | LTPDQVVAIASGGKQALETVQRLLPVLCRDHG | 1 |
| | LTPEQVVAIASGGKQALETVQRLLPMLCQAHG | 1 |
| | LTPEQVVAIACGGKQALETVQRLLPVLRHAHG | 1 |
| | LTPDQVVAIASGGKQALETVQRLLPVLCQHHG | 1 |
| | LIPDQVVAIASGGKQALETVQRLLPVLCQHHG | 1 |
| | LTRAQVVAIASGGKQALETVQRLLPVLCEQHG | 1 |
| | LTPDQVVAIANGGKQAVGTVQRLLPVLCQAHG | 1 |
| | LTLDQVVAIASGGKQALETVQRLLPVLCEQHG | 1 |
| | LTPAQVVAIASGGKQALETVQRLLPMLCQDHG | 1 |
| | LTPDQVVAIASGSKQALETMQRLLPVLCQDHG | 1 |
| | LTPDQVVAIASGGKQALETVQRLLPVLCKQHG | 1 |
| | LTLDQVVAIASGGKQALETVQRLLPVLCQTHG | 1 |
| | LTPDQVVAIASGGKQALEAVQRLLPVLCQDHG | 1 |
| | LTPAQVVTIASGGKQALETVQRLLPVLCEQHG | 1 |
| | LTPAQVMAIASGGKQALETVQRLLPVLCQDHG | 1 |
| | LTREQVVAIASGGKQALETVQRLLPVLRQAHG | 1 |
| | LTLAQVVAIANGGKQALETVQRLLPVLCQAHG | 1 |
| | LTLEQVVAIASGGKQALETVQRLLPVLCQAHG | 1 |
| | LTPQQVVAIASGGKQALETVQRLLPVLCEQHG | 1 |
| | LSPDQVVAIANGGKQALETVQRLLPVLCQDHG | 1 |
| | LTPDQVVAIANGGKQALETVQRLLPVLCQHHG | 1 |
| | LTPEQVVAIASGGKQALETVQALLPVLRQAHG | 1 |
| | LSQDQVVAIASGGKQALETVQRLLPVLCQDHG | 1 |
| | LPPEQVVAIASGGKQALETVQRLLPVLCQAHG | 1 |
| | LTPDQVVAIASGGKQALEAVQRLLPVLCQAHG | 1 |
| | LTPDQVVAIANGGKQALETVQRLLPVLCQEHG | 1 |
| | LTLDQVAAIASGGKQALETVQRLLPVLCQAHG | 1 |
| | LTPDQVVAIASGGKQALETVQRVLPVLCQDHG | 1 |
| | LIPAQVVAIASGGKQALETVQRLLPVLCQAHG | 1 |
| | LTPAQVVAIASGGKQALETVQRLLPVLRQAHG | 1 |
| | LTPAQVVAIASGSKQALETVQRLLPVLCQTHG | 1 |
| | LTPQQVVAIASGGKQALETVQRLLPVLCQDHG | 1 |
| | LTPDQVVAIANGGKQAVETVQRLLPVLCQAHG | 1 |
| | LSPDQVVTIASGGKQALETLQRLLPVLCQDHG | 1 |
| | LTPVQVVAIASGGKQALETVQRLLPVLCQAHG | 1 |
| | LTLDQVVAIASGSKQALETVQRLLPVLCQTHG | 1 |
| | LTPAQVVAIACGGKQALETVRRLLPVLCQAHG | 1 |
| | LTPAQVVAIASGSKQALETVQRLFPVLCQAHG | 1 |
| | LPPAQVVAIASGGKQALETVQRLLPVLCQAHG | 1 |
| | LTPDQVVAIASGGKQALETVQRLLPVLFQEHG | 1 |

FIG. 9E

| SEQ ID NO.s | Monomers (RVD removed) | Frequency |
|---|---|---|
| | LTPAKVVAIASGGKQALETVQRLLPVLCQDHG | 1 |
| | LTPVQVVAIASGGKQALATVQRLLPVLCQDHG | 1 |
| | LTPDQVVAIASGGKQALETVQRLLPGLCQDHG | 1 |
| | LTLAQVVAIANGGKQALETVQRLLPVLCQDHG | 1 |
| | LTPAQVVAIASGGKQALETVQRLLTVLCQDHG | 1 |
| | LPPAQVVAIASGGKQALETVQRLLPVLCQDHG | 1 |
| | LTPAQAVAIASGGKQALETVQRLLPVLCQAHG | 1 |
| | LTPAQVVAIVSGGKQALETVQRLLPVLCQTHG | 1 |
| | LTPDQVVAVAGGGKQALETVQRLLPVLCQDHG | 1 |
| | LTPDQVVAIASGGKQALGTVQRLLPVLCQAHG | 1 |
| | LPPAQVVAIASGGKQALETVQRLLPVLCEAHG | 1 |
| | LTTDQVVAIASGGKQALETVQRLLPVLCQDHG | 1 |
| | LTPDQVVAIANGGKQALETVQRLVPVLCQDHG | 1 |
| | LTPDQVVAIASGGKQALETVQRLLPVLCQTHA | 1 |
| | LTLAQVVAIASGGKQALETVQRLLPVLCQTHG | 1 |
| | LTPNQLVAIANGGKQALETVQRLLPVLCQDHG | 1 |
| | LSPAQVVAIASGSKQALETVQRLLPVLCQDHG | 1 |
| | LTPDQVVAIASGGKQALETVQRVLPVLCQAHG | 1 |
| | LTPDQVMAIANGGKQALETVQRLLPVLCQAHG | 1 |
| | LTPEQVVAIASGGRQALETVQRLLPVLCQAHG | 1 |
| | LTPAQVVAIASGGKQALETVQWLLPVLCQAHG | 1 |
| | LTPDKVVAIASGGKQALETVQRLLPVLCQDHG | 1 |
| | LTPAQVMAIANGGKQALETVQRLLPVLCQDHG | 1 |
| | LTQDQVVAIASGGKQALETVQRLLPVLCQANG | 1 |
| | LTPAQVVAIASGGKPALETVQRLLPVLCEQHG | 1 |
| | LTPDQVVAIASSGKQALETMQRLLPVLCQDHG | 1 |
| | LTPDQVVAIASGSKQALETVQRLLPVLRQDHG | 1 |
| | LTPYQVVAIASGSKQALETVQRLLPVLCQDHG | 1 |
| | LTPYQVVAIASGGKQALETVQRLLPVLCQAHG | 1 |
| | LTLDQVVAIASGGKQALETVQRLLPVLCQEHG | 1 |
| | LTLEQVVAIASGGKQALETVQRLLLVLCQAHG | 1 |
| | LTPDQVVAIASGGKQALETVRRLLQVLCQDHG | 1 |
| | LTPDQVVAIASGGKQALETVQRLLPVLRQDHG | 1 |
| | LTPDQVVSIANGGKQALETVQRLLPVLCQAHG | 1 |
| | LTPDQVVAIANGGKQALETVQRLLPVLCQTHG | 1 |
| | LTPDQVVAIASGGKQALETVKRLLPVLCQAHG | 1 |
| | LTTDQVVAIANGGKQALETVQRLLPVLCQDHG | 1 |
| | LIPQQVVAIASGGKQALETVQRLLPVLCQDHG | 1 |
| | LTLTQVVAIASGGKQALETVQRLLPVLCQAHG | 1 |
| | LTPTQVVAIASGGKQALETVQRLLPVLCQDHG | 1 |

FIG. 9F

| SEQ ID NO.s | Monomers (RVD removed) | Frequency |
|---|---|---|
| | LTPTQVMAIANGGKQALETVQRLLPVLCQAHG | 1 |
| | LTPDQVVAVASGGKQALETVQRLLPVLCQAHG | 1 |
| | LTPAQVVAIASGSKQALETVQRLLPVLCQDHG | 1 |
| | LTPGQVVAIASGGKRALETVQRLLPVLCQDHG | 1 |
| | LTPDQVVVIASGGKQALETVQRLLPVLCQAHG | 1 |
| | LPPDQVVAIASGSKQALETVQRLLPVLCQDHG | 1 |
| | LTPDQVVTIANGSKQALETVQRLLPVLCQAHG | 1 |
| | LTPAQVVAIASGGKQALETVQRLLQVLCQDHG | 1 |
| | LTPDHVVAIASGGKQALETVQRLLPVLCQDHG | 1 |
| | LTPDQVVAIASGGKQALETVQRLLQVLCQDHG | 1 |
| | LTPDQVVAIASGGRQALETVQRLLPVLCEQHG | 1 |
| | LHPGQVVAIASGGKQALETVQRLLPVLCQAHG | 1 |
| | LTLDQVVSIASGGKQALETVQRLLPVLCQDHG | 1 |
| | LTPDQVVAIASGGKQALETVQRLLPALCQDHG | 1 |
| | LTPDQVVAIASGGKPALETVQRLLPVLCEQHG | 1 |
| | LTPAQVVAIASGGKQALKTVQRLLPVLCQAHG | 1 |
| | LTPDQVVAIASGGKRALETVQRLLPVLCQAHG | 1 |
| | LNPDQVVAIASGGKQALETVQRLLPVLCQAHG | 1 |
| | LTPDQVVAIASGGKQALETVKRLLPVLCQDHG | 1 |
| | LTLDQVVAIANGGKQALETVQRLLPVLCQAHG | 1 |
| | LTPAQVVAIASGGKQALETVQRLLPVLCRDHG | 1 |
| | LTPAQVLAIASGGKQALETVQRLLTVLCQDHG | 1 |
| | LTPAQVVAIASGGKQALETMQRLLPVLCQDHG | 1 |
| | LTPDQVVAIASGGKQALETVQRLLPGLCQAHG | 1 |
| | LTREQVVAIASGGKQALETVQALLPVLRQAHG | 1 |
| | LTPAQVVAIASGGKQALETVQRLLPVLCQVHG | 1 |
| | LTPNQVVAIASGGKQALETVQRLLLVLCQDHG | 1 |
| | LTPDQVMAIASGGKQALETVQRLLPVLCQAHG | 1 |
| | LTREQVVAIASGGKQALETVQRLLPVLCQDHG | 1 |
| | LSTAQVVAIASGGKQALEGIGEQLLKLRTAPYG | |
| | LSTAQVVAVASGGKPALEAVRAQLLALRAAPYG | |

FIG. 23A-E
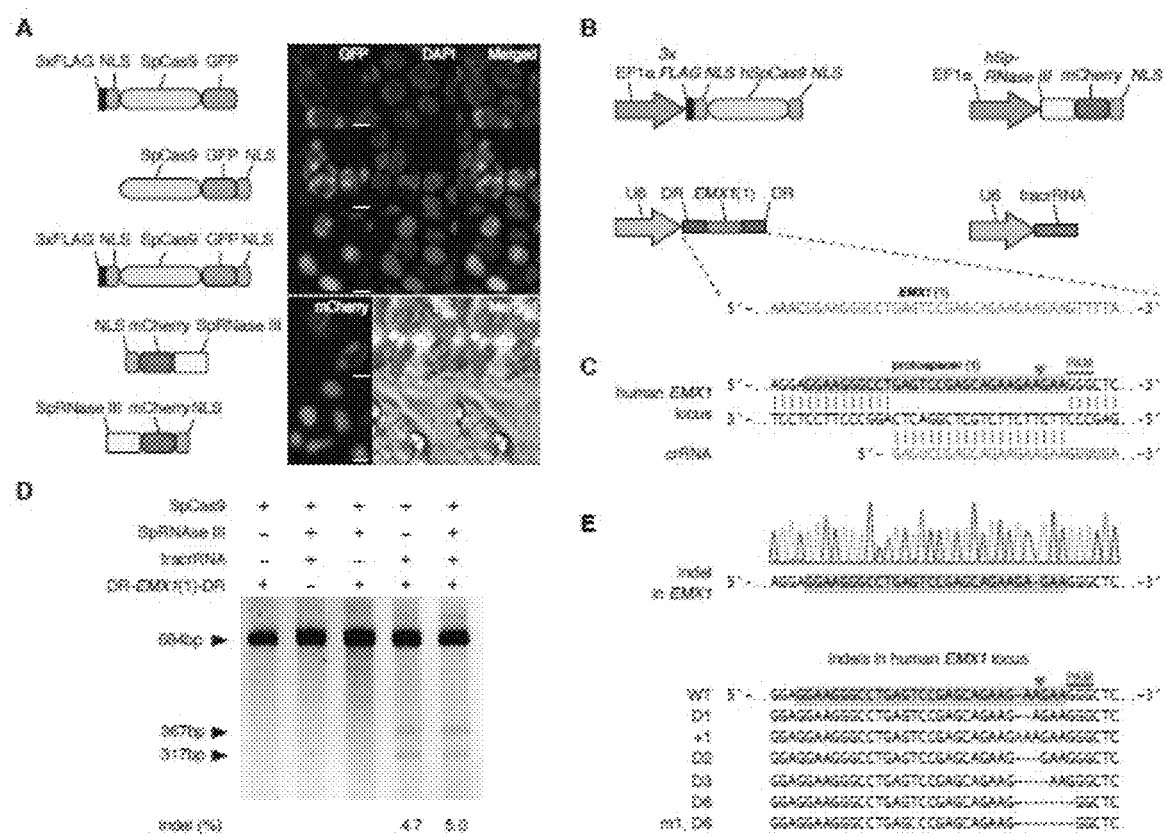

FIG. 24A-C
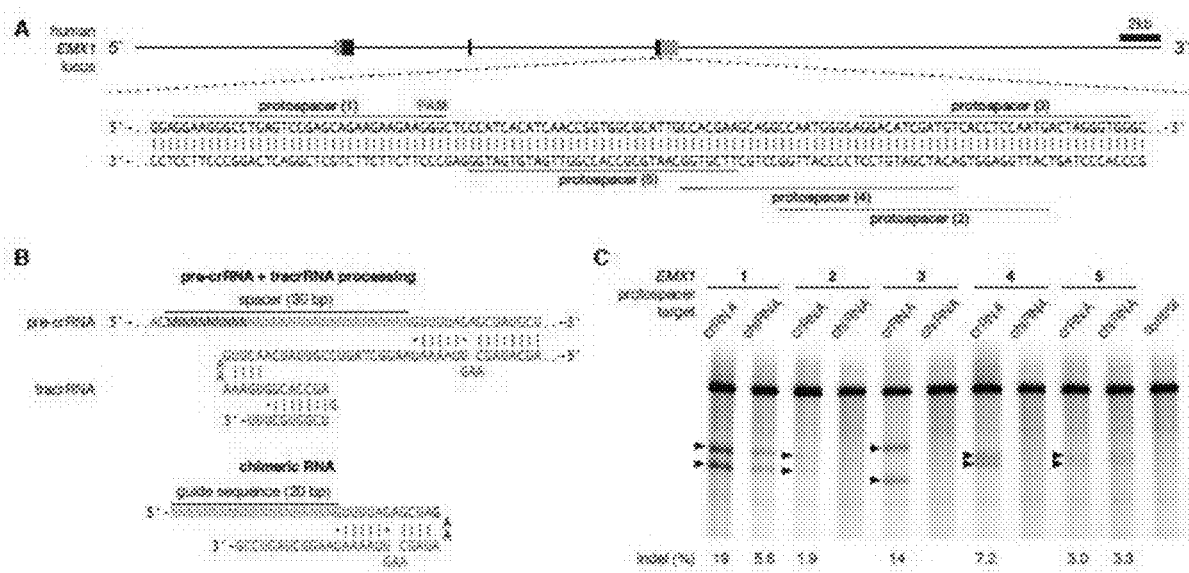

FIG. 25A-D
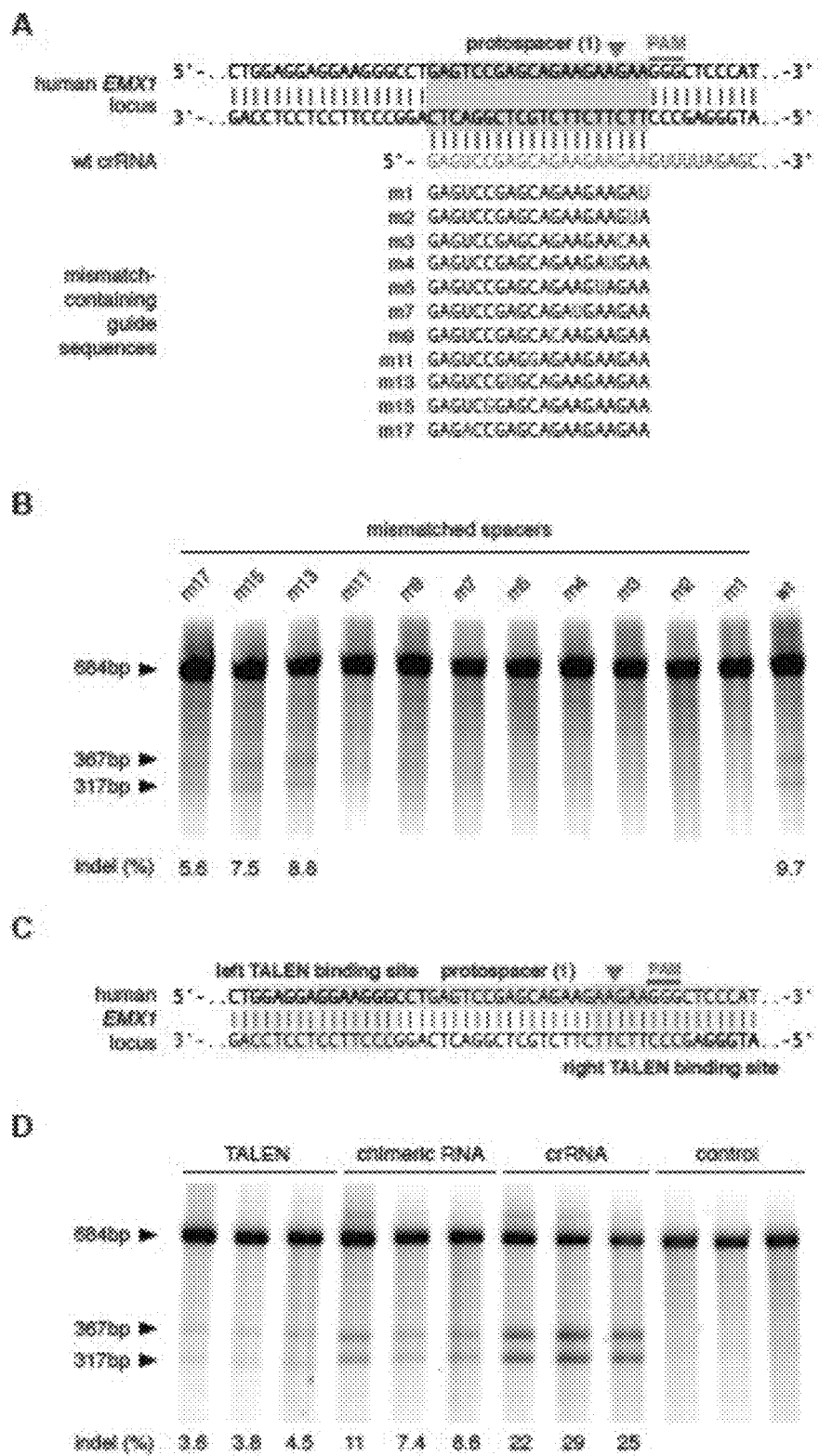

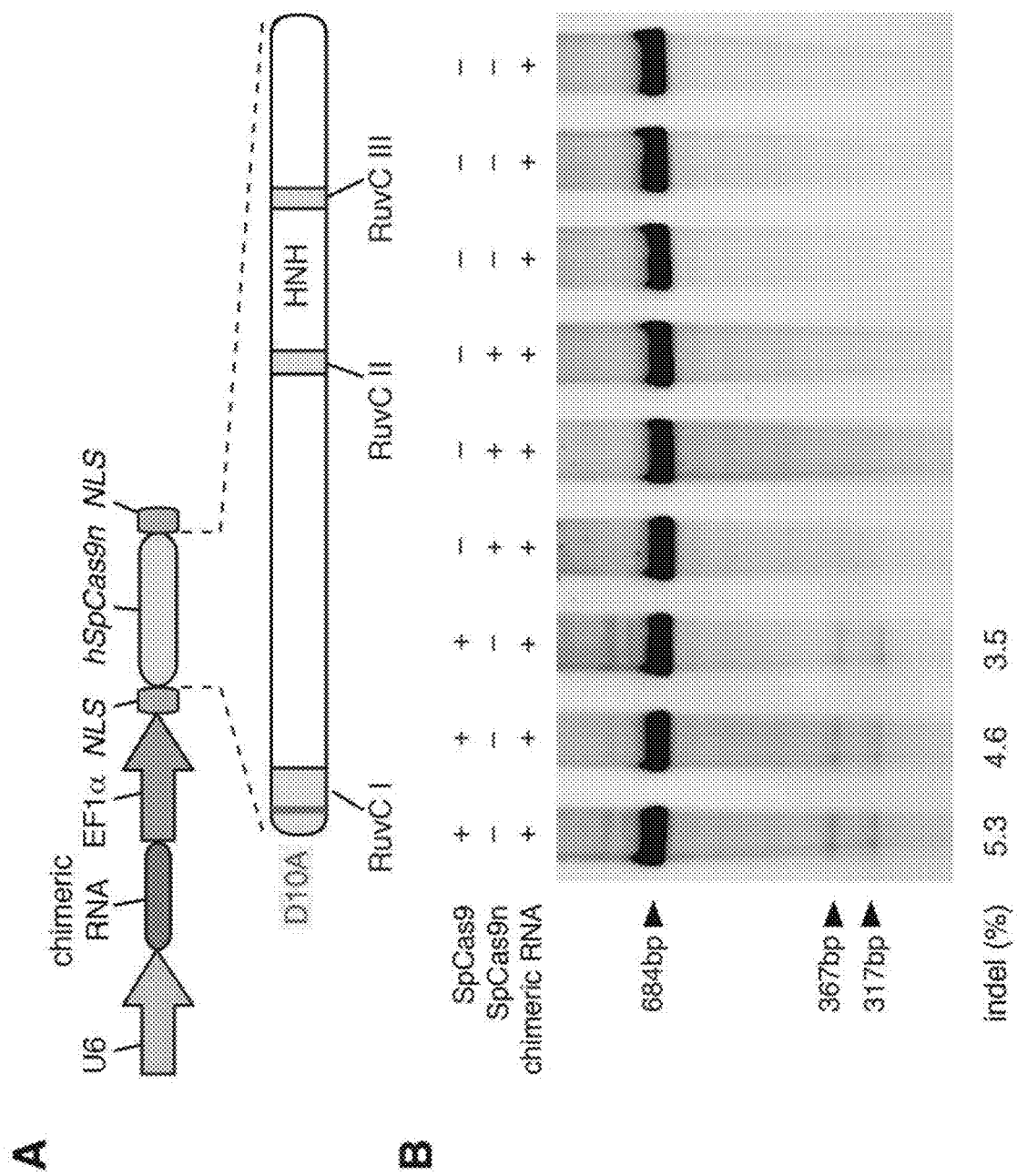
FIG. 26A-B

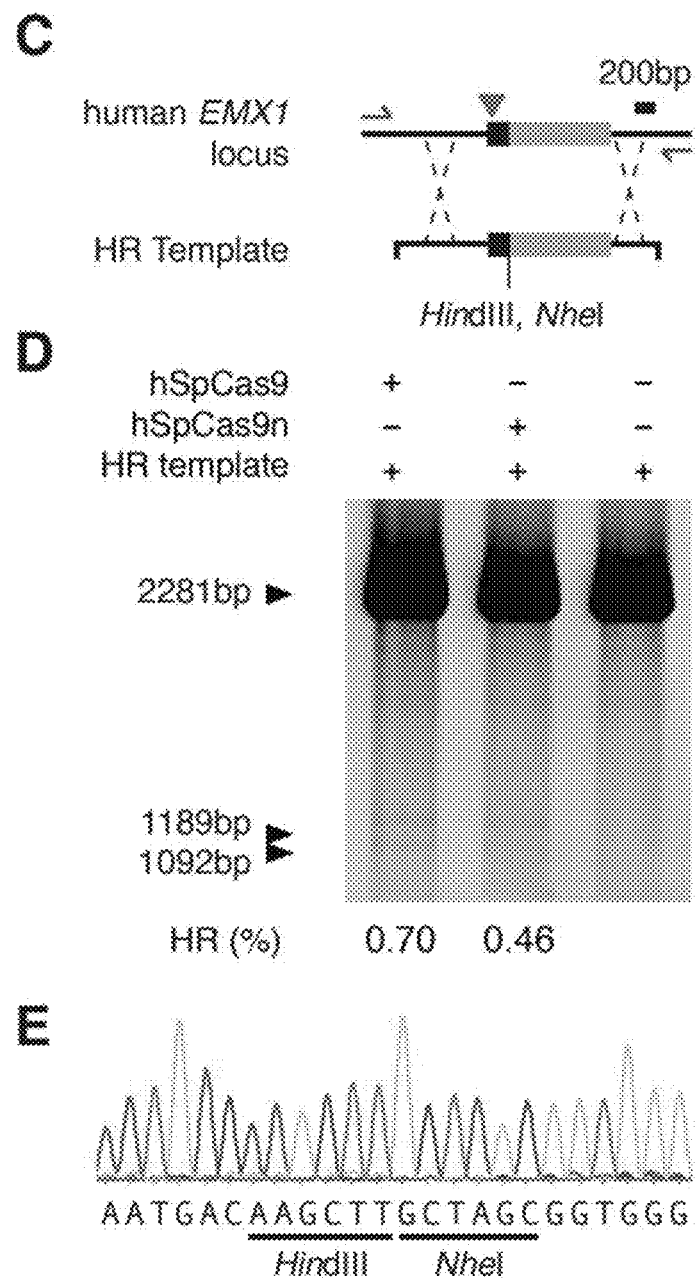
FIG. 26C-E

FIG. 28A-C

% indel = $(1-\sqrt{1-(a+b)/(a+b+c)})*100$

FIG. 30A-B
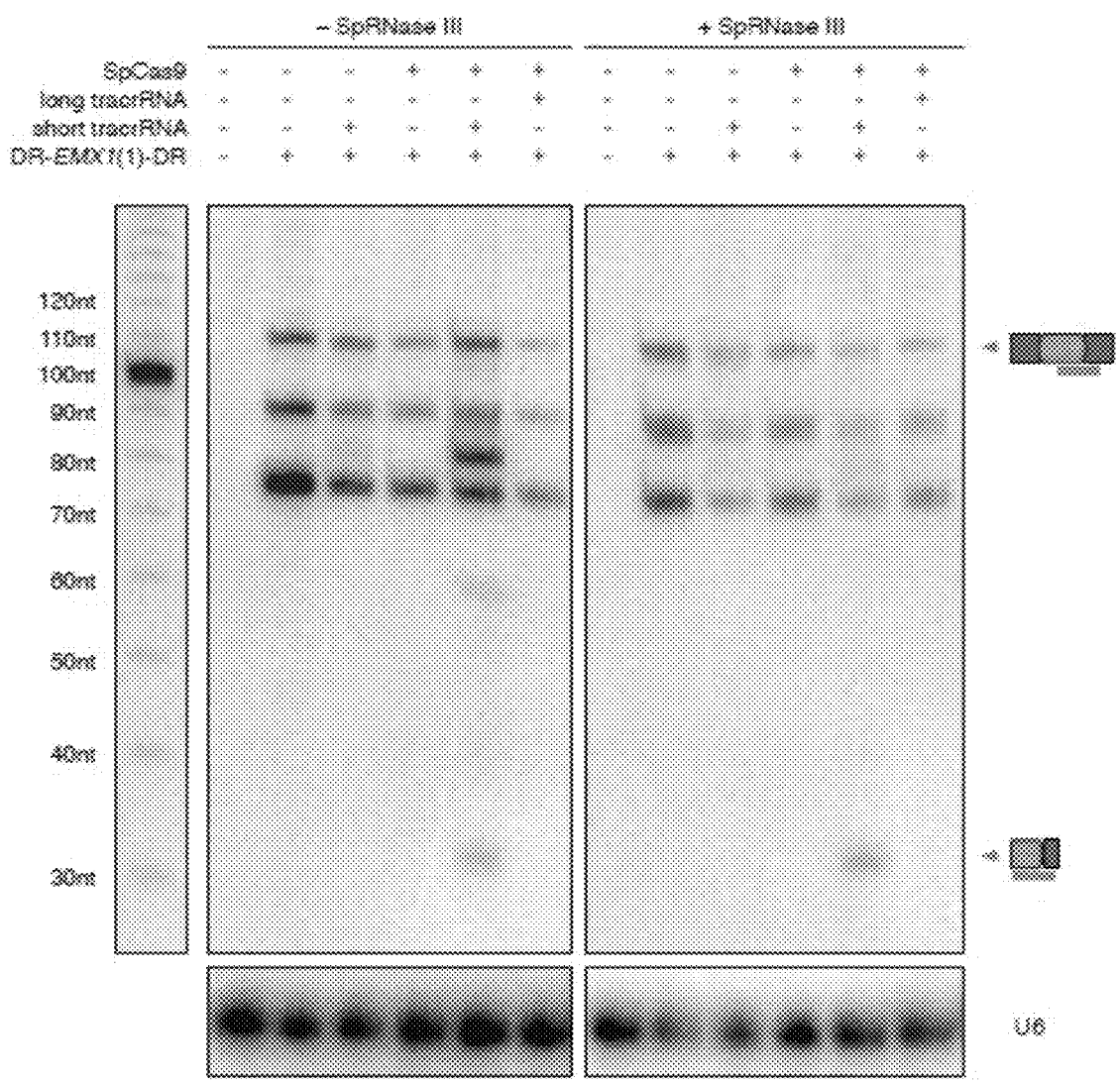

FIG. 31A-B
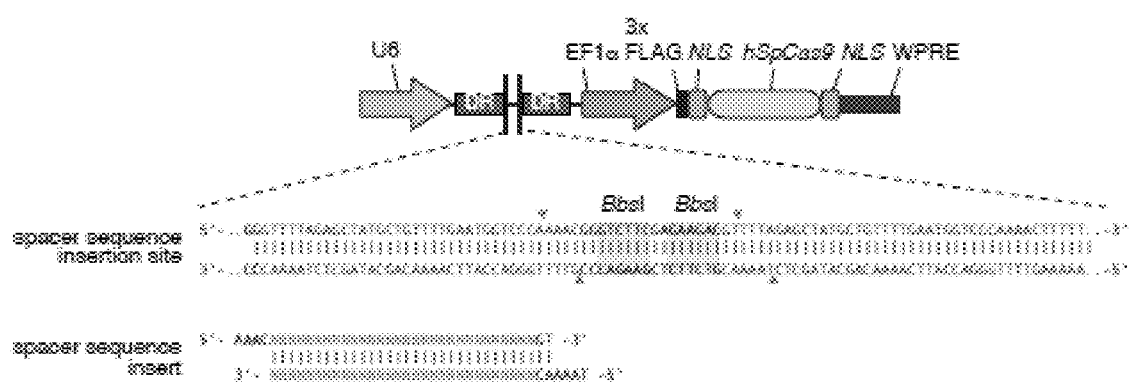
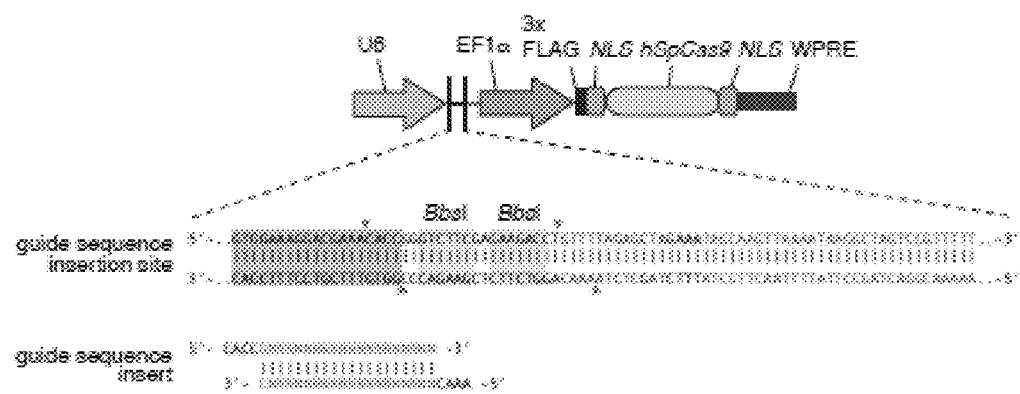

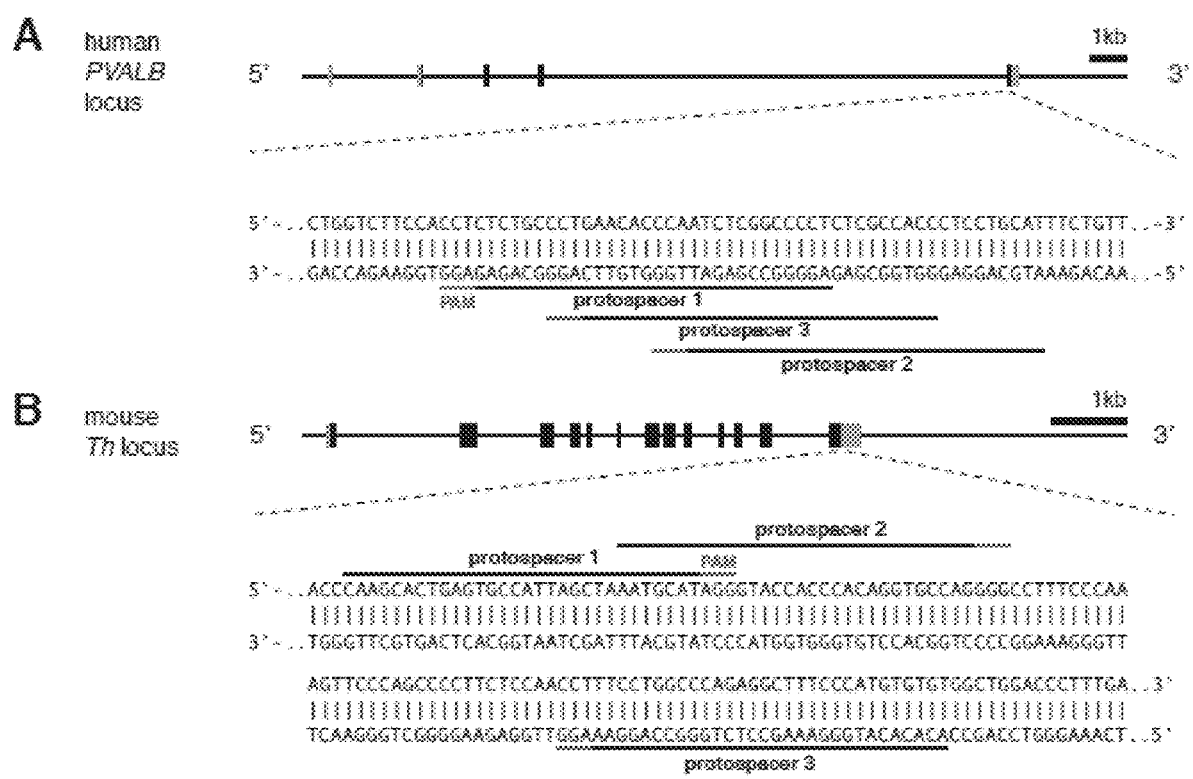
FIG. 32A-B

FIG. 33A-C
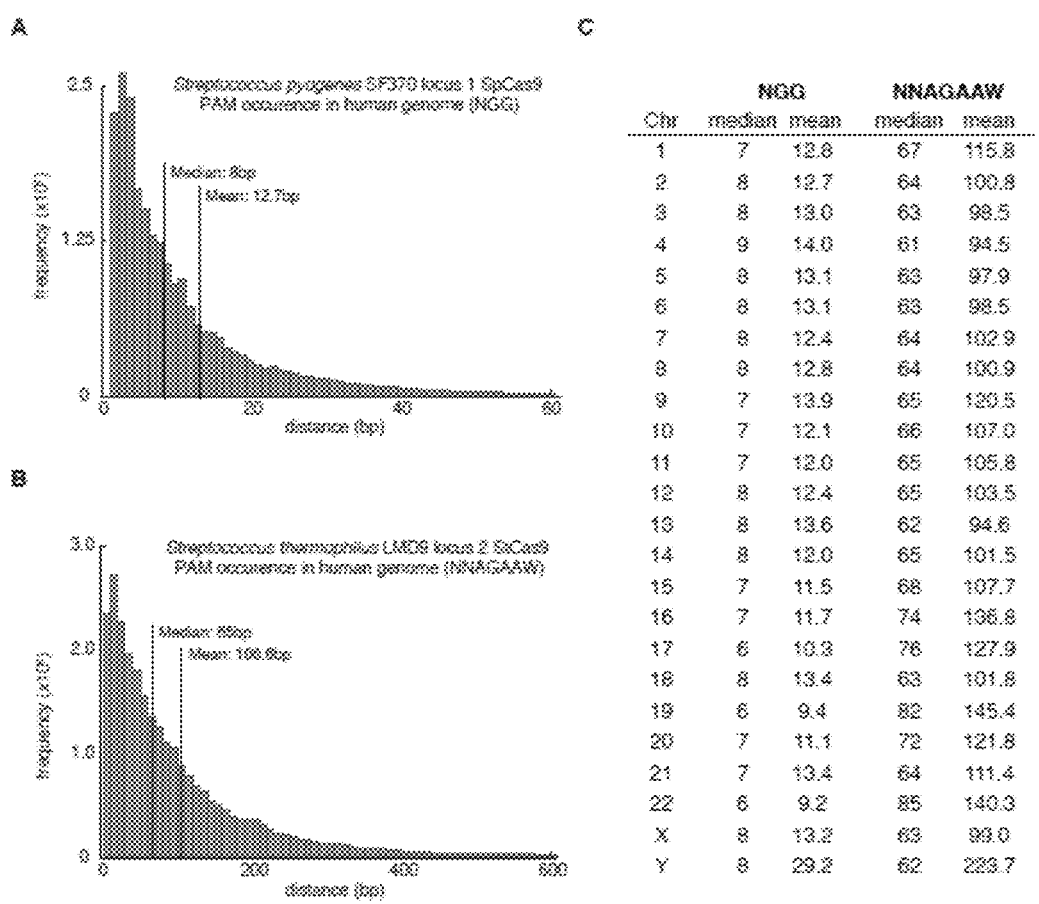

FIG. 34A-D
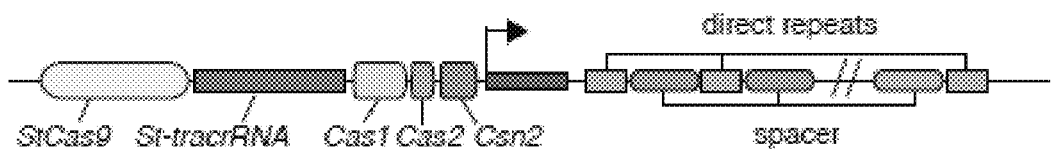
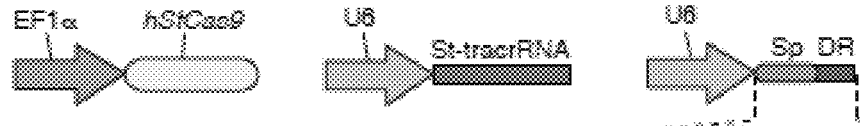
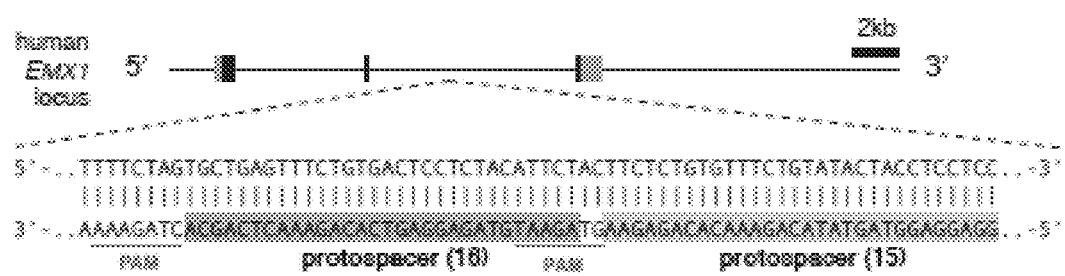
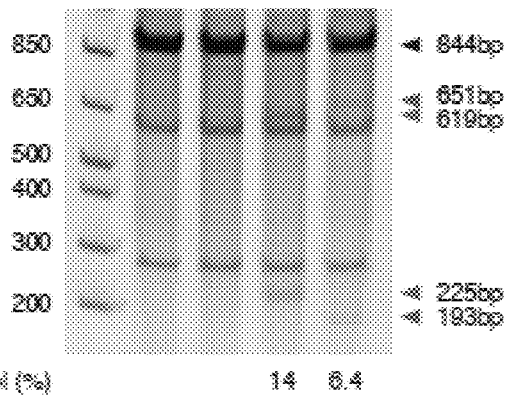

FIG. 35A-E
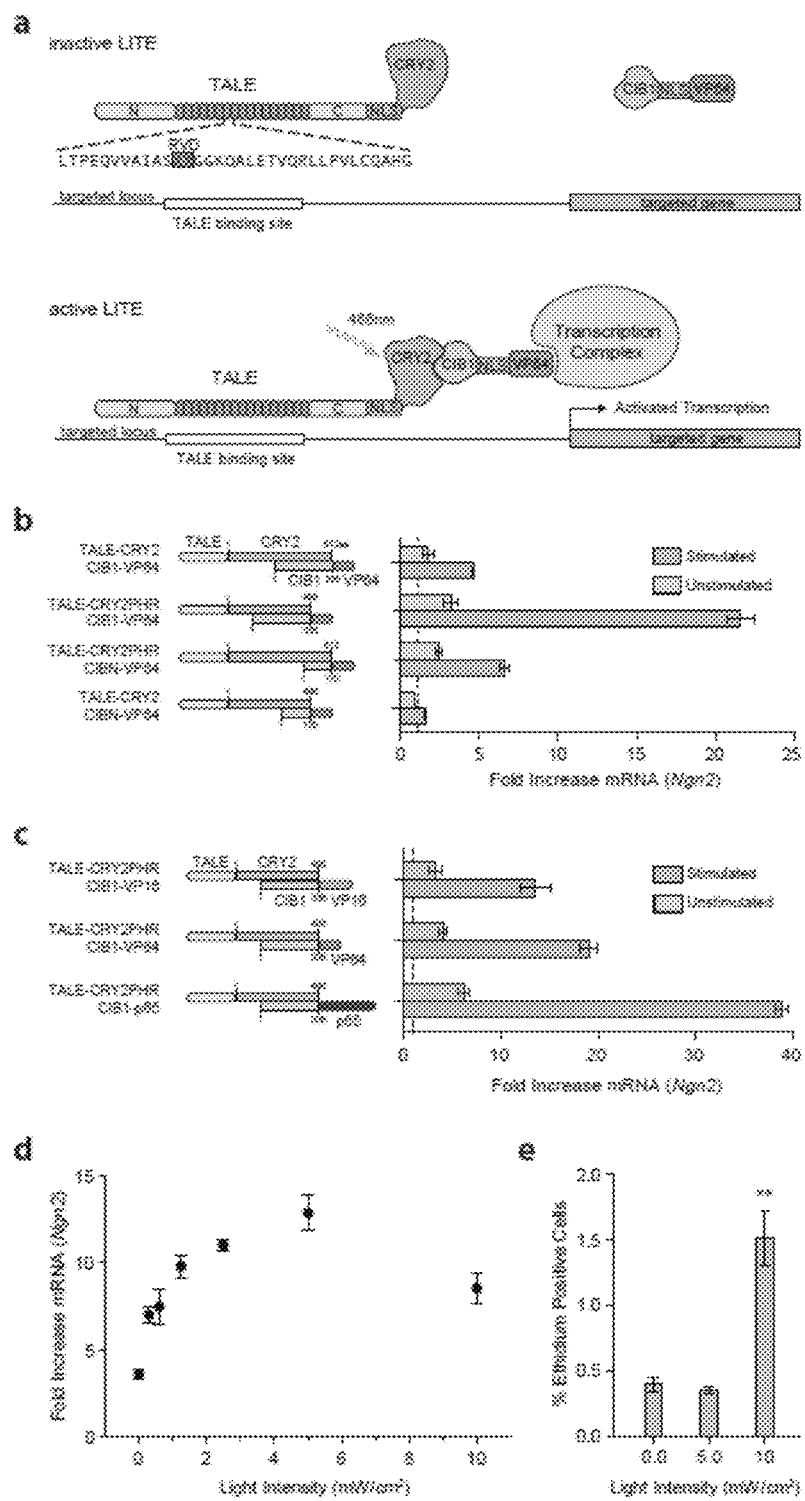

FIG. 36A-B
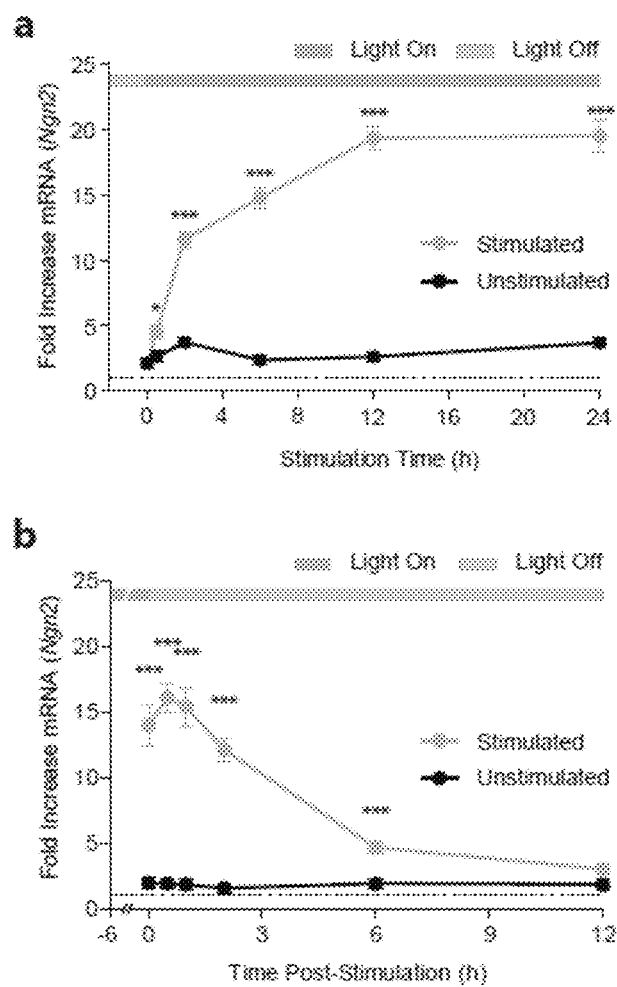

FIG. 37A-F
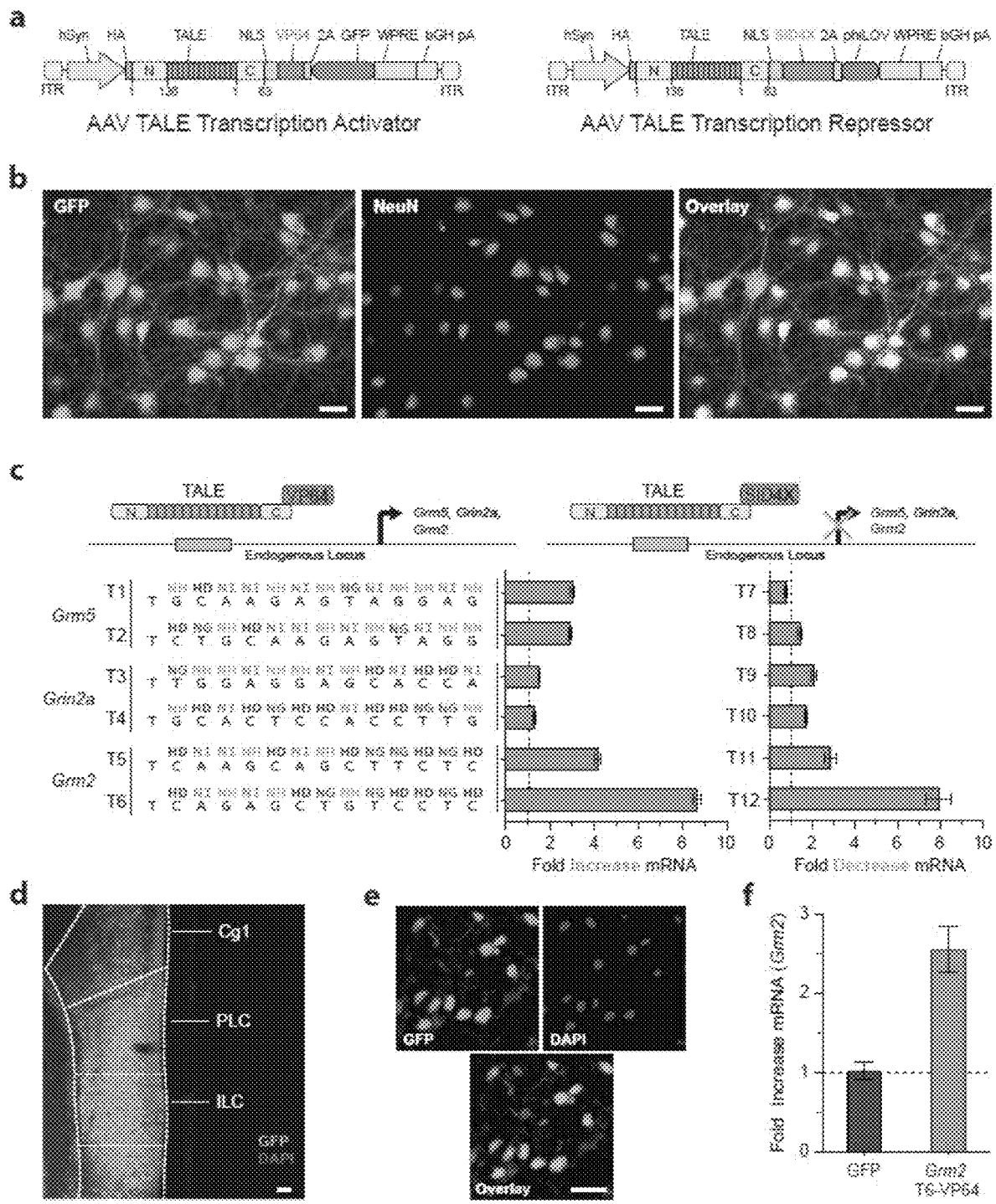

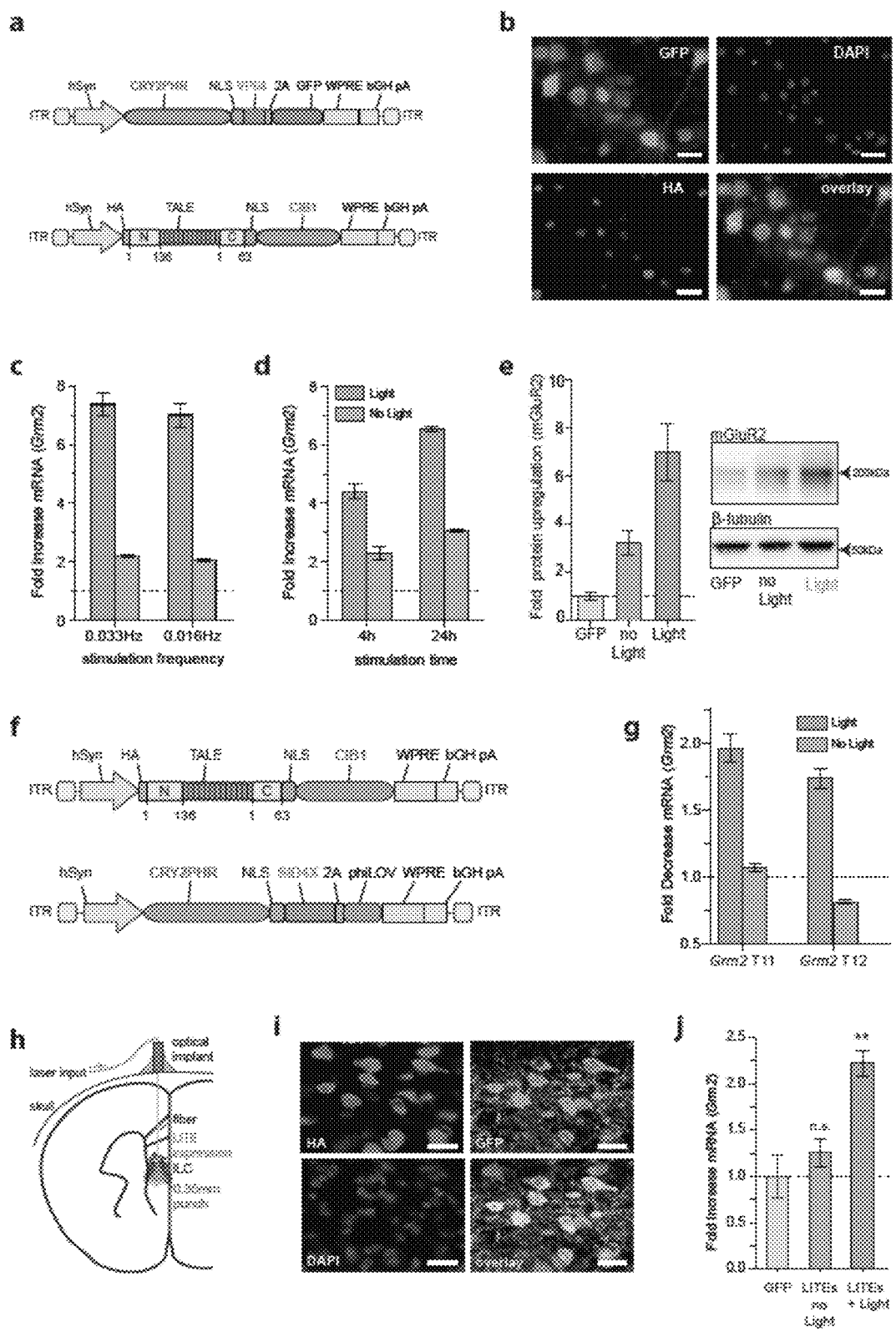
FIG. 38A-J

FIG. 42A-C

FIG. 43
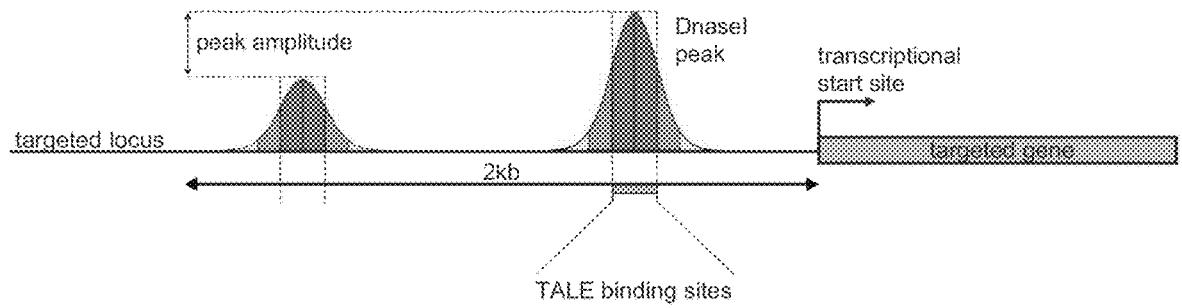
FIG. 44
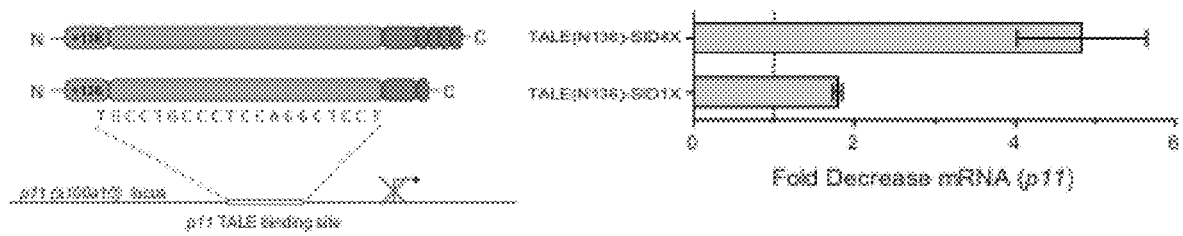
FIGS. 45A-B
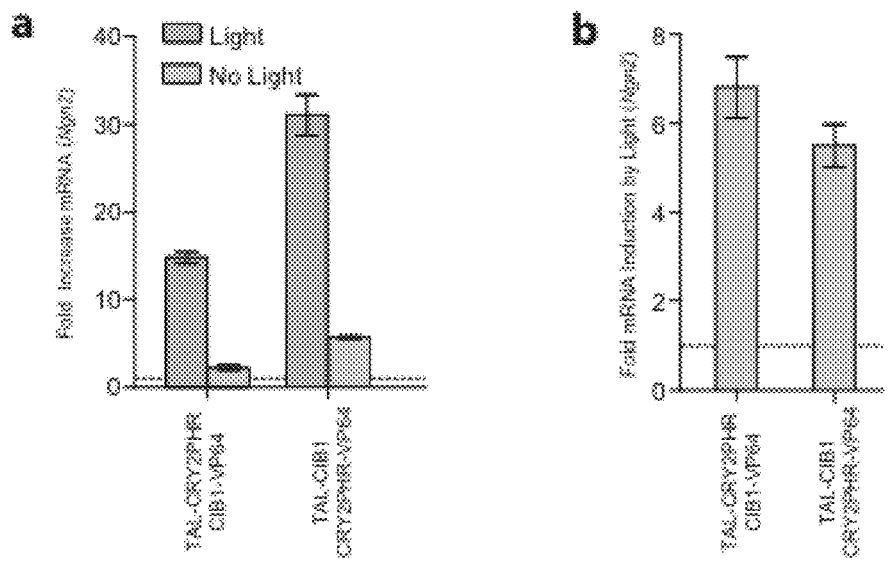

FIG. 47A-B
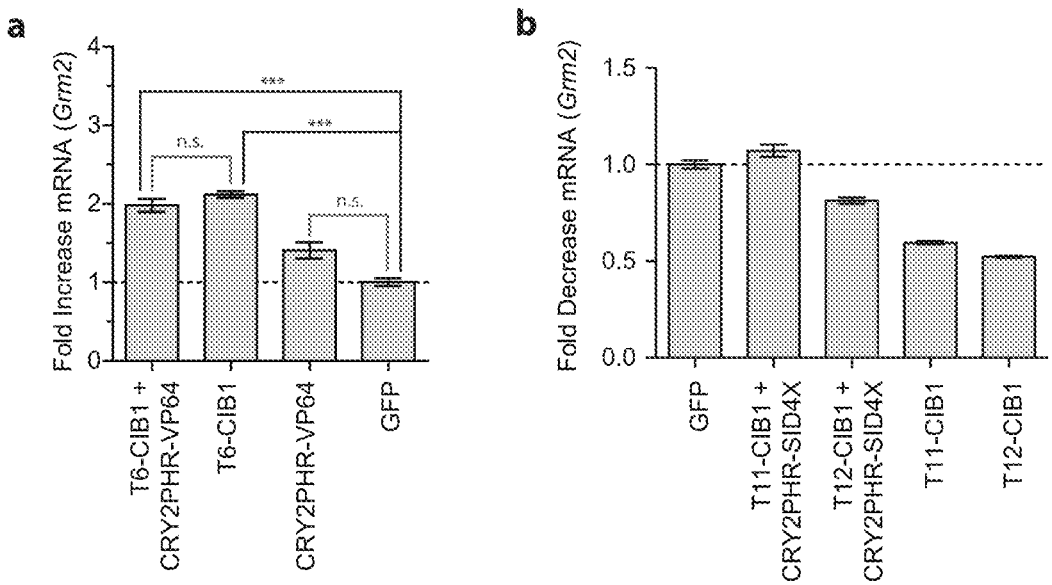
FIG. 48
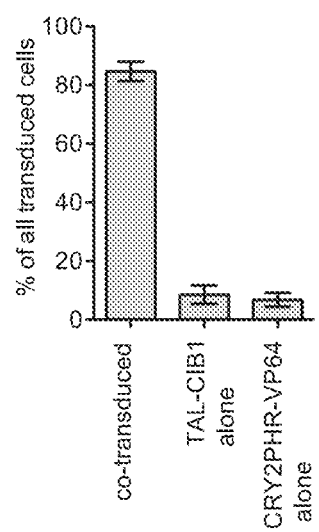

SEQUENCE LISTING

```
<160> NUMBER OF SEQ ID NOS: 350

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttattccct gacc                                                        14

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Thr Pro Asp Gln Val Val Ala Ile Ala Ser Gly Gly Lys Gln Ala
1               5                   10                  15
```

Leu Glu Thr Val Gln Arg Leu Leu Pro Val Leu Cys Gln Asp His Gly
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Thr Pro Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 13

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Thr Pro Asn Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Thr Pro Glu Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Thr Leu Asp Gln Val Val Ala Ile Ala Ser Gly Ser Lys Gln Ala
1               5                   10                  15
```

```
Leu Glu Thr Val Gln Arg Leu Leu Pro Val Leu Cys Gln Asp His Gly
            20                  25                  30
```

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Leu Ser Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Leu Thr Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Asp His Gly
            20                  25                  30
```

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Leu Thr Pro Asp Gln Val Val Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30
```

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Leu Thr Pro Asp Gln Val Val Ala Ile Ala Ser Gly Gly Asn Gln Ala
1               5                   10                  15

Leu Glu Thr Val Gln Arg Leu Leu Pro Val Leu Cys Gln Ala His Gly
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Leu Thr Pro Asp Gln Val Val Ala Ile Ala Ser Gly Gly Lys Gln Ala
1               5                   10                  15

Leu Ala Thr Val Gln Arg Leu Leu Pro Val Leu Cys Gln Ala His Gly
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

```
<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Thr Pro Glu Gln Val Val Ala Ile Ala Cys Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Thr Pro Ala Gln Val Val Ala Ile Ala Ser Gly Gly Lys Gln Ala
1               5                   10                  15

Leu Glu Thr Val Gln Gln Leu Leu Pro Val Leu Cys Glu Gln His Gly
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Leu Thr Pro Gln Gln Val Val Ala Ile Ala Ser Gly Gly Arg Pro Ala
1               5                   10                  15

Leu Glu Thr Val Gln Arg Leu Leu Pro Val Leu Cys Gln Ala His Gly
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Leu Thr Pro Asn Gln Val Val Ala Ile Ala Ser Gly Gly Lys Gln Ala
```

```
                1               5                   10                  15
Leu Glu Thr Val Gln Arg Leu Leu Pro Val Leu Cys Gln Ala His Gly
                20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Leu Thr Pro Asp Gln Val Val Ala Ile Ala Ser Gly Gly Lys Gln Ala
1               5                   10                  15

Leu Gly Thr Val Gln Arg Leu Leu Pro Val Leu Cys Gln Asp His Gly
                20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Leu Thr Pro Ala Gln Ala Val Ala Ile Ala Ser Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Leu Thr Pro Ala Gln Val Val Ala Ile Ala Ser Gly Gly Asn Gln Ala
1               5                   10                  15

Leu Glu Thr Val Gln Arg Leu Leu Pro Val Leu Cys Gln Asp His Gly
                20                  25                  30

<210> SEQ ID NO 36
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 36

Leu Thr Pro Asp Gln Val Val Ala Ile Ala Ser Gly Gly Lys Gln Ala
1               5                   10                  15

Leu Glu Thr Leu Gln Arg Leu Leu Pro Val Leu Cys Gln Ala His Gly
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Thr Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Ala His Gly
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Thr Pro Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Thr Pro Ala Gln Val Val Ala Ile Ala Asn Gly Gly Lys Gln Ala
1               5                   10                  15

Leu Glu Thr Val Arg Arg Leu Leu Pro Val Leu Cys Gln Asp His Gly
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Thr Pro Asp Gln Val Val Ala Ile Ala Ser Gly Gly Asn Gln Ala
1               5                   10                  15

Leu Glu Thr Val Gln Arg Leu Leu Pro Val Leu Cys Gln Asp His Gly
            20                  25                  30
```

```
<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Pro Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Thr Ser Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30
```

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Leu Thr Arg Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Leu Thr Pro Asp Gln Val Val Ala Thr Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Leu Ile Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 50
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 50

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asn His Gly
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Thr Leu Asp Gln Val Val Ala Ile Ala Ser Gly Gly Lys Lys Ala
1               5                   10                  15

Leu Glu Thr Val Gln Arg Leu Leu Pro Val Leu Cys Gln Asp His Gly
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Leu Thr Pro Asp Gln Leu Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Gly His Gly
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30
```

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Leu Thr Leu Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Thr Pro Asp Lys Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Tyr Gln Asp His Gly
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Thr Pro Ala Gln Val Val Ala Ile Val Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Leu Thr Pro Asp Lys Val Val Ala Ile Ala Asn Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Leu Thr Thr Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 64
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 64

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Thr Pro Asp Gln Val Val Ala Ile Ala Asn Gly Gly Lys Gln Ala
1               5                   10                  15

Leu Glu Thr Val Gln Arg Leu Leu Leu Val Leu Cys Gln Ala His Gly
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Thr Gln Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Leu Thr Pro Asp Gln Val Val Thr Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Leu Ser Pro Ala Gln Val Val Ala Ile Ala Ser Gly Gly Lys Gln Ala
1               5                   10                  15

Leu Glu Thr Val Gln Arg Leu Leu Pro Val Leu Cys His Asp His Gly
```

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 69

Leu Thr Pro Asp Gln Val Val Ala Ile Ala Ser Gly Gly Lys Gln Ala
1               5                   10                  15

Leu Glu Met Val Gln Arg Leu Leu Pro Val Leu Cys Gln Ala His Gly
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 70

Leu Ile Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 71

Leu Thr Pro Val Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 72

Leu Thr Pro Asp Gln Val Val Ala Ile Ala Ser Gly Gly Lys Gln Ala
1               5                   10                  15

Leu Lys Thr Val Gln Arg Leu Leu Pro Val Leu Cys Gln Asp His Gly
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide -continued

```
<400> SEQUENCE: 73

Leu Thr Pro Asp Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Thr Pro Ala Gln Val Val Ala Ile Ala Ser Gly Gly Lys Gln Ala
1               5                   10                  15

Leu Glu Thr Val Gln Arg Leu Phe Pro Val Leu Cys Gln Asp His Gly
            20                  25                  30

<210> SEQ ID NO 75
<211> LENGTH: 14
<212> TYPE: DNA
<213> ORGANISM: Homo sapiens

<400> SEQUENCE: 75
tttattccct gaca                                                           14

<210> SEQ ID NO 76
<211> LENGTH: 18
<212> TYPE: DNA
<213> ORGANISM: Homo sapiens

<400> SEQUENCE: 76
tcggcccctg ccggccca                                                       18

<210> SEQ ID NO 77
<211> LENGTH: 20
<212> TYPE: DNA
<213> ORGANISM: Mus musculus

<400> SEQUENCE: 77
tgcctgccct ccaggctcct                                                     20

<210> SEQ ID NO 78
<211> LENGTH: 40
<212> TYPE: DNA
<213> ORGANISM: Homo sapiens

<400> SEQUENCE: 78
aaacggaagg gcctgagtcc gagcagaaga agaagttta                                40

<210> SEQ ID NO 79
<211> LENGTH: 40
<212> TYPE: DNA
<213> ORGANISM: Homo sapiens

<400> SEQUENCE: 79
aggaggaagg gcctgagtcc gagcagaaga agaagggctc                               40

<210> SEQ ID NO 80
<211> LENGTH: 40
<212> TYPE: DNA
```

<213> ORGANISM: Homo sapiens

<400> SEQUENCE: 80
gagcccttct tcttctgctc ggactcaggc ccttcctcct                40

<210> SEQ ID NO 81
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gaguccgagc agaagaagaa guuuua                               26

<210> SEQ ID NO 82
<211> LENGTH: 39
<212> TYPE: DNA
<213> ORGANISM: Homo sapiens

<400> SEQUENCE: 82
aggaggaagg gcctgagtcc gagcagaaga gaagggctc                 39

<210> SEQ ID NO 83
<211> LENGTH: 39
<212> TYPE: DNA
<213> ORGANISM: Homo sapiens

<400> SEQUENCE: 83
ggaggaaggg cctgagtccg agcagaagaa gaagggctc                 39

<210> SEQ ID NO 84
<211> LENGTH: 38
<212> TYPE: DNA
<213> ORGANISM: Homo sapiens

<400> SEQUENCE: 84
ggaggaaggg cctgagtccg agcagaagag aagggctc                  38

<210> SEQ ID NO 85
<211> LENGTH: 40
<212> TYPE: DNA
<213> ORGANISM: Homo sapiens

<400> SEQUENCE: 85
ggaggaaggg cctgagtccg agcagaagaa agaagggctc                40

<210> SEQ ID NO 86
<211> LENGTH: 37
<212> TYPE: DNA
<213> ORGANISM: Homo sapiens

<400> SEQUENCE: 86
ggaggaaggg cctgagtccg agcagaagga agggctc                   37

<210> SEQ ID NO 87
<211> LENGTH: 36
<212> TYPE: DNA
<213> ORGANISM: Homo sapiens

<400> SEQUENCE: 87
ggaggaaggg cctgagtccg agcagaagaa gggctc                    36

```
<210> SEQ ID NO 88
<211> LENGTH: 33
<212> TYPE: DNA
<213> ORGANISM: Homo sapiens

<400> SEQUENCE: 88
ggaggaaggg cctgagtccg agcagaaggg ctc                                    33

<210> SEQ ID NO 89
<211> LENGTH: 33
<212> TYPE: DNA
<213> ORGANISM: Homo sapiens

<400> SEQUENCE: 89
ggaggaaggg cctgagcccg agcagaaggg ctc                                    33

<210> SEQ ID NO 90
<211> LENGTH: 122
<212> TYPE: DNA
<213> ORGANISM: Homo sapiens

<400> SEQUENCE: 90
ggaggaaggg cctgagtccg agcagaagaa gaagggctcc catcacatca accggtggcg       60
cattgccacg aagcaggcca atggggagga catcgatgtc acctccaatg actagggtgg      120
gc                                                                     122

<210> SEQ ID NO 91
<211> LENGTH: 122
<212> TYPE: DNA
<213> ORGANISM: Homo sapiens

<400> SEQUENCE: 91
gcccacccta gtcattggag gtgacatcga tgtcctcccc attggcctgc ttcgtggcaa       60
tgcgccaccg gttgatgtga tgggagccct tcttcttctg ctcggactca ggcccttcct      120
cc                                                                     122

<210> SEQ ID NO 92
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, u, g, unknown or other

<400> SEQUENCE: 92
acnnnnnnnn nnnnnnnnnn nnnnnnnnnn nnguuuuaga gcuaugcu                    48

<210> SEQ ID NO 93
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
```

```
agcauagcaa guuaaaauaa ggcuaguccg uuaucaacuu gaaaaagugg caccgagucg    60
gugcuuu                                                              67

<210> SEQ ID NO 94
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 94
nnnnnnnnnn nnnnnnnnnn guuuuagagc uagaaauagc aaguuaaaau aaggcuaguc    60
cg                                                                   62

<210> SEQ ID NO 95
<211> LENGTH: 48
<212> TYPE: DNA
<213> ORGANISM: Homo sapiens

<400> SEQUENCE: 95
ctggaggagg aagggcctga gtccgagcag aagaagaagg gctcccat                 48

<210> SEQ ID NO 96
<211> LENGTH: 48
<212> TYPE: DNA
<213> ORGANISM: Homo sapiens

<400> SEQUENCE: 96
atgggagccc ttcttcttct gctcggactc aggcccttcc tcctccag                 48

<210> SEQ ID NO 97
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
gaguccgagc agaagaagaa guuuuagagc                                     30

<210> SEQ ID NO 98
<211> LENGTH: 20
<212> TYPE: RNA
<213> ORGANISM: Homo sapiens

<400> SEQUENCE: 98
gaguccgagc agaagaagau                                                20

<210> SEQ ID NO 99
<211> LENGTH: 20
<212> TYPE: RNA
<213> ORGANISM: Homo sapiens

<400> SEQUENCE: 99
gaguccgagc agaagaagua                                                20

<210> SEQ ID NO 100
<211> LENGTH: 20
```

-continued

```
<212> TYPE: RNA
<213> ORGANISM: Homo sapiens

<400> SEQUENCE: 100
gaguccgagc agaagaacaa                                               20

<210> SEQ ID NO 101
<211> LENGTH: 20
<212> TYPE: RNA
<213> ORGANISM: Homo sapiens

<400> SEQUENCE: 101
gaguccgagc agaagaugaa                                               20

<210> SEQ ID NO 102
<211> LENGTH: 20
<212> TYPE: RNA
<213> ORGANISM: Homo sapiens

<400> SEQUENCE: 102
gaguccgagc agaaguagaa                                               20

<210> SEQ ID NO 103
<211> LENGTH: 20
<212> TYPE: RNA
<213> ORGANISM: Homo sapiens

<400> SEQUENCE: 103
gaguccgagc agaugaagaa                                               20

<210> SEQ ID NO 104
<211> LENGTH: 20
<212> TYPE: RNA
<213> ORGANISM: Homo sapiens

<400> SEQUENCE: 104
gaguccgagc acaagaagaa                                               20

<210> SEQ ID NO 105
<211> LENGTH: 20
<212> TYPE: RNA
<213> ORGANISM: Homo sapiens

<400> SEQUENCE: 105
gaguccgagg agaagaagaa                                               20

<210> SEQ ID NO 106
<211> LENGTH: 20
<212> TYPE: RNA
<213> ORGANISM: Homo sapiens

<400> SEQUENCE: 106
gaguccgugc agaagaagaa                                               20

<210> SEQ ID NO 107
<211> LENGTH: 20
<212> TYPE: RNA
<213> ORGANISM: Homo sapiens

<400> SEQUENCE: 107
gagucggagc agaagaagaa                                               20

<210> SEQ ID NO 108
```

```
<211> LENGTH: 20
<212> TYPE: RNA
<213> ORGANISM: Homo sapiens

<400> SEQUENCE: 108
gagaccgagc agaagaagaa                                                    20

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aatgacaagc ttgctagcgg tggg                                               24

<210> SEQ ID NO 110
<211> LENGTH: 39
<212> TYPE: DNA
<213> ORGANISM: Homo sapiens

<400> SEQUENCE: 110
aaaacggaag ggcctgagtc cgagcagaag aagaagttt                               39

<210> SEQ ID NO 111
<211> LENGTH: 39
<212> TYPE: DNA
<213> ORGANISM: Homo sapiens

<400> SEQUENCE: 111 aaacagggc cgagattggg tgttcagggc agaggtttt                                39

<210> SEQ ID NO 112
<211> LENGTH: 38
<212> TYPE: DNA
<213> ORGANISM: Homo sapiens

<400> SEQUENCE: 112
aaaacggaag ggcctgagtc cgagcagaag aagaagtt                                38

<210> SEQ ID NO 113
<211> LENGTH: 40
<212> TYPE: DNA
<213> ORGANISM: Homo sapiens

<400> SEQUENCE: 113
aacggaggga ggggcacaga tgagaaactc agggttttag                              40

<210> SEQ ID NO 114
<211> LENGTH: 38
<212> TYPE: DNA
<213> ORGANISM: Homo sapiens

<400> SEQUENCE: 114
agcccttctt cttctgctcg gactcaggcc cttcctcc                                38

<210> SEQ ID NO 115
<211> LENGTH: 40
<212> TYPE: DNA
<213> ORGANISM: Homo sapiens

<400> SEQUENCE: 115
```

```
cagggaggga ggggcacaga tgagaaactc aggaggcccc                           40
```

<210> SEQ ID NO 116
<211> LENGTH: 38
<212> TYPE: DNA
<213> ORGANISM: Homo sapiens

<400> SEQUENCE: 116

```
ggaggaaggg cctgagtccg agcagaagaa gaagggct                             38
```

<210> SEQ ID NO 117
<211> LENGTH: 40
<212> TYPE: DNA
<213> ORGANISM: Homo sapiens

<400> SEQUENCE: 117

```
ggggcctcct gagtttctca tctgtgcccc tccctccctg                           40
```

<210> SEQ ID NO 118
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
ggcaatgcgc caccggttga tgtgatggga gcccttctag gaggccccca gagcagccac     60
tggggcctca acactcaggc                                                 80
```

<210> SEQ ID NO 119
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
ggacgaaaca ccggaaccat tcaaaacagc atagcaagtt aaaataaggc tagtccgtta     60
tcaacttgaa aaagtggcac cgagtcggtg ctttttttt                            98
```

<210> SEQ ID NO 120
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
ggacgaaaca ccggtagtat taagtattgt tttatggctg ataaatttct ttgaatttct     60
ccttgattat ttgttataaa agttataaaa taatcttgtt ggaaccattc aaaacagcat    120
agcaagttaa aataaggcta gtccgttatc aacttgaaaa agtggcaccg agtcggtgct   180
tttttt                                                              186
```

<210> SEQ ID NO 121
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgaatggtcc caaaacggaa gggcctgagt ccgagcagaa gaagaagttt tagagctatg    60
ctgttttgaa tgg                                                      73

<210> SEQ ID NO 122
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gggttttaga gctatgctgt tttgaatggt cccaaaacgg gtcttcgaga agacgtttta    60
gagctatgct gttttgaatg gtcccaaaac ttttt                              95

<210> SEQ ID NO 123
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aaaaagtttt gggaccattc aaaacagcat agctctaaaa cgtcttctcg aagacccgtt    60
ttgggaccat tcaaaacagc atagctctaa aaccc                              95

<210> SEQ ID NO 124
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(34)
<223> OTHER INFORMATION: a, c, t, g, unknown or other

<400> SEQUENCE: 124
aaacnnnnnn nnnnnnnnnn nnnnnnnnnn nnnngt                             36

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(36)
<223> OTHER INFORMATION: a, c, t, g, unknown or other

<400> SEQUENCE: 125
taaaacnnnn nnnnnnnnnn nnnnnnnnnn nnnnnn                             36

<210> SEQ ID NO 126
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtggaaagga cgaaacaccg ggtcttcgag aagacctgtt ttagagctag aaatagcaag    60
ttaaaataag gctagtccgt tttt    84

<210> SEQ ID NO 127
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aaaaacggac tagccttatt ttaacttgct atttctagct ctaaaacagg tcttctcgaa    60
gacccggtgt ttcgtccttt ccac    84

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 128
caccgnnnnn nnnnnnnnnn nnnn    24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 129 aaacnnnnn nnnnnnnnnn nnnc    24

<210> SEQ ID NO 130
<211> LENGTH: 69
<212> TYPE: DNA
<213> ORGANISM: Homo sapiens

<400> SEQUENCE: 130
ctggtcttcc acctctctgc cctgaacacc caatctcggc ccctctcgcc accctcctgc    60
atttctgtt    69

<210> SEQ ID NO 131
<211> LENGTH: 69
<212> TYPE: DNA
<213> ORGANISM: Homo sapiens

<400> SEQUENCE: 131
aacagaaatg caggagggtg gcgagagggg ccgagattgg gtgttcaggg cagagaggtg    60
gaagaccag    69

<210> SEQ ID NO 132
<211> LENGTH: 138
<212> TYPE: DNA
<213> ORGANISM: Mus musculus

<400> SEQUENCE: 132
acccaagcac tgagtgccat tagctaaatg catagggtac cacccacagg tgccaggggc    60
ctttcccaaa gttcccagcc ccttctccaa cctttcctgg cccagaggct ttcccatgtg   120
tgtggctgga ccctttga                                                 138

<210> SEQ ID NO 133
<211> LENGTH: 138
<212> TYPE: DNA
<213> ORGANISM: Mus musculus

<400> SEQUENCE: 133
tcaaagggtc cagccacaca catgggaaag cctctgggcc aggaaaggtt ggagaagggg    60
ctgggaactt tgggaaaggc ccctggcacc tgtgggtggt accctatgca tttagctaat   120
ggcactcagt gcttgggt                                                 138

<210> SEQ ID NO 134
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other

<400> SEQUENCE: 134
nnnnnnnnnn nnnnnnnnng uuauuguacu cucaagauuu auuuuu                   46

<210> SEQ ID NO 135
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
guuacuuaaa ucuugcagaa gcuacaaaga uaaggcuuca ugccgaaauc aacacccugu    60
cauuuuaugg caggguguuu ucguuauuua a                                   91

<210> SEQ ID NO 136
<211> LENGTH: 70
<212> TYPE: DNA
<213> ORGANISM: Homo sapiens

<400> SEQUENCE: 136
ttttctagtg ctgagtttct gtgactcctc tacattctac ttctctgtgt ttctgtatac    60
tacctcctcc                                                          70

<210> SEQ ID NO 137
<211> LENGTH: 70
<212> TYPE: DNA
<213> ORGANISM: Homo sapiens -continued

```
<400> SEQUENCE: 137
ggaggaggta gtatacagaa acacagagaa gtagaatgta gaggagtcac agaaactcag    60
cactagaaaa                                                           70

<210> SEQ ID NO 138
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other

<400> SEQUENCE: 138 nnagaaw                                                               7

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 139

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 140
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tgcaagagta ggag                                                      14

<210> SEQ ID NO 141
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tctgcaagag tagg                                                      14

<210> SEQ ID NO 142
<211> LENGTH: 14
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 142
ttggaggagc acca                                                      14

<210> SEQ ID NO 143
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tgcactccac cttg                                                      14

<210> SEQ ID NO 144
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tcaagcagct tctc                                                      14

<210> SEQ ID NO 145
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tcagagctgt cctc                                                      14

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tgcctgccct ccaggctcct                                                20

<210> SEQ ID NO 147
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe

```
            50                  55                  60
Ser Ala Asp Ser Phe Ser Asp Leu Leu Arg Gln Phe Asp Pro Ser Leu
 65                  70                  75                  80

Phe Asn Thr Ser Leu Phe Asp Ser Leu Pro Pro Phe Gly Ala His His
                 85                  90                  95

Thr Glu Ala Ala Thr Gly Glu Trp Asp Glu Val Gln Ser Gly Leu Arg
             100                 105                 110

Ala Ala Asp Ala Pro Pro Thr Met Arg Val Ala Val Thr Ala Ala
         115                 120                 125

Arg Pro Pro Arg Ala Lys Pro Ala Pro Arg Arg Ala Ala Gln Pro
     130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                 165                 170                 175

Ala Gln His His Glu Ala Leu Val Gly His Gly Phe Thr His Ala His
             180                 185                 190

Ile Val Ala Leu Ser Gln His Pro Ala Ala Leu Gly Thr Val Ala Val
         195                 200                 205

Lys Tyr Gln Asp Met Ile Ala Ala Leu Pro Glu Ala Thr His Glu Ala
     210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                 245                 250                 255

Thr Gly Gln Leu Leu Lys Ile Ala Lys Arg Gly Gly Val Thr Ala Val
             260                 265                 270

Glu Ala Val His Ala Trp Arg Asn Ala Leu Thr Gly Ala Pro Leu Asn
         275                 280                 285

<210> SEQ ID NO 148
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Pro Ala Leu Glu Ser Ile Val Ala Gln Leu Ser Arg Pro Asp Pro
 1               5                  10                  15

Ala Leu Ala Ala Leu Thr Asn Asp His Leu Val Ala Leu Ala Cys Leu
                 20                  25                  30

Gly Gly Arg Pro Ala Leu Asp Ala Val Lys Lys Gly Leu Pro His Ala
             35                  40                  45

Pro Ala Leu Ile Lys Arg Thr Asn Arg Arg Ile Pro Glu Arg Thr Ser
         50                  55                  60

His Arg Val Ala Asp His Ala Gln Val Val Arg Val Leu Gly Phe Phe
 65                  70                  75                  80

Gln Cys His Ser His Pro Ala Gln Ala Phe Asp Asp Ala Met Thr Gln
                 85                  90                  95

Phe Gly Met Ser Arg His Gly Leu Leu Gln Leu Phe Arg Arg Val Gly
             100                 105                 110

Val Thr Glu Leu Glu Ala Arg Ser Gly Thr Leu Pro Pro Ala Ser Gln
         115                 120                 125
```

-continued

```
Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 149
<211> LENGTH: 18
<212> TYPE: DNA
<213> ORGANISM: Mus musculus

<400> SEQUENCE: 149
tgaatgatga taatacga                                                18

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ser Pro Lys Lys Lys Arg Lys Val Glu Ala Ser
1               5                   10

<210> SEQ ID NO 151
<211> LENGTH: 7
<212> TYPE: PRT
<213> ORGANISM: Simian virus 40

<400> SEQUENCE: 151

Pro Lys Lys Lys Arg Lys Val
1               5

<210> SEQ ID NO 152
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 152

Lys Arg Pro Ala Ala Thr Lys Lys Ala Gly Gln Ala Lys Lys Lys Lys
1               5                   10                  15

<210> SEQ ID NO 153
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 153

Pro Ala Ala Lys Arg Val Lys Leu Asp
1               5

<210> SEQ ID NO 154
<211> LENGTH: 11
<212> TYPE: PRT
```

```
<213> ORGANISM: Unknown
<220> FEATURE:
<223> OTHER INFORMATION: Description of Unknown:
      C-myc NLS sequence

<400> SEQUENCE: 154

Arg Gln Arg Arg Asn Glu Leu Lys Arg Ser Pro
1               5                   10

<210> SEQ ID NO 155
<211> LENGTH: 38
<212> TYPE: PRT
<213> ORGANISM: Homo sapiens

<400> SEQUENCE: 155

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 156
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 156

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 157
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 157

Val Ser Arg Lys Arg Pro Arg Pro
1               5

<210> SEQ ID NO 158
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 158

Pro Pro Lys Lys Ala Arg Glu Asp
1               5

<210> SEQ ID NO 159
<211> LENGTH: 8
<212> TYPE: PRT
```

-continued

```
<213> ORGANISM: Homo sapiens

<400> SEQUENCE: 159

Pro Gln Pro Lys Lys Pro Leu
1               5

<210> SEQ ID NO 160
<211> LENGTH: 12
<212> TYPE: PRT
<213> ORGANISM: Mus musculus

<400> SEQUENCE: 160

Ser Ala Leu Ile Lys Lys Lys Lys Lys Met Ala Pro
1               5                   10

<210> SEQ ID NO 161
<211> LENGTH: 5
<212> TYPE: PRT
<213> ORGANISM: Influenza virus

<400> SEQUENCE: 161

Asp Arg Leu Arg Arg
1               5

<210> SEQ ID NO 162
<211> LENGTH: 7
<212> TYPE: PRT
<213> ORGANISM: Influenza virus

<400> SEQUENCE: 162

Pro Lys Gln Lys Lys Arg Lys
1               5

<210> SEQ ID NO 163
<211> LENGTH: 10
<212> TYPE: PRT
<213> ORGANISM: Hepatitus delta virus

<400> SEQUENCE: 163

Arg Lys Leu Lys Lys Lys Ile Lys Lys Leu
1               5                   10

<210> SEQ ID NO 164
<211> LENGTH: 10
<212> TYPE: PRT
<213> ORGANISM: Mus musculus

<400> SEQUENCE: 164

Arg Glu Lys Lys Lys Phe Leu Lys Arg Arg
1               5                   10

<210> SEQ ID NO 165
<211> LENGTH: 20
<212> TYPE: PRT
<213> ORGANISM: Homo sapiens

<400> SEQUENCE: 165

Lys Arg Lys Gly Asp Glu Val Asp Gly Val Asp Glu Val Ala Lys Lys
1               5                   10                  15

Lys Ser Lys Lys
            20

<210> SEQ ID NO 166
<211> LENGTH: 17
```

<212> TYPE: PRT
<213> ORGANISM: Homo sapiens

<400> SEQUENCE: 166

Arg Lys Cys Leu Gln Ala Gly Met Asn Leu Glu Ala Arg Lys Thr Lys
1               5                   10                  15

Lys

<210> SEQ ID NO 167
<211> LENGTH: 14
<212> TYPE: DNA
<213> ORGANISM: Homo sapiens

<400> SEQUENCE: 167
ttcttactta taac                                                            14

<210> SEQ ID NO 168
<211> LENGTH: 1603
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Asn Gly Gly Lys
                245                 250                 255

```
Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Ile Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
        370                 375                 380

Ile Ala Ser Asn Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser Asn Gly Gly Lys Gln Ala Leu Glu Thr Val
            420                 425                 430

Gln Arg Leu Leu Pro Val Leu Cys Gln Ala His Gly Leu Thr Pro Glu
            435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Ile Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser His Asp Gly Gly Lys
        515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Gly Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser His Asp Gly Gly Lys Gln Ala Leu Glu Thr Val Gln Arg
            660                 665                 670

Leu Leu Pro Val Leu Cys Gln Ala His Gly Leu Thr Pro Glu Gln Val
```

```
                675                 680                 685
Val Ala Ile Ala Ser Asn Asn Gly Gly Lys Gln Ala Leu Glu Thr Val
    690                 695                 700
Gln Arg Leu Leu Pro Val Leu Cys Gln Ala His Gly Leu Thr Pro Glu
705                 710                 715                 720
Gln Val Val Ala Ile Ala Ser His Asp Gly Gly Lys Gln Ala Leu Glu
                725                 730                 735
Thr Val Gln Arg Leu Leu Pro Val Leu Cys Gln Ala His Gly Leu Thr
            740                 745                 750
Pro Glu Gln Val Val Ala Ile Ala Ser His Asp Gly Gly Lys Gln Ala
        755                 760                 765
Leu Glu Thr Val Gln Arg Leu Leu Pro Val Leu Cys Gln Ala His Gly
    770                 775                 780
Leu Thr Pro Glu Gln Val Val Ala Ile Ala Ser His Asp Gly Gly Arg
785                 790                 795                 800
Pro Ala Leu Glu Ser Ile Val Ala Gln Leu Ser Arg Pro Asp Pro Ala
                805                 810                 815
Leu Ala Ala Leu Thr Asn Asp His Leu Val Ala Leu Ala Cys Leu Gly
            820                 825                 830
Gly Arg Pro Ala Leu Asp Ala Val Lys Lys Gly Leu Pro His Ala Pro
        835                 840                 845
Ala Leu Ile Lys Arg Thr Asn Arg Arg Ile Pro Glu Arg Thr Ser His
    850                 855                 860
Arg Val Ala Asp His Ala Gln Val Val Arg Val Leu Gly Phe Phe Gln
865                 870                 875                 880
Cys His Ser His Pro Ala Gln Ala Phe Asp Asp Ala Met Thr Gln Phe
                885                 890                 895
Gly Met Ser Arg His Gly Leu Leu Gln Leu Phe Arg Arg Val Gly Val
            900                 905                 910
Thr Glu Leu Glu Ala Arg Ser Gly Thr Leu Pro Pro Ala Ser Gln Arg
        915                 920                 925
Trp Asp Arg Ile Leu Gln Ala Ser Gly Met Lys Arg Ala Lys Pro Ser
    930                 935                 940
Pro Thr Ser Thr Gln Thr Pro Asp Gln Ala Ser Leu His Ala Phe Ala
945                 950                 955                 960
Asp Ser Leu Glu Arg Asp Leu Asp Ala Pro Ser Pro Met His Glu Gly
                965                 970                 975
Asp Gln Thr Arg Ala Ser Ala Ser Pro Lys Lys Arg Lys Val Glu
            980                 985                 990
Ala Ser Lys Met Asp Lys Lys Thr Ile Val Trp Phe Arg Arg Asp Leu
        995                 1000                1005
Arg Ile Glu Asp Asn Pro Ala Leu Ala Ala Ala Ala His Glu Gly
    1010                1015                1020
Ser Val Phe Pro Val Phe Ile Trp Cys Pro Glu Glu Glu Gly Gln
    1025                1030                1035
Phe Tyr Pro Gly Arg Ala Ser Arg Trp Trp Met Lys Gln Ser Leu
    1040                1045                1050
Ala His Leu Ser Gln Ser Leu Lys Ala Leu Gly Ser Asp Leu Thr
    1055                1060                1065
Leu Ile Lys Thr His Asn Thr Ile Ser Ala Ile Leu Asp Cys Ile
    1070                1075                1080
Arg Val Thr Gly Ala Thr Lys Val Val Phe Asn His Leu Tyr Asp
    1085                1090                1095
```

-continued

Pro Val Ser Leu Val Arg Asp His Thr Val Lys Glu Lys Leu Val
    1100            1105            1110

Glu Arg Gly Ile Ser Val Gln Ser Tyr Asn Gly Asp Leu Leu Tyr
    1115            1120            1125

Glu Pro Trp Glu Ile Tyr Cys Glu Lys Gly Lys Pro Phe Thr Ser
    1130            1135            1140

Phe Asn Ser Tyr Trp Lys Lys Cys Leu Asp Met Ser Ile Glu Ser
    1145            1150            1155

Val Met Leu Pro Pro Pro Trp Arg Leu Met Pro Ile Thr Ala Ala
    1160            1165            1170

Ala Glu Ala Ile Trp Ala Cys Ser Ile Glu Glu Leu Gly Leu Glu
    1175            1180            1185

Asn Glu Ala Glu Lys Pro Ser Asn Ala Leu Leu Thr Arg Ala Trp
    1190            1195            1200

Ser Pro Gly Trp Ser Asn Ala Asp Lys Leu Leu Asn Glu Phe Ile
    1205            1210            1215

Glu Lys Gln Leu Ile Asp Tyr Ala Lys Asn Ser Lys Lys Val Val
    1220            1225            1230

Gly Asn Ser Thr Ser Leu Leu Ser Pro Tyr Leu His Phe Gly Glu
    1235            1240            1245

Ile Ser Val Arg His Val Phe Gln Cys Ala Arg Met Lys Gln Ile
    1250            1255            1260

Ile Trp Ala Arg Asp Lys Asn Ser Glu Gly Glu Glu Ser Ala Asp
    1265            1270            1275

Leu Phe Leu Arg Gly Ile Gly Leu Arg Glu Tyr Ser Arg Tyr Ile
    1280            1285            1290

Cys Phe Asn Phe Pro Phe Thr His Glu Gln Ser Leu Leu Ser His
    1295            1300            1305

Leu Arg Phe Phe Pro Trp Asp Ala Asp Val Asp Lys Phe Lys Ala
    1310            1315            1320

Trp Arg Gln Gly Arg Thr Gly Tyr Pro Leu Val Asp Ala Gly Met
    1325            1330            1335

Arg Glu Leu Trp Ala Thr Gly Trp Met His Asn Arg Ile Arg Val
    1340            1345            1350

Ile Val Ser Ser Phe Ala Val Lys Phe Leu Leu Leu Pro Trp Lys
    1355            1360            1365

Trp Gly Met Lys Tyr Phe Trp Asp Thr Leu Leu Asp Ala Asp Leu
    1370            1375            1380

Glu Cys Asp Ile Leu Gly Trp Gln Tyr Ile Ser Gly Ser Ile Pro
    1385            1390            1395

Asp Gly His Glu Leu Asp Arg Leu Asp Asn Pro Ala Leu Gln Gly
    1400            1405            1410

Ala Lys Tyr Asp Pro Glu Gly Glu Tyr Ile Arg Gln Trp Leu Pro
    1415            1420            1425

Glu Leu Ala Arg Leu Pro Thr Glu Trp Ile His His Pro Trp Asp
    1430            1435            1440

Ala Pro Leu Thr Val Leu Lys Ala Ser Gly Val Glu Leu Gly Thr
    1445            1450            1455

Asn Tyr Ala Lys Pro Ile Val Asp Ile Asp Thr Ala Arg Glu Leu
    1460            1465            1470

Leu Ala Lys Ala Ile Ser Arg Thr Arg Glu Ala Gln Ile Met Ile
    1475            1480            1485

-continued

```
Gly Ala  Ala Pro Asp Glu Ile Val Ala Asp Ser Phe  Glu Ala Leu
    1490             1495                 1500

Gly Ala  Asn Thr Ile Lys Glu Pro Gly Leu Cys Pro  Ser Val Ser
    1505             1510                 1515

Ser Asn  Asp Gln Gln Val Pro Ser Ala Val Arg Tyr  Asn Gly Ser
    1520             1525                 1530

Lys Arg  Val Lys Pro Glu Glu Glu Glu Arg Asp Met  Lys Lys
    1535             1540                 1545

Ser Arg  Gly Phe Asp Glu Arg Glu Leu Phe Ser Thr  Ala Glu Ser
    1550             1555                 1560

Ser Ser  Ser Ser Ser Val Phe Phe Val Ser Gln Ser  Cys Ser Leu
    1565             1570                 1575

Ala Ser  Glu Gly Lys Asn Leu Glu Gly Ile Gln Asp  Ser Ser Asp
    1580             1585                 1590

Gln Ile  Thr Thr Ser Leu Gly Lys Asn Gly
    1595             1600
```

<210> SEQ ID NO 169
<211> LENGTH: 1492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
                35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
                115                 120                 125

Ala Gln His His Glu Ala Leu Val Gly His Gly Phe Thr His Ala His
                130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
                195                 200                 205

Thr Gly Gln Leu Leu Lys Ile Ala Lys Arg Gly Gly Val Thr Ala Val
                210                 215                 220

Glu Ala Val His Ala Trp Arg Asn Ala Leu Thr Gly Ala Pro Leu Asn
225                 230                 235                 240
```

```
Leu Thr Pro Glu Gln Val Val Ala Ile Ala Ser Asn Asn Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser His Asp Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Ile Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
    370                 375                 380

Ile Ala Ser Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
            405                 410                 415

Val Ala Ile Ala Ser Asn Gly Gly Lys Gln Ala Leu Glu Thr Val
        420                 425                 430

Gln Arg Leu Leu Pro Val Leu Cys Gln Ala His Gly Leu Thr Pro Glu
    435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Ile Gly Gly Lys Gln Ala
            485                 490                 495

Leu Glu Thr Val Gln Arg Leu Leu Pro Val Leu Cys Gln Ala His Gly
        500                 505                 510

Leu Thr Pro Glu Gln Val Val Ala Ile Ala Ser His Asp Gly Gly Lys
    515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
            565                 570                 575

Gln Ala His Gly Leu Thr Pro Glu Gln Val Val Ala Ile Ala Ser Asn
        580                 585                 590

Gly Gly Lys Gln Ala Leu Glu Thr Val Gln Arg Leu Leu Pro Val
    595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655
```

```
Ile Ala Ser His Asp Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser Asn Asn Gly Gly Lys Gln Ala Leu Glu Thr Val
    690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750

Pro Glu Gln Val Val Ala Ile Ala Ser His Asp Gly Gly Lys Gln Ala
        755                 760                 765

Leu Glu Thr Val Gln Arg Leu Leu Pro Val Leu Cys Gln Ala His Gly
    770                 775                 780

Leu Thr Pro Glu Gln Val Val Ala Ile Ala Ser His Asp Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
        835                 840                 845

Ala Leu Ile Lys Arg Thr Asn Arg Arg Ile Pro Glu Arg Thr Ser His
    850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
    930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Lys Arg Lys Val Glu
            980                 985                 990

Ala Ser Lys Met Asp Lys Lys Thr Ile Val Trp Phe Arg Arg Asp Leu
        995                 1000                1005

Arg Ile Glu Asp Asn Pro Ala Leu Ala Ala Ala His Glu Gly
    1010                1015                1020

Ser Val Phe Pro Val Phe Ile Trp Cys Pro Glu Glu Glu Gly Gln
    1025                1030                1035

Phe Tyr Pro Gly Arg Ala Ser Arg Trp Trp Met Lys Gln Ser Leu
    1040                1045                1050

Ala His Leu Ser Gln Ser Leu Lys Ala Leu Gly Ser Asp Leu Thr
    1055                1060                1065

Leu Ile Lys Thr His Asn Thr Ile Ser Ala Ile Leu Asp Cys Ile
```

```
            1070                1075                1080
Arg Val Thr Gly Ala Thr Lys Val Val Phe Asn His Leu Tyr Asp
        1085                1090                1095

Pro Val Ser Leu Val Arg Asp His Thr Val Lys Glu Lys Leu Val
        1100                1105                1110

Glu Arg Gly Ile Ser Val Gln Ser Tyr Asn Gly Asp Leu Leu Tyr
        1115                1120                1125

Glu Pro Trp Glu Ile Tyr Cys Glu Lys Gly Lys Pro Phe Thr Ser
        1130                1135                1140

Phe Asn Ser Tyr Trp Lys Lys Cys Leu Asp Met Ser Ile Glu Ser
        1145                1150                1155

Val Met Leu Pro Pro Pro Trp Arg Leu Met Pro Ile Thr Ala Ala
        1160                1165                1170

Ala Glu Ala Ile Trp Ala Cys Ser Ile Glu Glu Leu Gly Leu Glu
        1175                1180                1185

Asn Glu Ala Glu Lys Pro Ser Asn Ala Leu Leu Thr Arg Ala Trp
        1190                1195                1200

Ser Pro Gly Trp Ser Asn Ala Asp Lys Leu Leu Asn Glu Phe Ile
        1205                1210                1215

Glu Lys Gln Leu Ile Asp Tyr Ala Lys Asn Ser Lys Lys Val Val
        1220                1225                1230

Gly Asn Ser Thr Ser Leu Leu Ser Pro Tyr Leu His Phe Gly Glu
        1235                1240                1245

Ile Ser Val Arg His Val Phe Gln Cys Ala Arg Met Lys Gln Ile
        1250                1255                1260

Ile Trp Ala Arg Asp Lys Asn Ser Glu Gly Glu Glu Ser Ala Asp
        1265                1270                1275

Leu Phe Leu Arg Gly Ile Gly Leu Arg Glu Tyr Ser Arg Tyr Ile
        1280                1285                1290

Cys Phe Asn Phe Pro Phe Thr His Glu Gln Ser Leu Leu Ser His
        1295                1300                1305

Leu Arg Phe Phe Pro Trp Asp Ala Asp Val Asp Lys Phe Lys Ala
        1310                1315                1320

Trp Arg Gln Gly Arg Thr Gly Tyr Pro Leu Val Asp Ala Gly Met
        1325                1330                1335

Arg Glu Leu Trp Ala Thr Gly Trp Met His Asn Arg Ile Arg Val
        1340                1345                1350

Ile Val Ser Ser Phe Ala Val Lys Phe Leu Leu Leu Pro Trp Lys
        1355                1360                1365

Trp Gly Met Lys Tyr Phe Trp Asp Thr Leu Leu Asp Ala Asp Leu
        1370                1375                1380

Glu Cys Asp Ile Leu Gly Trp Gln Tyr Ile Ser Gly Ser Ile Pro
        1385                1390                1395

Asp Gly His Glu Leu Asp Arg Leu Asp Asn Pro Ala Leu Gln Gly
        1400                1405                1410

Ala Lys Tyr Asp Pro Glu Gly Glu Tyr Ile Arg Gln Trp Leu Pro
        1415                1420                1425

Glu Leu Ala Arg Leu Pro Thr Glu Trp Ile His His Pro Trp Asp
        1430                1435                1440

Ala Pro Leu Thr Val Leu Lys Ala Ser Gly Val Glu Leu Gly Thr
        1445                1450                1455

Asn Tyr Ala Lys Pro Ile Val Asp Ile Asp Thr Ala Arg Glu Leu
        1460                1465                1470
```

```
Leu Ala Lys Ala Ile Ser Arg Thr Arg Glu Ala Gln Ile Met Ile
    1475                1480                1485

Gly Ala Ala Pro
    1490

<210> SEQ ID NO 170
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Asn Gly Ala Ile Gly Gly Asp Leu Leu Asn Phe Pro Asp Met
1               5                   10                  15

Ser Val Leu Glu Arg Gln Arg Ala His Leu Lys Tyr Leu Asn Pro Thr
                20                  25                  30

Phe Asp Ser Pro Leu Ala Gly Phe Phe Ala Asp Ser Ser Met Ile Thr
            35                  40                  45

Gly Gly Glu Met Asp Ser Tyr Leu Ser Thr Ala Gly Leu Asn Leu Pro
        50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
                85                  90                  95

Asp Thr Glu Thr Lys Asp Cys Asn Glu Lys Lys Lys Lys Met Thr Met
            100                 105                 110

Asn Arg Asp Asp Leu Val Glu Glu Gly Glu Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
                165                 170                 175

Gly Gln Ala Thr Asp Ser His Ser Ile Ala Glu Arg Val Arg Arg Glu
            180                 185                 190

Lys Ile Ser Glu Arg Met Lys Phe Leu Gln Asp Leu Val Pro Gly Cys
        195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
                245                 250                 255

Glu Val Ala Ser Thr Pro Met Thr Val Val Pro Ser Pro Glu Met Val
            260                 265                 270

Leu Ser Gly Tyr Ser His Glu Met Val His Ser Gly Tyr Ser Ser Glu
        275                 280                 285

Met Val Asn Ser Gly Tyr Leu His Val Asn Pro Met Gln Gln Val Asn
    290                 295                 300

Thr Ser Ser Asp Pro Leu Ser Cys Phe Asn Asn Gly Glu Ala Pro Ser
305                 310                 315                 320

Met Trp Asp Ser His Val Gln Asn Leu Tyr Gly Asn Leu Gly Val Ala
```

325                 330                 335

Ser Pro Lys Lys Lys Arg Lys Val Glu Ala Ser Gly Ser Gly Arg Ala
            340                 345                 350

Asp Ala Leu Asp Asp Phe Asp Leu Asp Met Leu Gly Ser Asp Ala Leu
        355                 360                 365

Asp Asp Phe Asp Leu Asp Met Leu Gly Ser Asp Ala Leu Asp Asp Phe
    370                 375                 380

Asp Leu Asp Met Leu Gly Ser Asp Ala Leu Asp Asp Phe Asp Leu Asp
385                 390                 395                 400

Met Leu Ile Asn Ser Arg Gly Ser Gly Glu Gly Arg Gly Ser Leu Leu
            405                 410                 415

Thr Cys Gly Asp Val Glu Glu Asn Pro Gly Pro Val Ser Lys Gly Glu
        420                 425                 430

Glu Leu Phe Thr Gly Val Val Pro Ile Leu Val Glu Leu Asp Gly Asp
    435                 440                 445

Val Asn Gly His Lys Phe Ser Val Ser Gly Glu Gly Glu Gly Asp Ala
450                 455                 460

Thr Tyr Gly Lys Leu Thr Leu Lys Phe Ile Cys Thr Thr Gly Lys Leu
465                 470                 475                 480

Pro Val Pro Trp Pro Thr Leu Val Thr Thr Leu Thr Tyr Gly Val Gln
            485                 490                 495

Cys Phe Ser Arg Tyr Pro Asp His Met Lys Gln His Asp Phe Phe Lys
        500                 505                 510

Ser Ala Met Pro Glu Gly Tyr Val Gln Glu Arg Thr Ile Phe Phe Lys
    515                 520                 525

Asp Asp Gly Asn Tyr Lys Thr Arg Ala Glu Val Lys Phe Glu Gly Asp
530                 535                 540

Thr Leu Val Asn Arg Ile Glu Leu Lys Gly Ile Asp Phe Lys Glu Asp
545                 550                 555                 560

Gly Asn Ile Leu Gly His Lys Leu Glu Tyr Asn Tyr Asn Ser His Asn
            565                 570                 575

Val Tyr Ile Met Ala Asp Lys Gln Lys Asn Gly Ile Lys Val Asn Phe
        580                 585                 590

Lys Ile Arg His Asn Ile Glu Asp Gly Ser Val Gln Leu Ala Asp His
    595                 600                 605

Tyr Gln Gln Asn Thr Pro Ile Gly Asp Gly Pro Val Leu Leu Pro Asp
610                 615                 620

Asn His Tyr Leu Ser Thr Gln Ser Ala Leu Ser Lys Asp Pro Asn Glu
625                 630                 635                 640

Lys Arg Asp His Met Val Leu Leu Glu Phe Val Thr Ala Ala Gly Ile
            645                 650                 655

Thr Leu Gly Met Asp Glu Leu Tyr Lys
        660                 665

<210> SEQ ID NO 171
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Asn Gly Ala Ile Gly Gly Asp Leu Leu Leu Asn Phe Pro Asp Met
1               5                   10                  15

-continued

Ser Val Leu Glu Arg Gln Arg Ala His Leu Lys Tyr Leu Asn Pro Thr
        20                  25                  30

Phe Asp Ser Pro Leu Ala Gly Phe Ala Asp Ser Ser Met Ile Thr
        35                  40                  45

Gly Gly Glu Met Asp Ser Tyr Leu Ser Thr Ala Gly Leu Asn Leu Pro
50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
                85                  90                  95

Asp Thr Glu Thr Lys Asp Cys Asn Glu Lys Lys Lys Met Thr Met
            100                 105                 110

Asn Arg Asp Asp Leu Val Glu Glu Gly Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile Ala Ser Pro Lys Lys Lys
                165                 170                 175

Arg Lys Val Glu Ala Ser Gly Ser Gly Arg Ala Asp Ala Leu Asp Asp
            180                 185                 190

Phe Asp Leu Asp Met Leu Gly Ser Asp Ala Leu Asp Asp Phe Asp Leu
        195                 200                 205

Asp Met Leu Gly Ser Asp Ala Leu Asp Asp Phe Asp Leu Asp Met Leu
    210                 215                 220

Gly Ser Asp Ala Leu Asp Asp Phe Asp Leu Asp Met Leu Ile Asn Ser
225                 230                 235                 240

Arg Gly Ser Gly Glu Gly Arg Gly Ser Leu Leu Thr Cys Gly Asp Val
                245                 250                 255

Glu Glu Asn Pro Gly Pro Val Ser Lys Gly Glu Glu Leu Phe Thr Gly
            260                 265                 270

Val Val Pro Ile Leu Val Glu Leu Asp Gly Asp Val Asn Gly His Lys
        275                 280                 285

Phe Ser Val Ser Gly Glu Gly Glu Gly Asp Ala Thr Tyr Gly Lys Leu
    290                 295                 300

Thr Leu Lys Phe Ile Cys Thr Thr Gly Lys Leu Pro Val Pro Trp Pro
305                 310                 315                 320

Thr Leu Val Thr Thr Leu Thr Tyr Gly Val Gln Cys Phe Ser Arg Tyr
                325                 330                 335

Pro Asp His Met Lys Gln His Asp Phe Phe Lys Ser Ala Met Pro Glu
            340                 345                 350

Gly Tyr Val Gln Glu Arg Thr Ile Phe Phe Lys Asp Asp Gly Asn Tyr
        355                 360                 365

Lys Thr Arg Ala Glu Val Lys Phe Glu Gly Asp Thr Leu Val Asn Arg
    370                 375                 380

Ile Glu Leu Lys Gly Ile Asp Phe Lys Glu Asp Gly Asn Ile Leu Gly
385                 390                 395                 400

His Lys Leu Glu Tyr Asn Tyr Asn Ser His Asn Val Tyr Ile Met Ala
                405                 410                 415

Asp Lys Gln Lys Asn Gly Ile Lys Val Asn Phe Lys Ile Arg His Asn
            420                 425                 430

Ile Glu Asp Gly Ser Val Gln Leu Ala Asp His Tyr Gln Gln Asn Thr

-continued

```
                435                 440                 445
Pro Ile Gly Asp Gly Pro Val Leu Leu Pro Asp Asn His Tyr Leu Ser
        450                 455                 460

Thr Gln Ser Ala Leu Ser Lys Asp Pro Asn Glu Lys Arg Asp His Met
465                 470                 475                 480

Val Leu Leu Glu Phe Val Thr Ala Ala Gly Ile Thr Leu Gly Met Asp
                    485                 490                 495

Glu Leu Tyr Lys
            500

<210> SEQ ID NO 172
<211> LENGTH: 693
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
            85                  90                  95

Asp Thr Glu Thr Lys Asp Cys Asn Glu Lys Lys Lys Met Thr Met
        100                 105                 110

Asn Arg Asp Asp Leu Val Glu Glu Gly Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
                165                 170                 175

Gly Gln Ala Thr Asp Ser His Ser Ile Ala Glu Arg Val Arg Arg Glu
            180                 185                 190

Lys Ile Ser Glu Arg Met Lys Phe Leu Gln Asp Leu Val Pro Gly Cys
        195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
                245                 250                 255

Glu Val Ala Ser Thr Pro Met Thr Val Val Pro Ser Pro Glu Met Val
            260                 265                 270

Leu Ser Gly Tyr Ser His Glu Met Val His Ser Gly Tyr Ser Ser Glu
        275                 280                 285
```

```
Met Val Asn Ser Gly Tyr Leu His Val Asn Pro Met Gln Gln Val Asn
    290                 295                 300
Thr Ser Ser Asp Pro Leu Ser Cys Phe Asn Asn Gly Glu Ala Pro Ser
305                 310                 315                 320
Met Trp Asp Ser His Val Gln Asn Leu Tyr Gly Asn Leu Gly Val Ala
                325                 330                 335
Ser Pro Lys Lys Arg Lys Val Glu Ala Ser Ala Pro Pro Thr Asp
            340                 345                 350
Val Ser Leu Gly Asp Glu Leu His Leu Asp Gly Glu Asp Val Ala Met
        355                 360                 365
Ala His Ala Asp Ala Leu Asp Asp Phe Asp Leu Asp Met Leu Gly Asp
    370                 375                 380
Gly Asp Ser Pro Gly Pro Gly Phe Thr Pro His Asp Ser Ala Pro Tyr
385                 390                 395                 400
Gly Ala Leu Asp Met Ala Asp Phe Glu Phe Glu Gln Met Phe Thr Asp
                405                 410                 415
Ala Leu Gly Ile Asp Glu Tyr Gly Gly Glu Phe Pro Gly Ile Arg Arg
            420                 425                 430
Ser Arg Gly Ser Gly Glu Gly Arg Gly Ser Leu Leu Thr Cys Gly Asp
        435                 440                 445
Val Glu Glu Asn Pro Gly Pro Val Ser Lys Gly Glu Glu Leu Phe Thr
    450                 455                 460
Gly Val Val Pro Ile Leu Val Glu Leu Asp Gly Asp Val Asn Gly His
465                 470                 475                 480
Lys Phe Ser Val Ser Gly Glu Gly Glu Gly Asp Ala Thr Tyr Gly Lys
                485                 490                 495
Leu Thr Leu Lys Phe Ile Cys Thr Thr Gly Lys Leu Pro Val Pro Trp
            500                 505                 510
Pro Thr Leu Val Thr Thr Leu Thr Tyr Gly Val Gln Cys Phe Ser Arg
        515                 520                 525
Tyr Pro Asp His Met Lys Gln His Asp Phe Phe Lys Ser Ala Met Pro
    530                 535                 540
Glu Gly Tyr Val Gln Glu Arg Thr Ile Phe Phe Lys Asp Asp Gly Asn
545                 550                 555                 560
Tyr Lys Thr Arg Ala Glu Val Lys Phe Glu Gly Asp Thr Leu Val Asn
                565                 570                 575
Arg Ile Glu Leu Lys Gly Ile Asp Phe Lys Glu Asp Gly Asn Ile Leu
            580                 585                 590
Gly His Lys Leu Glu Tyr Asn Tyr Asn Ser His Asn Val Tyr Ile Met
        595                 600                 605
Ala Asp Lys Gln Lys Asn Gly Ile Lys Val Asn Phe Lys Ile Arg His
    610                 615                 620
Asn Ile Glu Asp Gly Ser Val Gln Leu Ala Asp His Tyr Gln Gln Asn
625                 630                 635                 640
Thr Pro Ile Gly Asp Gly Pro Val Leu Leu Pro Asp Asn His Tyr Leu
                645                 650                 655
Ser Thr Gln Ser Ala Leu Ser Lys Asp Pro Asn Glu Lys Arg Asp His
            660                 665                 670
Met Val Leu Leu Glu Phe Val Thr Ala Ala Gly Ile Thr Leu Gly Met
        675                 680                 685
Asp Glu Leu Tyr Lys
    690
```

<210> SEQ ID NO 173
<211> LENGTH: 792
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

```
Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
            85                  90                  95

Asp Thr Glu Thr Lys Asp Cys Asn Glu Lys Lys Lys Met Thr Met
        100                 105                 110

Asn Arg Asp Asp Leu Val Glu Glu Gly Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
            165                 170                 175

Gly Gln Ala Thr Asp Ser His Ser Ile Ala Glu Arg Val Arg Arg Glu
        180                 185                 190

Lys Ile Ser Glu Arg Met Lys Phe Leu Gln Asp Leu Val Pro Gly Cys
    195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
            245                 250                 255

Glu Val Ala Ser Thr Pro Met Thr Val Val Pro Ser Pro Glu Met Val
        260                 265                 270

Leu Ser Gly Tyr Ser His Glu Met Val His Ser Gly Tyr Ser Ser Glu
    275                 280                 285

Met Val Asn Ser Gly Tyr Leu His Val Asn Pro Met Gln Gln Val Asn
    290                 295                 300

Thr Ser Ser Asp Pro Leu Ser Cys Phe Asn Asn Gly Glu Ala Pro Ser
305                 310                 315                 320

Met Trp Asp Ser His Val Gln Asn Leu Tyr Gly Asn Leu Gly Val Ala
            325                 330                 335

Ser Pro Lys Lys Lys Arg Lys Val Glu Ala Ser Ser Gly Gln Ile
        340                 345                 350

Ser Asn Gln Ala Leu Ala Leu Ala Pro Ser Ser Ala Pro Val Leu Ala
    355                 360                 365
```

```
Gln Thr Met Val Pro Ser Ser Ala Met Val Pro Leu Ala Gln Pro Pro
    370                 375                 380
Ala Pro Ala Pro Val Leu Thr Pro Gly Pro Pro Gln Ser Leu Ser Ala
385                 390                 395                 400
Pro Val Pro Lys Ser Thr Gln Ala Gly Glu Gly Thr Leu Ser Glu Ala
                405                 410                 415
Leu Leu His Leu Gln Phe Asp Ala Asp Glu Asp Leu Gly Ala Leu Leu
            420                 425                 430
Gly Asn Ser Thr Asp Pro Gly Val Phe Thr Asp Leu Ala Ser Val Asp
        435                 440                 445
Asn Ser Glu Phe Gln Gln Leu Leu Asn Gln Gly Val Ser Met Ser His
    450                 455                 460
Ser Thr Ala Glu Pro Met Leu Met Glu Tyr Pro Glu Ala Ile Thr Arg
465                 470                 475                 480
Leu Val Thr Gly Ser Gln Arg Pro Pro Asp Pro Ala Pro Thr Pro Leu
                485                 490                 495
Gly Thr Ser Gly Leu Pro Asn Gly Leu Ser Gly Asp Glu Asp Phe Ser
            500                 505                 510
Ser Ile Ala Asp Met Asp Phe Ser Ala Leu Leu Ser Gln Ile Ser Ser
        515                 520                 525
Ser Gly Gln Ser Arg Gly Ser Gly Glu Gly Arg Gly Ser Leu Leu Thr
    530                 535                 540
Cys Gly Asp Val Glu Glu Asn Pro Gly Pro Val Ser Lys Gly Glu Glu
545                 550                 555                 560
Leu Phe Thr Gly Val Val Pro Ile Leu Val Glu Leu Asp Gly Asp Val
                565                 570                 575
Asn Gly His Lys Phe Ser Val Ser Gly Glu Gly Glu Gly Asp Ala Thr
            580                 585                 590
Tyr Gly Lys Leu Thr Leu Lys Phe Ile Cys Thr Thr Gly Lys Leu Pro
        595                 600                 605
Val Pro Trp Pro Thr Leu Val Thr Thr Leu Thr Tyr Gly Val Gln Cys
    610                 615                 620
Phe Ser Arg Tyr Pro Asp His Met Lys Gln His Asp Phe Phe Lys Ser
625                 630                 635                 640
Ala Met Pro Glu Gly Tyr Val Gln Glu Arg Thr Ile Phe Phe Lys Asp
                645                 650                 655
Asp Gly Asn Tyr Lys Thr Arg Ala Glu Val Lys Phe Glu Gly Asp Thr
            660                 665                 670
Leu Val Asn Arg Ile Glu Leu Lys Gly Ile Asp Phe Lys Glu Asp Gly
        675                 680                 685
Asn Ile Leu Gly His Lys Leu Glu Tyr Asn Tyr Asn Ser His Asn Val
    690                 695                 700
Tyr Ile Met Ala Asp Lys Gln Lys Asn Gly Ile Lys Val Asn Phe Lys
705                 710                 715                 720
Ile Arg His Asn Ile Glu Asp Gly Ser Val Gln Leu Ala Asp His Tyr
                725                 730                 735
Gln Gln Asn Thr Pro Ile Gly Asp Gly Pro Val Leu Leu Pro Asp Asn
            740                 745                 750
His Tyr Leu Ser Thr Gln Ser Ala Leu Ser Lys Asp Pro Asn Glu Lys
        755                 760                 765
Arg Asp His Met Val Leu Leu Glu Phe Val Thr Ala Ala Gly Ile Thr
    770                 775                 780
Leu Gly Met Asp Glu Leu Tyr Lys
```

-continued

```
<210> SEQ ID NO 174
<211> LENGTH: 967
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (158)..(159)
<223> OTHER INFORMATION: Any amino acid
<220> FEATURE:
<221> NAME/KEY: MOD_RES
<222> LOCATION: (192)..(193)
<223> OTHER INFORMATION: Any amino acid
<220> FEATURE:
<221> NAME/KEY: MOD_RES
<222> LOCATION: (226)..(227)
<223> OTHER INFORMATION: Any amino acid
<220> FEATURE:
<221> NAME/KEY: MOD_RES
<222> LOCATION: (260)..(261)
<223> OTHER INFORMATION: Any amino acid
<220> FEATURE:
<221> NAME/KEY: MOD_RES
<222> LOCATION: (294)..(295)
<223> OTHER INFORMATION: Any amino acid
<220> FEATURE:
<221> NAME/KEY: MOD_RES
<222> LOCATION: (328)..(329)
<223> OTHER INFORMATION: Any amino acid
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (396)..(397)
<223> OTHER INFORMATION: Any amino acid
<220> FEATURE:
<221> NAME/KEY: MOD_RES
<222> LOCATION: (430)..(431)
<223> OTHER INFORMATION: Any amino acid
<220> FEATURE:
<221> NAME/KEY: MOD_RES
<222> LOCATION: (464)..(465)
<223> OTHER INFORMATION: Any amino acid
<220> FEATURE:
<221> NAME/KEY: MOD_RES
<222> LOCATION: (498)..(499)
<223> OTHER INFORMATION: Any amino acid
<220> FEATURE:
<221> NAME/KEY: MOD_RES
<222> LOCATION: (532)..(533)
<223> OTHER INFORMATION: Any amino acid
<220> FEATURE:
<221> NAME/KEY: MOD_RES
<222> LOCATION: (566)..(567)
<223> OTHER INFORMATION: Any amino acid

<400> SEQUENCE: 174

Met Tyr Pro Tyr Asp Val Pro Asp Tyr Ala Val Asp Leu Arg Thr Leu
1               5                   10                  15

Gly Tyr Ser Gln Gln Gln Glu Lys Ile Lys Pro Lys Val Arg Ser
            20                  25                  30

Thr Val Ala Gln His His Glu Ala Leu Val Gly His Gly Phe Thr His
        35                  40                  45

Ala His Ile Val Ala Leu Ser Gln His Pro Ala Ala Leu Gly Thr Val
    50                  55                  60

Ala Val Lys Tyr Gln Asp Met Ile Ala Ala Leu Pro Glu Ala Thr His
65                  70                  75                  80
```

```
Glu Ala Ile Val Gly Val Gly Lys Gln Trp Ser Gly Arg Ala Leu
                85                  90                  95

Glu Ala Leu Leu Thr Val Ala Gly Glu Leu Arg Gly Pro Pro Leu Gln
            100                 105                 110

Leu Asp Thr Gly Gln Leu Leu Lys Ile Ala Lys Arg Gly Gly Val Thr
            115                 120                 125

Ala Val Glu Ala Val His Ala Trp Arg Asn Ala Leu Thr Gly Ala Pro
130                 135                 140

Leu Asn Leu Thr Pro Glu Gln Val Val Ala Ile Ala Ser Xaa Xaa Gly
145                 150                 155                 160

Gly Lys Gln Ala Leu Glu Thr Val Gln Arg Leu Leu Pro Val Leu Cys
                165                 170                 175

Gln Ala His Gly Leu Thr Pro Glu Gln Val Val Ala Ile Ala Ser Xaa
            180                 185                 190

Xaa Gly Gly Lys Gln Ala Leu Glu Thr Val Gln Arg Leu Leu Pro Val
            195                 200                 205

Leu Cys Gln Ala His Gly Leu Thr Pro Glu Gln Val Val Ala Ile Ala
210                 215                 220

Ser Xaa Xaa Gly Gly Lys Gln Ala Leu Glu Thr Val Gln Arg Leu Leu
225                 230                 235                 240

Pro Val Leu Cys Gln Ala His Gly Leu Thr Pro Glu Gln Val Val Ala
                245                 250                 255

Ile Ala Ser Xaa Xaa Gly Gly Lys Gln Ala Leu Glu Thr Val Gln Arg
            260                 265                 270

Leu Leu Pro Val Leu Cys Gln Ala His Gly Leu Thr Pro Glu Gln Val
            275                 280                 285

Val Ala Ile Ala Ser Xaa Xaa Gly Gly Lys Gln Ala Leu Glu Thr Val
290                 295                 300

Gln Arg Leu Leu Pro Val Leu Cys Gln Ala His Gly Leu Thr Pro Glu
305                 310                 315                 320

Gln Val Val Ala Ile Ala Ser Xaa Xaa Gly Gly Lys Gln Ala Leu Glu
                325                 330                 335

Thr Val Gln Arg Leu Leu Pro Val Leu Cys Gln Ala His Gly Leu Thr
            340                 345                 350

Pro Glu Gln Val Val Ala Ile Ala Ser Xaa Xaa Gly Gly Lys Gln Ala
            355                 360                 365

Leu Glu Thr Val Gln Arg Leu Leu Pro Val Leu Cys Gln Ala His Gly
370                 375                 380

Leu Thr Pro Glu Gln Val Val Ala Ile Ala Ser Xaa Xaa Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser Xaa Xaa Gly
            420                 425                 430

Gly Lys Gln Ala Leu Glu Thr Val Gln Arg Leu Leu Pro Val Leu Cys
            435                 440                 445

Gln Ala His Gly Leu Thr Pro Glu Gln Val Val Ala Ile Ala Ser Xaa
450                 455                 460

Xaa Gly Gly Lys Gln Ala Leu Glu Thr Val Gln Arg Leu Leu Pro Val
465                 470                 475                 480

Leu Cys Gln Ala His Gly Leu Thr Pro Glu Gln Val Val Ala Ile Ala
                485                 490                 495
```

```
Ser Xaa Xaa Gly Gly Lys Gln Ala Leu Glu Thr Val Gln Arg Leu Leu
            500                 505                 510

Pro Val Leu Cys Gln Ala His Gly Leu Thr Pro Glu Gln Val Val Ala
        515                 520                 525

Ile Ala Ser Xaa Xaa Gly Gly Lys Gln Ala Leu Glu Thr Val Gln Arg
        530                 535                 540

Leu Leu Pro Val Leu Cys Gln Ala His Gly Leu Thr Pro Glu Gln Val
545                 550                 555                 560

Val Ala Ile Ala Ser Xaa Xaa Gly Gly Arg Pro Ala Leu Glu Ser Ile
                565                 570                 575

Val Ala Gln Leu Ser Arg Pro Asp Pro Ala Leu Ala Ala Leu Thr Asn
            580                 585                 590

Asp His Leu Val Ala Leu Ala Cys Leu Gly Gly Arg Pro Ala Leu Asp
            595                 600                 605

Ala Val Lys Lys Gly Leu Pro His Ala Pro Ala Leu Ile Lys Arg Thr
            610                 615                 620

Asn Arg Arg Ile Pro Glu Arg Thr Ser His Arg Val Ala Ala Ser Pro
625                 630                 635                 640

Lys Lys Lys Arg Lys Val Glu Ala Ser Gly Ser Gly Arg Ala Asp Ala
                645                 650                 655

Leu Asp Asp Phe Asp Leu Asp Met Leu Gly Ser Asp Ala Leu Asp Asp
            660                 665                 670

Phe Asp Leu Asp Met Leu Gly Ser Asp Ala Leu Asp Asp Phe Asp Leu
            675                 680                 685

Asp Met Leu Gly Ser Asp Ala Leu Asp Asp Phe Asp Leu Asp Met Leu
            690                 695                 700

Ile Asn Ser Arg Gly Ser Gly Glu Gly Arg Gly Ser Leu Leu Thr Cys
705                 710                 715                 720

Gly Asp Val Glu Glu Asn Pro Gly Pro Val Ser Lys Gly Glu Glu Leu
                725                 730                 735

Phe Thr Gly Val Val Pro Ile Leu Val Glu Leu Asp Gly Asp Val Asn
            740                 745                 750

Gly His Lys Phe Ser Val Ser Gly Glu Gly Glu Gly Asp Ala Thr Tyr
            755                 760                 765

Gly Lys Leu Thr Leu Lys Phe Ile Cys Thr Thr Gly Lys Leu Pro Val
770                 775                 780

Pro Trp Pro Thr Leu Val Thr Thr Leu Thr Tyr Gly Val Gln Cys Phe
785                 790                 795                 800

Ser Arg Tyr Pro Asp His Met Lys Gln His Asp Phe Phe Lys Ser Ala
            805                 810                 815

Met Pro Glu Gly Tyr Val Gln Glu Arg Thr Ile Phe Phe Lys Asp Asp
            820                 825                 830

Gly Asn Tyr Lys Thr Arg Ala Glu Val Lys Phe Glu Gly Asp Thr Leu
            835                 840                 845

Val Asn Arg Ile Glu Leu Lys Gly Ile Asp Phe Lys Glu Asp Gly Asn
850                 855                 860

Ile Leu Gly His Lys Leu Glu Tyr Asn Tyr Asn Ser His Asn Val Tyr
865                 870                 875                 880

Ile Met Ala Asp Lys Gln Lys Asn Gly Ile Lys Val Asn Phe Lys Ile
            885                 890                 895

Arg His Asn Ile Glu Asp Gly Ser Val Gln Leu Ala Asp His Tyr Gln
            900                 905                 910

Gln Asn Thr Pro Ile Gly Asp Gly Pro Val Leu Leu Pro Asp Asn His
```

```
                915                 920                 925
Tyr Leu Ser Thr Gln Ser Ala Leu Ser Lys Asp Pro Asn Glu Lys Arg
    930                 935                 940

Asp His Met Val Leu Leu Glu Phe Val Thr Ala Ala Gly Ile Thr Leu
945                 950                 955                 960

Gly Met Asp Glu Leu Tyr Lys
                965

<210> SEQ ID NO 175
<211> LENGTH: 922
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (158)..(159)
<223> OTHER INFORMATION: Any amino acid
<220> FEATURE:
<221> NAME/KEY: MOD_RES
<222> LOCATION: (192)..(193)
<223> OTHER INFORMATION: Any amino acid
<220> FEATURE:
<221> NAME/KEY: MOD_RES
<222> LOCATION: (226)..(227)
<223> OTHER INFORMATION: Any amino acid
<220> FEATURE:
<221> NAME/KEY: MOD_RES
<222> LOCATION: (260)..(261)
<223> OTHER INFORMATION: Any amino acid
<220> FEATURE:
<221> NAME/KEY: MOD_RES
<222> LOCATION: (294)..(295)
<223> OTHER INFORMATION: Any amino acid
<220> FEATURE:
<221> NAME/KEY: MOD_RES
<222> LOCATION: (328)..(329)
<223> OTHER INFORMATION: Any amino acid
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (396)..(397)
<223> OTHER INFORMATION: Any amino acid
<220> FEATURE:
<221> NAME/KEY: MOD_RES
<222> LOCATION: (430)..(431)
<223> OTHER INFORMATION: Any amino acid
<220> FEATURE:
<221> NAME/KEY: MOD_RES
<222> LOCATION: (464)..(465)
<223> OTHER INFORMATION: Any amino acid
<220> FEATURE:
<221> NAME/KEY: MOD_RES
<222> LOCATION: (498)..(499)
<223> OTHER INFORMATION: Any amino acid
<220> FEATURE:
<221> NAME/KEY: MOD_RES
<222> LOCATION: (532)..(533)
<223> OTHER INFORMATION: Any amino acid
<220> FEATURE:
<221> NAME/KEY: MOD_RES
<222> LOCATION: (566)..(567)
<223> OTHER INFORMATION: Any amino acid

<400> SEQUENCE: 175

Met Tyr Pro Tyr Asp Val Pro Asp Tyr Ala Val Asp Leu Arg Thr Leu
1               5                   10                  15

Gly Tyr Ser Gln Gln Gln Gln Glu Lys Ile Lys Pro Lys Val Arg Ser
            20                  25                  30
```

```
Thr Val Ala Gln His His Glu Ala Leu Val Gly His Gly Phe Thr His
            35                  40                  45

Ala His Ile Val Ala Leu Ser Gln His Pro Ala Ala Leu Gly Thr Val
50                  55                  60

Ala Val Lys Tyr Gln Asp Met Ile Ala Ala Leu Pro Glu Ala Thr His
65                  70                  75                  80

Glu Ala Ile Val Gly Val Gly Lys Gln Trp Ser Gly Ala Arg Ala Leu
                    85                  90                  95

Glu Ala Leu Leu Thr Val Ala Gly Glu Leu Arg Gly Pro Pro Leu Gln
            100                 105                 110

Leu Asp Thr Gly Gln Leu Leu Lys Ile Ala Lys Arg Gly Gly Val Thr
        115                 120                 125

Ala Val Glu Ala Val His Ala Trp Arg Asn Ala Leu Thr Gly Ala Pro
    130                 135                 140

Leu Asn Leu Thr Pro Glu Gln Val Val Ala Ile Ala Ser Xaa Xaa Gly
145                 150                 155                 160

Gly Lys Gln Ala Leu Glu Thr Val Gln Arg Leu Leu Pro Val Leu Cys
                165                 170                 175

Gln Ala His Gly Leu Thr Pro Glu Gln Val Val Ala Ile Ala Ser Xaa
            180                 185                 190

Xaa Gly Gly Lys Gln Ala Leu Glu Thr Val Gln Arg Leu Leu Pro Val
        195                 200                 205

Leu Cys Gln Ala His Gly Leu Thr Pro Glu Gln Val Val Ala Ile Ala
    210                 215                 220

Ser Xaa Xaa Gly Gly Lys Gln Ala Leu Glu Thr Val Gln Arg Leu Leu
225                 230                 235                 240

Pro Val Leu Cys Gln Ala His Gly Leu Thr Pro Glu Gln Val Val Ala
                245                 250                 255

Ile Ala Ser Xaa Xaa Gly Gly Lys Gln Ala Leu Glu Thr Val Gln Arg
            260                 265                 270

Leu Leu Pro Val Leu Cys Gln Ala His Gly Leu Thr Pro Glu Gln Val
        275                 280                 285

Val Ala Ile Ala Ser Xaa Xaa Gly Gly Lys Gln Ala Leu Glu Thr Val
    290                 295                 300

Gln Arg Leu Leu Pro Val Leu Cys Gln Ala His Gly Leu Thr Pro Glu
305                 310                 315                 320

Gln Val Val Ala Ile Ala Ser Xaa Xaa Gly Gly Lys Gln Ala Leu Glu
                325                 330                 335

Thr Val Gln Arg Leu Leu Pro Val Leu Cys Gln Ala His Gly Leu Thr
            340                 345                 350

Pro Glu Gln Val Val Ala Ile Ala Ser Xaa Xaa Gly Gly Lys Gln Ala
        355                 360                 365

Leu Glu Thr Val Gln Arg Leu Leu Pro Val Leu Cys Gln Ala His Gly
    370                 375                 380

Leu Thr Pro Glu Gln Val Val Ala Ile Ala Ser Xaa Xaa Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser Xaa Xaa Gly
            420                 425                 430

Gly Lys Gln Ala Leu Glu Thr Val Gln Arg Leu Leu Pro Val Leu Cys
        435                 440                 445
```

```
Gln Ala His Gly Leu Thr Pro Glu Gln Val Val Ala Ile Ala Ser Xaa
    450                 455                 460
Xaa Gly Gly Lys Gln Ala Leu Glu Thr Val Gln Arg Leu Leu Pro Val
465                 470                 475                 480
Leu Cys Gln Ala His Gly Leu Thr Pro Glu Gln Val Val Ala Ile Ala
                    485                 490                 495
Ser Xaa Xaa Gly Gly Lys Gln Ala Leu Glu Thr Val Gln Arg Leu Leu
        500                 505                 510
Pro Val Leu Cys Gln Ala His Gly Leu Thr Pro Glu Gln Val Val Ala
            515                 520                 525
Ile Ala Ser Xaa Xaa Gly Gly Lys Gln Ala Leu Glu Thr Val Gln Arg
530                 535                 540
Leu Leu Pro Val Leu Cys Gln Ala His Gly Leu Thr Pro Glu Gln Val
545                 550                 555                 560
Val Ala Ile Ala Ser Xaa Xaa Gly Gly Arg Pro Ala Leu Glu Ser Ile
                565                 570                 575
Val Ala Gln Leu Ser Arg Pro Asp Pro Ala Leu Ala Ala Leu Thr Asn
            580                 585                 590
Asp His Leu Val Ala Leu Ala Cys Leu Gly Gly Arg Pro Ala Leu Asp
        595                 600                 605
Ala Val Lys Lys Gly Leu Pro His Ala Pro Ala Leu Ile Lys Arg Thr
610                 615                 620
Asn Arg Arg Ile Pro Glu Arg Thr Ser His Arg Val Ala Ala Ser Pro
625                 630                 635                 640
Lys Lys Lys Arg Lys Val Glu Ala Ser Pro Lys Lys Lys Arg Lys Val
                645                 650                 655
Glu Ala Ser Gly Ser Gly Met Asn Ile Gln Met Leu Leu Glu Ala Ala
            660                 665                 670
Asp Tyr Leu Glu Arg Arg Glu Arg Glu Ala Glu His Gly Tyr Ala Ser
        675                 680                 685
Met Leu Pro Gly Ser Gly Met Asn Ile Gln Met Leu Leu Glu Ala Ala
    690                 695                 700
Asp Tyr Leu Glu Arg Arg Glu Arg Glu Ala Glu His Gly Tyr Ala Ser
705                 710                 715                 720
Met Leu Pro Gly Ser Gly Met Asn Ile Gln Met Leu Leu Glu Ala Ala
                725                 730                 735
Asp Tyr Leu Glu Arg Arg Glu Arg Glu Ala Glu His Gly Tyr Ala Ser
            740                 745                 750
Met Leu Pro Gly Ser Gly Met Asn Ile Gln Met Leu Leu Glu Ala Ala
        755                 760                 765
Asp Tyr Leu Glu Arg Arg Glu Arg Glu Ala Glu His Gly Tyr Ala Ser
    770                 775                 780
Met Leu Pro Ser Arg Ser Arg Gly Ser Gly Glu Gly Arg Gly Ser Leu
785                 790                 795                 800
Leu Thr Cys Gly Asp Val Glu Glu Asn Pro Gly Pro Ile Glu Lys Ser
                805                 810                 815
Phe Val Ile Thr Asp Pro Arg Leu Pro Asp Tyr Pro Ile Ile Phe Ala
            820                 825                 830
Ser Asp Gly Phe Leu Glu Leu Thr Glu Tyr Ser Arg Glu Glu Ile Met
        835                 840                 845
Gly Arg Asn Ala Arg Phe Leu Gln Gly Pro Glu Thr Asp Gln Ala Thr
    850                 855                 860
Val Gln Lys Ile Arg Asp Ala Ile Arg Asp Gln Arg Glu Thr Thr Val
```

```
                865                 870                 875                 880
Gln Leu Ile Asn Tyr Thr Lys Ser Gly Lys Lys Phe Trp Asn Leu Leu
                885                 890                 895

His Leu Gln Pro Val Arg Asp Arg Lys Gly Gly Leu Gln Tyr Phe Ile
                900                 905                 910

Gly Val Gln Leu Val Gly Ser Asp His Val
                915                 920
```

```
<210> SEQ ID NO 176
<211> LENGTH: 983
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (158)..(159)
<223> OTHER INFORMATION: Any amino acid
<220> FEATURE:
<221> NAME/KEY: MOD_RES
<222> LOCATION: (192)..(193)
<223> OTHER INFORMATION: Any amino acid
<220> FEATURE:
<221> NAME/KEY: MOD_RES
<222> LOCATION: (226)..(227)
<223> OTHER INFORMATION: Any amino acid
<220> FEATURE:
<221> NAME/KEY: MOD_RES
<222> LOCATION: (260)..(261)
<223> OTHER INFORMATION: Any amino acid
<220> FEATURE:
<221> NAME/KEY: MOD_RES
<222> LOCATION: (294)..(295)
<223> OTHER INFORMATION: Any amino acid
<220> FEATURE:
<221> NAME/KEY: MOD_RES
<222> LOCATION: (328)..(329)
<223> OTHER INFORMATION: Any amino acid
<220> FEATURE:
<221> NAME/KEY: MOD_RES
<222> LOCATION: (362)..(363)
<223> OTHER INFORMATION: Any amino acid
<220> FEATURE:
<221> NAME/KEY: MOD_RES
<222> LOCATION: (396)..(397)
<223> OTHER INFORMATION: Any amino acid
<220> FEATURE:
<221> NAME/KEY: MOD_RES
<222> LOCATION: (430)..(431)
<223> OTHER INFORMATION: Any amino acid
<220> FEATURE:
<221> NAME/KEY: MOD_RES
<222> LOCATION: (464)..(465)
<223> OTHER INFORMATION: Any amino acid
<220> FEATURE:
<221> NAME/KEY: MOD_RES
<222> LOCATION: (498)..(499)
<223> OTHER INFORMATION: Any amino acid
<220> FEATURE:
<221> NAME/KEY: MOD_RES
<222> LOCATION: (532)..(533)
<223> OTHER INFORMATION: Any amino acid
<220> FEATURE:
<221> NAME/KEY: MOD_RES
<222> LOCATION: (566)..(567)
<223> OTHER INFORMATION: Any amino acid

<400> SEQUENCE: 176

Met Tyr Pro Tyr Asp Val Pro Asp Tyr Ala Val Asp Leu Arg Thr Leu
1               5                   10                  15

Gly Tyr Ser Gln Gln Gln Gln Glu Lys Ile Lys Pro Lys Val Arg Ser
                20                  25                  30
```

```
Thr Val Ala Gln His His Glu Ala Leu Val Gly His Gly Phe Thr His
            35                  40                  45
Ala His Ile Val Ala Leu Ser Gln His Pro Ala Ala Leu Gly Thr Val
 50                  55                  60
Ala Val Lys Tyr Gln Asp Met Ile Ala Ala Leu Pro Glu Ala Thr His
 65                  70                  75                  80
Glu Ala Ile Val Gly Val Gly Lys Gln Trp Ser Gly Ala Arg Ala Leu
                 85                  90                  95
Glu Ala Leu Leu Thr Val Ala Gly Glu Leu Arg Gly Pro Pro Leu Gln
            100                 105                 110
Leu Asp Thr Gly Gln Leu Leu Lys Ile Ala Lys Arg Gly Gly Val Thr
            115                 120                 125
Ala Val Glu Ala Val His Ala Trp Arg Asn Ala Leu Thr Gly Ala Pro
            130                 135                 140
Leu Asn Leu Thr Pro Glu Gln Val Val Ala Ile Ala Ser Xaa Xaa Gly
145                 150                 155                 160
Gly Lys Gln Ala Leu Glu Thr Val Gln Arg Leu Leu Pro Val Leu Cys
                165                 170                 175
Gln Ala His Gly Leu Thr Pro Glu Gln Val Val Ala Ile Ala Ser Xaa
            180                 185                 190
Xaa Gly Gly Lys Gln Ala Leu Glu Thr Val Gln Arg Leu Leu Pro Val
            195                 200                 205
Leu Cys Gln Ala His Gly Leu Thr Pro Glu Gln Val Val Ala Ile Ala
210                 215                 220
Ser Xaa Xaa Gly Gly Lys Gln Ala Leu Glu Thr Val Gln Arg Leu Leu
225                 230                 235                 240
Pro Val Leu Cys Gln Ala His Gly Leu Thr Pro Glu Gln Val Val Ala
                245                 250                 255
Ile Ala Ser Xaa Xaa Gly Gly Lys Gln Ala Leu Glu Thr Val Gln Arg
            260                 265                 270
Leu Leu Pro Val Leu Cys Gln Ala His Gly Leu Thr Pro Glu Gln Val
            275                 280                 285
Val Ala Ile Ala Ser Xaa Xaa Gly Gly Lys Gln Ala Leu Glu Thr Val
            290                 295                 300
Gln Arg Leu Leu Pro Val Leu Cys Gln Ala His Gly Leu Thr Pro Glu
305                 310                 315                 320
Gln Val Val Ala Ile Ala Ser Xaa Xaa Gly Gly Lys Gln Ala Leu Glu
                325                 330                 335
Thr Val Gln Arg Leu Leu Pro Val Leu Cys Gln Ala His Gly Leu Thr
            340                 345                 350
Pro Glu Gln Val Val Ala Ile Ala Ser Xaa Xaa Gly Gly Lys Gln Ala
            355                 360                 365
Leu Glu Thr Val Gln Arg Leu Leu Pro Val Leu Cys Gln Ala His Gly
            370                 375                 380
Leu Thr Pro Glu Gln Val Val Ala Ile Ala Ser Xaa Xaa Gly Gly Lys
385                 390                 395                 400
Gln Ala Leu Glu Thr Val Gln Arg Leu Leu Pro Val Leu Cys Gln Ala
                405                 410                 415
His Gly Leu Thr Pro Glu Gln Val Val Ala Ile Ala Ser Xaa Xaa Gly
            420                 425                 430
Gly Lys Gln Ala Leu Glu Thr Val Gln Arg Leu Leu Pro Val Leu Cys
            435                 440                 445
```

-continued

```
Gln Ala His Gly Leu Thr Pro Glu Gln Val Val Ala Ile Ala Ser Xaa
450                 455                 460
Xaa Gly Gly Lys Gln Ala Leu Glu Thr Val Gln Arg Leu Leu Pro Val
465                 470                 475                 480
Leu Cys Gln Ala His Gly Leu Thr Pro Glu Gln Val Val Ala Ile Ala
            485                 490                 495
Ser Xaa Xaa Gly Gly Lys Gln Ala Leu Glu Thr Val Gln Arg Leu Leu
        500                 505                 510
Pro Val Leu Cys Gln Ala His Gly Leu Thr Pro Glu Gln Val Val Ala
    515                 520                 525
Ile Ala Ser Xaa Xaa Gly Gly Lys Gln Ala Leu Glu Thr Val Gln Arg
530                 535                 540
Leu Leu Pro Val Leu Cys Gln Ala His Gly Leu Thr Pro Glu Gln Val
545                 550                 555                 560
Val Ala Ile Ala Ser Xaa Xaa Gly Gly Arg Pro Ala Leu Glu Ser Ile
                565                 570                 575
Val Ala Gln Leu Ser Arg Pro Asp Pro Ala Leu Ala Ala Leu Thr Asn
            580                 585                 590
Asp His Leu Val Ala Leu Ala Cys Leu Gly Gly Arg Pro Ala Leu Asp
        595                 600                 605
Ala Val Lys Lys Gly Leu Pro His Ala Pro Ala Leu Ile Lys Arg Thr
    610                 615                 620
Asn Arg Arg Ile Pro Glu Arg Thr Ser His Arg Val Ala Ala Ser Pro
625                 630                 635                 640
Lys Lys Lys Arg Lys Val Glu Ala Ser Asn Gly Ala Ile Gly Gly Asp
                645                 650                 655
Leu Leu Leu Asn Phe Pro Asp Met Ser Val Leu Glu Arg Gln Arg Ala
            660                 665                 670
His Leu Lys Tyr Leu Asn Pro Thr Phe Asp Ser Pro Leu Ala Gly Phe
        675                 680                 685
Phe Ala Asp Ser Ser Met Ile Thr Gly Gly Glu Met Asp Ser Tyr Leu
    690                 695                 700
Ser Thr Ala Gly Leu Asn Leu Pro Met Met Tyr Gly Glu Thr Thr Val
705                 710                 715                 720
Glu Gly Asp Ser Arg Leu Ser Ile Ser Pro Glu Thr Thr Leu Gly Thr
                725                 730                 735
Gly Asn Phe Lys Lys Arg Lys Phe Asp Thr Glu Thr Lys Asp Cys Asn
            740                 745                 750
Glu Lys Lys Lys Met Thr Met Asn Arg Asp Asp Leu Val Glu Glu
        755                 760                 765
Gly Glu Glu Glu Lys Ser Lys Ile Thr Glu Gln Asn Asn Gly Ser Thr
    770                 775                 780
Lys Ser Ile Lys Lys Met Lys His Lys Ala Lys Glu Glu Asn Asn
785                 790                 795                 800
Phe Ser Asn Asp Ser Ser Lys Val Thr Lys Glu Leu Glu Lys Thr Asp
                805                 810                 815
Tyr Ile His Val Arg Ala Arg Arg Gly Gln Ala Thr Asp Ser His Ser
            820                 825                 830
Ile Ala Glu Arg Val Arg Arg Glu Lys Ile Ser Glu Arg Met Lys Phe
        835                 840                 845
Leu Gln Asp Leu Val Pro Gly Cys Asp Lys Ile Thr Gly Lys Ala Gly
    850                 855                 860
Met Leu Asp Glu Ile Ile Asn Tyr Val Gln Ser Leu Gln Arg Gln Ile
```

```
                865                 870                 875                 880
Glu Phe Leu Ser Met Lys Leu Ala Ile Val Asn Pro Arg Pro Asp Phe
                    885                 890                 895

Asp Met Asp Asp Ile Phe Ala Lys Glu Val Ala Ser Thr Pro Met Thr
                900                 905                 910

Val Val Pro Ser Pro Glu Met Val Leu Ser Gly Tyr Ser His Glu Met
                915                 920                 925

Val His Ser Gly Tyr Ser Ser Glu Met Val Asn Ser Gly Tyr Leu His
                930                 935                 940

Val Asn Pro Met Gln Gln Val Asn Thr Ser Ser Asp Pro Leu Ser Cys
945                 950                 955                 960

Phe Asn Asn Gly Glu Ala Pro Ser Met Trp Asp Ser His Val Gln Asn
                    965                 970                 975

Leu Tyr Gly Asn Leu Gly Val
                980

<210> SEQ ID NO 177
<211> LENGTH: 830
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
        50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240
```

```
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Ser Ala Asp Leu Phe Leu
        275                 280                 285
Arg Gly Ile Gly Leu Arg Glu Tyr Ser Arg Tyr Ile Cys Phe Asn Phe
    290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
        355                 360                 365
Phe Leu Leu Leu Pro Trp Lys Trp Gly Met Lys Tyr Phe Trp Asp Thr
    370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Glu Ala Gln Ile Met Ile Gly
                485                 490                 495
Ala Ala Pro Ala Ser Pro Lys Lys Lys Arg Lys Val Glu Ala Ser Gly
            500                 505                 510
Ser Gly Arg Ala Asp Ala Leu Asp Asp Phe Asp Leu Asp Met Leu Gly
        515                 520                 525
Ser Asp Ala Leu Asp Asp Phe Asp Leu Asp Met Leu Gly Ser Asp Ala
    530                 535                 540
Leu Asp Asp Phe Asp Leu Asp Met Leu Gly Ser Asp Ala Leu Asp Asp
545                 550                 555                 560
Phe Asp Leu Asp Met Leu Ile Asn Ser Arg Gly Ser Gly Glu Gly Arg
                565                 570                 575
Gly Ser Leu Leu Thr Cys Gly Asp Val Glu Glu Asn Pro Gly Pro Val
            580                 585                 590
Ser Lys Gly Glu Glu Leu Phe Thr Gly Val Val Pro Ile Leu Val Glu
        595                 600                 605
Leu Asp Gly Asp Val Asn Gly His Lys Phe Ser Val Ser Gly Glu Gly
    610                 615                 620
Glu Gly Asp Ala Thr Tyr Gly Lys Leu Thr Leu Lys Phe Ile Cys Thr
625                 630                 635                 640
Thr Gly Lys Leu Pro Val Pro Trp Pro Thr Leu Val Thr Thr Leu Thr
                645                 650                 655
Tyr Gly Val Gln Cys Phe Ser Arg Tyr Pro Asp His Met Lys Gln His
```

```
                660              665                670
Asp Phe Phe Lys Ser Ala Met Pro Glu Gly Tyr Val Gln Glu Arg Thr
            675                680                685
Ile Phe Phe Lys Asp Asp Gly Asn Tyr Lys Thr Arg Ala Glu Val Lys
            690                695                700
Phe Glu Gly Asp Thr Leu Val Asn Arg Ile Glu Leu Lys Gly Ile Asp
705                710                715                720
Phe Lys Glu Asp Gly Asn Ile Leu Gly His Lys Leu Glu Tyr Asn Tyr
                725                730                735
Asn Ser His Asn Val Tyr Ile Met Ala Asp Lys Gln Lys Asn Gly Ile
            740                745                750
Lys Val Asn Phe Lys Ile Arg His Asn Ile Glu Asp Gly Ser Val Gln
            755                760                765
Leu Ala Asp His Tyr Gln Gln Asn Thr Pro Ile Gly Asp Gly Pro Val
            770                775                780
Leu Leu Pro Asp Asn His Tyr Leu Ser Thr Gln Ser Ala Leu Ser Lys
785                790                795                800
Asp Pro Asn Glu Lys Arg Asp His Met Val Leu Leu Glu Phe Val Thr
                805                810                815
Ala Ala Gly Ile Thr Leu Gly Met Asp Glu Leu Tyr Lys Val
            820                825                830

<210> SEQ ID NO 178
<211> LENGTH: 774
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Lys Met Asp Lys Lys Thr Ile Val Trp Phe Arg Arg Asp Leu Arg
1               5                   10                  15
Ile Glu Asp Asn Pro Ala Leu Ala Ala Ala His Glu Gly Ser Val
            20                  25                  30
Phe Pro Val Phe Ile Trp Cys Pro Glu Glu Gly Gln Phe Tyr Pro
            35                  40                  45
Gly Arg Ala Ser Arg Trp Trp Met Lys Gln Ser Leu Ala His Leu Ser
50                  55                  60
Gln Ser Leu Lys Ala Leu Gly Ser Asp Leu Thr Leu Ile Lys Thr His
65                  70                  75                  80
Asn Thr Ile Ser Ala Ile Leu Asp Cys Ile Arg Val Thr Gly Ala Thr
                85                  90                  95
Lys Val Val Phe Asn His Leu Tyr Asp Pro Val Ser Leu Val Arg Asp
            100                 105                 110
His Thr Val Lys Glu Lys Leu Val Glu Arg Gly Ile Ser Val Gln Ser
            115                 120                 125
Tyr Asn Gly Asp Leu Leu Tyr Glu Pro Trp Glu Ile Tyr Cys Glu Lys
            130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Pro Trp Arg Leu Met Pro
                165                 170                 175
Ile Thr Ala Ala Ala Glu Ala Ile Trp Ala Cys Ser Ile Glu Glu Leu
            180                 185                 190
```

```
Gly Leu Glu Asn Glu Ala Glu Lys Pro Ser Asn Ala Leu Leu Thr Arg
        195                 200                 205
Ala Trp Ser Pro Gly Trp Ser Asn Ala Asp Lys Leu Leu Asn Glu Phe
210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
                260                 265                 270
Ala Arg Asp Lys Asn Ser Glu Gly Glu Glu Ser Ala Asp Leu Phe Leu
                275                 280                 285
Arg Gly Ile Gly Leu Arg Glu Tyr Ser Arg Tyr Ile Cys Phe Asn Phe
290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
                340                 345                 350
Trp Met His Asn Arg Ile Arg Val Ile Val Ser Ser Phe Ala Val Lys
                355                 360                 365
Phe Leu Leu Leu Pro Trp Lys Trp Gly Met Lys Tyr Phe Trp Asp Thr
                370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
                435                 440                 445
Trp Asp Ala Pro Leu Thr Val Leu Lys Ala Ser Gly Val Glu Leu Gly
450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Glu Ala Gln Ile Met Ile Gly
                485                 490                 495
Ala Ala Pro Ala Ser Pro Lys Lys Lys Arg Lys Val Glu Ala Ser Gly
                500                 505                 510
Ser Gly Met Asn Ile Gln Met Leu Leu Glu Ala Ala Asp Tyr Leu Glu
                515                 520                 525
Arg Arg Glu Arg Glu Ala Glu His Gly Tyr Ala Ser Met Leu Pro Gly
                530                 535                 540
Ser Gly Met Asn Ile Gln Met Leu Leu Glu Ala Ala Asp Tyr Leu Glu
545                 550                 555                 560
Arg Arg Glu Arg Glu Ala Glu His Gly Tyr Ala Ser Met Leu Pro Gly
                565                 570                 575
Ser Gly Met Asn Ile Gln Met Leu Leu Glu Ala Ala Asp Tyr Leu Glu
                580                 585                 590
Arg Arg Glu Arg Glu Ala Glu His Gly Tyr Ala Ser Met Leu Pro Gly
                595                 600                 605
Ser Gly Met Asn Ile Gln Met Leu Leu Glu Ala Ala Asp Tyr Leu Glu
```

```
                    610                 615                 620
Arg Arg Glu Arg Glu Ala Glu His Gly Tyr Ala Ser Met Leu Pro Ser
625                 630                 635                 640

Arg Ser Arg Gly Ser Glu Gly Arg Gly Ser Leu Leu Thr Cys Gly
                645                 650                 655

Asp Val Glu Glu Asn Pro Gly Pro Ile Glu Lys Ser Phe Val Ile Thr
                660                 665                 670

Asp Pro Arg Leu Pro Asp Tyr Pro Ile Ile Phe Ala Ser Asp Gly Phe
                675                 680                 685

Leu Glu Leu Thr Glu Tyr Ser Arg Glu Glu Ile Met Gly Arg Asn Ala
                690                 695                 700

Arg Phe Leu Gln Gly Pro Glu Thr Asp Gln Ala Thr Val Gln Lys Ile
705                 710                 715                 720

Arg Asp Ala Ile Arg Asp Arg Glu Thr Thr Val Gln Leu Ile Asn
                    725                 730                 735

Tyr Thr Lys Ser Gly Lys Lys Phe Trp Asn Leu Leu His Leu Gln Pro
                740                 745                 750

Val Arg Asp Arg Lys Gly Gly Leu Gln Tyr Phe Ile Gly Val Gln Leu
                755                 760                 765

Val Gly Ser Asp His Val
    770

<210> SEQ ID NO 179
<211> LENGTH: 1356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
                35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
                115                 120                 125

Ala Gln His His Glu Ala Leu Val Gly His Gly Phe Thr His Ala His
                130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190
```

-continued

```
Leu Leu Thr Val Ala Gly Glu Leu Arg Gly Pro Pro Leu Gln Leu Asp
        195                 200                 205
Thr Gly Gln Leu Leu Lys Ile Ala Lys Arg Gly Gly Val Thr Ala Val
    210                 215                 220
Glu Ala Val His Ala Trp Arg Asn Ala Leu Thr Gly Ala Pro Leu Asn
225                 230                 235                 240
Leu Thr Pro Glu Gln Val Val Ala Ile Ala Ser Asn Gly Gly Gly Lys
                245                 250                 255
Gln Ala Leu Glu Thr Val Gln Arg Leu Leu Pro Val Leu Cys Gln Ala
            260                 265                 270
His Gly Leu Thr Pro Glu Gln Val Val Ala Ile Ala Ser His Asp Gly
        275                 280                 285
Gly Lys Gln Ala Leu Glu Thr Val Gln Arg Leu Leu Pro Val Leu Cys
    290                 295                 300
Gln Ala His Gly Leu Thr Pro Glu Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
            340                 345                 350
Ser Asn Gly Gly Gly Lys Gln Ala Leu Glu Thr Val Gln Arg Leu Leu
        355                 360                 365
Pro Val Leu Cys Gln Ala His Gly Leu Thr Pro Glu Gln Val Val Ala
    370                 375                 380
Ile Ala Ser Asn Ile Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Ala His Gly Leu Thr Pro Glu
        435                 440                 445
Gln Val Val Ala Ile Ala Ser Asn Gly Gly Gly Lys Gln Ala Leu Glu
    450                 455                 460
Thr Val Gln Arg Leu Leu Pro Val Leu Cys Gln Ala His Gly Leu Thr
465                 470                 475                 480
Pro Glu Gln Val Val Ala Ile Ala Ser Asn Gly Gly Lys Gln Ala
                485                 490                 495
Leu Glu Thr Val Gln Arg Leu Leu Pro Val Leu Cys Gln Ala His Gly
            500                 505                 510
Leu Thr Pro Glu Gln Val Val Ala Ile Ala Ser Asn Ile Gly Gly Lys
        515                 520                 525
Gln Ala Leu Glu Thr Val Gln Arg Leu Leu Pro Val Leu Cys Gln Ala
    530                 535                 540
His Gly Leu Thr Pro Glu Gln Val Val Ala Ile Ala Ser Asn Gly Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser Asn
            580                 585                 590
Ile Gly Gly Lys Gln Ala Leu Glu Thr Val Gln Arg Leu Leu Pro Val
        595                 600                 605
Leu Cys Gln Ala His Gly Leu Thr Pro Glu Gln Val Val Ala Ile Ala
```

```
              610                 615                 620
Ser Asn Ile Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser His Asp Gly Gly Arg Pro Ala Leu Glu Ser Ile Val Ala
                660                 665                 670

Gln Leu Ser Arg Pro Asp Pro Ala Leu Ala Ala Leu Thr Asn Asp His
                675                 680                 685

Leu Val Ala Leu Ala Cys Leu Gly Gly Arg Pro Ala Leu Asp Ala Val
690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
                740                 745                 750

Phe Asp Asp Ala Met Thr Gln Phe Gly Met Ser Arg His Gly Leu Leu
                755                 760                 765

Gln Leu Phe Arg Arg Val Gly Val Thr Glu Leu Glu Ala Arg Ser Gly
770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
                820                 825                 830

Ala Pro Ser Pro Met His Glu Gly Asp Gln Thr Arg Ala Ser Ala Ser
                835                 840                 845

Pro Lys Lys Lys Arg Lys Val Glu Ala Ser Lys Met Asp Lys Lys Thr
850                 855                 860

Ile Val Trp Phe Arg Arg Asp Leu Arg Ile Glu Asp Asn Pro Ala Leu
865                 870                 875                 880

Ala Ala Ala Ala His Glu Gly Ser Val Phe Pro Val Phe Ile Trp Cys
                885                 890                 895

Pro Glu Glu Glu Gly Gln Phe Tyr Pro Gly Arg Ala Ser Arg Trp Trp
                900                 905                 910

Met Lys Gln Ser Leu Ala His Leu Ser Gln Ser Leu Lys Ala Leu Gly
                915                 920                 925

Ser Asp Leu Thr Leu Ile Lys Thr His Asn Thr Ile Ser Ala Ile Leu
930                 935                 940

Asp Cys Ile Arg Val Thr Gly Ala Thr Lys Val Val Phe Asn His Leu
945                 950                 955                 960

Tyr Asp Pro Val Ser Leu Val Arg Asp His Thr Val Lys Glu Lys Leu
                965                 970                 975

Val Glu Arg Gly Ile Ser Val Gln Ser Tyr Asn Gly Asp Leu Leu Tyr
                980                 985                 990

Glu Pro Trp Glu Ile Tyr Cys Glu Lys Gly Lys Pro Phe Thr Ser Phe
                995                 1000                1005

Asn Ser Tyr Trp Lys Lys Cys Leu Asp Met Ser Ile Glu Ser Val
     1010                1015                1020

Met Leu Pro Pro Pro Trp Arg Leu Met Pro Ile Thr Ala Ala Ala
     1025                1030                1035
```

Glu Ala Ile Trp Ala Cys Ser Ile Glu Glu Leu Gly Leu Glu Asn
    1040                1045                1050

Glu Ala Glu Lys Pro Ser Asn Ala Leu Leu Thr Arg Ala Trp Ser
    1055                1060                1065

Pro Gly Trp Ser Asn Ala Asp Lys Leu Leu Asn Glu Phe Ile Glu
    1070                1075                1080

Lys Gln Leu Ile Asp Tyr Ala Lys Asn Ser Lys Lys Val Val Gly
    1085                1090                1095

Asn Ser Thr Ser Leu Leu Ser Pro Tyr Leu His Phe Gly Glu Ile
    1100                1105                1110

Ser Val Arg His Val Phe Gln Cys Ala Arg Met Lys Gln Ile Ile
    1115                1120                1125

Trp Ala Arg Asp Lys Asn Ser Glu Gly Glu Ser Ala Asp Leu
    1130                1135                1140

Phe Leu Arg Gly Ile Gly Leu Arg Glu Tyr Ser Arg Tyr Ile Cys
    1145                1150                1155

Phe Asn Phe Pro Phe Thr His Glu Gln Ser Leu Leu Ser His Leu
    1160                1165                1170

Arg Phe Phe Pro Trp Asp Ala Asp Val Asp Lys Phe Lys Ala Trp
    1175                1180                1185

Arg Gln Gly Arg Thr Gly Tyr Pro Leu Val Asp Ala Gly Met Arg
    1190                1195                1200

Glu Leu Trp Ala Thr Gly Trp Met His Asn Arg Ile Arg Val Ile
    1205                1210                1215

Val Ser Ser Phe Ala Val Lys Phe Leu Leu Leu Pro Trp Lys Trp
    1220                1225                1230

Gly Met Lys Tyr Phe Trp Asp Thr Leu Leu Asp Ala Asp Leu Glu
    1235                1240                1245

Cys Asp Ile Leu Gly Trp Gln Tyr Ile Ser Gly Ser Ile Pro Asp
    1250                1255                1260

Gly His Glu Leu Asp Arg Leu Asp Asn Pro Ala Leu Gln Gly Ala
    1265                1270                1275

Lys Tyr Asp Pro Glu Gly Glu Tyr Ile Arg Gln Trp Leu Pro Glu
    1280                1285                1290

Leu Ala Arg Leu Pro Thr Glu Trp Ile His His Pro Trp Asp Ala
    1295                1300                1305

Pro Leu Thr Val Leu Lys Ala Ser Gly Val Glu Leu Gly Thr Asn
    1310                1315                1320

Tyr Ala Lys Pro Ile Val Asp Ile Asp Thr Ala Arg Glu Leu Leu
    1325                1330                1335

Ala Lys Ala Ile Ser Arg Thr Arg Glu Ala Gln Ile Met Ile Gly
    1340                1345                1350

Ala Ala Pro
    1355

<210> SEQ ID NO 180
<211> LENGTH: 1001
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Tyr Pro Tyr Asp Val Pro Asp Tyr Ala Ser Pro Lys Lys Lys Arg

```
             1               5                   10                  15
          Lys Val Glu Ala Ser Val Asp Leu Arg Thr Leu Gly Tyr Ser Gln Gln
                           20                  25                  30

Gln Gln Glu Lys Ile Lys Pro Lys Val Arg Ser Thr Val Ala Gln His
                           35                  40                  45

His Glu Ala Leu Val Gly His Gly Phe Thr His Ala His Ile Val Ala
           50                          55                  60

Leu Ser Gln His Pro Ala Ala Leu Gly Thr Val Ala Val Lys Tyr Gln
           65                  70                  75                  80

Asp Met Ile Ala Ala Leu Pro Glu Ala Thr His Glu Ala Ile Val Gly
                           85                  90                  95

Val Gly Lys Gln Trp Ser Gly Ala Arg Ala Leu Glu Ala Leu Leu Thr
                          100                 105                 110

Val Ala Gly Glu Leu Arg Gly Pro Leu Gln Leu Asp Thr Gly Gln
                          115                 120                 125

Leu Leu Lys Ile Ala Lys Arg Gly Gly Val Thr Ala Val Glu Ala Val
                          130                 135                 140

His Ala Trp Arg Asn Ala Leu Thr Gly Ala Pro Leu Asn Leu Thr Pro
          145                 150                 155                 160

Glu Gln Val Val Ala Ile Ala Ser Asn Asn Gly Gly Lys Gln Ala Leu
                          165                 170                 175

Glu Thr Val Gln Arg Leu Leu Pro Val Leu Cys Gln Ala His Gly Leu
                          180                 185                 190

Thr Pro Glu Gln Val Val Ala Ile Ala Ser His Asp Gly Gly Lys Gln
                          195                 200                 205

Ala Leu Glu Thr Val Gln Arg Leu Leu Pro Val Leu Cys Gln Ala His
                          210                 215                 220

Gly Leu Thr Pro Glu Gln Val Val Ala Ile Ala Ser His Asp Gly Gly
          225                 230                 235                 240

Lys Gln Ala Leu Glu Thr Val Gln Arg Leu Leu Pro Val Leu Cys Gln
                          245                 250                 255

Ala His Gly Leu Thr Pro Glu Gln Val Val Ala Ile Ala Ser Asn Gly
                          260                 265                 270

Gly Gly Lys Gln Ala Leu Glu Thr Val Gln Arg Leu Leu Pro Val Leu
                          275                 280                 285

Cys Gln Ala His Gly Leu Thr Pro Glu Gln Val Val Ala Ile Ala Ser
                          290                 295                 300

Asn Asn Gly Gly Lys Gln Ala Leu Glu Thr Val Gln Arg Leu Leu Pro
          305                 310                 315                 320

Val Leu Cys Gln Ala His Gly Leu Thr Pro Glu Gln Val Val Ala Ile
                          325                 330                 335

Ala Ser His Asp Gly Gly Lys Gln Ala Leu Glu Thr Val Gln Arg Leu
                          340                 345                 350

Leu Pro Val Leu Cys Gln Ala His Gly Leu Thr Pro Glu Gln Val Val
                          355                 360                 365

Ala Ile Ala Ser His Asp Gly Gly Lys Gln Ala Leu Glu Thr Val Gln
                          370                 375                 380

Arg Leu Leu Pro Val Leu Cys Gln Ala His Gly Leu Thr Pro Glu Gln
          385                 390                 395                 400

Val Val Ala Ile Ala Ser His Asp Gly Gly Lys Gln Ala Leu Glu Thr
                          405                 410                 415

Val Gln Arg Leu Leu Pro Val Leu Cys Gln Ala His Gly Leu Thr Pro
                          420                 425                 430
```

```
Glu Gln Val Val Ala Ile Ala Ser Asn Gly Gly Lys Gln Ala Leu
        435                 440                 445
Glu Thr Val Gln Arg Leu Leu Pro Val Leu Cys Gln Ala His Gly Leu
    450                 455                 460
Thr Pro Glu Gln Val Val Ala Ile Ala Ser His Asp Gly Gly Lys Gln
465                 470                 475                 480
Ala Leu Glu Thr Val Gln Arg Leu Leu Pro Val Leu Cys Gln Ala His
                485                 490                 495
Gly Leu Thr Pro Glu Gln Val Val Ala Ile Ala Ser His Asp Gly Gly
                500                 505                 510
Lys Gln Ala Leu Glu Thr Val Gln Arg Leu Leu Pro Val Leu Cys Gln
                515                 520                 525
Ala His Gly Leu Thr Pro Glu Gln Val Val Ala Ile Ala Ser Asn Ile
            530                 535                 540
Gly Gly Lys Gln Ala Leu Glu Thr Val Gln Arg Leu Leu Pro Val Leu
545                 550                 555                 560
Cys Gln Ala His Gly Leu Thr Pro Glu Gln Val Val Ala Ile Ala Ser
                565                 570                 575
Asn Asn Gly Gly Lys Gln Ala Leu Glu Thr Val Gln Arg Leu Leu Pro
            580                 585                 590
Val Leu Cys Gln Ala His Gly Leu Thr Pro Glu Gln Val Val Ala Ile
            595                 600                 605
Ala Ser Asn Asn Gly Gly Lys Gln Ala Leu Glu Thr Val Gln Arg Leu
        610                 615                 620
Leu Pro Val Leu Cys Gln Ala His Gly Leu Thr Pro Glu Gln Val Val
625                 630                 635                 640
Ala Ile Ala Ser His Asp Gly Gly Lys Gln Ala Leu Glu Thr Val Gln
                645                 650                 655
Arg Leu Leu Pro Val Leu Cys Gln Ala His Gly Leu Thr Pro Glu Gln
                660                 665                 670
Val Val Ala Ile Ala Ser Asn Gly Gly Gly Lys Gln Ala Leu Glu Thr
            675                 680                 685
Val Gln Arg Leu Leu Pro Val Leu Cys Gln Ala His Gly Leu Thr Pro
    690                 695                 700
Glu Gln Val Val Ala Ile Ala Ser His Asp Gly Gly Lys Gln Ala Leu
705                 710                 715                 720
Glu Thr Val Gln Arg Leu Leu Pro Val Leu Cys Gln Ala His Gly Leu
                725                 730                 735
Thr Pro Glu Gln Val Val Ala Ile Ala Ser His Asp Gly Gly Lys Gln
                740                 745                 750
Ala Leu Glu Thr Val Gln Arg Leu Leu Pro Val Leu Cys Gln Ala His
                755                 760                 765
Gly Leu Thr Pro Glu Gln Val Val Ala Ile Ala Ser His Asp Gly Gly
    770                 775                 780
Arg Pro Ala Leu Glu Ser Ile Val Ala Gln Leu Ser Arg Pro Asp Pro
785                 790                 795                 800
Ala Leu Ala Ala Leu Thr Asn Asp His Leu Val Ala Leu Ala Cys Leu
                805                 810                 815
Gly Gly Arg Pro Ala Leu Asp Ala Val Lys Lys Gly Leu Pro His Ala
                820                 825                 830
Pro Ala Leu Ile Lys Arg Thr Asn Arg Arg Ile Pro Glu Arg Thr Ser
            835                 840                 845
```

```
His Arg Val Ala Asp His Ala Gln Val Val Arg Val Leu Gly Phe Phe
    850                 855                 860

Gln Cys His Ser His Pro Ala Gln Ala Phe Asp Asp Ala Met Thr Gln
865                 870                 875                 880

Phe Gly Met Ser Arg His Gly Leu Leu Gln Leu Phe Arg Arg Val Gly
                885                 890                 895

Val Thr Glu Leu Glu Ala Arg Ser Gly Thr Leu Pro Pro Ala Ser Gln
            900                 905                 910

Arg Trp Asp Arg Ile Leu Gln Ala Ser Gly Met Lys Arg Ala Lys Pro
        915                 920                 925

Ser Pro Thr Ser Thr Gln Thr Pro Asp Gln Ala Ser Leu His Ala Phe
    930                 935                 940

Ala Asp Ser Leu Glu Arg Asp Leu Asp Ala Pro Ser Pro Met His Glu
945                 950                 955                 960

Gly Asp Gln Thr Arg Ala Ser Ala Ser Gly Ser Gly Met Asn Ile Gln
                965                 970                 975

Met Leu Leu Glu Ala Ala Asp Tyr Leu Glu Arg Arg Glu Arg Glu Ala
            980                 985                 990

Glu His Gly Tyr Ala Ser Met Leu  Pro
        995                 1000

<210> SEQ ID NO 181
<211> LENGTH: 1099
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Tyr Pro Tyr Asp Val Pro Asp Tyr Ala Ser Pro Lys Lys Lys Arg
1               5                   10                  15

Lys Val Glu Ala Ser Val Asp Leu Arg Thr Leu Gly Tyr Ser Gln Gln
            20                  25                  30

Gln Gln Glu Lys Ile Lys Pro Lys Val Arg Ser Thr Val Ala Gln His
        35                  40                  45

His Glu Ala Leu Val Gly His Gly Phe Thr His Ala His Ile Val Ala
    50                  55                  60

Leu Ser Gln His Pro Ala Ala Leu Gly Thr Val Ala Val Lys Tyr Gln
65                  70                  75                  80

Asp Met Ile Ala Ala Leu Pro Glu Ala Thr His Glu Ala Ile Val Gly
                85                  90                  95

Val Gly Lys Gln Trp Ser Gly Ala Arg Ala Leu Glu Ala Leu Leu Thr
            100                 105                 110

Val Ala Gly Glu Leu Arg Gly Pro Pro Leu Gln Leu Asp Thr Gly Gln
        115                 120                 125

Leu Leu Lys Ile Ala Lys Arg Gly Gly Val Thr Ala Val Glu Ala Val
    130                 135                 140

His Ala Trp Arg Asn Ala Leu Thr Gly Ala Pro Leu Asn Leu Thr Pro
145                 150                 155                 160

Glu Gln Val Val Ala Ile Ala Ser Asn Asn Gly Gly Lys Gln Ala Leu
                165                 170                 175

Glu Thr Val Gln Arg Leu Leu Pro Val Leu Cys Gln Ala His Gly Leu
            180                 185                 190

Thr Pro Glu Gln Val Val Ala Ile Ala Ser His Asp Gly Gly Lys Gln
        195                 200                 205
```

```
Ala Leu Glu Thr Val Gln Arg Leu Leu Pro Val Leu Cys Gln Ala His
    210                 215                 220

Gly Leu Thr Pro Glu Gln Val Val Ala Ile Ala Ser His Asp Gly Gly
225                 230                 235                 240

Lys Gln Ala Leu Glu Thr Val Gln Arg Leu Leu Pro Val Leu Cys Gln
                245                 250                 255

Ala His Gly Leu Thr Pro Glu Gln Val Val Ala Ile Ala Ser Asn Gly
                260                 265                 270

Gly Gly Lys Gln Ala Leu Glu Thr Val Gln Arg Leu Leu Pro Val Leu
            275                 280                 285

Cys Gln Ala His Gly Leu Thr Pro Glu Gln Val Val Ala Ile Ala Ser
290                 295                 300

Asn Asn Gly Gly Lys Gln Ala Leu Glu Thr Val Gln Arg Leu Leu Pro
305                 310                 315                 320

Val Leu Cys Gln Ala His Gly Leu Thr Pro Glu Gln Val Val Ala Ile
                325                 330                 335

Ala Ser His Asp Gly Gly Lys Gln Ala Leu Glu Thr Val Gln Arg Leu
                340                 345                 350

Leu Pro Val Leu Cys Gln Ala His Gly Leu Thr Pro Glu Gln Val Val
            355                 360                 365

Ala Ile Ala Ser His Asp Gly Gly Lys Gln Ala Leu Glu Thr Val Gln
370                 375                 380

Arg Leu Leu Pro Val Leu Cys Gln Ala His Gly Leu Thr Pro Glu Gln
385                 390                 395                 400

Val Val Ala Ile Ala Ser His Asp Gly Gly Lys Gln Ala Leu Glu Thr
                405                 410                 415

Val Gln Arg Leu Leu Pro Val Leu Cys Gln Ala His Gly Leu Thr Pro
                420                 425                 430

Glu Gln Val Val Ala Ile Ala Ser Asn Gly Gly Gly Lys Gln Ala Leu
            435                 440                 445

Glu Thr Val Gln Arg Leu Leu Pro Val Leu Cys Gln Ala His Gly Leu
450                 455                 460

Thr Pro Glu Gln Val Val Ala Ile Ala Ser His Asp Gly Gly Lys Gln
465                 470                 475                 480

Ala Leu Glu Thr Val Gln Arg Leu Leu Pro Val Leu Cys Gln Ala His
                485                 490                 495

Gly Leu Thr Pro Glu Gln Val Val Ala Ile Ala Ser His Asp Gly Gly
                500                 505                 510

Lys Gln Ala Leu Glu Thr Val Gln Arg Leu Leu Pro Val Leu Cys Gln
            515                 520                 525

Ala His Gly Leu Thr Pro Glu Gln Val Val Ala Ile Ala Ser Asn Ile
530                 535                 540

Gly Gly Lys Gln Ala Leu Glu Thr Val Gln Arg Leu Leu Pro Val Leu
545                 550                 555                 560

Cys Gln Ala His Gly Leu Thr Pro Glu Gln Val Val Ala Ile Ala Ser
                565                 570                 575

Asn Asn Gly Gly Lys Gln Ala Leu Glu Thr Val Gln Arg Leu Leu Pro
                580                 585                 590

Val Leu Cys Gln Ala His Gly Leu Thr Pro Glu Gln Val Val Ala Ile
            595                 600                 605

Ala Ser Asn Asn Gly Gly Lys Gln Ala Leu Glu Thr Val Gln Arg Leu
610                 615                 620
```

```
Leu Pro Val Leu Cys Gln Ala His Gly Leu Thr Pro Glu Gln Val Val
625                 630                 635                 640

Ala Ile Ala Ser His Asp Gly Lys Gln Ala Leu Glu Thr Val Gln
            645                 650                 655

Arg Leu Leu Pro Val Leu Cys Gln Ala His Gly Leu Thr Pro Glu Gln
                660                 665                 670

Val Val Ala Ile Ala Ser Asn Gly Gly Lys Gln Ala Leu Glu Thr
        675                 680                 685

Val Gln Arg Leu Leu Pro Val Leu Cys Gln Ala His Gly Leu Thr Pro
690                 695                 700

Glu Gln Val Val Ala Ile Ala Ser His Asp Gly Gly Lys Gln Ala Leu
705                 710                 715                 720

Glu Thr Val Gln Arg Leu Leu Pro Val Leu Cys Gln Ala His Gly Leu
            725                 730                 735

Thr Pro Glu Gln Val Val Ala Ile Ala Ser His Asp Gly Gly Lys Gln
                740                 745                 750

Ala Leu Glu Thr Val Gln Arg Leu Leu Pro Val Leu Cys Gln Ala His
        755                 760                 765

Gly Leu Thr Pro Glu Gln Val Val Ala Ile Ala Ser His Asp Gly Gly
770                 775                 780

Arg Pro Ala Leu Glu Ser Ile Val Ala Gln Leu Ser Arg Pro Asp Pro
785                 790                 795                 800

Ala Leu Ala Ala Leu Thr Asn Asp His Leu Val Ala Leu Ala Cys Leu
            805                 810                 815

Gly Gly Arg Pro Ala Leu Asp Ala Val Lys Lys Gly Leu Pro His Ala
                820                 825                 830

Pro Ala Leu Ile Lys Arg Thr Asn Arg Arg Ile Pro Glu Arg Thr Ser
        835                 840                 845

His Arg Val Ala Asp His Ala Gln Val Val Arg Val Leu Gly Phe Phe
850                 855                 860

Gln Cys His Ser His Pro Ala Gln Ala Phe Asp Asp Ala Met Thr Gln
865                 870                 875                 880

Phe Gly Met Ser Arg His Gly Leu Leu Gln Leu Phe Arg Arg Val Gly
            885                 890                 895

Val Thr Glu Leu Glu Ala Arg Ser Gly Thr Leu Pro Pro Ala Ser Gln
                900                 905                 910

Arg Trp Asp Arg Ile Leu Gln Ala Ser Gly Met Lys Arg Ala Lys Pro
        915                 920                 925

Ser Pro Thr Ser Thr Gln Thr Pro Asp Gln Ala Ser Leu His Ala Phe
930                 935                 940

Ala Asp Ser Leu Glu Arg Asp Leu Asp Ala Pro Ser Pro Met His Glu
945                 950                 955                 960

Gly Asp Gln Thr Arg Ala Ser Ala Ser Gly Ser Gly Met Asn Ile Gln
            965                 970                 975

Met Leu Leu Glu Ala Ala Asp Tyr Leu Glu Arg Arg Glu Arg Glu Ala
                980                 985                 990

Glu His Gly Tyr Ala Ser Met Leu Pro Gly Ser Gly Met Asn Ile Gln
        995                 1000                1005

Met Leu Leu Glu Ala Ala Asp Tyr Leu Glu Arg Arg Glu Arg Glu
            1010                1015                1020

Ala Glu His Gly Tyr Ala Ser Met Leu Pro Gly Ser Gly Met Asn
            1025                1030                1035

Ile Gln Met Leu Leu Glu Ala Ala Asp Tyr Leu Glu Arg Arg Glu
```

| | | | | | | | | | | |
|---|---|---|---|---|---|---|---|---|---|---|
| Arg | Glu | Ala | Glu | His | Gly | Tyr | Ala | Ser | Met | Leu | Pro | Gly | Ser | Gly |
| | 1055 | | | | 1060 | | | | 1065 | |

Met Asn Ile Gln Met Leu Leu Glu Ala Ala Asp Tyr Leu Glu Arg
 1070                1075                1080

Arg Glu Arg Glu Ala Glu His Gly Tyr Ala Ser Met Leu Pro Ser
 1085                1090                1095

Arg

<210> SEQ ID NO 182
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggttcc t                                                141

<210> SEQ ID NO 183
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcctgcag g                                               141

<210> SEQ ID NO 184
<211> LENGTH: 485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184
gtgtctagac tgcagagggc cctgcgtatg agtgcaagtg gttttaggac caggatgag      60 gcggggtggg ggtgcctacc tgacgaccga ccccgaccca ctggacaagc acccaacccc    120
cattccccaa attgcgcatc ccctatcaga gaggggagg ggaaacagga tgcggcgagg     180
cgcgtgcgca ctgccagctt cagcaccgcg gacagtgcct tcgcccccgc ctggcggcgc    240
gcgccaccgc cgcctcagca ctgaaggcgc gctgacgtca ctcgccggtc ccccgcaaac    300
tccccttccc ggccaccttg gtcgcgtccg cgccgccgcc ggcccagccg accgcacca    360 cgcgaggcgc gagatagggg ggcacgggcg cgaccatctg cgctgcggcg ccggcgactc    420
agcgctgcct cagtctgcgg tgggcagcgg aggagtcgtg tcgtgcctga gagcgcagtc    480
gagaa                                                                 485

<210> SEQ ID NO 185
<211> LENGTH: 408

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185

```
gtagatttga gaactttggg atattcacag cagcagcagg aaaagatcaa gcccaaagtg      60
aggtcgacag tcgcgcagca tcacgaagcg ctggtgggtc atgggtttac acatgcccac     120
atcgtagcct tgtcgcagca ccctgcagcc cttggcacgg tcgccgtcaa gtaccaggac     180
atgattgcgg cgttgccgga agccacacat gaggcgatcg tcggtgtggg gaaacagtgg     240
agcggagccc gagcgcttga ggccctgttg acggtcgcgg gagagctgag agggcctccc     300
cttcagctgg acacgggcca gttgctgaag atcgcgaagc ggggaggagt cacggcggtc     360
gaggcggtgc acgcgtggcg caatgcgctc acgggagcac ccctcaac                  408
```

<210> SEQ ID NO 186
<211> LENGTH: 164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186

```
cggaccccgc gctggccgca ctcactaatg atcatcttgt agcgctggcc tgcctcggcg      60
gacgacccgc cttggatgcg gtgaagaagg ggctcccgca cgcgcctgca ttgattaagc     120
ggaccaacag aaggattccc gagaggacat cacatcgagt ggca                      164
```

<210> SEQ ID NO 187
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187

```
atgagtattc aacatttccg tgtcgccctt attccttttt tgcggcatt ttgccttcct      60
gtttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattgg                                                   858
```

```
<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Asp Leu Ala Ser Leu Ile Leu
1               5

<210> SEQ ID NO 189
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Leu Thr Pro Ala Gln Val Val Ala Ile Ala Ser Gly Gly Lys Gln Ala
1               5                   10                  15

Leu Glu Thr Val Gln Gln Leu Leu Pro Val Leu Cys Gln Ala His Gly
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Leu Thr Pro Ala Gln Val Val Ala Leu Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Leu Thr Pro Asp Gln Val Val Ala Ile Ala Ser Gly Gly Arg Pro Ala
1               5                   10                  15

Leu Glu Thr Val Gln Arg Leu Leu Pro Val Leu Cys Glu Gln His Gly
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Leu Thr Pro Asp Gln Val Val Ala Ile Ala Ser Gly Gly Lys Gln Ala
1               5                   10                  15
```

Leu Ala Thr Val Gln Arg Leu Leu Pro Val Leu Cys Gln Asp His Gly
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Leu Thr Gln Val Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Leu Thr Pro Asp Gln Val Val Ala Ile Ala Arg Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Leu Pro Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 197

Leu Ser Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Thr His Ala
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Leu Asn Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Leu Thr Pro Asp Gln Val Met Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Leu Thr Pro Ala Gln Val Val Ala Ile Ala Ser Gly Gly Lys Gln Ala
1               5                   10                  15

Leu Glu Thr Val Arg Arg Leu Leu Pro Val Leu Cys Gln Ala His Gly
            20                  25                  30

<210> SEQ ID NO 201
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Leu Thr Pro Asp Gln Val Val Ala Ile Ala Ser Gly Gly Lys Gln Thr
1               5                   10                  15

Leu Glu Thr Val Gln Arg Leu Leu Pro Val Leu Cys Gln Asp His Gly
            20                  25                  30

```
<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Leu Thr Pro Asp Gln Val Met Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Leu Thr Pro Ala Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Arg Ala His Gly
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Leu Ser Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 206
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Leu Thr Pro Asp Gln Val Val Gly Ile Ala Ser Gly Gly Lys Gln Ala
```

```
                1               5                  10                  15
Leu Glu Thr Val Gln Arg Leu Leu Pro Val Leu Cys Gln Asp His Gly
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Leu Thr Pro Asp Gln Val Val Ala Ile Ala Ser Gly Gly Lys Gln Ala
1               5                  10                  15

Leu Glu Thr Val Gln Arg Leu Leu Pro Val Leu Cys Gln Ala Asn Gly
            20                  25                  30

<210> SEQ ID NO 208
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Leu Thr Pro Ala Gln Val Val Ala Ile Ala Ser Gly Gly Lys Gln Ala
1               5                  10                  15

Leu Glu Thr Val Gln Arg Leu Leu Pro Val Leu Cys Gln Thr His Gly
            20                  25                  30

<210> SEQ ID NO 209
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Leu Thr Pro Asp Gln Val Val Ala Ile Ala Ser Gly Gly Lys Gln Ala
1               5                  10                  15

Leu Glu Met Val Gln Arg Leu Leu Pro Val Leu Cys Gln Asp His Gly
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Leu Thr Pro Asp Gln Val Val Ala Ile Ala Ser Gly Gly Lys Gln Ala
1               5                  10                  15

Leu Glu Thr Met Gln Arg Leu Leu Pro Val Leu Cys Gln Asp His Gly
            20                  25                  30

<210> SEQ ID NO 211
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 211

Leu Thr Pro Asp Gln Val Val Ala Ile Ala Asn Gly Gly Lys Gln Ala
1               5                   10                  15

Leu Ala Thr Val Gln Arg Leu Leu Pro Val Leu Cys Gln Asp His Gly
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Leu Thr Pro Asp Gln Val Val Thr Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Leu Thr Pro Asp Gln Val Val Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Met Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Leu Ala Pro Asp Gln Val Val Ala Val Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Leu Thr Pro Ala Gln Val Val Ala Ile Ala Ser Gly Gly Lys Gln Ala
1               5                   10                  15

Leu Lys Thr Val Gln Gln Leu Leu Pro Val Leu Cys Glu Gln His Gly
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Leu Thr Pro Asp Gln Val Val Ala Ile Ala Arg Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 218
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Ala His Gly
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Leu Thr Pro Asp Gln Val Leu Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Leu Thr Pro Glu Gln Val Val Ala Ile Ala Arg Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 221
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Arg Ala His Gly
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Leu Thr Pro Asp Gln Val Val Ala Ile Ala Asn Gly Gly Lys Gln Ala
1               5                   10                  15

Leu Glu Met Val Gln Arg Leu Leu Pro Val Leu Cys Gln Asp His Gly
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Leu Thr Thr Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 225
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 225

Leu Thr Pro Gln Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Leu Thr Pro Asp Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Leu Thr Ser Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Asp His Gly
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Leu Thr Pro Asp Gln Val Val Ala Ile Ala Asn Gly Gly Lys Gln Ala
1               5                   10                  15

Leu Ala Thr Val Gln Arg Leu Leu Pro Val Leu Cys Gln Ala His Gly
            20                  25                  30
```

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Ala Arg Gly
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Leu Thr Pro Ala Gln Val Val Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asn His Gly
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

-continued

```
Leu Thr Pro Asp Gln Val Val Thr Ile Ala Ser Gly Gly Lys Gln Ala
1               5                   10                  15

Leu Glu Met Val Gln Arg Leu Leu Pro Val Leu Cys Gln Asp His Gly
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Leu Thr Pro Asp Gln Val Val Ala Ile Ala Ser Gly Gly Lys Gln Ala
1               5                   10                  15

Leu Glu Arg Val Gln Arg Leu Leu Pro Val Leu Cys Glu Gln His Gly
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Leu Thr Pro Glu Gln Val Val Ala Ile Ala Cys Gly Gly Lys Gln Ala
1               5                   10                  15

Leu Glu Thr Val Gln Ala Leu Leu Pro Val Leu Arg Gln Ala His Gly
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Arg Asp His Gly
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Leu Thr Pro Glu Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30

<210> SEQ ID NO 239
<211> LENGTH: 32
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 239

Leu Thr Pro Glu Gln Val Val Ala Ile Ala Cys Gly Gly Lys Gln Ala
1               5                  10                  15

Leu Glu Thr Val Gln Arg Leu Leu Pro Val Leu Arg His Ala His Gly
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Leu Thr Pro Asp Gln Val Val Ala Ile Ala Ser Gly Gly Lys Gln Ala
1               5                  10                  15

Leu Glu Thr Val Gln Arg Leu Leu Pro Val Leu Cys Gln His His Gly
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Leu Ile Pro Asp Gln Val Val Ala Ile Ala Ser Gly Gly Lys Gln Ala
1               5                  10                  15

Leu Glu Thr Val Gln Arg Leu Leu Pro Val Leu Cys Gln His His Gly
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Leu Thr Arg Ala Gln Val Val Ala Ile Ala Ser Gly Gly Lys Gln Ala
1               5                  10                  15

Leu Glu Thr Val Gln Arg Leu Leu Pro Val Leu Cys Glu Gln His Gly
            20                  25                  30

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Leu Thr Pro Asp Gln Val Val Ala Ile Ala Asn Gly Gly Lys Gln Ala
1               5                  10                  15

Val Gly Thr Val Gln Arg Leu Leu Pro Val Leu Cys Gln Ala His Gly
```

20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Leu Thr Pro Asp Gln Val Val Ala Ile Ala Ser Gly Ser Lys Gln Ala
1               5                   10                  15

Leu Glu Thr Met Gln Arg Leu Leu Pro Val Leu Cys Gln Asp His Gly
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Lys Gln His Gly
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 248

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Leu Thr Pro Asp Gln Val Val Ala Ile Ala Ser Gly Gly Lys Gln Ala
1               5                   10                  15

Leu Glu Ala Val Gln Arg Leu Leu Pro Val Leu Cys Gln Asp His Gly
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Leu Thr Pro Ala Gln Val Val Thr Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Leu Thr Pro Ala Gln Val Met Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Leu Thr Arg Glu Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30

<210> SEQ ID NO 253
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Leu Thr Leu Ala Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 254
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Leu Thr Leu Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 256
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Leu Ser Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 257
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Leu Thr Pro Asp Gln Val Val Ala Ile Ala Asn Gly Gly Lys Gln Ala
1               5                   10                  15
```

```
Leu Glu Thr Val Gln Arg Leu Leu Pro Val Leu Cys Gln His His Gly
            20                  25                  30
```

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

```
Leu Thr Pro Glu Gln Val Val Ala Ile Ala Ser Gly Gly Lys Gln Ala
1               5                   10                  15

Leu Glu Thr Val Gln Ala Leu Leu Pro Val Leu Arg Gln Ala His Gly
            20                  25                  30
```

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

```
Leu Ser Gln Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 260
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

```
Leu Pro Pro Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

```
Leu Thr Pro Asp Gln Val Val Ala Ile Ala Ser Gly Gly Lys Gln Ala
1               5                   10                  15

Leu Glu Ala Val Gln Arg Leu Leu Pro Val Leu Cys Gln Ala His Gly
            20                  25                  30
```

<210> SEQ ID NO 262
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 262

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Glu His Gly
            20                  25                  30

<210> SEQ ID NO 263
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Leu Thr Leu Asp Gln Val Ala Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 264
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Leu Thr Pro Asp Gln Val Val Ala Ile Ala Ser Gly Gly Lys Gln Ala
1               5                   10                  15

Leu Glu Thr Val Gln Arg Val Leu Pro Val Leu Cys Gln Asp His Gly
            20                  25                  30

<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 266
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30

<210> SEQ ID NO 267
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Thr His Gly
            20                  25                  30

<210> SEQ ID NO 268
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Leu Thr Pro Asp Gln Val Val Ala Ile Ala Asn Gly Gly Lys Gln Ala
1               5                   10                  15

Val Glu Thr Val Gln Arg Leu Leu Pro Val Leu Cys Gln Ala His Gly
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Leu Ser Pro Asp Gln Val Val Thr Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 271
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Leu Thr Pro Val Gln Val Val Ala Ile Ala Ser Gly Gly Lys Gln Ala
1               5                   10                  15
```

Leu Glu Thr Val Gln Arg Leu Leu Pro Val Leu Cys Gln Ala His Gly
            20                  25                  30

<210> SEQ ID NO 272
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Thr His Gly
            20                  25                  30

<210> SEQ ID NO 273
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Leu Thr Pro Ala Gln Val Val Ala Ile Ala Cys Gly Gly Lys Gln Ala
1               5                   10                  15

Leu Glu Thr Val Arg Arg Leu Leu Pro Val Leu Cys Gln Ala His Gly
            20                  25                  30

<210> SEQ ID NO 274
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Leu Thr Pro Ala Gln Val Val Ala Ile Ala Ser Gly Ser Lys Gln Ala
1               5                   10                  15

Leu Glu Thr Val Gln Arg Leu Phe Pro Val Leu Cys Gln Ala His Gly
            20                  25                  30

<210> SEQ ID NO 275
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 276
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 276

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Phe Gln Glu His Gly
            20                  25                  30

<210> SEQ ID NO 277
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Leu Thr Pro Ala Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 278
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Leu Thr Pro Val Gln Val Val Ala Ile Ala Ser Gly Gly Lys Gln Ala
1               5                   10                  15

Leu Ala Thr Val Gln Arg Leu Leu Pro Val Leu Cys Gln Asp His Gly
            20                  25                  30

<210> SEQ ID NO 279
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Leu Thr Pro Asp Gln Val Val Ala Ile Ala Ser Gly Gly Lys Gln Ala
1               5                   10                  15

Leu Glu Thr Val Gln Arg Leu Leu Pro Gly Leu Cys Gln Asp His Gly
            20                  25                  30

<210> SEQ ID NO 280
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Leu Thr Leu Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

```
<210> SEQ ID NO 281
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Leu Thr Pro Ala Gln Val Val Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 282
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Leu Thr Pro Ala Gln Ala Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 284
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Leu Thr Pro Ala Gln Val Val Ala Ile Val Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 285
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Leu Thr Pro Asp Gln Val Val Ala Val Ala Gly Gly Gly Lys Gln Ala
```

```
                1               5                   10                  15
Leu Glu Thr Val Gln Arg Leu Leu Pro Val Leu Cys Gln Asp His Gly
            20                  25                  30

<210> SEQ ID NO 286
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Leu Thr Pro Asp Gln Val Val Ala Ile Ala Ser Gly Gly Lys Gln Ala
1               5                   10                  15

Leu Gly Thr Val Gln Arg Leu Leu Pro Val Leu Cys Gln Ala His Gly
            20                  25                  30

<210> SEQ ID NO 287
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Glu Ala His Gly
            20                  25                  30

<210> SEQ ID NO 288
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Leu Thr Thr Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 289
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Leu Thr Pro Asp Gln Val Val Ala Ile Ala Asn Gly Gly Lys Gln Ala
1               5                   10                  15

Leu Glu Thr Val Gln Arg Leu Val Pro Val Leu Cys Gln Asp His Gly
            20                  25                  30

<210> SEQ ID NO 290
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 290

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Ala
            20                  25                  30

<210> SEQ ID NO 291
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Leu Thr Pro Asn Gln Leu Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 293
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Leu Ser Pro Ala Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Leu Thr Pro Asp Gln Val Val Ala Ile Ala Ser Gly Gly Lys Gln Ala
1               5                   10                  15

Leu Glu Thr Val Gln Arg Val Leu Pro Val Leu Cys Gln Ala His Gly
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 296
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Leu Thr Pro Glu Gln Val Val Ala Ile Ala Ser Gly Gly Arg Gln Ala
1               5                   10                  15

Leu Glu Thr Val Gln Arg Leu Leu Pro Val Leu Cys Gln Ala His Gly
            20                  25                  30

<210> SEQ ID NO 297
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Leu Thr Pro Ala Gln Val Val Ala Ile Ala Ser Gly Gly Lys Gln Ala
1               5                   10                  15

Leu Glu Thr Val Gln Trp Leu Leu Pro Val Leu Cys Gln Ala His Gly
            20                  25                  30

<210> SEQ ID NO 298
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Leu Thr Pro Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 299
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Leu Thr Pro Ala Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 300
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Ala Asn Gly
            20                  25                  30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Leu Thr Pro Ala Gln Val Val Ala Ile Ala Ser Gly Gly Lys Pro Ala
1               5                   10                  15

Leu Glu Thr Val Gln Arg Leu Leu Pro Val Leu Cys Glu Gln His Gly
            20                  25                  30

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Leu Thr Pro Asp Gln Val Val Ala Ile Ala Ser Ser Gly Lys Gln Ala
1               5                   10                  15

Leu Glu Thr Met Gln Arg Leu Leu Pro Val Leu Cys Gln Asp His Gly
            20                  25                  30

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Arg Gln Asp His Gly
            20                  25                  30

<210> SEQ ID NO 304
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 304

Leu Thr Pro Tyr Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Leu Thr Pro Tyr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Leu Thr Leu Glu Gln Val Val Ala Ile Ala Ser Gly Gly Lys Gln Ala
1               5                   10                  15

Leu Glu Thr Val Gln Arg Leu Leu Leu Val Leu Cys Gln Ala His Gly
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Leu Thr Pro Asp Gln Val Val Ala Ile Ala Ser Gly Gly Lys Gln Ala
1               5                   10                  15

Leu Glu Thr Val Arg Arg Leu Leu Gln Val Leu Cys Gln Asp His Gly
            20                  25                  30
```

<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Arg Gln Asp His Gly
            20                  25                  30

<210> SEQ ID NO 310
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Leu Thr Pro Asp Gln Val Val Ser Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Leu Thr Pro Asp Gln Val Val Ala Ile Ala Ser Gly Gly Lys Gln Ala
1               5                   10                  15

Leu Glu Thr Val Lys Arg Leu Leu Pro Val Leu Cys Gln Ala His Gly
            20                  25                  30

<210> SEQ ID NO 313
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

```
Leu Thr Thr Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 314
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Leu Ile Pro Gln Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 315
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Leu Thr Leu Thr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Leu Thr Pro Thr Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 318
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 318

Leu Thr Pro Asp Gln Val Val Ala Val Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 319
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 320
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Leu Thr Pro Gly Gln Val Val Ala Ile Ala Ser Gly Gly Lys Arg Ala
1               5                   10                  15

Leu Glu Thr Val Gln Arg Leu Leu Pro Val Leu Cys Gln Asp His Gly
            20                  25                  30

<210> SEQ ID NO 321
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Leu Thr Pro Asp Gln Val Val Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 322
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Leu Pro Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
```

20                  25                  30

<210> SEQ ID NO 323
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Leu Thr Pro Asp Gln Val Val Thr Ile Ala Asn Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 324
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Leu Thr Pro Ala Gln Val Val Ala Ile Ala Ser Gly Gly Lys Gln Ala
1               5                   10                  15

Leu Glu Thr Val Gln Arg Leu Leu Gln Val Leu Cys Gln Asp His Gly
            20                  25                  30

<210> SEQ ID NO 325
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Leu Thr Pro Asp His Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Leu Thr Pro Asp Gln Val Val Ala Ile Ala Ser Gly Gly Lys Gln Ala
1               5                   10                  15

Leu Glu Thr Val Gln Arg Leu Leu Gln Val Leu Cys Gln Asp His Gly
            20                  25                  30

<210> SEQ ID NO 327
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Leu Thr Pro Asp Gln Val Val Ala Ile Ala Ser Gly Gly Arg Gln Ala
1               5                   10                  15

Leu Glu Thr Val Gln Arg Leu Leu Pro Val Leu Cys Glu Gln His Gly
            20                  25                  30

<210> SEQ ID NO 328
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Leu His Pro Gly Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 329
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Leu Thr Leu Asp Gln Val Val Ser Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 330
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Leu Thr Pro Asp Gln Val Val Ala Ile Ala Ser Gly Gly Lys Gln Ala
1               5                   10                  15

Leu Glu Thr Val Gln Arg Leu Leu Pro Ala Leu Cys Gln Asp His Gly
            20                  25                  30

<210> SEQ ID NO 331
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Leu Thr Pro Asp Gln Val Val Ala Ile Ala Ser Gly Gly Lys Pro Ala
1               5                   10                  15

Leu Glu Thr Val Gln Arg Leu Leu Pro Val Leu Cys Glu Gln His Gly
            20                  25                  30

<210> SEQ ID NO 332
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Leu Thr Pro Ala Gln Val Val Ala Ile Ala Ser Gly Gly Lys Gln Ala
1               5                   10                  15

Leu Lys Thr Val Gln Arg Leu Leu Pro Val Leu Cys Gln Ala His Gly
            20                  25                  30

<210> SEQ ID NO 333
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Ala His Gly
            20                  25                  30

<210> SEQ ID NO 334
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Leu Asn Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 335
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Leu Thr Pro Asp Gln Val Val Ala Ile Ala Ser Gly Gly Lys Gln Ala
1               5                   10                  15

Leu Glu Thr Val Lys Arg Leu Leu Pro Val Leu Cys Gln Asp His Gly
            20                  25                  30

<210> SEQ ID NO 336
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Leu Thr Leu Asp Gln Val Val Ala Ile Ala Asn Gly Gly Lys Gln Ala
1               5                   10                  15
```

Leu Glu Thr Val Gln Arg Leu Leu Pro Val Leu Cys Gln Ala His Gly
            20                  25                  30

<210> SEQ ID NO 337
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Arg Asp His Gly
            20                  25                  30

<210> SEQ ID NO 338
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Leu Thr Pro Ala Gln Val Leu Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 339
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Gln Asp His Gly
            20                  25                  30

<210> SEQ ID NO 340
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Leu Thr Pro Asp Gln Val Val Ala Ile Ala Ser Gly Gly Lys Gln Ala
1               5                   10                  15

Leu Glu Thr Val Gln Arg Leu Leu Pro Gly Leu Cys Gln Ala His Gly
            20                  25                  30

<210> SEQ ID NO 341
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Leu Thr Arg Glu Gln Val Val Ala Ile Ala Ser Gly Gly Lys Gln Ala
1               5                   10                  15

Leu Glu Thr Val Gln Ala Leu Leu Pro Val Leu Arg Gln Ala His Gly
            20                  25                  30

<210> SEQ ID NO 342
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Val His Gly
            20                  25                  30

<210> SEQ ID NO 343
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Leu Thr Pro Asn Gln Val Val Ala Ile Ala Ser Gly Gly Lys Gln Ala
1               5                   10                  15

Leu Glu Thr Val Gln Arg Leu Leu Leu Val Leu Cys Gln Asp His Gly
            20                  25                  30

<210> SEQ ID NO 344
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Leu Thr Pro Asp Gln Val Met Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 345
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Leu Thr Arg Glu Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 346

<211> LENGTH: 33
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 346

Leu Ser Thr Ala Gln Val Val Ala Ile Ala Ser Gly Gly Lys Gln Ala
1               5                   10                  15
Leu Glu Gly Ile Gly Glu Gln Leu Leu Lys Leu Arg Thr Ala Pro Tyr
            20                  25                  30
Gly

<210> SEQ ID NO 347
<211> LENGTH: 33
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 347

Leu Ser Thr Ala Gln Val Val Ala Val Ala Ser Gly Gly Lys Pro Ala
1               5                   10                  15
Leu Glu Ala Val Arg Ala Gln Leu Leu Ala Leu Arg Ala Ala Pro Tyr
            20                  25                  30
Gly

<210> SEQ ID NO 348
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 348

Leu Thr Gln Val Gln Val Val Ala Ile Ala Ser Gly Gly Lys Gln Ala
1               5                   10                  15
Leu Glu Thr Val Gln Arg Leu Leu Pro Val Leu Cys Gln Asp His Gly
            20                  25                  30

<210> SEQ ID NO 349
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 349

Leu Thr Pro Asp Gln Val Val Ala Ile Ala Ser Asn Gly Lys Gln Ala
1               5                   10                  15
Leu Glu Thr Val Gln Arg Leu Leu Pro Val Leu Cys Gln Asp His Gly
            20                  25                  30

<210> SEQ ID NO 350
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

```
<400> SEQUENCE: 350

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Asp His Gly
            20                  25                  30
```

RECOMBINANT VIRUS AND PREPARATIONS THEREOF

RELATED APPLICATIONS AND INCORPORATION BY REFERENCE

This application claims priority to U.S. Provisional Application 61/799,800 filed on Mar. 15, 2013. Reference is made to US applications having Broad reference BI-2011/008 to US Provisional Application Nos. 61/736,527 filed Dec. 12, 2012; 61/748,427 filed Jan. 2, 2013; 61/757,972 filed Jan. 29, 2013, 61/768,959, filed Feb. 25, 2013 and 61/791,409 filed Mar. 15, 2013, titled SYSTEMS METHODS AND COMPOSITIONS FOR SEQUENCE MANIPULATION; Broad reference BI-2011/020 to US Provisional Application Nos. 61/675,778 filed Jul. 25, 2012; 61/721,283 filed Nov. 1, 2012; 61/726,465 filed Dec. 12, 2012 and 61/794,458 filed Mar. 15, 2013, titled INDUCIBLE DNA BINDING PROTEINS AND GENOME PERTURBATION TOOLS AND APPLICATIONS THEREOF; Broad reference BI-2011/021 to U.S. Provisional Application No. 61/565,171 filed Nov. 30, 2011 and U.S. application Ser. No. 13/554,922 filed Jul. 30, 2012 and Ser. No. 13/604,945 filed Sep. 6, 2012, titled NUCLEOTIDE-SPECIFIC RECOGNITION SEQUENCES FOR DESIGNER TAL EFFECTORS and Broad references BI-2013/003 and BI-2013/004 to U.S. Provisional Application No. 61/836,123 filed on Jun. 17, 2013 and U.S. Provisional Application Nos. 61/758,468; 61/769,046; 61/802,174; 61/806,375; 61/814,263; 61/819,803 and 61/828,130 each entitled ENGINEERING AND OPTIMIZATION OF SYSTEMS, METHODS AND COMPOSITIONS FOR SEQUENCE MANIPULATION, filed on Jan. 30, 2013; Feb. 25, 2013; Mar. 15, 2013; Mar. 28, 2013; Apr. 20, 2013; May 6, 2013 and May 28, 2013 respectively.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. MH100706 awarded by the National Institutes of Health. The Government has certain rights in the invention.

FIELD OF THE INVENTION

The present invention generally relates to methods for preparation of viral vector and methods and compositions for advantageous delivery of nucleic acid molecule(s) for expression of Transcription Activation Like Effector (TALE) and nucleic acid molecule(s) for expression of a CRISPR (Clustered Regularly Interspaced Short Palindromic Repeats) system, or nucleic acid molecule(s) for expression of a light-inducible transcriptional effector (LITE), or a cassette or plurality of cassette comprising or consisting essentially of a promoter and exogenous nucleic acid molecule encoding same particularly for gene editing in a eukaryote cell. TALEs, LITEs and CRISPRs expressed via a recombinant construct, e.g., an AAV, can advantageously provide activator, repressor or nuclease activity in vivo, in vitro or ex vivo.

The method of the invention can provide a readily accessible, reproducible aliquot of recombinant construct that can be used for testing, e.g., testing whether construction of the recombinant construct was successful, or whether the recombinant construct expresses the exogenous DNA in an amount that may be sufficient for an intended use and/or for a duration that may be sufficient for an intended use, i.e., for screening, such as high throughput screening. And hence the invention relates to a method that may advantageously be for screening or high throughput screening, wherein the method additionally comprises or consists essentially of contacting the aliquot with cells and determining whether the exogenous DNA is expressed in an amount and/or duration sufficient for an intended use.

SEQUENCE LISTING

The instant application contains a Sequence Listing which has been submitted electronically in ASCII format and is hereby incorporated by reference in its entirety. Said ASCII copy, created on Apr. 29, 2014, is named U.S. Ser. No. 14/213,991.txt and is 250,735 bytes in size.

BACKGROUND OF THE INVENTION

Normal gene expression is a dynamic process with carefully orchestrated temporal and spatial components, the precision of which are necessary for normal development, homeostasis, and advancement of the organism. In turn, the dysregulation of required gene expression patterns, either by increased, decreased, or altered function of a gene or set of genes, has been linked to a wide array of pathologies. Technologies capable of modulating gene expression in a spatiotemporally precise fashion will enable the elucidation of the genetic cues responsible for normal biological processes and disease mechanisms. To address this technological need, Applicants developed molecular tools that may regulate gene expression.

There is an evident need for methods and compositions that allow for efficient and precise spatial and temporal control of a genomic locus of interest. These methods and compositions may provide for the regulation and modulation of genomic expression both in vivo and in vitro as well as provide for novel treatment methods for a number of disease pathologies.

Adeno-associated virus (AAV) is a single-stranded DNA parvovirus which is endogenous to the human population. Although capable of productive infection in cells from a variety of species, AAV is a dependovirus, requiring helper functions from either adenovirus, herpesvirus or a poxvirus such as vaccinia virus for its own replication. In the absence of helper functions from any of these helper viruses, AAV will infect cells, uncoat in the nucleus, and integrate its genome into the host chromosome, but will not replicate or produce new viral particles. There are at least 12 recognized AAV serotypes, There are recombinant AAVs. A recombinant AAV can accommodate approximately 4300 bases of exogenous DNA, and AAVs having a hybrid or mosaic capsid have been produced.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and vital gene expression. The right side of the vital genome contains the cap genes that encode the structural capsid proteins VP1, VP2 and VP3. The proteins encoded by both the rep and cap genes function in trans during productive AAV replication.

Citation or identification of any document in this application is not an admission that such document is available as prior art to the present invention.

SUMMARY OF THE INVENTION

The present invention particularly relates to methods for preparation of viral vector and methods and compositions for advantageous delivery of Transcription Activation Like Effector (TALE) and nucleic acid molecule(s) for expression or a CRISPR (Clustered Regularly Interspaced Short Palindromic Repeats) system, or a cassette or plurality of cassette comprising or consisting essentially of a promoter and exogenous nucleic acid molecule encoding same particularly for gene editing in a eukaryote cell.

The present invention encompasses nucleic acid encoding the polypeptides of the present invention. The nucleic acid may comprise a promoter, advantageously human Synapsin I promoter (hSyn). In one embodiment, the nucleic acid is packaged into a viral vector. In some embodiments, the nucleic acid is packaged into a parvovirus-based vector. In some embodiments, the nucleic acid is packaged into an adeno associated viral vector (AAV).

The invention further relates to methods of treatment or therapy that encompass the methods and compositions described herein.

As discussed herein, the present invention generally relates to recombinant parvovirus (Group II viruses according to the Baltimore classification; e.g., Parvovirus B19, e.g. Dependovirus (e.g. Adeno-Associated Virus or AAV), Erythrovirus (e.g. Parvovirus B19) or Bocavirus), advantageously AAV. AAV is a protytpical Dependovirus, The invention will be discussed with regard to advantageous AAV embodiments with it understood that the invention comprehends any of "parvovirus", "Parvovirus B19", "Dependovirus", "Erythrovirus" or "Bocavirus" or species or serotypes of any of the foregoing in place of "AAV" in discussion herein. It is also understood that "AAV", unless specified as being a particular serotype or specified as having a particular capsid can be any of the herein identified AAVs.

There is a need for TALEs and LITEs to be expressed via a recombinant construct, e.g., an AAV, e.g., to provide activator, repressor or nuclease activity in vivo, in vitro or ex vivo.

There is a need for expression of a CRISPR system via a recombinant construct, e.g., an AAV, e.g., to provide knockdown in vivo, in vitro or ex vivo by the CRISPR introducing a spacer, which inhibits a target gene.

As traditional AAV or rAAV production requires a laborious production and purification process from cells, e.g., HEK-293FT cells, and this can make testing many constructs in parallel impractical. There is a need for a simple yet highly effective method of preparing AAV or rAAV, including testing or screening thereof, e.g., high throughput screening, and methods of using the resulting AAV or rAAV to integrate into the genome of cells otherwise difficult to infect, such as non-dividing cells, although AAV is able to infect both dividing and quiescent cells. In one aspect neuronal cells are targetted e.g., via neuronal transduction. Means for neuronal transduction also can be ascertained via Mason et al, "Comparison of AAV Serotypes for Gene Delivery to Dorsal Root Ganglion Neurons," Mol Ther. 2010 April; 18(4): 715-724 (2010 Feb. 23). All types of AAV and other Dependovirus are known to infect multiple diverse tissue types, and various AAV serotypes are known to have natural tropism to different tissues depending on their capsid proteins. Target tissues include, but are not limited to, e.g., brain, neurons, liver, eye, cardiac, muscle, and even cancer. See, e.g., Alam et al., Mol Cancer. 2011 Aug. 9; 10:97; Bartel et al. Gene Ther. 2012 June; 19(6):694-700.

There is also a need for a readily accessible, reproducible aliquot of recombinant construct that can be used for testing whether construction of the recombinant construct was successful, or whether the recombinant construct expresses the exogenous DNA in an amount that may be sufficient for an intended use and/or for a duration that may be sufficient for an intended use, i.e., for screening, such as high throughput screening, for therapeutic uses such as gene therapy, and targeting a broad range of tissues, whether of dividing or quiescent cells. Thus, there is a need for methods of the invention including those that may advantageously be for screening or high throughput screening, wherein the method includes or consists essentially of contacting the aliquot with cells and determining whether the exogenous DNA is expressed in an amount and/or duration sufficient for an intended use, e.g., gene therapy, genetic engineering or screening.

AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV compositions and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by one or more methods that comprise or consist essentially of, infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant construct lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant construct lacks functioning cap and/or rep, wherein said cells supply cap and/or rep function that the recombinant construct lacks; or transfecting the susceptible cells with an AAV lacking functioning cap and/or rep and plasmids for inserting exogenous DNA into the recombinant construct so that the exogenous DNA is expressed by the recombinant construct and for supplying rep and/or cap functions whereby transfection results in an rAAV containing the exogenous DNA including DNA for expression that lacks functioning cap and/or rep.

In addition to methods for preparing rAAV, the invention provides methods for using such recombinant constructs, and compositions or preparations of such recombinant constructs, including without limitation compositions or preparations resulting from a method for obtaining and optionally storing a sample containing a set amount of rAAV; and, this method can further optionally include testing the rAAV.

The method advantageously may comprise or consist essentially of, and hence the invention pertains to a method for obtaining and optionally storing a sample containing a set amount of rAAV comprising or consisting essentially of:
  preparing the rAAV as herein described, e.g.,
    plasmid(s) containing or consisting essentially of the desired viral construct are transfected into AAV-infected cells along with another helper plasmid that provide the AAV rep and/or cap genes which are obligatory for replication and packaging of the recombinant viral construct; or
    infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or
    infecting susceptible cells with a rAAV containing exogenous DNA including DNA for expression, wherein the recombinant construct lacks functioning cap and/or rep, and transfecting said cells with a plasmid supplying cap and/or rep function that the rAAV lacks; or
    infecting susceptible cells with a rAAV containing exogenous DNA including DNA for expression, wherein the recombinant construct lacks functioning cap and/or rep, wherein said cells supply cap and/or rep function that the recombinant lacks; or
    transfecting the susceptible cells with an AAV lacking functioning cap and/or rep and plasmids for inserting exogenous DNA into the recombinant construct so that the exogenous DNA is expressed by the recombinant construct and for supplying rep and/or cap functions whereby transfection results in an rAAV containing the exogenous DNA including DNA for expression that lacks functioning cap and/or rep; and
  incubating the infected or transfected cells, whereby there results infected or transfected cells and supernatant containing the rAAV lacking functioning cap and/or rep;
  after incubating, extracting an aliquot from the supernatant;
  filtering the aliquot, whereby the filtered aliquot contains and the method obtains a sample containing set amount of the rAAV relative to the type and amount of susceptible cells infected or transfected; and
  optionally freezing the filtered aliquot, whereby the method optionally includes storing a sample containing set amount of the rAAV relative to the type and amount of susceptible cells infected or transfected.

The rAAV can be from an AAV as herein described, and advantageously can be an rAAV1, rAAV2, AAV5 or rAAV having a hybrid capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue.

The susceptible cells are advantageously 293FT cells. The method advantageously includes or consists essentially of freezing (e.g., about −80° C.) the filtered aliquot. A secretion enhancer (e.g., polyethylenimine (PEI)) may be added to the cells before, during or after and within the incubating. The incubating can be typically up to 48 or 72 hours. $2\times10^5$ cells are advantageously transfected or infected, especially when the cells are 293FT cells. The filtered aliquot advantageously has a volume of 250 µL.

When the cells are 293FT cells and $2\times10^5$ cells are advantageously transfected or infected, the rAAV concentration in the filtered 250 µL aliquot is approximately $5.6+/-0.24\times10^5$. When cells other than 293FT are used, there should be a linear relationship with regard to the amount of rAAV in the supernatant, aliquot and filtered aliquot. Thus, from $2\times10^5$ 293FT cells obtaining the rAAV concentration in the filtered 250 µL aliquot of approximately $5.6+/-0.24\times10^5$, the skilled person can transfect the same number of other cells and measure the viral output (e.g., via qPCR) and ascertain the linear relationship amongst cells. Other cells that can be used in the practice of the invention and the relative infectivity of certain AAV serotypes in vitro as to these cells (see Grimm, D. et al, J. Virol. 82: 5887-5911 (2008)) are as follows:

| Cell Line | AAV-1 | AAV-2 | AAV-3 | AAV-4 | AAV-5 | AAV-6 | AAV-8 | AAV-9 |
| --- | --- | --- | --- | --- | --- | --- | --- | --- |
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |

-continued

| Cell Line | AAV-1 | AAV-2 | AAV-3 | AAV-4 | AAV-5 | AAV-6 | AAV-8 | AAV-9 |
|---|---|---|---|---|---|---|---|---|
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a transcriptional effector such as a Transcription Activation Like Effector (TALE) and nucleic acid molecule(s) for expression or a cassette comprising or consisting essentially of a promoter and a nucleic acid molecule encoding a transcriptional effector such as a TALE.

The invention provides rAAV that contains or consists essentially of an exogenous nucleic acid molecule encoding an inducible transcriptional effector such as a light-inducible transcriptional effector (LITE) and nucleic acid molecule(s) for expression or a cassette comprising or consisting essentially of a promoter and a nucleic acid molecule encoding an inducible transcriptional effector such as a LITE.

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector).

As rAAV is a DNA virus, the nucleic acid molecules in the herein discussion are advantageously DNA.

The invention also provides a readily accessible, reproducible aliquot of rAAV that can be used for testing, e.g., testing whether construction of the rAAV was successful, or whether the rAAV expresses the exogenous DNA in an amount that may be sufficient for an intended use and/or for a duration that may be sufficient for an intended use, i.e., for screening, such as high throughput screening.

Hence, the invention provides a method for screening or high throughput screening, wherein the method comprises or consists essentially of preparing the filtered aliquot or the stored filtered aliquot as herein described, if necessary, thawing the stored filtered aliquot, contacting the filtered aliquot with cells and determining whether the exogenous DNA is expressed in an amount and/or duration sufficient for an intended use. The contacting with cells can be transducing said cells (e.g., contacting can take 5-6 days with observation whereby suitable levels of rAAV expression are reached). For instance, the rAAV can express a TALE and the contacting can include detecting nuclease, activator or repressor activity. The rAAV can express an inducible transcriptional effector such as a LITE, and the contacting can include inducing gene expression or subjecting the contacted cells to a suitable stimulus, and if detecting whether transcriptional effector has been induced, e.g., via detecting a color change. The rAAV can express a CRISPR system, and the contacting can include detecting gene knockdown or other effects of the CRISPR system.

The invention further provides advantageous methods of AAV or rAAV production. In one aspect, as further described in the Examples herein, the invention encompasses AAV supernatant production. The methods of the invention described herein comprehend varying the DNA ratios of the vectors used, e.g. the ratios of vector of interest plasmid: AAV serotype plasmid:pHelper plasmid may be varied. In a preferred embodiment of the invention, this value may be 1:1.7:2 for AAV supernatant production down to 24-well scale. In another preferred embodiment of the invention, this value may be 1:2:1 for a 96-well format.

The invention also comprehends the scaling up of the AAV supernatant production to higher throughput formats. Aspects of the invention may be carried out in a 15 cm dish. In a further embodiment, aspects of the invention comprehend scaling up from a 15 cm dish to 96-well plates for production. In another aspect, the invention also encompasses scaling up which incudes but is not limited to 384-well plates or 1536-well plates. In a further embodiment, the invention also comprehends a microfluidic device capable of maintaining cell cultures in individual chambers. In a preferred embodiment, the AAV supernatant produced in the methods of the invention may be produced at the same scale as it may be applied.

The invention provides for methods of filtration or purification of the supernatant containing AAV generated in the methods described herein. Methods of filtration or purification may include but are not limited to the use of filters or centrifugation. In one aspect of the invention, filtration with specific pore size filters may be employed to remove any potential 293FT cells and large cell debris. In a preferred embodiment, a 22 micron or 45 micron pore size low protein binding filter may be used. When filtration is utilized the flow-through is harvested and subsequently used. In another aspect of the invention, centrifugation may be employed to pellet cells and cell debris. In a preferred embodiment, centrifugation at speeds in the range of 200 g for 20 min to 6000 g for 1-10 min may be utilized. When centrifugation is utilized the supernatant is collected and subsequently used. In a further embodiment of the invention, these steps may be followed by subsequent purification steps when more stringent purification is desired. In a preferred embodiment a sequence of molecular weight cutoff filters (e.g. amicon filters, Millipore) may be used.

The invention also provides for methods of AAV supernatant production which do not use fetal bovine serum (FBS). In a preferred embodiment, the culture medium used to support AAV producing 293FT cells may be replaced with a chemically-defined serum-free medium. e.g. Pro293a.

The invention also provides for AAV supernatant production methods being used to generate functional pooled AAV supernatant. Furthermore, the invention also provides for multiple supernatant AAV batches being harvested from a single AAV producing 293FT culture.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The invention further also provides other recombinant constructs, compositions, preparations, and methods described herein.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 shows a schematic indicating the need for spatial and temporal precision.

FIG. 3 shows a design of a LITE: TALE/Cryptochrome transcriptional activation. Each LITE is a two-component system which may comprise a TALE fused to CRY2 and the cryptochrome binding partner CIB1 fused to VP64, a transcription activator. In the inactive state, the TALE localizes its fused CRY2 domain to the promoter region of the gene of interest. At this point, CIB1 is unable to bind CRY2, leaving the CIB1-VP64 unbound in the nuclear space. Upon stimulation with 488 nm (blue) light, CRY2 undergoes a conformational change, revealing its CIB1 binding site (Liu, H et al., Science, 2008). Rapid binding of CIB1 results in recruitment of the fused VP64 domain, which induces transcription of the target gene.

FIG. 6 shows activation kinetics of Neurog2 LITE and inactivation kinetics of Neurog2 LITE.

Figure 7A:
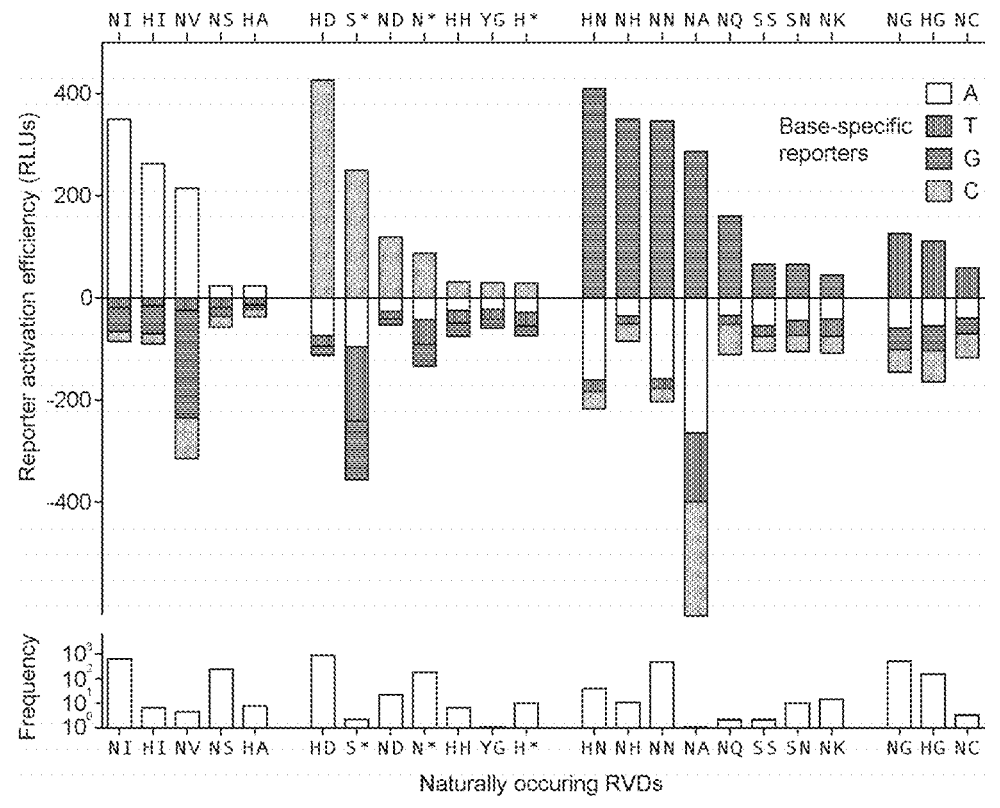

FIG. 7A shows the base-preference of various RVDs as determined using the Applicants' RVD screening system.

FIGS. 8A-D show in (a) Natural structure of TALEs derived from *Xanthomonas* sp. Each DNA-binding module consists of 34 amino acids (SEQ ID NO:1), where the RVDs in the 12th and 13th amino acid positions of each repeat specify the DNA base being targeted (e.g., SEQ ID NO:2) according to the cipher NG=T, HD=C, NI=A, and NN=G or A. The DNA-binding modules are flanked by nonrepetitive N and C termini, which carry the translocation, nuclear localization (NLS) and transcription activation (AD) domains. A cryptic signal within the N terminus specifies a thymine as the first base of the target site. (b) The TALE toolbox allows rapid and inexpensive construction of custom TALE-TFs and TALENs. The kit consists of 12 plasmids in total: four monomer plasmids to be used as templates for PCR amplification, four TALE-TF and four TALEN cloning backbones corresponding to four different bases targeted by the 0.5 repeat. CMV, cytomegalovirus promoter; N term, nonrepetitive N terminus from the Hax3 TALE; C term, nonrepetitive C terminus from the Hax3 TALE; BsaI, type IIs restriction sites used for the insertion of custom TALE DNA-binding domains; ccdB+CmR, negative selection cassette containing the ccdB negative selection gene and chloramphenicol resistance gene; NLS, nuclear localization signal; VP64, synthetic transcriptional activator derived from VP16 protein of herpes simplex virus; 2A, 2A self-cleavage linker; EGFP, enhanced green fluorescent protein; polyA signal, polyadenylation signal; FokI, catalytic domain from the FokI endonuclease. (c) TALEs may be used to generate custom TALE-TFs and modulate the transcription of endogenous genes from the genome. The TALE DNA-binding domain is fused to the synthetic VP64 transcriptional activator, which recruits RNA polymerase and other factors needed to initiate transcription. (d) TALENs may be used to generate site-specific double-strand breaks to facilitate genome editing through nonhomologous repair or homology directed repair. Two TALENs target a pair of binding sites flanking a 16-bp spacer. The left and right TALENs recognize the top and bottom strands of the target sites, respectively. Each TALE DNA-binding domain is fused to the catalytic domain of FokI endonuclease; when FokI dimerizes, it cuts the DNA in the region between the left and right TALEN-binding sites.

FIG. 9A-F shows a table listing monomer sequences (excluding the RVDs at positions 12 and 13)(SEQ ID NOS:3-74 and 189-347, respectively, in order of appearance) and the frequency with which monomers having a particular sequence occur.

FIGS. 23A-E depict a Type II CRISPR locus from *Streptococcus pyogenes* SF370 can be reconstituted in mammalian cells to facilitate targeted DSBs of DNA. (A) Engineering of SpCas9 and SpRNase III with NLSs enables import into the mammalian nucleus. (B) Mammalian expression of SpCas9 and SpRNase III are driven by the EF1a promoter, whereas tracrRNA and pre-crRNA array (DR-Spacer-DR) are driven by the U6 promoter. A protospacer (blue highlight) from the human EMX1 locus (SEQ ID NO:78) with PAM is used as template for the spacer in the pre-crRNA array. (C) Schematic representation of base pairing between target locus (SEQ ID NOS:79-80) and EMX1-targeting crRNA (SEQ ID NO:81). Red arrow indicates putative cleavage site. (D) SURVEYOR assay for SpCas9-mediated indels. (E) An example chromatogram showing a microdeletion, as well as representative sequences of mutated alleles (SEQ ID NOS:82-89) identified from 187 clonal amplicons. Red dashes, deleted bases; red bases, insertions or mutations. Scale bar=10 μm.

FIGS. 24A-C depict a SpCas9 can be reprogrammed to target multiple genomic loci in mammalian cells. (A) Schematic of the human EMX1 locus (SEQ ID NOS:90-91) showing the location of five protospacers, indicated by blue lines with corresponding PAM in magenta. (B) Schematic of the pre-crRNA:tracrRNA complex (SEQ ID NOS:92-93) (top) showing hybridization between the direct repeat (gray) region of the pre-crRNA and tracrRNA. Schematic of a chimeric RNA design (SEQ ID NO:94) (M. Jinek et al., A programmable dual-RNA-guided DNA endonuclease in adaptive bacterial immunity. Science 337, 816 (Aug. 17, 2012)) (bottom). tracrRNA sequence is shown in red and the 20 bp spacer sequence in blue. (C) SURVEYOR assay comparing the efficacy of Cas9-mediated cleavage at five protospacers in the human EMX1 locus. Each protospacer is targeted using either processed pre-crRNA:tracrRNA complex (crRNA) or chimeric RNA (chiRNA).

FIGS. 25A-D depict an evaluation of the SpCas9 specificity and comparison of efficiency with TALENs. (A) EMX1-targeting chimeric crRNAs with single point mutations were generated to evaluate the effects of spacer-protospacer mismatches (SEQ ID NOS:95-96, 97-108). (B) SURVEYOR assay comparing the cleavage efficiency of different mutant chimeric RNAs. (C) Schematic showing the design of TALENs targeting EMX1 (SEQ ID NOS:95-96). (D) SURVEYOR gel comparing the efficiency of TALEN and SpCas9 (N=3).

FIGS. 26A-G depict applications of Cas9 for homologous recombination and multiplex genome engineering. (A) Mutation of the RuvC I domain converts Cas9 into a nicking enzyme (SpCas9n) (B) Co-expression of EMX1-targeting chimeric RNA with SpCas9 leads to indels, whereas SpCas9n does not (N=3). (C) Schematic representation of the recombination strategy. A repair template is designed to insert restriction sites into EMX1 locus. Primers used to amplify the modified region are shown as red arrows. (D) Restriction fragments length polymorphism gel analysis. Arrows indicate fragments generated by HindIII digestion. (E) Example chromatogram showing successful recombination (SEQ ID NO:109). (F) SpCas9 can facilitate multiplex genome modification using a crRNA array containing two spacers (SEQ ID NOS:110, 111) targeting EMX1 and PVALB. Schematic showing the design of the crRNA array (top). Both spacers mediate efficient protospacer cleavage (bottom). (G) SpCas9 can be used to achieve precise genomic deletion. Two spacers (SEQ ID NOS:112, 113) targeting EMX1 (top) mediated a 118 bp genomic deletion (SEQ ID NOS:114-118) (bottom).

FIG. 30A-B depict a Northern blot analysis of crRNA processing in mammalian cells. (A) Schematic showing the expression vector for a single spacer flanked by two direct repeats (DR-EMX1(1)-DR) (SEQ ID NO: 121). The 30 bp spacer targeting the human EMX1 locus protospacer 1 (Table 1) is shown in blue and direct repeats are in shown in gray. Orange line indicates the region whose reverse complement sequence is used to generate northern blot probes for EMX1(1) crRNA detection. (B) Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA, and was not dependent on the presence of SpRNase III. The mature crRNA detected from transfected 293FT total RNA is-33 bp and is shorter than the 39-42 bp mature crRNA from *S. pyogenes* (E. Deltcheva et al., Nature 471, 602 (Mar. 31, 2011)), suggesting that the processed mature crRNA in human 293FT cells is likely different from the bacterial mature crRNA in *S. pyogenes*.

FIG. 31A-B depict bicistronic expression vectors for pre-crRNA array or chimeric crRNA with Cas9 (SEQ ID NOS:122-129). (A) Schematic showing the design of an expression vector for the pre-crRNA array. Spacers can be inserted between two BbsI sites using annealed oligonucleotides. Sequence design for the oligonucleotides are shown below with the appropriate ligation adapters indicated. (B) Schematic of the expression vector for chimeric crRNA. The guide sequence can be inserted between two BbsI sites using annealed oligonucleotides. The vector already contains the partial direct repeat (gray) and partial tracrRNA (red) sequences. WPRE, Woodchuck hepatitis virus posttranscriptional regulatory element.

FIGS. 32A-B depict a selection of protospacers in the human PVALB (SEQ ID NOS: 130-131) and mouse (SEQ ID NOS: 132-133) Th loci. Schematic of the human PVALB (A) and mouse Th (B) loci and the location of the three protospacers within the last exon of the PVALB and Th genes, respectively. The 30 bp protospacers are indicated by black lines and the adjacent PAM sequences are indicated by the magenta bar. Protospacers on the sense and anti-sense strands are indicated above and below the DNA sequences respectively.

FIGS. 33A-C depict occurrences of PAM sequences in the human genome. Histograms of distances between adjacent *Streptococcus pyogenes* SF370 locus 1 PAM (NGG) (A) and *Streptococcus thermophilus* LMD9 locus 1 PAM (NNA-GAAW) (SEQ ID NO: 138) (B) in the human genome. (C) Distances for each PAM by chromosome. Chr, chromosome. Putative targets were identified using both the plus and minus strands of human chromosomal sequences. Given that there may be chromatin, DNA methylation-, RNA structure, and other factors that may limit the cleavage activity at some protospacer targets, it is important to note that the actual targeting ability might be less than the result of this computational analysis.

FIGS. 34A-D depict type II CRISPR from *Streptococcus thermophilus* LMD-9 can also function in eukaryotic cells. (A) Schematic of CRISPR locus 2 from *Streptococcus thermophilus* LMD-9. (B) Design of the expression system for the *S. thermophilus* CRISPR system. Human codon-optimized hStCas9 is expressed using a constitutive EF1a promoter. Mature versions of tracrRNA and crRNA are expressed using the U6 promoter to ensure precise transcription initiation. Sequences for the mature crRNA and tracrRNA are shown (SEQ ID NOS: 134-135). A single based indicated by the lower case "a" in the crRNA sequence was used to remove the polyU sequence, which serves as a RNA Pol III transcriptional terminator. (C) Schematic showing protospacer and corresponding PAM sequences targets in the human EMX1 locus (SEQ ID NOS: 136-137). Two protospacer sequences are highlighted and their corresponding PAM sequences satisfying the NNAGAAW motif (SEQ ID NO:138) are indicated by magenta lines. Both protospacers are targeting the anti-sense strand. (D) SURVEYOR assay showing StCas9-mediated cleavage in the target locus. RNA guide spacers 1 and 2 induced 14% and 6.4% respectively. Statistical analysis of cleavage activity across biological replica at these two protospacer sites can be found in Table 1.

FIGS. 35A-E depict design and optimization of the LITE system. (A) A TALE DNA-binding domain (SEQ ID NO: 139) is fused to CRY2 and a transcriptional effector domain is fused to CIB1. In the inactive state, TALE-CRY2 binds the promoter region of the target gene while CIB1-effector remains unbound in the nucleus. The VP64 transcriptional activator is shown above. Upon illumination with blue light, TALE-CRY2 and CIB1-effector rapidly dimerize, recruiting CIB1-effector to the target promoter. The effector in turn modulates transcription of the target gene. (B) Light-dependent upregulation of the endogenous target Ngn2 mRNA with LITEs containing functional truncations of its light-sensitive binding partners. LITE-transfected Neuro-2a cells were stimulated for 24 h with 466 nm light at an intensity of 5 mW/cm$^2$ and a duty cycle of 7% (1 s pulses at 0.066 Hz). (C) Ngn2 upregulation with and without light by LITEs using different transcriptional activation domains VP16, VP64, and p65. Stimulation parameters are the same as (b). (D) The transcriptional activity of CRY2 PHR-CIB1 LITE was found to vary according to the intensity of 466 nm blue light. Neuro 2a cells were stimulated for 24 h hours at a 7% duty cycle (1s pulses at 0.066 Hz) (E) Light-induced toxicity measured as the percentage of cells positive for red-fluorescent ethidium homodimer-1 versus calcein-positive cells. All Ngn2 mRNA levels were measured relative to cells expressing YFP only (mean±s.e.m.; n=3-4)

FIGS. 36A-B depict kinetics of light-induced transcriptional activation. (A) Time course of light-dependent Ngn2 upregulation by TALE-CRY2 PHR and CIB1-VP64 LITEs. LITE-transfected Neuro-2a cells were stimulated with 466 nm light at an intensity of 5 mW/cm$^2$ and a duty cycle of 7% (1 s pulses at 0.066 Hz). (B) Decrease of Ngn2 mRNA levels after 6 h of light stimulation. All Ngn2 mRNA levels were measured relative to expressing YFP control cells (mean±s.e.m.; n=3-4) (*=p<0.05 and ***=p<0.001).

FIGS. 37A-F depict virus-mediated TALE delivery enabling bimodal control of endogenous gene expression in neurons (A) General schematic of constitutive TALE transcriptional activator and repressor packaged into AAV. Effector domains VP64 and SID4X are highlighted. (B) Representative images showing transduction with AAV-TALE-VP64 constructs from (a) in primary cortical neurons. Cells were stained for virally delivered GFP and neuronal marker NeuN. Scale bars=25 (C) 6 TALEs were designed, with two TALEs targeting each of the endogenous mouse loci Grm5, Grin2a, and Grm2 (SEQ ID NOS:140-145). TALEs were fused to the transcriptional activator domain VP64 or the repressor domain SID4X and virally transduced into primary neurons. Both the target gene upregulation via VP64 and downregulation via SID4X are shown for each TALE relative to levels in neurons expressing GFP only. (D) Efficient delivery of TALE-VP64 by AAV into the ILC of mice. Scale bar=100 um. (Cg1=cingulate cortex, PLC=prelimbic cortex, ILC=infralimbic cortex). (E) Higher magnification image of efficient transduction of neurons in ILC. (F) Grm2 mRNA upregulation by TALE-VP64 in vivo in ILC (mean±s.e.m.; n=3).

FIGS. 38A-J depict light-mediated manipulation of Grm2 expression in primary neurons and in vivo (A) AAV LITE activator construct with switched CRY2 PHR and CIB1 architecture. (B) Representative images showing co-transduction of AAV-delivered LITE constructs in primary neurons. Cells were stained for GFP, HA-tag, and DAPI. (Scale bars=25 µm). (C) Light-induced activation of Grm2 expression in primary neurons after 24 h of stimulation with 0.8% duty cycle pulsed 466 nm light (250 ms pulses at 0.033 Hz or 500 ms pulses at 0.016 Hz; 5 mW/cm$^2$). (D) Upregulation of Grm2 mRNA in primary cortical neurons with and without light stimulation at 4 h and 24 h time points. Expression levels are shown relative to neurons transduced with GFP only. (E) Quantification of mGluR2 protein levels in GFP only control transductions, unstimulated neurons with LITEs, and light-stimulated neurons with LITEs. A representative western blot is shown with β-tubulin-III as a loading control. (F) LITE repressor construct highlighting SID4X repressor domain. (G) Light-induced repression of endogenous Grm2 expression in primary cortical neurons using Grm2 T1-LITE and Grm2 T2-LITE. Fold downregulation is shown relative to neurons transduced with GFP only (mean±s.e.m.; n=3-4 for all subpanels). (H) Schematic showing transduction of ILC with the LITE system, the optical fiber implant, and the 0.35 mm diameter brain punch used for tissue isolation. (I) Representative images of ILC co-transduced with both LITE components. Stains are shown for HA-tag (red), GFP (green), and DAPI (blue). (Scale bar=25 μm). (J) Light-induced activation of endogenous Grm2 expression using LITEs transduced into ILC.

FIG. 43 depicts a selection of TALE target sites guided by DNaseI-sensitive chromatin regions. High DNaseI sensitivity based on mouse cortical tissue data from ENCODE (at the website of genome.ucsc.edu) was used to identify open chromatin regions. The peak with the highest amplitude within the region 2 kb upstream of the transcriptional start site was selected for targeting. TALE binding targets were then picked within a 200 bp region at the center of the peak.

FIG. 44 depicts a TALE SID4X repressor characterization. A synthetic repressor was constructed by concatanating 4 SID domains (SID4X). To identify the optimal TALE-repressor architecture, SID or SID4X was fused to a TALE designed to target the mouse p11 gene (SEQ ID NO:146). Fold decrease in p11 mRNA was assayed using qRT-PCR.

FIGS. 45A-B depict exchanging CRY2 PHR and CIB1 components. (A) TALE-CIB1::CRY2 PHR-VP64 was able to activate Ngn2 at higher levels than TALE-CRY2 PHR:: CIB1-VP64. (B) Fold activation ratios (light versus no light) ratios of Ngn2 LITEs show similar efficiency for both designs. Stimulation parameters were the same as those used in FIG. 35B.

FIGS. 47A-B depict a contribution of individual LITE components to baseline transcription modulation. (A) Grm2 mRNA levels were determined in primary neurons transfected with individual LITE components. Primary neurons expressing T6-CIB1 alone led to a similar increase in Grm2 mRNA levels as unstimulated cells expressing the complete LITE system. (B) Transcription repression by individual LITE repressor components targeting the Grm2 gene was compared.

FIG. 48 depicts a co-transduction efficiency of LITE components by AAV1/2 in mouse infralimbic cortex. Cells transduced by T6-CIB1 alone, CRY2 PHR-VP64 alone, or co-transduced were calculated as a percentage of all transduced cells.

DETAILED DESCRIPTION OF THE INVENTION

Figure 2:
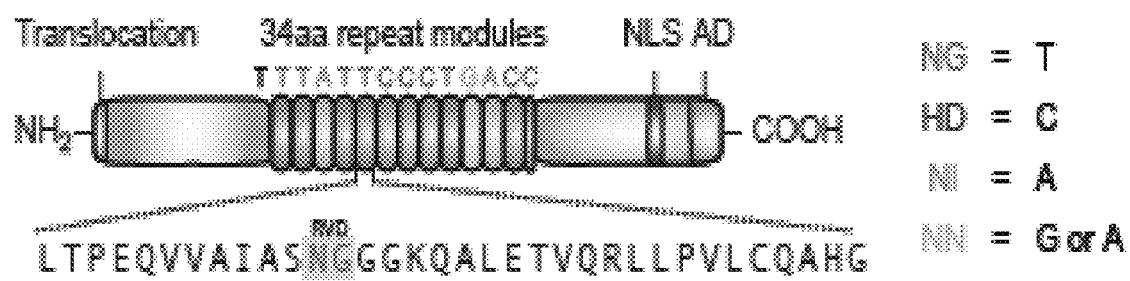
FIG. 2 shows transcription activator like effectors (TALEs). TALEs consist of 34 aa repeats (SEQ ID NO:1) at the core of their sequence. Each repeat corresponds to a base in the target DNA that is bound by the TALE, with one example shown as SEQ ID NO:2. Repeats differ only by 2 variable amino acids at positions 12 and 13. The code of this correspondence has been elucidated (Boch, J et al., Science, 2009 and Moscou, M et al., Science, 2009) and is shown in this figure. Applicants have developed a method for the synthesis of designer TALEs incorporating this code and capable of binding a sequence of choice within the genome (Zhang, F et al., Nature Biotechnology, 2011).
Figure 4:
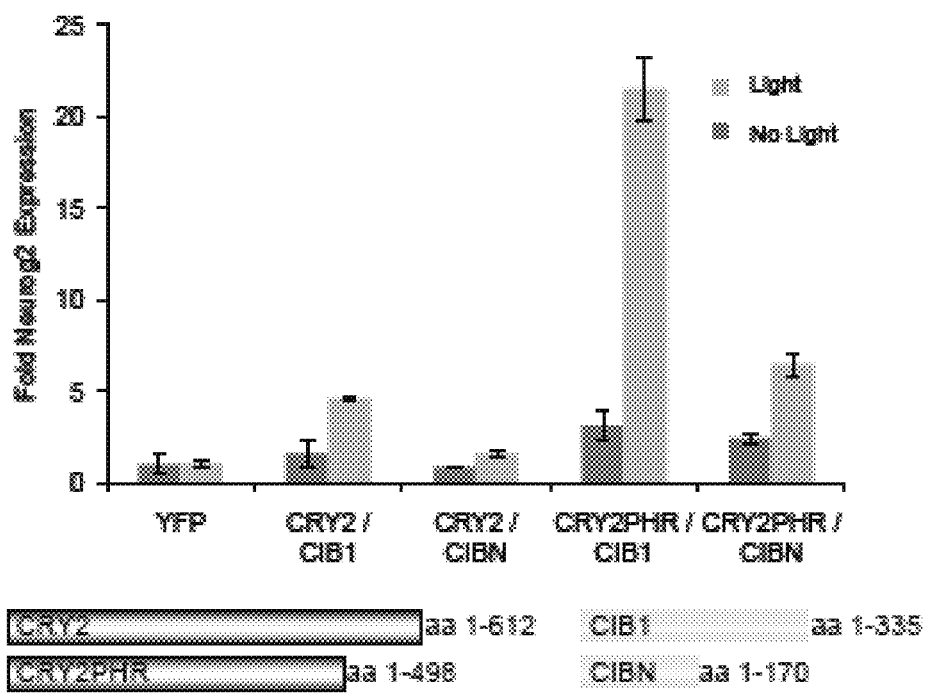
FIG. 4 shows effects of cryptochrome dimer truncations on LITE activity. Truncations known to alter the activity of CRY2 and CIB1 (Kennedy M et al., Nature Methods 2010) were compared against the full length proteins. A LITE targeted to the promoter of Neurog2 was tested in Neuro-2a cells for each combination of domains. Following stimulation with 488 nm light, transcript levels of Neurog2 were quantified using qPCR for stimulated and unstimulated samples.
Figure 5:
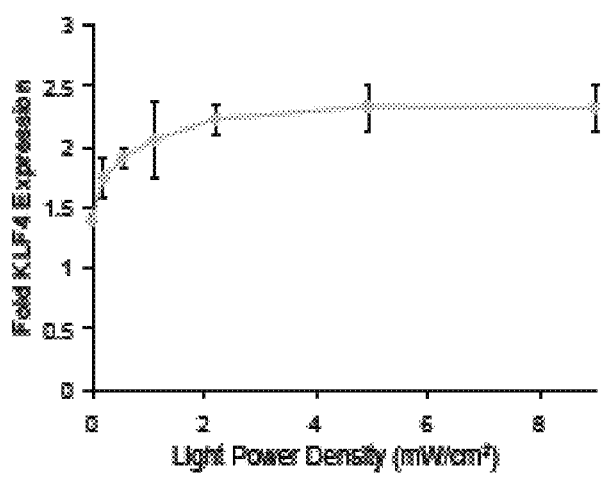
FIG. 5 shows a light-intensity dependent response of KLF4 LITE.
Figure 7B:
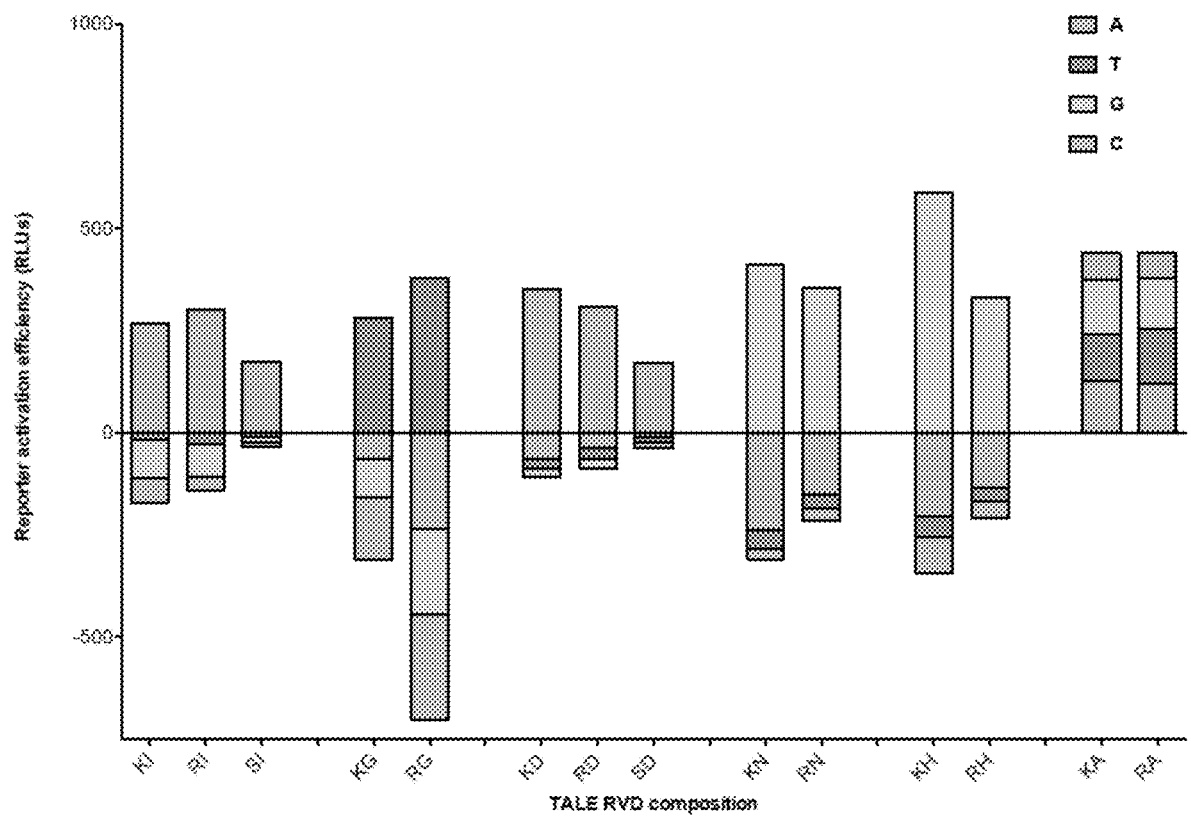
FIG. 7B shows the base-preference of additional RVDs as determined using the Applicants' RVD screening system.
Figure 10:
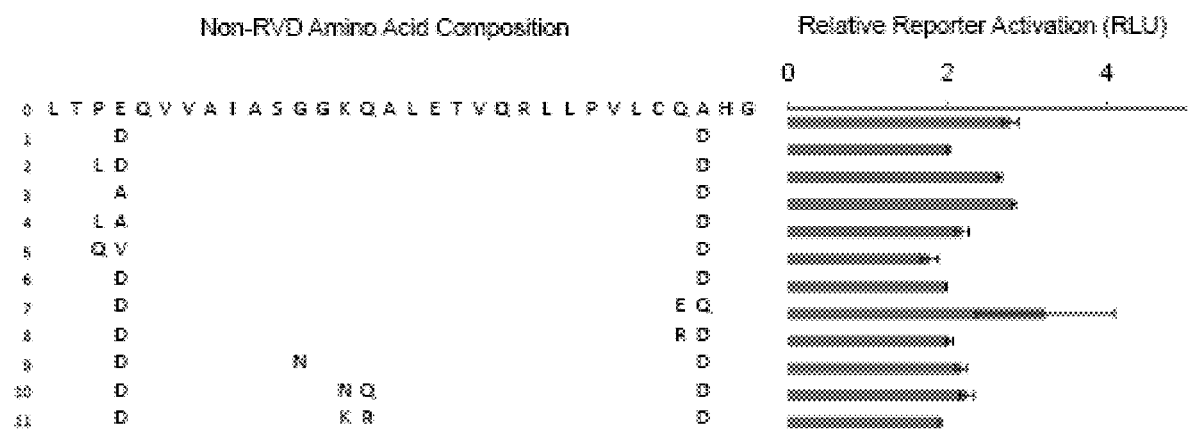
FIG. 10 shows the comparison of the effect of non-RVD amino acid on TALE activity (SEQ ID NO: 4 and variants thereof SEQ ID NOS 3, 10, 7, 33, 348, 3, 8, 237, 349, 40, and 350, respectively in order of appearance).
Figure 11:
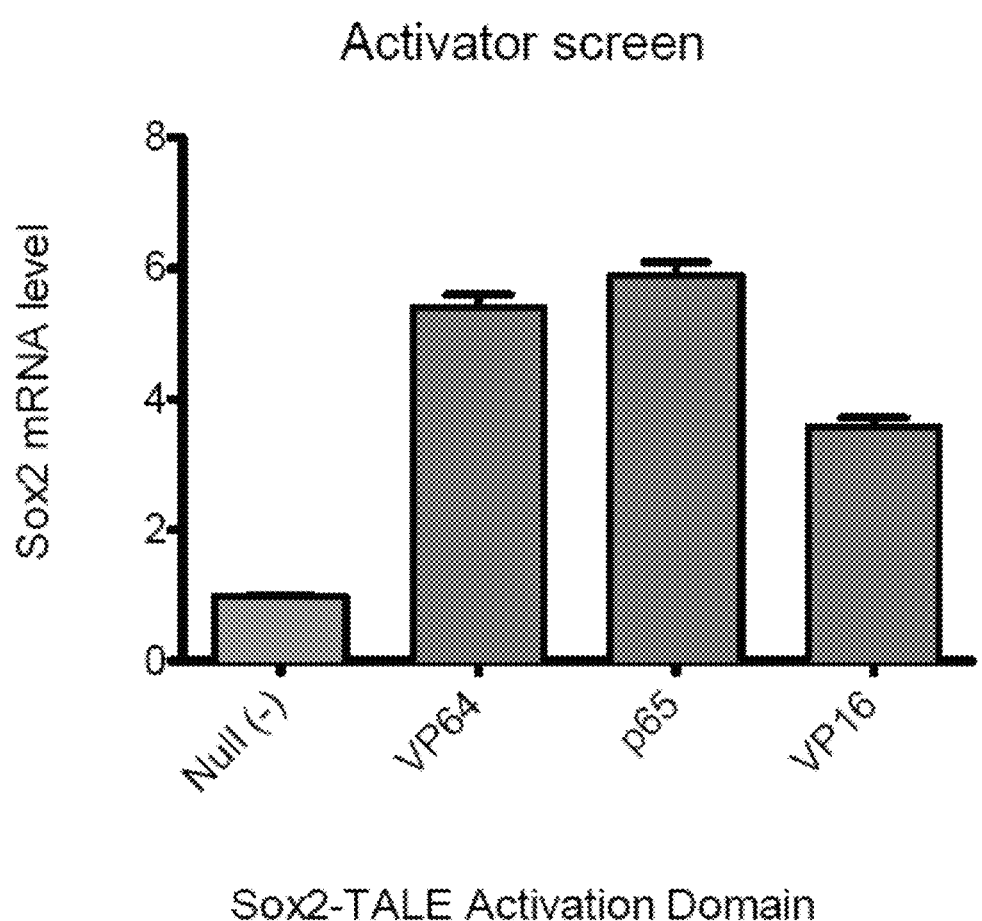
FIG. 11 shows an activator screen comparing levels of activation between VP64, p65 and VP16.
Figure 12:
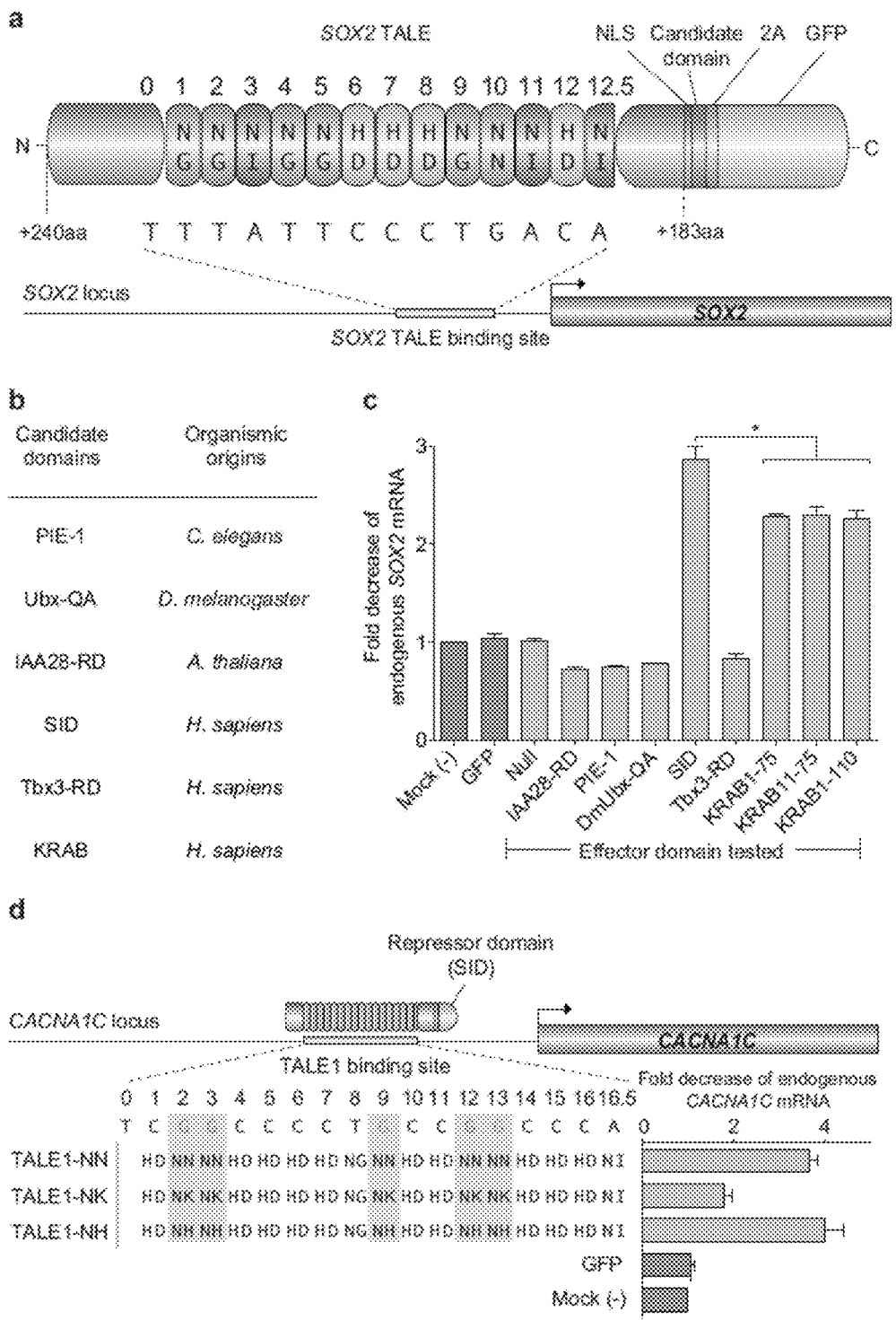
FIGS. 12A-D show the development of a TALE transcriptional repressor architecture. (a) Design of SOX2 TALE for TALE repressor screening. A TALE targeting a 14 bp sequence within the SOX2 locus of the human genome (SEQ ID NO:75) was synthesized. (b) List of all repressors screened and their host origin (left). Eight different candidate repressor domains were fused to the C-term of the SOX2 TALE. (c) The fold decrease of endogenous SOX2 mRNA is measured using qRTPCR by dividing the SOX2 mRNA levels in mock transfected cells by SOX2 mRNA levels in cells transfected with each candidate TALE repressor. (d) Transcriptional repression of endogenous CACNA1C. TALEs using NN, NK, and NH as the G-targeting RVD were constructed to target a 18 bp target site (SEQ ID NO:76) within the human CACNA1C locus. Each TALE is fused to the SID repression domain. NLS, nuclear localization signal; KRAB, Krüppel-associated box; SID, mSin interaction domain. All results are collected from three independent experiments in HEK 293FT cells. Error bars indicate s.e.m.; n=3. * p<0.05, Student's t test.
Figure 13:
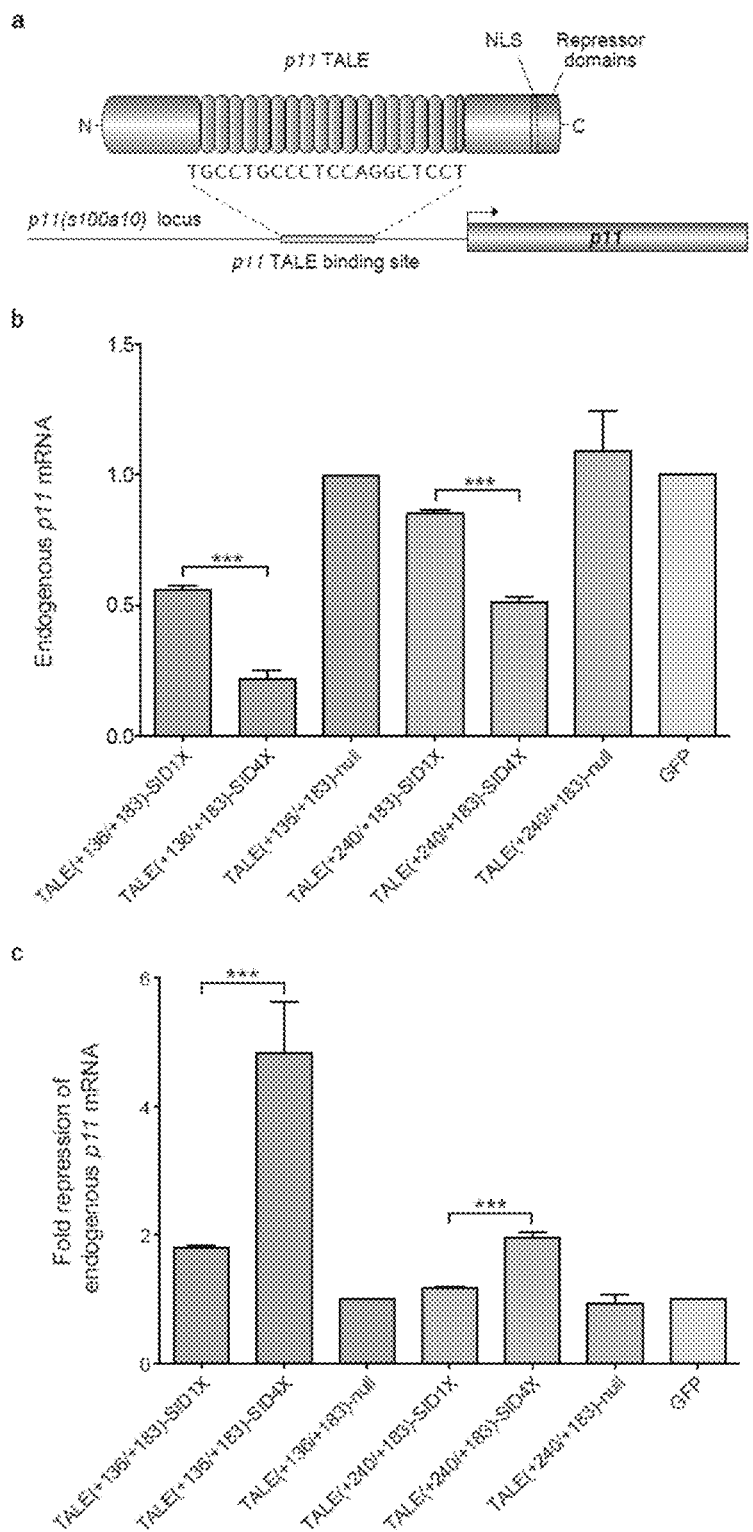
FIGS. 13A-C shows the optimization of TALE transcriptional repressor architecture using SID and SID4X. (a) Design of p11 TALE for testing of TALE repressor architecture. A TALE targeting a 20 bp sequence (p11 TALE binding site, SEQ ID NO:77) within the p11 (s100a10) locus of the mouse (Mus musculus) genome was synthesized. (b) Transcriptional repression of endogenous mouse p11 mRNA. TALEs targeting the mouse p11 locus harboring two different truncations of the wild type TALE architecture were fused to different repressor domains as indicated on the x-axis. The value in the bracket indicate the number of amino acids at the N- and C-termini of the TALE DNA binding domain flanking the DNA binding repeats, followed by the repressor domain used in the construct. The endogenous p11 mRNA levels were measured using qRT-PCR and normalized to the level in the negative control cells transfected with a GFP-encoding construct. (c) Fold of transcriptional repression of endogenous mouse p11. The fold decrease of endogenous p11 mRNA is measured using qRT-PCR through dividing the p11 mRNA levels in cells transfected with a negative control GFP construct by p11 mRNA levels in cells transfected with each candidate TALE repressors. The labeling of the constructs along the x-axis is the same as previous panel. NLS, nuclear localization signal; SID, mSin interaction domain; SID4X, an optimized four-time tandem repeats of SID domain linked by short peptide linkers. All results are collected from three independent experiments in Neuro2A cells. Error bars indicate s.e.m.; n=3. *** p<0.001, Student's t test.
Figure 14:
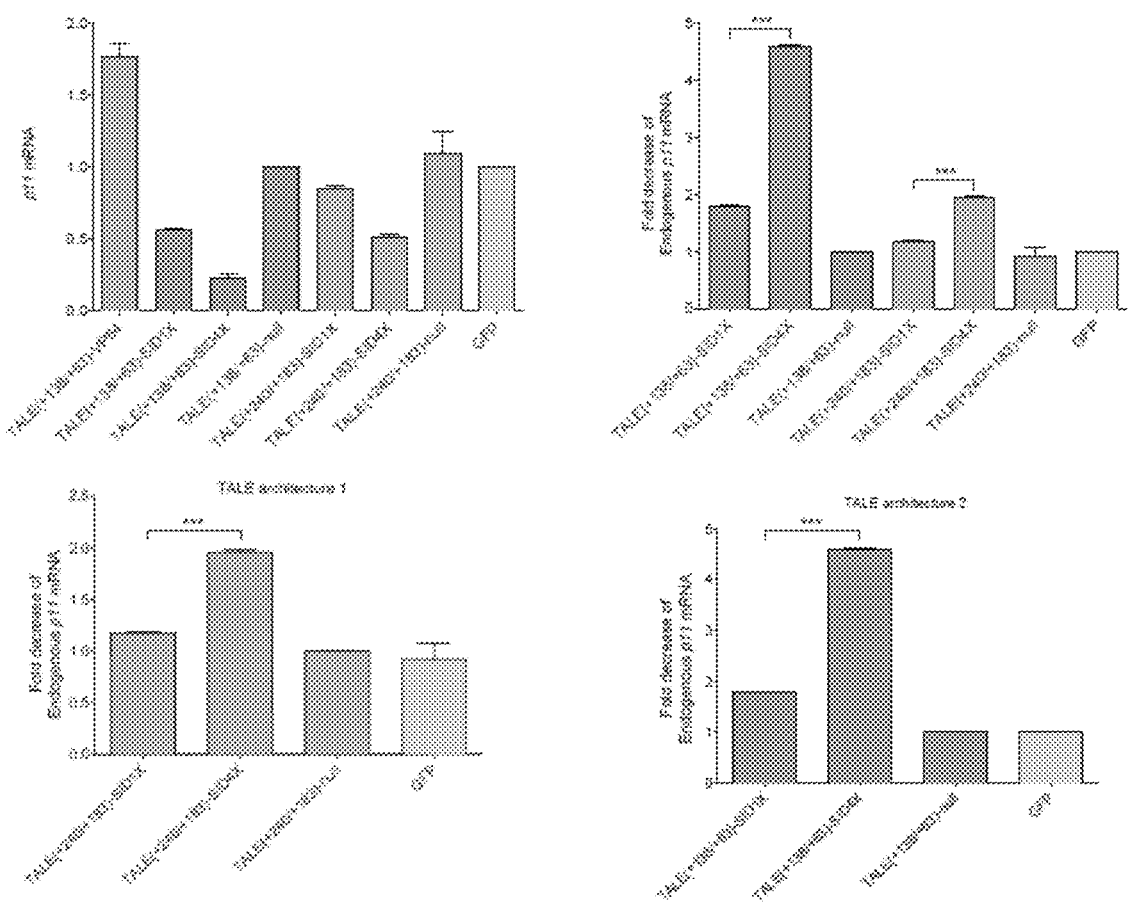
FIG. 14 shows a comparison of two different types of TALE architecture.
Figure 15A:
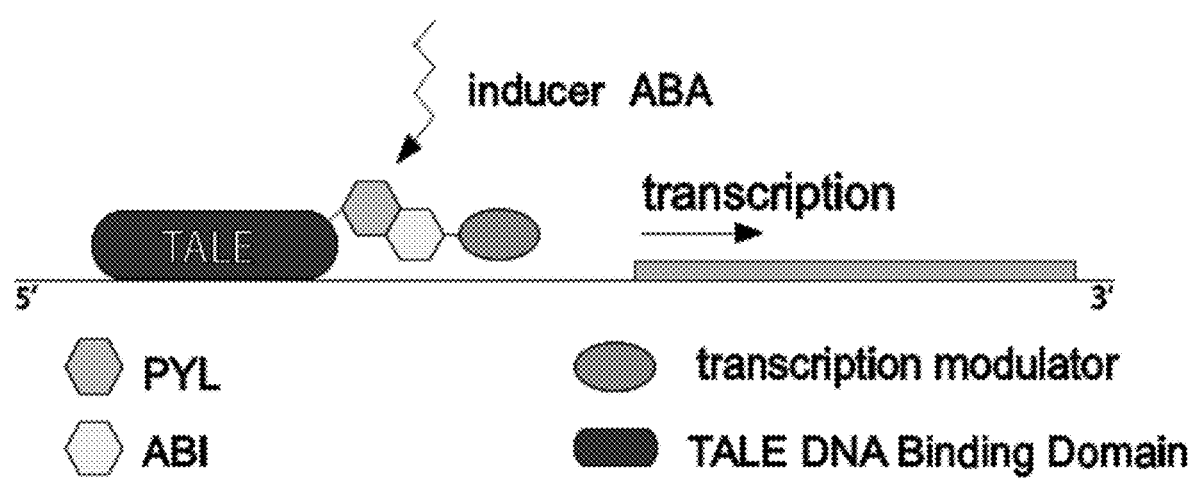
FIGS. 15A-C show a chemically inducible TALE ABA inducible system. ABI (ABA insensitive 1) and PYL (PYL protein: pyrabactin resistance (PYR)/PYR1-like (PYL)) are domains from two proteins listed below that will dimerize upon binding of plant hormone Abscisic Acid (ABA). This plant hormone is a small molecule chemical that Applicants used in Applicants' inducible TALE system. In this system, the TALE DNA-binding polypeptide is fused to the ABI domain, whereas the VP64 activation domain or SID repressor domain or any effector domains are linked to the PYL domain. Thus, upon the induction by the presence of ABA molecule, the two interacting domains, ABI and PYL, will dimerize and allow the TALE to be linked to the effector domains to perform its activity in regulating target gene expression.
Figure 15B:
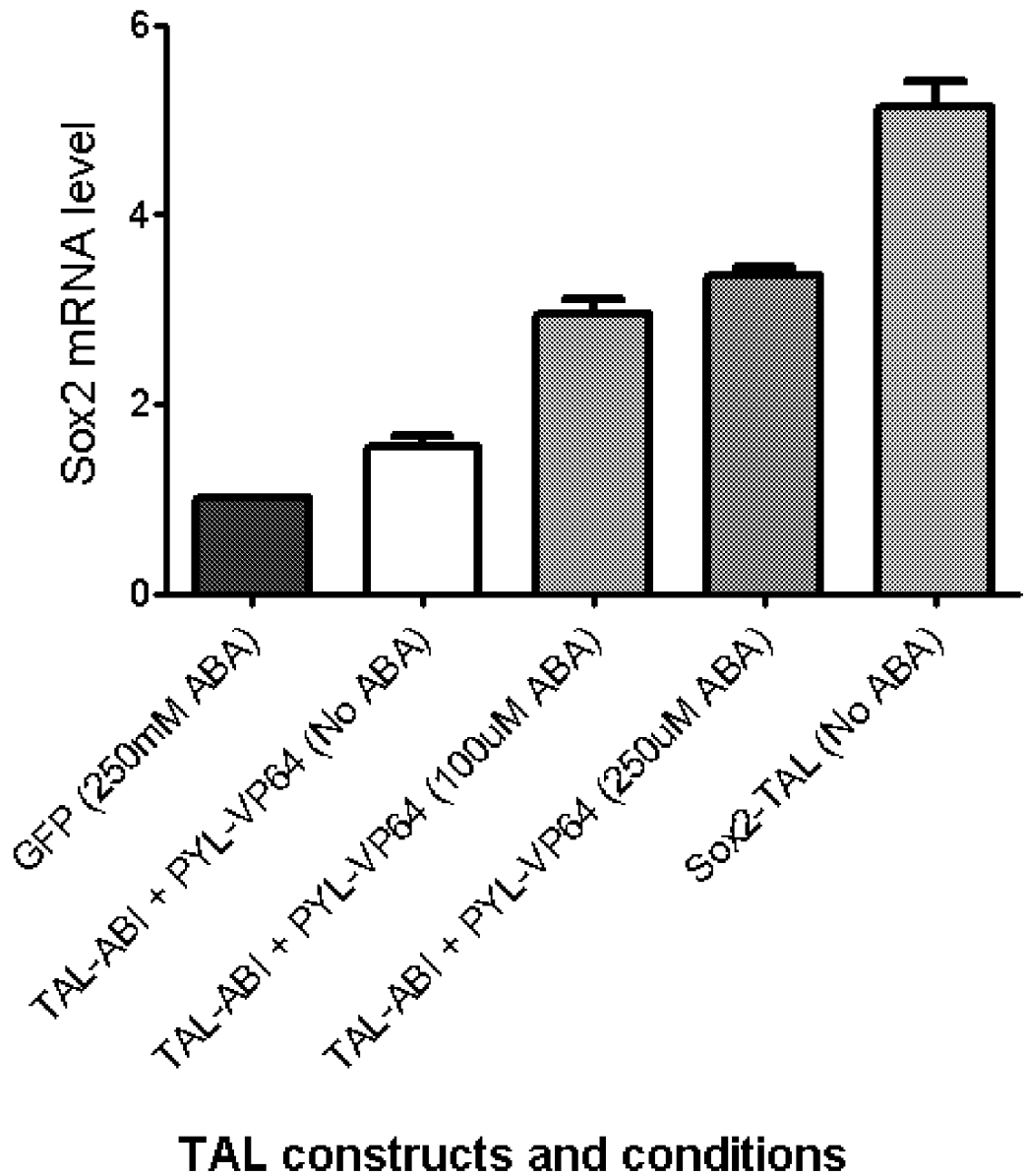
Figure 15C:
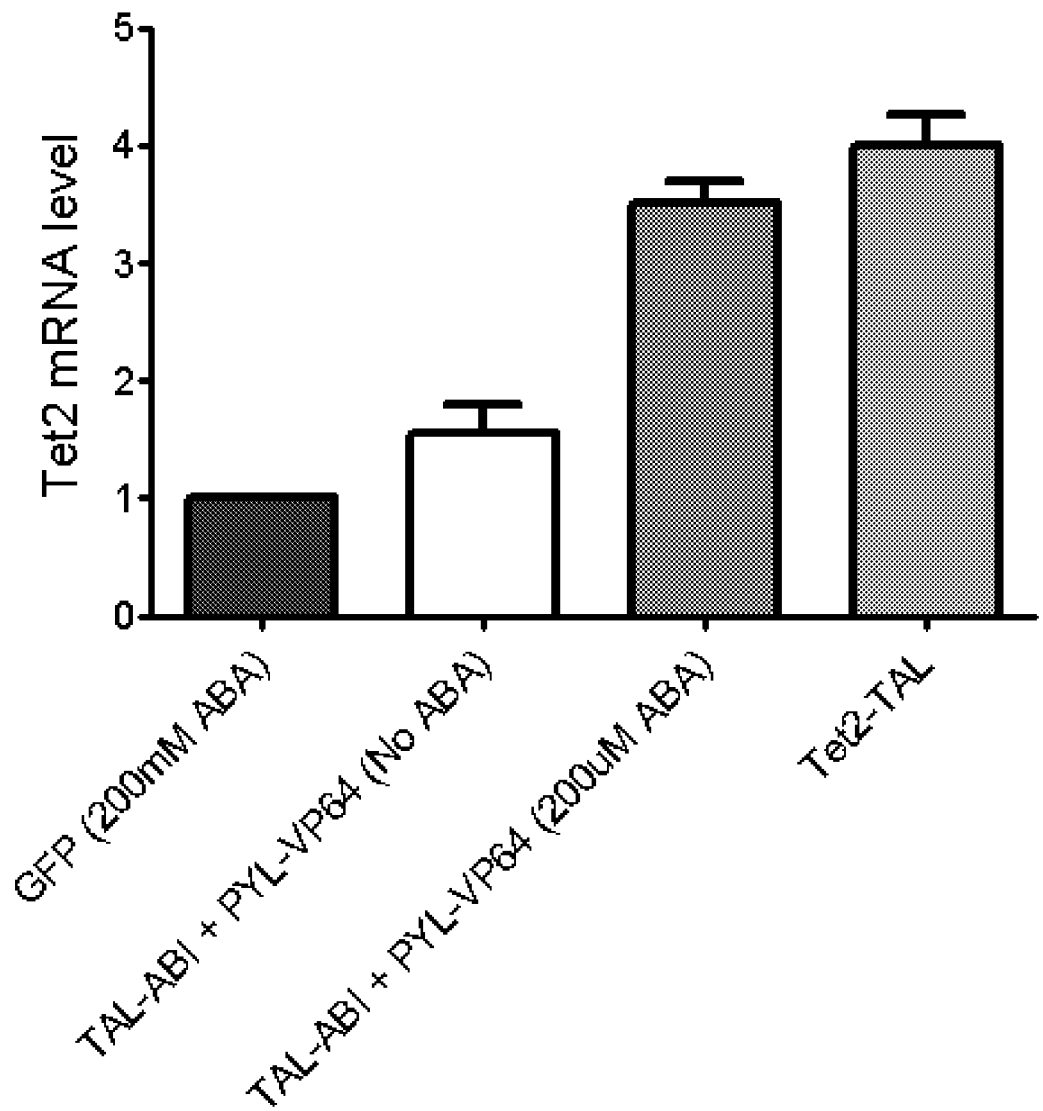
Figure 16A:
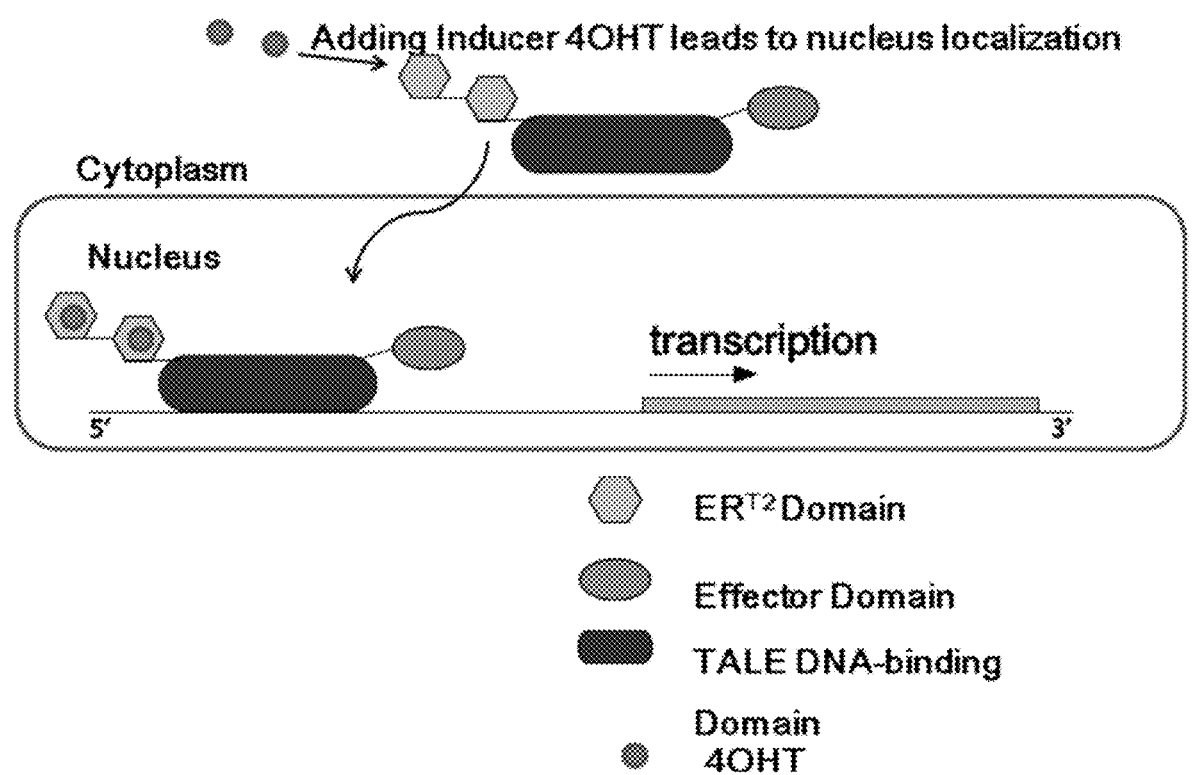
FIGS. 16A-B show a chemically inducible TALE 4OHT inducible system.
Figure 16B:
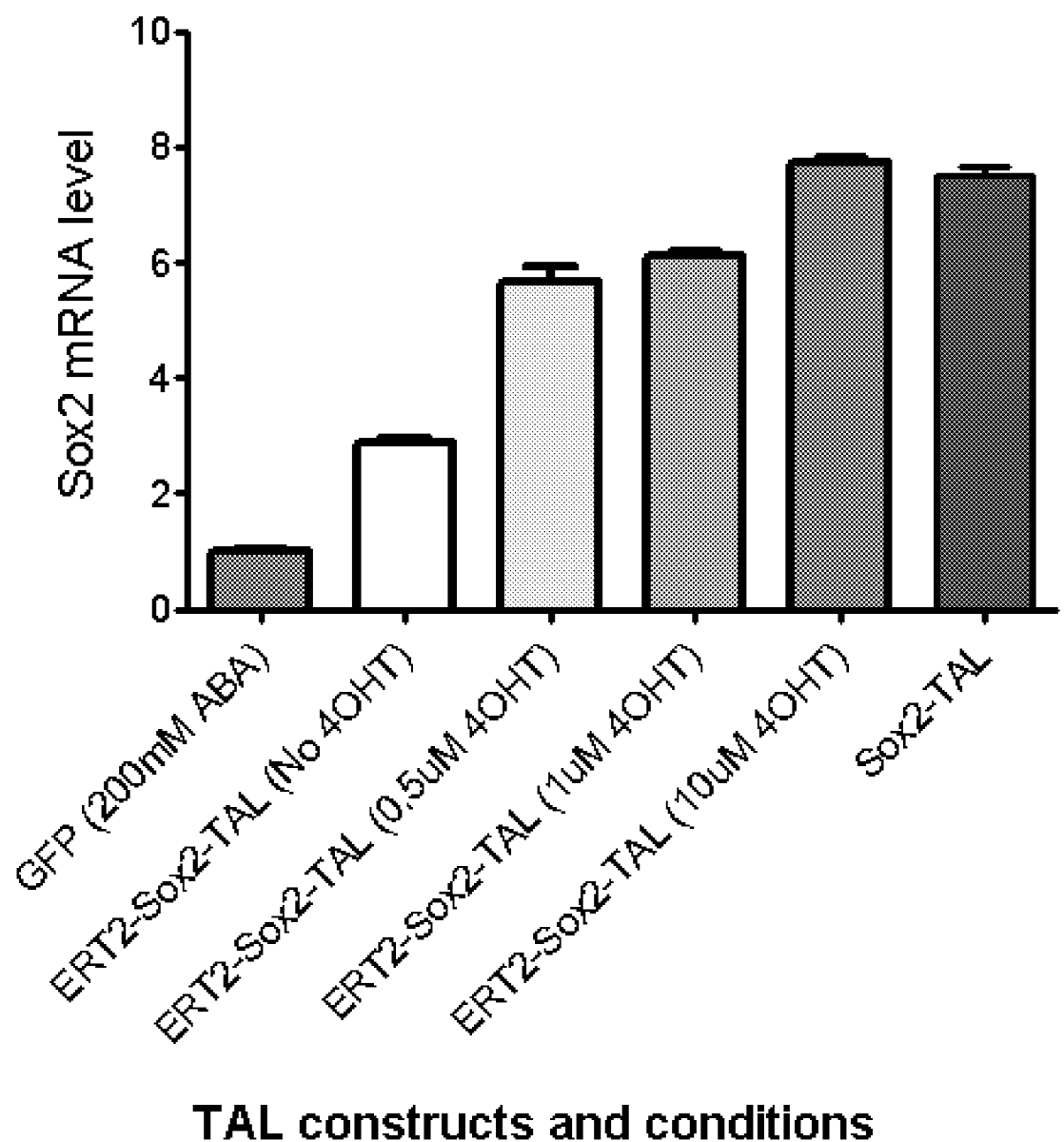

The term "nucleic acid" or "nucleic acid sequence" refers to a deoxyribonucleic or ribonucleic oligonucleotide in either single- or double-stranded form. The term encompasses nucleic acids, i.e., oligonucleotides, containing known analogues of natural nucleotides. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996.

As used herein, "recombinant" refers to a non-naturally occurring composition comprising materials from more than one origin and, in some embodiments, materials derived from more than one organism. A "recombinant construct" may be a polynucleotide synthesized or otherwise manipulated in vitro (e.g., "recombinant polynucleotide"), and the invention includes methods of using recombinant polynucleotides to produce gene products in cells or other biological systems, or to a polypeptide ("recombinant protein") encoded by a recombinant polynucleotide. "Recombinant means" encompasses methods of recombining compositions, e.g., ligation of nucleic acids having various coding regions or domains or promoter sequences from different sources into an expression cassette or vector for expression of, e.g., inducible or constitutive expression of polypeptide coding sequences in the vectors of invention.

The term "heterologous" when used with reference to a nucleic acid, indicates that the nucleic acid is in a cell or a virus where it is not normally found in nature; or, comprises two or more subsequences that are not found in the same relationship to each other as normally found in nature, or is recombinantly engineered so that its level of expression, or physical relationship to other nucleic acids or other molecules in a cell, or structure, is not normally found in nature. A similar term used in this context is "exogenous". For instance, a heterologous nucleic acid is typically recombinantly produced, having two or more sequences from unrelated genes arranged in a manner not found in nature; e.g., a human gene operably linked to a promoter sequence inserted into an adenovirus-based vector of the invention. As an example, a heterologous nucleic acid of interest may encode an immunogenic gene product, wherein the adenovirus is administered therapeutically or prophylactically as a carrier or drug-vaccine composition. Heterologous sequences may comprise various combinations of promoters and sequences, examples of which are described in detail herein.

A "therapeutic ligand" may be a substance which may bind to a receptor of a target cell with therapeutic effects.

A "therapeutic effect" may be a consequence of a medical treatment of any kind, the results of which are judged by one of skill in the field to be desirable and beneficial. The "therapeutic effect" may be a behavioral or physiologic change which occurs as a response to the medical treatment. The result may be expected, unexpected, or even an unintended consequence of the medical treatment. A "therapeutic effect" may include, for example, a reduction of symptoms in a subject suffering from infection by a pathogen.

A "target cell" may be a cell in which an alteration in its activity may induce a desired result or response.

A "ligand" may be any substance that binds to and forms a complex with a biomolecule to serve a biological purpose. As used herein, "ligand" may also refer to an "antigen" or "immunogen". As used herein "antigen" and "immunogen" are used interchangeably.

"Expression" of a gene or nucleic acid encompasses not only cellular gene expression, but also the transcription and translation of nucleic acid(s) in cloning systems and in any other context.

As used herein, a "vector" is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. The present invention comprehends recombinant vectors that may include viral vectors, bacterial vectors, protozoan vectors, DNA vectors, or recombinant constructs thereof.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents of record in the prosecution of that patent and those PCT applications, and other documents cited herein or otherwise incorporated herein by reference, may be consulted in the practice of this invention; and, all exogenous nucleic acid molecules, promoters, and vectors cited therein may be used in the practice of this invention. In this regard, mention is also made of U.S. Pat. Nos. 6,706,693; 6,716,823; 6,348,450; U.S. patent application Ser. Nos. 10/424,409; 10/052,323; 10/116,963; 10/346,021; and WO 99/08713, published Feb. 25, 1999, from PCT/US98/16739.

As used herein, the terms "drug composition" and "drug", "vaccinal composition", "vaccine", "vaccine composition", "therapeutic composition" and "therapeutic-immunologic composition" cover any composition that induces protection against an antigen or pathogen. In some embodiments, the protection may be due to an inhibition or prevention of infection by a pathogen. In other embodiments, the protection may be induced by an immune response against the antigen(s) of interest, or which efficaciously protects against the antigen; for instance, after administration or injection into the subject, elicits a protective immune response against the targeted antigen or immunogen or provides efficacious protection against the antigen or immunogen expressed from the inventive adenovirus vectors of the invention. The term "pharmaceutical composition" means any composition that is delivered to a subject. In some embodiments, the composition may be delivered to inhibit or prevent infection by a pathogen.

A "therapeutically effective amount" is an amount or concentration of the recombinant vector encoding the gene of interest, that, when administered to a subject, produces a therapeutic response or an immune response to the gene product of interest.

The term "viral vector" as used herein includes but is not limited to retroviruses, adenoviruses, adeno-associated viruses, alphaviruses, and herpes simplex virus.

The present invention enables spatiotemporal control of endogenous gene expression using a form of energy. The form of energy by include but is not limited to electromagnetic radiation, sound energy, chemical energy and thermal energy. In a preferred embodiment of the invention, the form of energy is electromagnetic radiation, preferably, light energy. Previous approaches to control expression of endogenous genes, such as transcription activators linked to DNA binding zinc finger proteins provided no mechanism for temporal or spatial control. The capacity for photoactivation of the system described herein allows the induction of gene expression modulation to begin at a precise time within a localized population of cells.

Two key molecular tools were leveraged in the design of the photoresponsive transcription activator-like (TAL) effector system. First, the DNA binding specificity of engineered TAL effectors is utilized to localize the complex to a particular region in the genome. Second, light-induced protein dimerization is used to attract an activating or repressing domain to the region specified by the TAL effector, resulting in modulation of the downstream gene.

Inducible effectors are contemplated for in vitro or in vivo application in which temporally or spatially specific gene expression control is desired. In vitro examples: temporally precise induction/suppression of developmental genes to elucidate the timing of developmental cues, spatially controlled induction of cell fate reprogramming factors for the generation of cell-type patterned tissues. In vivo examples: combined temporal and spatial control of gene expression within specific brain regions.

In a preferred embodiment of the invention, the inducible effector is a Light Inducible Transcriptional Effector (LITE). The modularity of the LITE system allows for any number of effector domains to be employed for transcriptional modulation. In a particularly advantageous embodiment, transcription activator like effector (TALE) and the activation domain VP64 are utilized in the present invention.

LITEs are designed to modulate or alter expression of individual endogenous genes in a temporally and spatially precise manner. Each LITE may comprise a two component system consisting of a customized DNA-binding transcription activator like effector (TALE) protein, a light-responsive cryptochrome heterodimer from *Arabadopsis thaliana*, and a transcriptional activation/repression domain. The TALE is designed to bind to the promoter sequence of the gene of interest. The TALE protein is fused to one half of the cryptochrome heterodimer (cryptochrome-2 or CIB1), while the remaining cryptochrome partner is fused to a transcriptional effector domain. Effector domains may be either activators, such as VP16, VP64, or p65, or repressors, such as KRAB, EnR, or SID. In a LITE's unstimulated state, the TALE-cryptochrome2 protein localizes to the promoter of the gene of interest, but is not bound to the CIB1-effector protein. Upon stimulation of a LITE with blue spectrum light, cryptochrome-2 becomes activated, undergoes a conformational change, and reveals its binding domain. CIB1, in turn, binds to cryptochrome-2 resulting in localization of the effector domain to the promoter region of the gene of interest and initiating gene overexpression or silencing.

Activator and repressor domains may selected on the basis of species, strength, mechanism, duration, size, or any number of other parameters. Preferred effector domains include, but are not limited to, a transposase domain, integrase domain, recombinase domain, resolvase domain, invertase domain, protease domain, DNA methyltransferase domain, DNA demethylase domain, histone acetylase domain, histone deacetylases domain, nuclease domain, repressor domain, activator domain, nuclear-localization signal domains, transcription-protein recruiting domain, cellular uptake activity associated domain, nucleic acid binding domain or antibody presentation domain.

Gene targeting in a LITE or in any other inducible effector may be achieved via the specificity of customized TALE DNA binding proteins. A target sequence in the promoter region of the gene of interest is selected and a TALE customized to this sequence is designed. The central portion of the TALE consists of tandem repeats 34 amino acids in length. Although the sequences of these repeats are nearly identical, the 12th and 13th amino acids (termed repeat variable diresidues) of each repeat vary, determining the nucleotide-binding specificity of each repeat. Thus, by synthesizing a construct with the appropriate ordering of TALE monomer repeats, a DNA binding protein specific to the target promoter sequence is created.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable diresidues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as ($X_{1-11}$-($X_{12}X_{13}$)-$X_{14-33}$ or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 147)
M D P I R S R T P S P A R E L L S S P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N

An exemplary amino acid sequence of a C-terminal capping region is:

(SEQ ID NO: 148)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

As described in Zhang et al., Nature Biotechnology 29:149-153 (2011), a TALE polypeptide having a nucleic acid binding domain and an effector domain may be used to target the effector domain's activity to a genomic position having a predetermined nucleic acid sequence recognized by the nucleic acid binding domain. In some embodiments of the invention described herein, TALE polypeptides are designed and used for targeting gene regulatory activity, such as transcriptional or translational modifier activity, to a regulatory, coding, and/or intergenic region, such as enhancer and/or repressor activity, that may affect transcription upstream and downstream of coding regions, and may be used to enhance or repress gene expression. For example, TALEs polypeptide may comprise effector domains having DNA-binding domains from transcription factors, effector domains from transcription factors (activators, repressors, co-activators, co-repressors), silencers, nuclear hormone receptors, and/or chromatin associated proteins and their modifiers (e.g., methylases, kinases, phosphatases, acetylases and deacetylases). In a preferred embodiment, the TALE polypeptide may comprise a nuclease domain. In a more preferred embodiment the nuclease domain is a non-specific FokI endonucleases catalytic domain.

In a further embodiment, useful domains for regulating gene expression may also be obtained from the gene products of oncogenes. In yet further advantageous embodiments of the invention, effector domains having integrase or transposase activity may be used to promote integration of exogenous nucleic acid sequence into specific nucleic acid sequence regions, eliminate (knock-out) specific endogenous nucleic acid sequence, and/or modify epigenetic signals and consequent gene regulation, such as by promoting DNA methyltransferase, DNA demethylase, histone acetylase and histone deacetylase activity. In other embodiments, effector domains having nuclease activity may be used to alter genome structure by nicking or digesting target sequences to which the polypeptides of the invention specifically bind, and may allow introduction of exogenous genes at those sites. In still further embodiments, effector domains having invertase activity may be used to alter genome structure by swapping the orientation of a DNA fragment.

In particularly advantageous embodiments, the polypeptides used in the methods of the invention may be used to target transcriptional activity. As used herein, the term "transcription factor" refers to a protein or polypeptide that binds specific DNA sequences associated with a genomic locus or gene of interest to control transcription. Transcription factors may promote (as an activator) or block (as a repressor) the recruitment of RNA polymerase to a gene of interest. Transcription factors may perform their function alone or as a part of a larger protein complex. Mechanisms of gene regulation used by transcription factors include but are not limited to a) stabilization or destabilization of RNA polymerase binding, b) acetylation or deacetylation of histone proteins and c) recruitment of co-activator or co-repressor proteins. Furthermore, transcription factors play roles in biological activities that include but are not limited to basal transcription, enhancement of transcription, development, response to intercellular signaling, response to environmental cues, cell-cycle control and pathogenesis. With regards to information on transcriptional factors, mention is made of Latchman and DS (1997) Int. J. Biochem. Cell Biol. 29 (12): 1305-12; Lee TI, Young RA (2000) Annu. Rev. Genet. 34: 77-137 and Mitchell P J, Tjian R (1989) Science 245 (4916): 371-8, herein incorporated by reference in their entirety.

Light responsiveness of a LITE is achieved via the activation and binding of cryptochrome-2 and CIB1. As mentioned above, blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a LITE system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a LITE stimulated region, allowing for greater precision than vector delivery alone may offer.

The modularity of the LITE system allows for any number of effector domains to be employed for transcriptional modulation. Thus, activator and repressor domains may be selected on the basis of species, strength, mechanism, duration, size, or any number of other parameters.

Applicants next present two prototypical manifestations of the LITE system. The first example is a LITE designed to activate transcription of the mouse gene NEUROG2. The sequence TGAATGATGATAATACGA (SEQ ID NO:149), located in the upstream promoter region of mouse NEUROG2, was selected as the target and a TALE was designed and synthesized to match this sequence. The TALE sequence was linked to the sequence for cryptochrome-2 via a nuclear localization signal (amino acids: SPKKKRKVEAS; SEQ ID NO: 150) to facilitate transport of the protein from the cytosol to the nuclear space. A second vector was synthesized comprising the CIB1 domain linked to the transcriptional activator domain VP64 using the same nuclear localization signal. This second vector, also a GFP sequence, is separated from the CIB1-VP64 fusion sequence by a 2A translational skip signal. Expression of each construct was driven by a ubiquitous, constitutive promoter (CMV or EF1-α). Mouse neuroblastoma cells from the Neuro 2A cell line were co-transfected with the two vectors. After incubation to allow for vector expression, samples were stimulated by periodic pulsed blue light from an array of 488 nm LEDs. Unstimulated co-transfected samples and samples transfected only with the fluorescent reporter YFP were used as controls. At the end of each experiment, mRNA was purified from the samples analyzed via qPCR.

Truncated versions of cryptochrome-2 and CIB1 were cloned and tested in combination with the full-length versions of cryptochrome-2 and CIB1 in order to determine the effectiveness of each heterodimer pair. The combination of the CRY2 PHR domain, consisting of the conserved photoresponsive region of the cryptochrome-2 protein, and the full-length version of CIB1 resulted in the highest upregulation of Neurog2 mRNA levels (~22 fold over YFP samples and ~7 fold over unstimulated co-transfected samples). The combination of full-length cryptochrome-2 (CRY2) with full-length CIB1 resulted in a lower absolute activation level (~4.6 fold over YFP), but also a lower baseline activation (~1.6 fold over YFP for unstimulated co-transfected samples). These cryptochrome protein pairings may be selected for particular uses depending on absolute level of induction required and the necessity to minimize baseline "leakiness" of the LITE system.

Speed of activation and reversibility are critical design parameters for the LITE system. The invention contemplates energy sources such as electromagnetic radiation, sound energy or thermal energy.

The cells of the present invention are preferably a eukaryotic cell, advantageously an animal cell, more advantageously a mammalian cell.

The present invention also contemplates a multiplex genome engineering using CRISPR/Cas systems. Functional elucidation of causal genetic variants and elements requires precise genome editing technologies. The type II prokaryotic CRISPR (clustered regularly interspaced short palindromic repeats) adaptive immune system has been shown to facilitate RNA-guided site-specific DNA cleavage. Applicants engineered two different type II CRISPR systems and demonstrate that Cas9 nucleases can be directed by short RNAs to induce precise cleavage at endogenous genomic loci in human and mouse cells. Cas9 can also be converted into a nicking enzyme to facilitate homology-directed repair with minimal mutagenic activity. Finally, multiple guide sequences can be encoded into a single CRISPR array to enable simultaneous editing of several sites within the mammalian genome, demonstrating easy programmability and wide applicability of the CRISPR technology.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, all or a portion of the tracr sequence may also form part of a CRISPR complex, such as by hybridization to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000"Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 151); the NLS from nucleoplasmin (e.g. the nucleoplasmin bipartite NLS with the sequence KRPAATKKAGQAKKKK; SEQ ID NO: 152); the c-myc NLS having the amino acid sequence PAAKRVKLD (SEQ ID NO: 153) or RQRRNELKRSP (SEQ ID NO: 154); the hRNPA1 M9 NLS having the sequence NQSSNFGPMKGGNFGGRSSGPYGGGGQYFAK-PRNQGGY (SEQ ID NO: 155); the sequence RMRIZFKNKGKDTAELRRRRVEVSVELRKAKKD-EQILKRRNV (SEQ ID NO: 156) of the IBB domain from importin-alpha; the sequences VSRKRPRP (SEQ ID NO: 157) and PPKKARED (SEQ ID NO: 158) of the myoma T protein; the sequence PQPKKKPL (SEQ ID NO: 159) of human p53; the sequence SALIKKKKKMAP (SEQ ID NO: 160) of mouse c-abl IV; the sequences DRLRR (SEQ ID NO: 161) and PKQKKRK (SEQ ID NO: 162) of the influenza virus NS1; the sequence RKLKKKIKKL (SEQ ID NO: 163) of the Hepatitis virus delta antigen; the sequence REKKKFLKRR (SEQ ID NO: 164) of the mouse Mx1 protein; the sequence KRKGDEVDGVDEVAKKKSKK (SEQ ID NO: 165) of the human poly(ADP-ribose) polymerase; and the sequence RKCLQAGMNLEARKTKK (SEQ ID NO: 166) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

The present invention also encompasses nucleic acid encoding the polypeptides of the present invention. The nucleic acid may comprise a promoter, advantageously human Synapsin I promoter (hSyn). In a particularly advantageous embodiment, the nucleic acid may be packaged into an adeno associated viral vector (AAV).

Also contemplated by the present invention are recombinant vectors and recombinant adenoviruses that may comprise subviral particles from more than one adenovirus serotype. For example, it is known that adenovirus vectors may display an altered tropism for specific tissues or cell types (Havenga, M. J. E. et al., 2002), and therefore, mixing and matching of different adenoviral capsids, i.e., fiber, or penton proteins from various adenoviral serotypes may be advantageous. Modification of the adenoviral capsids, including fiber and penton may result in an adenoviral vector with a tropism that is different from the unmodified adenovirus. Adenovirus vectors that are modified and optimized in their ability to infect target cells may allow for a significant reduction in the therapeutic or prophylactic dose, resulting in reduced local and disseminated toxicity.

Viral vector gene delivery systems are commonly used in gene transfer and gene therapy applications. Different viral vector systems have their own unique advantages and disadvantages. Viral vectors that may be used to express the pathogen-derived ligand of the present invention include but are not limited to adenoviral vectors, adeno-associated viral vectors, alphavirus vectors, herpes simplex viral vectors, and retroviral vectors, described in more detail below.

Additional general features of adenoviruses are such that the biology of the adenovirus is characterized in detail; the adenovirus is not associated with severe human pathology; the adenovirus is extremely efficient in introducing its DNA into the host cell; the adenovirus may infect a wide variety of cells and has a broad host range; the adenovirus may be produced in large quantities with relative ease; and the adenovirus may be rendered replication defective and/or non-replicating by deletions in the early region 1 ("E1") of the viral genome. Adenovirus is a non-enveloped DNA virus. The genome of adenovirus is a linear double-stranded DNA molecule of approximately 36,000 base pairs ("bp") with a 55-kDa terminal protein covalently bound to the 5'-terminus of each strand. The adenovirus DNA contains identical inverted terminal repeats ("ITRs") of about 100 bp, with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single stranded and may form a "panhandle" intermediate, which allows replication initiation and generation of a daughter duplex molecule. Alternatively, replication may proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase, only the early gene products, encoded by regions E1, E2, E3 and E4, are expressed, which carry out a number of functions that prepare the cell for synthesis of viral structural proteins (Berk, A. J., 1986). During the late phase, the late viral gene products are expressed in addition to the early gene products and host cell DNA and protein synthesis are shut off. Consequently, the cell becomes dedicated to the production of viral DNA and of viral structural proteins (Tooze, J., 1981).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone may induce unlimited proliferation (immortalization), but does not result in complete transformation. However, expression of E1A, in most cases, results in induction of programmed cell death (apoptosis), and only occasionally is immortalization obtained (Jochemsen et al., 1987). Co-expression of the E1B gene is required to prevent induction of apoptosis and for complete morphological transformation to occur. In established immortal cell lines, high-level expression of E1A may cause complete transformation in the absence of E1B (Roberts, B. E. et al., 1985).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype; Telling et al., 1994). The deg and cyt phenotypes are suppressed when in addition the E1A gene is mutated, indicating that these phenotypes are a function of E1A (White, E. et al., 1988). Furthermore, the E1B 21 kDa protein slows down the rate by which E1A switches on the other viral genes. It is not yet known by which mechanisms EIB 21 kD quenches these E1A dependent functions.

In contrast to, for example, retroviruses, adenoviruses do not efficiently integrate into the host cell's genome, are able to infect non-dividing cells, and are able to efficiently transfer recombinant genes in vivo (Brody et al., 1994). These features make adenoviruses attractive candidates for in vivo gene transfer of, for example, an antigen or immunogen of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective and/or non-replicating adenovirus. As long as one of the deletions renders the adenovirus replication defective or non-replicating, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective and/or non-replicating and/or attenuated. More preferably, all of the deletions are deletions that would render the adenovirus replication-defective and/or non-replicating and/or attenuated. However, the invention also encompasses adenovirus and adenovirus vectors that are replication competent and/or wild-type, i.e. comprises all of the adenoviral genes necessary for infection and replication in a subject.

Embodiments of the invention employing adenovirus recombinants may include E1-defective or deleted, or E3-defective or deleted, or E4-defective or deleted or adenovirus vectors comprising deletions of E1 and E3, or E1 and E4, or E3 and E4, or E1, E3, and E4 deleted, or the "gutless" adenovirus vector in which all viral genes are deleted. The adenovirus vectors may comprise mutations in E1, E3, or E4 genes, or deletions in these or all adenoviral genes. The E1 mutation raises the safety margin of the vector because E1-defective adenovirus mutants are said to be replication-defective and/or non-replicating in non-permissive cells, and are, at the very least, highly attenuated. The E3 mutation enhances the immunogenicity of the antigen by disrupting the mechanism whereby adenovirus down-regulates WIC class I molecules. The E4 mutation reduces the immunogenicity of the adenovirus vector by suppressing the late gene expression, thus may allow repeated re-vaccination utilizing the same vector. The present invention comprehends adenovirus vectors of any serotype or serogroup that are deleted or mutated in E1, or E3, or E4, or E1 and E3, or E1 and E4. Deletion or mutation of these adenoviral genes result in impaired or substantially complete loss of activity of these proteins.

The "gutless" adenovirus vector is another type of vector in the adenovirus vector family. Its replication requires a helper virus and a special human 293 cell line expressing both E1a and Cre, a condition that does not exist in a natural environment; the vector is deprived of all viral genes, thus the vector as a vaccine carrier is non-immunogenic and may be inoculated multiple times for re-vaccination. The "gutless" adenovirus vector also contains 36 kb space for accommodating antigen or immunogen(s) of interest, thus allowing co-delivery of a large number of antigen or immunogens into cells.

Adeno-associated virus (AAV) is a single-stranded DNA parvovirus which is endogenous to the human population. Although capable of productive infection in cells from a variety of species, AAV is a dependovirus, requiring helper functions from either adenovirus or herpes virus for its own replication. In the absence of helper functions from either of these helper viruses, AAV will infect cells, uncoat in the nucleus, and integrate its genome into the host chromosome, but will not replicate or produce new viral particles.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and vital gene expression. The right side of the vital genome contains the cap genes that encode the structural capsid proteins VP1, VP2 and VP3. The proteins encoded by both the rep and cap genes function in trans during productive AAV replication.

AAV is considered an ideal candidate for use as a transducing vector, and it has been used in this manner. Such AAV transducing vectors comprise sufficient cis-acting functions to replicate in the presence of adenovirus or herpes virus helper functions provided in trans. Recombinant AAV (rAAV) have been constructed in a number of laboratories and have been used to carry exogenous genes into cells of a variety of lineages. In these vectors, the AAV cap and/or rep genes are deleted from the viral genome and replaced with a DNA segment of choice. Current vectors may accommodate up to 4300 bases of inserted DNA.

To produce rAAV, plasmids containing the desired vital construct are transfected into adenovirus-infected cells. In addition, a second helper plasmid is cotransfected into these cells to provide the AAV rep and cap genes which are obligatory for replication and packaging of the recombinant viral construct. Under these conditions, the rep and cap proteins of AAV act in trans to stimulate replication and packaging of the rAAV construct. Three days after transfection, rAAV is harvested from the cells along with adenovirus. The contaminating adenovirus is then inactivated by heat treatment.

Herpes Simplex Virus 1 (HSV-1) is an enveloped, double-stranded DNA virus with a genome of 153 kb encoding more than 80 genes. Its wide host range is due to the binding of viral envelope glycoproteins to the extracellular heparin sulphate molecules found in cell membranes (WuDunn & Spear, 1989). Internalization of the virus then requires envelope glycoprotein gD and fibroblast growth factor receptor (Kaner, 1990). HSV is able to infect cells lytically or may establish latency. HSV vectors have been used to infect a wide variety of cell types (Lowenstein, 1994; Huard, 1995; Miyanohara, 1992; Liu, 1996; Goya, 1998).

There are two types of HSV vectors, called the recombinant HSV vectors and the amplicon vectors. Recombinant HSV vectors are generated by the insertion of transcription units directly into the HSV genome, through homologous recombination events. The amplicon vectors are based on plasmids bearing the transcription unit of choice, an origin of replication, and a packaging signal.

HSV vectors have the obvious advantages of a large capacity for insertion of foreign genes, the capacity to establish latency in neurons, a wide host range, and the ability to confer transgene expression to the CNS for up to 18 months (Carpenter & Stevens, 1996).

Retroviruses are enveloped single-stranded RNA viruses, which have been widely used in gene transfer protocols. Retroviruses have a diploid genome of about 7-10 kb, composed of four gene regions termed gag, pro, pol and env. These gene regions encode for structural capsid proteins, viral protease, integrase and viral reverse transcriptase, and envelope glycoproteins, respectively. The genome also has a packaging signal and cis-acting sequences, termed long-terminal repeats (LTRs), at each end, which have a role in transcriptional control and integration.

The viral vectors of the present invention are useful for the delivery of nucleic acids expressing antigens or immunogens to cells both in vitro and in vivo. In particular, the inventive vectors may be advantageously employed to deliver or transfer nucleic acids to cells, more preferably mammalian cells. Nucleic acids of interest include nucleic acids encoding peptides and proteins, preferably therapeutic (e.g., for medical or veterinary uses) or immunogenic (e.g., for vaccines) peptides or proteins.

Preferably, the codons encoding the antigen or immunogen of interest are "optimized" codons, i.e., the codons are those that appear frequently in, e.g., highly expressed genes in the subject's species, instead of those codons that are frequently used by, for example, an influenza virus. Such codon usage provides for efficient expression of the antigen or immunogen in animal cells. In other embodiments, for example, when the antigen or immunogen of interest is expressed in bacteria, yeast or another expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al., 1998; McEwan et al. 1998).

As a further alternative, the viral vectors may be used to infect a cell in culture to express a desired gene product, e.g., to produce a protein or peptide of interest. Preferably, the protein or peptide is secreted into the medium and may be purified therefrom using routine techniques known in the art. Signal peptide sequences that direct extracellular secretion of proteins are known in the art and nucleotide sequences encoding the same may be operably linked to the nucleotide sequence encoding the peptide or protein of interest by routine techniques known in the art. Alternatively, the cells may be lysed and the expressed recombinant protein may be purified from the cell lysate. Preferably, the cell is an animal cell, more preferably a mammalian cell. Also preferred are cells that are competent for transduction by particular viral vectors of interest. Such cells include PER.C6 cells, 911 cells, and HEK293 cells.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

The present invention also relates to cell lines or transgenic animals which are capable of expressing or overexpressing LITEs or at least one agent useful in the present invention. Preferably the cell line or animal expresses or overexpresses one or more LITEs.

The transgenic animal is typically a vertebrate, more preferably a rodent, such as a rat or a mouse, but also includes other mammals such as human, goat, pig or cow etc.

Such transgenic animals are useful as animal models of disease and in screening assays for new useful compounds. By specifically expressing one or more polypeptides, as defined above, the effect of such polypeptides on the development of disease may be studied. Furthermore, therapies including gene therapy and various drugs may be tested on transgenic animals. Methods for the production of transgenic animals are known in the art. For example, there are several possible routes for the introduction of genes into embryos. These include (i) direct transfection or retroviral infection of embryonic stem cells followed by introduction of these cells into an embryo at the blastocyst stage of development; (ii) retroviral infection of early embryos; and (iii) direct microinjection of DNA into zygotes or early embryo cells. The gene and/or transgene may also include genetic regulatory elements and/or structural elements known in the art. A type of target cell for transgene introduction is the embryonic stem cell (ES). ES cells may be obtained from pre-implantation embryos cultured in vitro and fused with embryos (Evans et al., 1981, Nature 292: 154-156; Bradley et al., 1984, Nature 309:255-258; Gossler et al., 1986, Proc. Natl. Acad. Sci. USA 83:9065-9069; and Robertson et al., 1986 Nature 322:445-448). Transgenes may be efficiently introduced into the ES cells by a variety of standard techniques such as DNA transfection, microinjection, or by retrovirus-mediated transduction. The resultant transformed ES cells may thereafter be combined with blastocysts from a non-human animal. The introduced ES cells thereafter colonize the embryo and contribute to the germ line of the resulting chimeric animal (Jaenisch, 1988, Science 240: 1468-1474).

LITEs may also offer valuable temporal precision in vivo. LITEs may be used to alter gene expression during a particular stage of development, for example, by repressing a particular apoptosis gene only during a particular stage of C. elegans growth. LITEs may be used to time a genetic cue to a particular experimental window. For example, genes implicated in learning may be overexpressed or repressed only during the learning stimulus in a precise region of the intact rodent or primate brain. Further, LITEs may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the LITE system, they highlight some of the areas in which LITEs may be a powerful technology.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient may be administered in a wide variety of therapeutic dosage forms in conventional vehicles for administration. For example, the compounds may be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention may be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents may be administered concurrently, or they each may be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the one patient; and the particular compound thereof employed. A physician of ordinary skill may readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

EXAMPLES

Example 1

The ability to directly modulate gene expression from the endogenous mammalian genome is critical for elucidating normal gene function and disease mechanism. Advances that further refine the spatial and temporal control of gene expression within cell populations have the potential to expand the utility of gene modulation. Applicants previously developed transcription activator-like effectors (TALEs) from Xanthamonas oryze to enable the rapid design and construction of site-specific DNA binding proteins. Applicants developed a set of molecular tools for enabling light-regulated gene expression in the endogenous mammalian genome. The system consists of engineered artificial transcription factors linked to light-sensitive dimerizing protein domains from Arabidopsis thaliana. The system responds to light in the range of 450 nm-500 nm and is capable of inducing a significant increase in the expression of pluripotency factors after stimulation with light at an intensity of 6.2 mW/cm$^2$ in mammalian cells. Applicants are developing tools for the targeting of a wide range of genes. Applicants believe that a toolbox for the light-mediated control of gene expression would complement the existing optogenetic methods and may in the future help elucidate the timing-, cell type- and concentration dependent role of specific genes in the brain.

The ability to directly modulate gene expression from the endogenous mammalian genome is critical for elucidating normal gene function and disease mechanisms. Applicants present the development of a set of molecular tools for enabling light-regulated gene expression in the endogenous mammalian genome. This system consists of a transcription activator like effector (TALE) and the activation domain VP64 linked to the light-sensitive dimerizing protein domains cryptochrome 2 (CRY2) and CIB1 from Arabidopsis thaliana. Applicants show that blue-light stimulation of HEK293FT and Neuro-2a cells transfected with these LITE constructs designed to target the promoter region of KLF4 and Neurog2 results in a significant increase in target expression, demonstrating the functionality of TALE-based optical gene expression modulation technology.

FIG. 2 shows transcription activator like effectors (TALEs). TALEs consist of 34 aa repeats (SEQ ID NO:1) at the core of their sequence. Each repeat corresponds to a base in the target DNA that is bound by the TALE. Repeats differ only by 2 variable amino acids at positions 12 and 13. The code of this correspondence has been elucidated (Boch, J et al; Science, 2009 and Moscou, M et al., Science, 2009) and is shown in this figure. One example of a binding site is shown as SEQ ID NO: 2. Applicants developed a method for the synthesis of designer TALEs incorporating this code and capable of binding a sequence of choice within the genome (Zhang, F et al., Nature Biotechnology, 2011).

FIG. 3 depicts a design of a LITE: TALE/Cryptochrome transcriptional activation. Each LITE is a two-component system which may comprise a TALE fused to CRY2 and the cryptochrome binding partner CIB1 fused to VP64, a transcription activator. In the inactive state, the TALE localizes its fused CRY2 domain to the promoter region of the gene of interest. At this point, CIB1 is unable to bind CRY2, leaving the CIB1-VP64 unbound in the nuclear space. Upon stimulation with 488 nm (blue) light, CRY2 undergoes a conformational change, revealing its CIB1 binding site (Liu, H et al., Science, 2008). Rapid binding of CIB1 results in recruitment of the fused VP64 domain, which induces transcription of the target gene.

Example 2

Normal gene expression is a dynamic process with carefully orchestrated temporal and spatial components, the precision of which are necessary for normal development, homeostasis, and advancement of the organism. In turn, the dysregulation of required gene expression patterns, either by increased, decreased, or altered function of a gene or set of genes, has been linked to a wide array of pathologies. Technologies capable of modulating gene expression in a spatiotemporally precise fashion will enable the elucidation of the genetic cues responsible for normal biological processes and disease mechanisms. To address this technological need, Applicants developed light-inducible transcriptional effectors (LITEs), which provide light-mediated control of endogenous gene expression.

Inducible gene expression systems have typically been designed to allow for chemically inducible activation of an inserted open reading frame or shRNA sequence, resulting in gene overexpression or repression, respectively. Disadvantages of using open reading frames for overexpression include loss of splice variation and limitation of gene size. Gene repression via RNA interference, despite its transformative power in human biology, may be hindered by complicated off-target effects. Certain inducible systems including estrogen, ecdysone, and FKBP12/FRAP based systems are known to activate off-target endogenous genes. The potentially deleterious effects of long-term antibiotic treatment may complicate the use of tetracycline transactivator (TET) based systems. In vivo, the temporal precision of these chemically inducible systems is dependent upon the kinetics of inducing agent uptake and elimination. Further, because inducing agents are generally delivered systemically, the spatial precision of such systems is bounded by the precision of exogenous vector delivery.

In response to these limitations, LITEs are designed to modulate expression of individual endogenous genes in a temporally and spatially precise manner. Each LITE is a two component system consisting of a customized DNA-binding transcription activator like effector (TALE) protein, a light-responsive cryptochrome heterodimer from *Arabadopsis thaliana*, and a transcriptional activation/repression domain. The TALE is designed to bind to the promoter sequence of the gene of interest. The TALE protein is fused to one half of the cryptochrome heterodimer (cryptochrome-2 or CIB1), while the remaining cryptochrome partner is fused to a transcriptional effector domain. Effector domains may be either activators, such as VP16, VP64, or p65, or repressors, such as KRAB, EnR, or SID. In a LITE's unstimulated state, the TALE-cryptochrome2 protein localizes to the promoter of the gene of interest, but is not bound to the CIB1-effector protein. Upon stimulation of a LITE with blue spectrum light, cryptochrome-2 becomes activated, undergoes a conformational change, and reveals its binding domain. CIB1, in turn, binds to cryptochrome-2 resulting in localization of the effector domain to the promoter region of the gene of interest and initiating gene overexpression or silencing.

Gene targeting in a LITE is achieved via the specificity of customized TALE DNA binding proteins. A target sequence in the promoter region of the gene of interest is selected and a TALE customized to this sequence is designed. The central portion of the TALE consists of tandem repeats 34 amino acids in length. Although the sequences of these repeats are nearly identical, the 12th and 13th amino acids (termed repeat variable diresidues) of each repeat vary, determining the nucleotide-binding specificity of each repeat. Thus, by synthesizing a construct with the appropriate ordering of TALE monomer repeats, a DNA binding protein specific to the target promoter sequence is created.

Light responsiveness of a LITE is achieved via the activation and binding of cryptochrome-2 and CIB1. As mentioned above, blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a LITE system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a LITE stimulated region, allowing for greater precision than vector delivery alone may offer.

The modularity of the LITE system allows for any number of effector domains to be employed for transcriptional modulation. Thus, activator and repressor domains may be selected on the basis of species, strength, mechanism, duration, size, or any number of other parameters.

Applicants next present two prototypical manifestations of the LITE system. The first example is a LITE designed to activate transcription of the mouse gene NEUROG2. The sequence TGAATGATGATAATACGA (SEQ ID NO:149), located in the upstream promoter region of mouse NEUROG2, was selected as the target and a TALE was designed and synthesized to match this sequence. The TALE sequence was linked to the sequence for cryptochrome-2 via a nuclear localization signal (amino acids: SPKKKRKVEAS; SEQ ID NO: 150) to facilitate transport of the protein from the cytosol to the nuclear space. A second vector was synthesized comprising the CIB1 domain linked to the transcriptional activator domain VP64 using the same nuclear localization signal. This second vector, also a GFP sequence, is separated from the CIB1-VP64 fusion sequence by a 2A translational skip signal. Expression of each construct was driven by a ubiquitous, constitutive promoter (CMV or EF1-α). Mouse neuroblastoma cells from the Neuro 2A cell line were co-transfected with the two vectors. After incubation to allow for vector expression, samples were stimulated by periodic pulsed blue light from an array of 488 nm LEDs. Unstimulated co-transfected samples and samples transfected only with the fluorescent reporter YFP were used as controls. At the end of each experiment, mRNA was purified from the samples analyzed via qPCR.

Truncated versions of cryptochrome-2 and CIB1 were cloned and tested in combination with the full-length versions of cryptochrome-2 and CIB1 in order to determine the effectiveness of each heterodimer pair. The combination of the CRY2 PHR domain, consisting of the conserved photoresponsive region of the cryptochrome-2 protein, and the full-length version of CIB1 resulted in the highest upregulation of Neurog2 mRNA levels (~22 fold over YFP samples and ~7 fold over unstimulated co-transfected samples). The combination of full-length cryptochrome-2 (CRY2) with full-length CIB1 resulted in a lower absolute activation level (~4.6 fold over YFP), but also a lower baseline activation (~1.6 fold over YFP for unstimulated co-transfected samples). These cryptochrome protein pairings may be selected for particular uses depending on absolute level of induction required and the necessity to minimize baseline "leakiness" of the LITE system.

Speed of activation and reversibility are critical design parameters for the LITE system. To characterize the kinetics of the LITE system, constructs consisting of the Neurog2 TALE-CRY2 PHR and CIB1-VP64 version of the system were tested to determine its activation and inactivation speed. Samples were stimulated for as little as 0.5 h to as long as 24 h before extraction. Upregulation of Neurog2 expression was observed at the shortest, 0.5 h, time point (~5 fold vs YFP samples). Neurog2 expression peaked at 12 h of stimulation (~19 fold vs YFP samples). Inactivation kinetics were analyzed by stimulating co-transfected samples for 6 h, at which time stimulation was stopped, and samples were kept in culture for 0 to 12 h to allow for mRNA degradation. Neurog2 mRNA levels peaked at 0.5 h after the end of stimulation (~16 fold vs. YFP samples), after which the levels degraded with an ~3 h half-life before returning to near baseline levels by 12 h.

The second prototypical example is a LITE designed to activate transcription of the human gene KLF4. The sequence TTCTTACTTATAAC (SEQ ID NO: 167), located in the upstream promoter region of human KLF4, was selected as the target and a TALE was designed and synthesized to match this sequence. The TALE sequence was linked to the sequence for CRY2 PHR via a nuclear localization signal (amino acids: SPKKKRKVEAS; SEQ ID NO: 150). The identical CIB1-VP64 activator protein described above was also used in this manifestation of the LITE system. Human embryonal kidney cells from the HEK293FT cell line were co-transfected with the two vectors. After incubation to allow for vector expression, samples were stimulated by periodic pulsed blue light from an array of 488 nm LEDs. Unstimulated co-transfected samples and samples transfected only with the fluorescent reporter YFP were used as controls. At the end of each experiment, mRNA was purified from the samples analyzed via qPCR.

The light-intensity response of the LITE system was tested by stimulating samples with increased light power (0-9 mW/cm2). Upregulation of KLF4 mRNA levels was observed for stimulation as low as 0.2 mW/cm2. KLF4 upregulation became saturated at 5 mW/cm2 (2.3 fold vs. YFP samples). Cell viability tests were also performed for powers up to 9 mW/cm2 and showed >98% cell viability. Similarly, the KLF4 LITE response to varying duty cycles of stimulation was tested (1.6-100%). No difference in KLF4 activation was observed between different duty cycles indicating that a stimulation paradigm of as low as 0.25 sec every 15 sec should result in maximal activation.

There are potential applications for which LITEs represent an advantageous choice for gene expression control. There exist a number of in vitro applications for which LITEs are particularly attractive. In all these cases, LITEs have the advantage of inducing endogenous gene expression with the potential for correct splice variant expression.

Because LITE activation is photoinducible, spatially defined light patterns, created via masking or rasterized laser scanning, may be used to alter expression levels in a confined subset of cells. For example, by overexpressing or silencing an intercellular signaling molecule only in a spatially constrained set of cells, the response of nearby cells relative to their distance from the stimulation site may help elucidate the spatial characteristics of cell non-autonomous processes. Additionally, recent advances in cell reprogramming biology have shown that overexpression of sets of transcription factors may be utilized to transform one cell type, such as fibroblasts, into another cell type, such as neurons or cardiomyocytes. Further, the correct spatial distribution of cell types within tissues is critical for proper organotypic function. Overexpression of reprogramming factors using LITEs may be employed to reprogram multiple cell lineages in a spatially precise manner for tissue engineering applications.

The rapid transcriptional response and endogenous targeting of LITEs make for an ideal system for the study of transcriptional dynamics. For example, LITEs may be used to study the dynamics of mRNA splice variant production upon induced expression of a target gene. On the other end of the transcription cycle, mRNA degradation studies are often performed in response to a strong extracellular stimulus, causing expression level changes in a plethora of genes. LITEs may be utilized to reversibly induce transcription of an endogenous target, after which point stimulation may be stopped and the degradation kinetics of the unique target may be tracked.

The temporal precision of LITEs may provide the power to time genetic regulation in concert with experimental interventions. For example, targets with suspected involvement in long-term potentiation (LTP) may be modulated in organotypic or dissociated neuronal cultures, but only during stimulus to induce LTP, so as to avoid interfering with the normal development of the cells. Similarly, in cellular models exhibiting disease phenotypes, targets suspected to be involved in the effectiveness of a particular therapy may be modulated only during treatment. Conversely, genetic targets may be modulated only during a pathological stimulus. Any number of experiments in which timing of genetic cues to external experimental stimuli is of relevance may potentially benefit from the utility of LITE modulation.

The in vivo context offers equally rich opportunities for the use of LITEs to control gene expression. As mentioned above, photoinducibility provides the potential for previously unachievable spatial precision. Taking advantage of the development of optrode technology, a stimulating fiber optic lead may be placed in a precise brain region. Stimulation region size may then be tuned by light intensity. This may be done in conjunction with the delivery of LITEs via viral vectors, or, if transgenic LITE animals were to be made available, may eliminate the use of viruses while still allowing for the modulation of gene expression in precise brain regions. LITEs may be used in a transparent organism, such as an immobilized zebrafish, to allow for extremely precise laser induced local gene expression changes.

LITEs may also offer valuable temporal precision in vivo. LITEs may be used to alter gene expression during a particular stage of development, for example, by repressing a particular apoptosis gene only during a particular stage of C. elegans growth. LITEs may be used to time a genetic cue to a particular experimental window. For example, genes implicated in learning may be overexpressed or repressed only during the learning stimulus in a precise region of the intact rodent or primate brain. Further, LITEs may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the LITE system, they highlight some of the areas in which LITEs may be a powerful technology.

Example 3: Development of Mammalian TALE ToolBox

Customized TALEs may be used for a wide variety of genome engineering applications, including transcriptional modulation and genome editing. Here, Applicants describe a toolbox for rapid construction of custom TALE transcription factors (TALE-TFs) and nucleases (TALENs) using a hierarchical ligation procedure. This toolbox facilitates affordable and rapid construction of custom TALE-TFs and TALENs within 1 week and may be easily scaled up to construct TALEs for multiple targets in parallel. Applicants also provide details for testing the activity in mammalian cells of custom TALE-TFs and TALENs using quantitative reverse-transcription PCR and Surveyor nuclease, respectively. The TALE toolbox will enable a broad range of biological applications.

TALEs are natural bacterial effector proteins used by Xanthomonas sp. to modulate gene transcription in host plants to facilitate bacterial colonization (7, 8). The central region of the protein contains tandem repeats of 34-aa sequences (termed monomers; e.g., SEQ ID NO: 1) that are required for DNA recognition and binding (9, 10, 11, 12) (FIG. 8). Naturally occurring TALEs have been found to have a variable number of monomers, ranging from 1.5 to 33.5 (7). Although the sequence of each monomer is highly conserved, they differ primarily in two positions termed the repeat variable diresidues (RVDs, 12th and 13th positions). Recent reports have found that the identity of these two residues determines the nucleotide-binding specificity of each TALE repeat and that a simple cipher specifies the target base of each RVD (NI=A, HD=C, NG=T, NN=G or A) (1, 2). Thus, each monomer targets one nucleotide and the linear sequence of monomers in a TALE specifies the target DNA sequence in the 5' to 3' orientation. The natural TALE-binding sites within plant genomes always begin with a thymine (1, 2), which is presumably specified by a cryptic signal within the nonrepetitive N terminus of TALEs. The tandem repeat DNA-binding domain always ends with a half-length repeat (0.5 repeat, FIG. 8). Therefore, the length of the DNA sequence being targeted is equal to the number of full repeat monomers plus two.

Applicants have further improved the TALE assembly system with a few optimizations, including maximizing the dissimilarity of ligation adaptors to minimize misligations and combining separate digest and ligation steps into single Golden Gate (13, 14, 15) reactions. Briefly, each nucleotide-specific monomer sequence is amplified with ligation adaptors that uniquely specify the monomer position within the TALE tandem repeats. Once this monomer library is produced, it may conveniently be reused for the assembly of many TALEs. For each TALE desired, the appropriate monomers are first ligated into hexamers, which are then amplified via PCR. Then, a second Golden Gate digestion-ligation with the appropriate TALE cloning backbone (FIG. 8) yields a fully assembled, sequence-specific TALE. The backbone contains a ccdB negative selection cassette flanked by the TALE N and C termini, which is replaced by the tandem repeat DNA-binding domain when the TALE has been successfully constructed. ccdB selects against cells transformed with an empty backbone, thereby yielding clones with tandem repeats inserted (5).

Assemblies of monomeric DNA-binding domains may be inserted into the appropriate TALE-TF or TALEN cloning backbones to construct customized TALE-TFs and TALENs. TALE-TFs are constructed by replacing the natural activation domain within the TALE C terminus with the synthetic transcription activation domain VP64 (3; FIG. 8).

REFERENCES

1. Boch, J. et al. Breaking the code of DNA binding specificity of TAL-type III effectors. *Science* 326, 1509-1512 (2009).
2. Moscou, M. J. & Bogdanove, A. J. A simple cipher governs DNA recognition by TAL effectors. *Science* 326, 1501 (2009).
3. Zhang, F. et al. Efficient construction of sequence-specific TAL effectors for modulating mammalian transcription. *Nat. Biotechnol.* 29, 149-153 (2011).
4. Miller, J. C. et al. A TALE nuclease architecture for efficient genome editing. *Nat. Biotechnol.* 29, 143-148 (2011).
5. Cermak, T. et al. Efficient design and assembly of custom TALEN and other TAL effector-based constructs for DNA targeting. *Nucleic Acids Res.* 39, e82 (2011).
6. Hockemeyer, D. et al. Genetic engineering of human pluripotent cells using TALE nucleases. *Nat. Biotechnol.* 29, 731-734 (2011).
7. Boch, J. & Bonas, U. Xanthomonas AvrBs3 family-type III effectors: discovery and function. *Annu. Rev. Phytopathol.* 48, 419-436 (2010).
8. Bogdanove, A. J., Schornack, S. & Lahaye, T. TAL effectors: finding plant genes for disease and defense. *Curr. Opin. Plant Biol.* 13, 394-401 (2010).
9. Romer, P. et al. Plant pathogen recognition mediated by promoter activation of the pepper Bs3 resistance gene. *Science* 318, 645-648 (2007).
10. Kay, S., Hahn, S., Marois, E., Hause, G. & Bonas, U. A bacterial effector acts as a plant transcription factor and induces a cell size regulator. *Science* 318, 648-651 (2007).
11. Kay, S., Hahn, S., Marois, E., Wieduwild, R. & Bonas, U. Detailed analysis of the DNA recognition motifs of the Xanthomonas type III effectors AvrBs3 and AvrBs3Deltarep16. *Plant J.* 59, 859-871 (2009).

12. Romer, P. et al. Recognition of AvrBs3-like proteins is mediated by specific binding to promoters of matching pepper Bs3 alleles. *Plant Physiol.* 150, 1697-1712 (2009).
13. Engler, C., Kandzia, R. & Marillonnet, S. A one pot, one step, precision cloning method with high throughput capability. *PLoS ONE* 3, e3647 (2008).
14. Engler, C., Gruetzner, R., Kandzia, R. & Marillonnet, S. Golden gate shuffling: a one-pot DNA shuffling method based on type IIs restriction enzymes. *PLoS ONE* 4, e5553 (2009).
15. Weber, E., Engler, C., Gruetzner, R., Werner, S. & Marillonnet, S. A modular cloning system for standardized assembly of multigene constructs. *PLoS ONE* 6, e16765 (2011).
16. Huertas, P. DNA resection in eukaryotes: deciding how to fix the break. *Nat. Struct. Mol. Biol.* 17, 11-16 (2010).

Example 4

Figure 17:
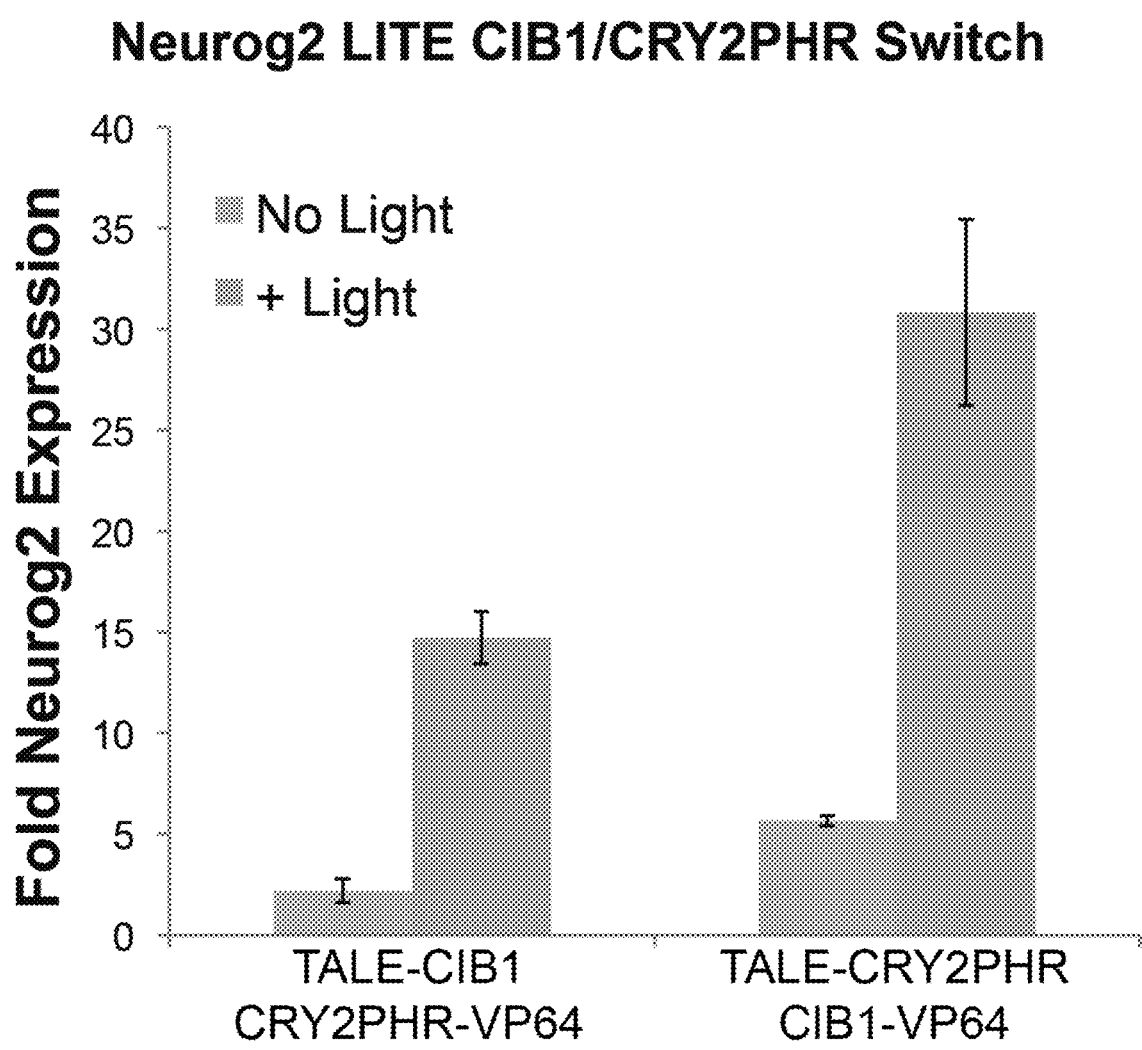
FIG. 17 depicts an effect of cryptochrome2 heterodimer orientation on LITE functionality.

FIG. 17 depicts an effect of cryptochrome2 heterodimer orientation on LITE functionality. Two versions of the Neurogenin 2 (Neurog2) LITE were synthesized to investigate the effects of cryptochrome 2 photolyase homology region (CRY2 PHR)/calcium and integrin-binding protein 1 (CIB1) dimer orientation. In one version, the CIB1 domain was fused to the C-terminus of the TALE (Neurog2) domain, while the CRY2 PHR domain was fused to the N-terminus of the VP64 domain. In the converse version, the CRY2 PHR domain was fused to the C-terminus of the TALE (Neurog2) domain, while the CIB1 domain was fused to the N-terminus of the VP64 domain. Each set of plasmids were transfected in Neuro2a cells and stimulated (466 nm, 5 mW/cm$^2$, 1 sec pulse per 15 sec, 12 h) before harvesting for qPCR analysis. Stimulated LITE and unstimulated LITE Neurog2 expression levels were normalized to Neurog2 levels from stimulated GFP control samples. The TALE-CRY2 PHR/CIB1-VP64 LITE exhibited elevated basal activity and higher light induced Neurog2 expression, and suggested its suitability for situations in which higher absolute activation is required. Although the relative light inducible activity of the TALE-CIB1/CRY2 PHR-VP64 LITE was lower that its counterpart, the lower basal activity suggested its utility in applications requiring minimal baseline activation. Further, the TALE-CIB1 construct was smaller in size, compared to the TALE-CRY2 PHR construct, a potential advantage for applications such as viral packaging.

Figure 18:
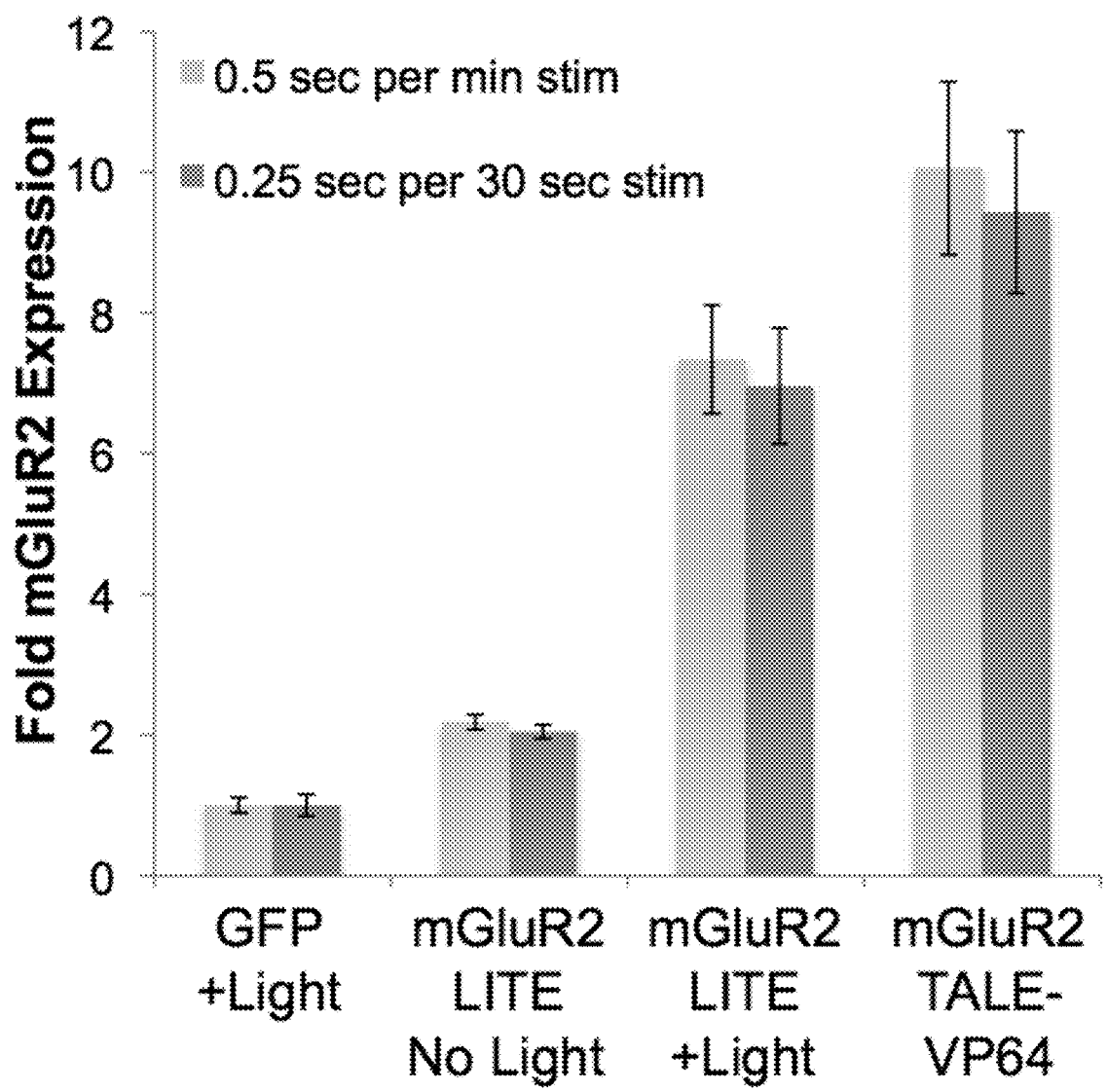
FIG. 18 depicts mGlur2 LITE activity in mouse cortical neuron culture.

FIG. 18 depicts metabotropic glutamate receptor 2 (mGlur2) LITE activity in mouse cortical neuron culture. A mGluR2 targeting LITE was constructed via the plasmids pAAV-human Synapsin I promoter (hSyn)-HA-TALE (mGluR2)-CIB1 and pAAV-hSyn-CRY2 PHR-VP64-2A-GFP. These fusion constructs were then packaged into adeno associated viral vectors (AAV). Additionally, AAV carrying hSyn-TALE-VP64-2A-GFP and GFP only were produced. Embryonic mouse (E16) cortical cultures were plated on Poly-L-lysine coated 24 well plates. After 5 days in vitro neural cultures were co-transduced with a mixture of TALE (mGluR2)-CIB1 and CRY2 PHR-VP64 AAV stocks. Control samples were transduced with either TALE(mGluR2)-VP64 AAV or GFP AAV. 6 days after AAV transduction, experimental samples were stimulated using either of two light pulsing paradigms: 0.5 s per min and 0.25 sec per 30 sec. Neurons were stimulated for 24 h and harvested for qPCR analysis. All mGluR2 expression levels were normalized to the respective stimulated GFP control. The data suggested that the LITE system could be used to induce the light-dependent activation of a target gene in primary neuron cultures in vitro.

Figure 19:
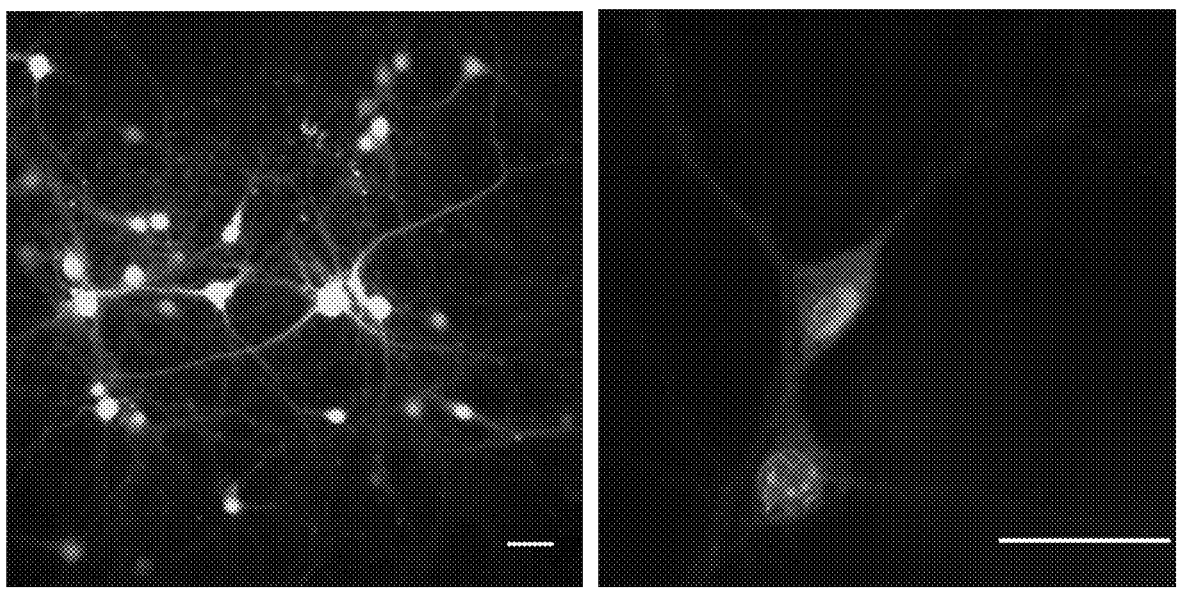
FIG. 19 depicts transduction of primary mouse neurons with LITE AAV vectors.

FIG. 19 depicts transduction of primary mouse neurons with LITE AAV vectors. Primary mouse cortical neuron cultures were co-transduced at 5 days in vitro with AAV vectors encoding hSyn-CRY2 PHR-VP64-2A-GFP and hSyn-HA-TALE-CIB1, the two components of the LITE system. Left panel: at 6 days after transduction, neural cultures exhibited high expression of GFP from the hSyn-CRY2 PHR-VP64-2A-GFP vector. Right panel: Co-transduced neuron cultures were fixed and stained with an antibody specific to the HA epitope on the N-terminus of the TALE domain in hSyn-HA-TALE-CIB1. Red signal indicated HA expression, with particularly strong nuclear signal (DNA stained by DAPI in blue channel). Together these images suggested that the expression of each LITE component could be achieved in primary mouse neuron cultures. (scale bars=50 um).

Figure 20:
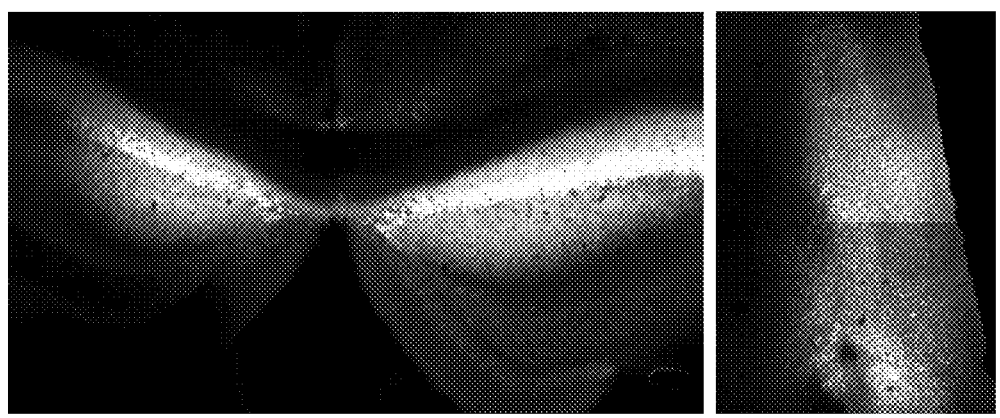
FIG. 20 depicts expression of LITE component in vivo.
Figure 21:
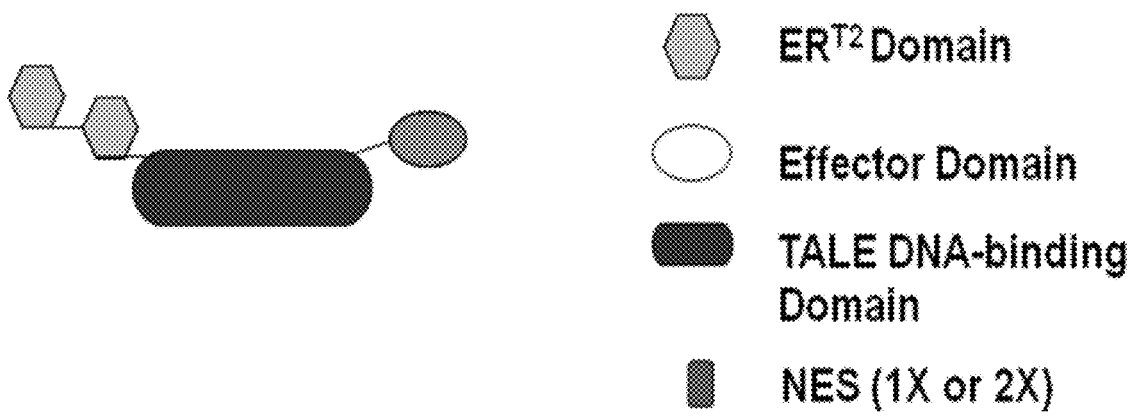
FIG. 21 depicts an improved design of the construct where the specific NES peptide sequence used is LDLASLIL (SEQ ID NO: 188).
Figure 22:
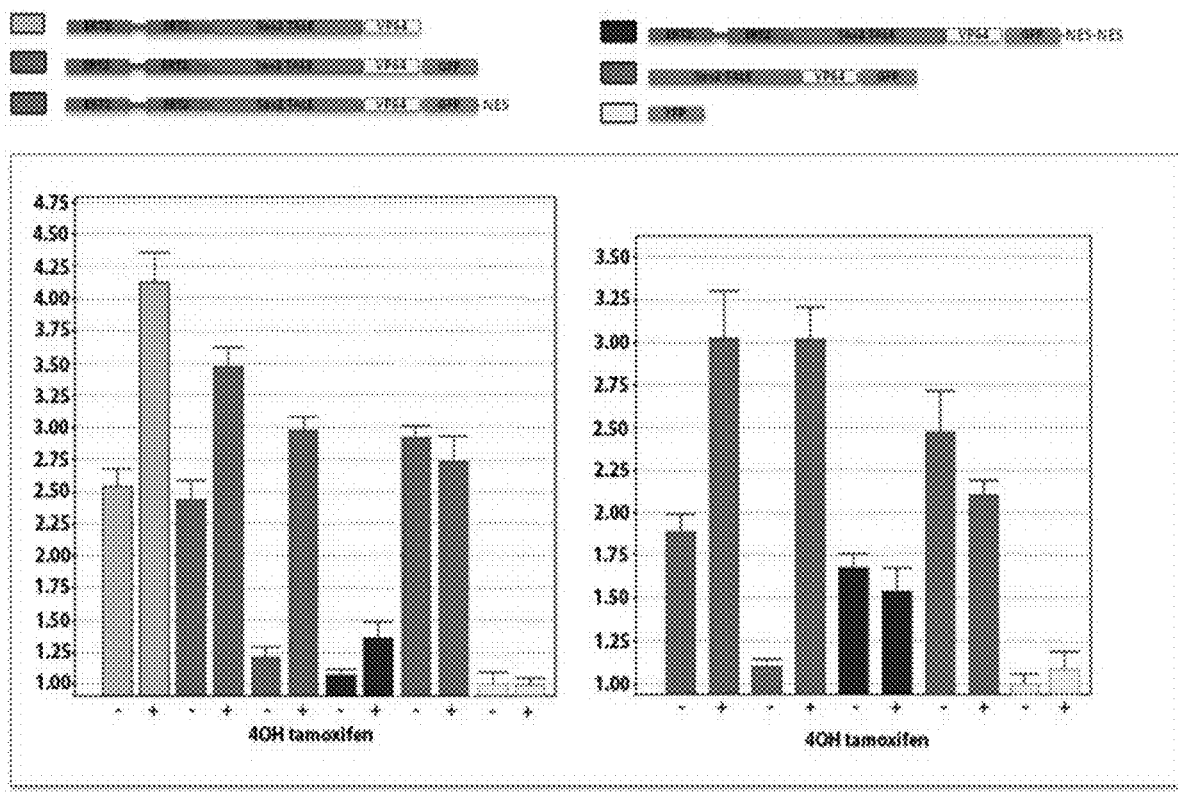
FIG. 22 depicts Sox2 mRNA levels in the absence and presence of 4OH tamoxifen.
Figure 26F:
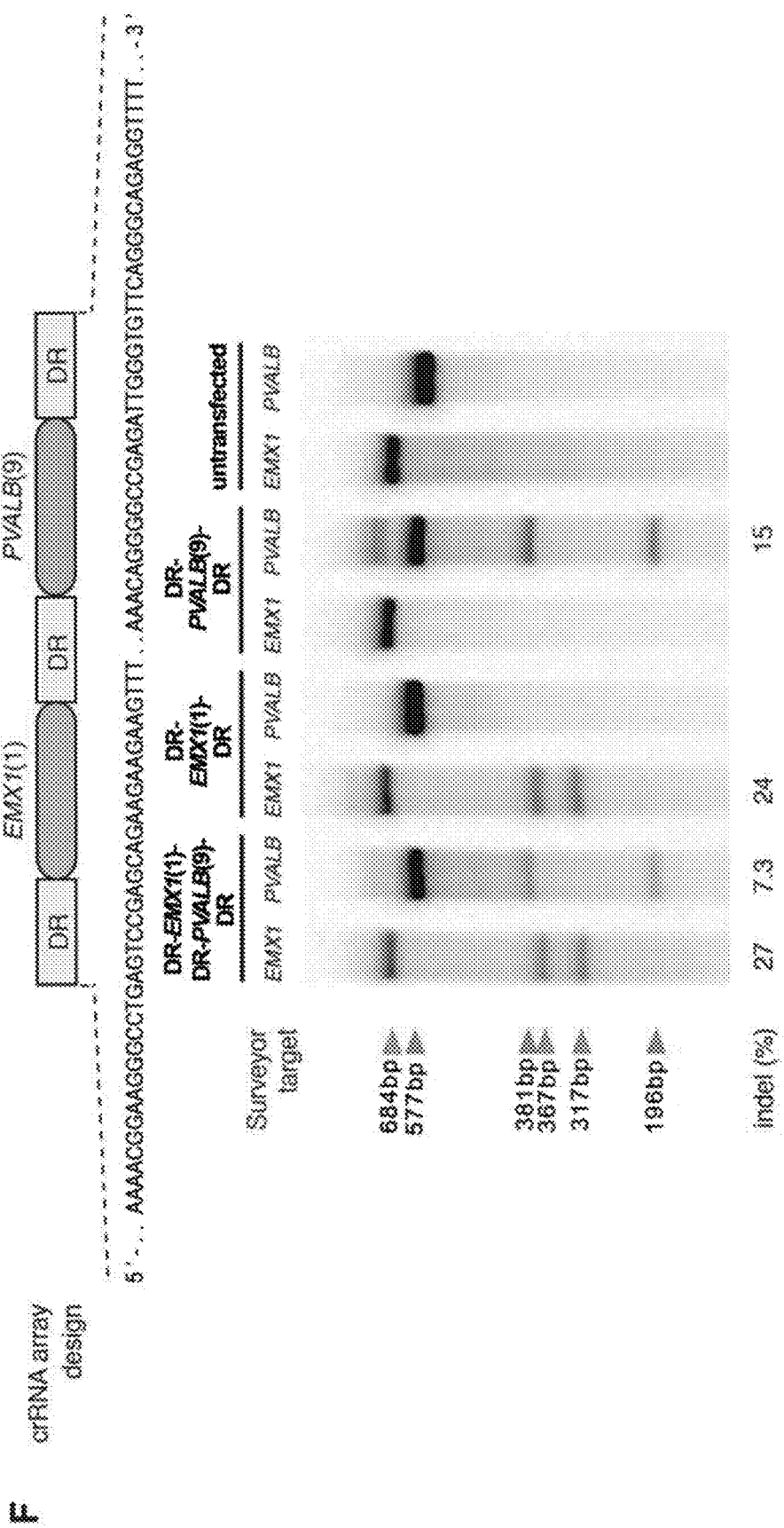
Figure 26G:
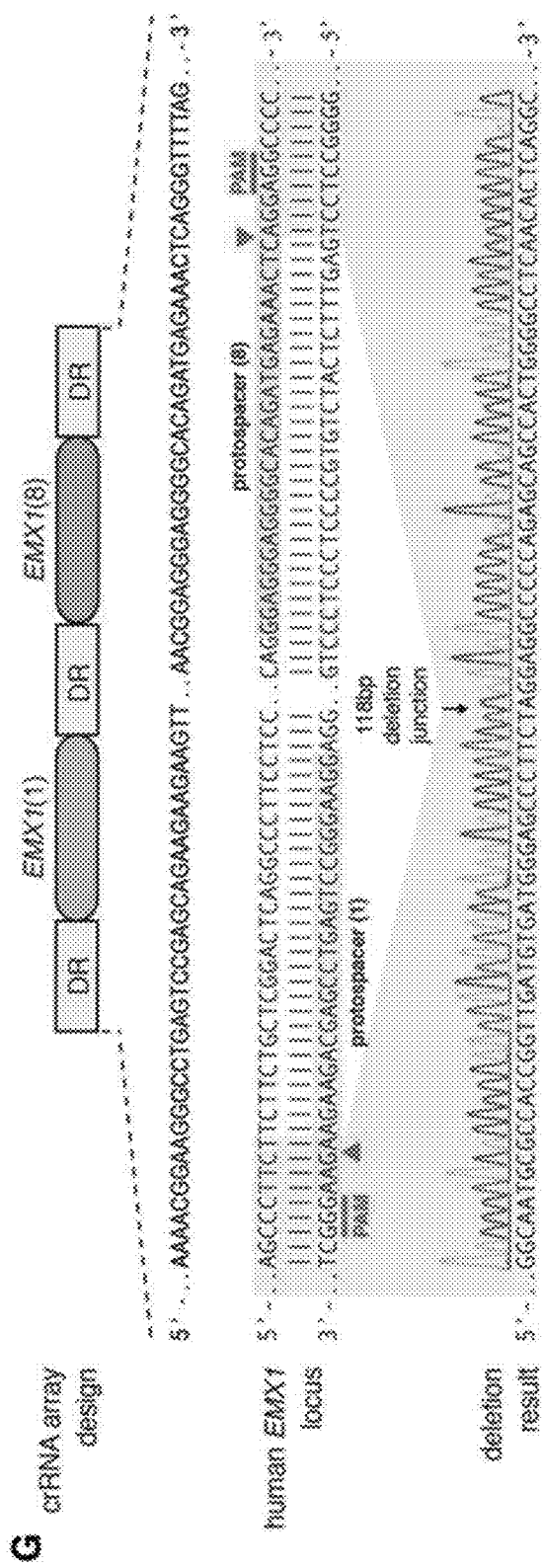

FIG. 20 depicts expression of a LITE component in vivo. An AAV vector of serotype 1/2 carrying hSyn-CRY2 PHR-VP64 was produced via transfection of HEK293FT cells and purified via heparin column binding. The vector was concentrated for injection into the intact mouse brain. 1 uL of purified AAV stock was injected into the hippocampus and infralimbic cortex of an 8 week old male C57BL/6 mouse by steroeotaxic surgery and injection. 7 days after in vivo transduction, the mouse was euthanized and the brain tissue was fixed by paraformaldehyde perfusion. Slices of the brain were prepared on a vibratome and mounted for imaging. Strong and widespread GFP signals in the hippocampus and infralimbic cortex suggested efficient transduction and high expression of the LITE component CRY2 PHR-VP64.

Example 5: Multiplex Genome Engineering Using CRISPR/Cas Systems

Functional elucidation of causal genetic variants and elements requires precise genome editing technologies. The type II prokaryotic CRISPR (clustered regularly interspaced short palindromic repeats) adaptive immune system has been shown to facilitate RNA-guided site-specific DNA cleavage. Applicants engineered two different type II CRISPR systems and demonstrate that Cas9 nucleases can be directed by short RNAs to induce precise cleavage at endogenous genomic loci in human and mouse cells. Cas9 can also be converted into a nicking enzyme to facilitate homology-directed repair with minimal mutagenic activity. Finally, multiple guide sequences can be encoded into a single CRISPR array to enable simultaneous editing of several sites within the mammalian genome, demonstrating easy programmability and wide applicability of the CRISPR technology.

Prokaryotic CRISPR adaptive immune systems can be reconstituted and engineered to mediate multiplex genome editing in eukaryote cells, advantageously mammalian cells.

Precise and efficient genome targeting technologies are needed to enable systematic reverse engineering of causal genetic variations by allowing selective perturbation of individual genetic elements. Although genome-editing technologies such as designer zinc fingers (ZFs) (1-4), transcription activator-like effectors (TALEs) (4-10), and homing meganucleases (11) have begun to enable targeted genome modifications, there remains a need for new technologies that are scalable, affordable, and easy to engineer. Here, Applicants report the development of a new class of precision genome engineering tools based on the RNA-guided Cas9 nuclease (12-14) from the type II prokaryotic CRISPR adaptive immune system (15-18).

Figure 27:
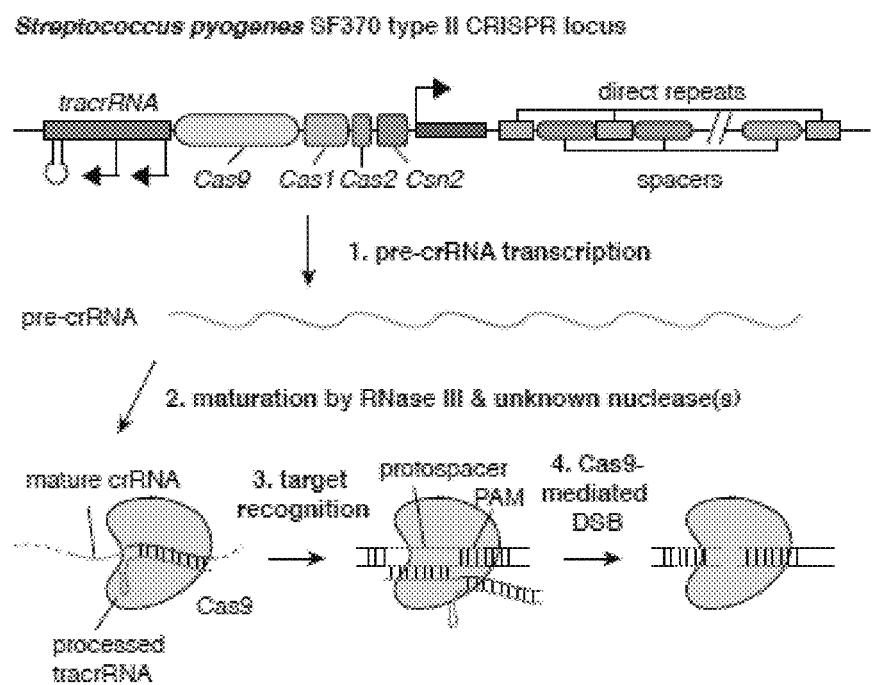
FIG. 27 depicts a schematic of the type II CRISPR-mediated DNA double-strand break. The type II CRISPR locus from *Streptococcus pyogenes* SF370 contains a cluster of four genes, Cas9, Cas1, Cas2, and Csn1, as well as two non-coding RNA elements, tracrRNA and a characteristic array of repetitive sequences (direct repeats) interspaced by short stretches of non-repetitive sequences (spacers, 30 bp each) (15-18, 30, 31). Each spacer is typically derived from foreign genetic material (protospacer), and directs the specificity of CRISPR-mediated nucleic acid cleavage. In the target nucleic acid, each protospacer is associated with a protospacer adjacent motif (PAM) whose recognition is specific to individual CRISPR systems (22, 23). The Type II CRISPR system carries out targeted DNA double-strand break (DSB) in sequential steps (M. Jinek et al., Science 337, 816 (Aug. 17, 2012); Gasiunas, R. et al. Proc Natl Acad Sci USA 109, E2579 (Sep. 25, 2012); J. E. Garneau et al., Nature 468, 67 (Nov. 4, 2010); R. Sapranauskas et al., Nucleic Acids Res 39, 9275 (November, 2011); A. H. Magadan et al. PLoS One 7, e40913 (2012)). First, the pre-crRNA array and tracrRNA are transcribed from the CRISPR locus. Second, tracrRNA hybridizes to the direct repeats of pre-crRNA and associates with Cas9 as a duplex, which mediates the processing of the pre-crRNA into mature crRNAs containing individual, truncated spacer sequences. Third, the mature crRNA:tracrRNA duplex directs Cas9 to the DNA target consisting of the protospacer and the requisite PAM via heteroduplex formation between the spacer region of the crRNA and the protospacer DNA. Finally, Cas9 mediates cleavage of target DNA upstream of PAM to create a DSB within the protospacer.
Figure 28:
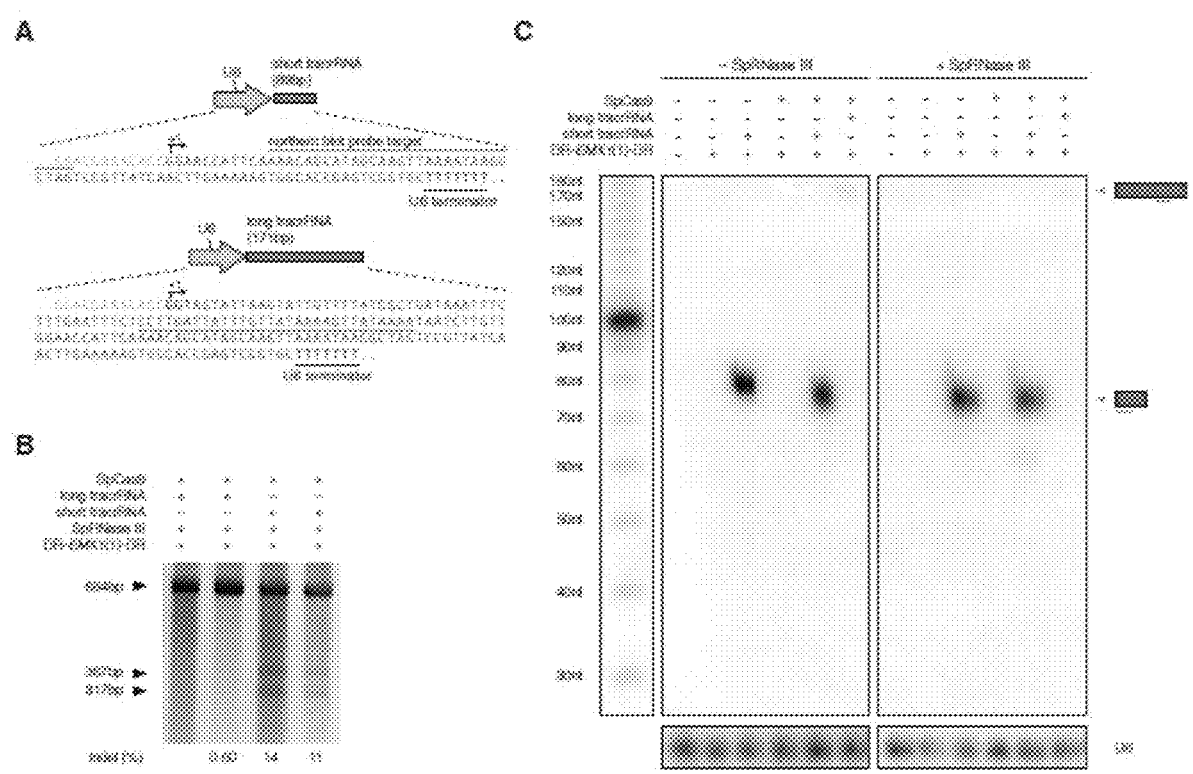
FIGS. 28A-C depict a comparison of different tracrRNA transcripts for Cas9-mediated gene targeting. (A) Schematic showing the design and sequences of two tracrRNA transcripts (SEQ ID NOS:119-120) tested (short and long). Each transcript is driven by a U6 promoter. Transcription start site is marked as +1 and transcription terminator is as indicated. Blue line indicates the region whose reverse-complement sequence is used to generate northern blot probes for tracrRNA detection. (B) SURVEYOR assay comparing the efficiency of hSpCas9-mediated cleavage of the EMX1 locus. Two biological replicas are shown for each tracrRNA transcript. (C) Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III respectively. U6 indicate loading control blotted with a probe targeting human U6 snRNA. Transfection of the short tracrRNA expression construct led to abundant levels of the processed form of tracrRNA (~75 bp) (E. Deltcheva et al., Nature 471, 602 (Mar. 31, 2011)). Very low amounts of long tracrRNA are detected on the Northern blot. As a result of these experiments, Applicants chose to use short tracrRNA for application in mammalian cells.
Figure 29:
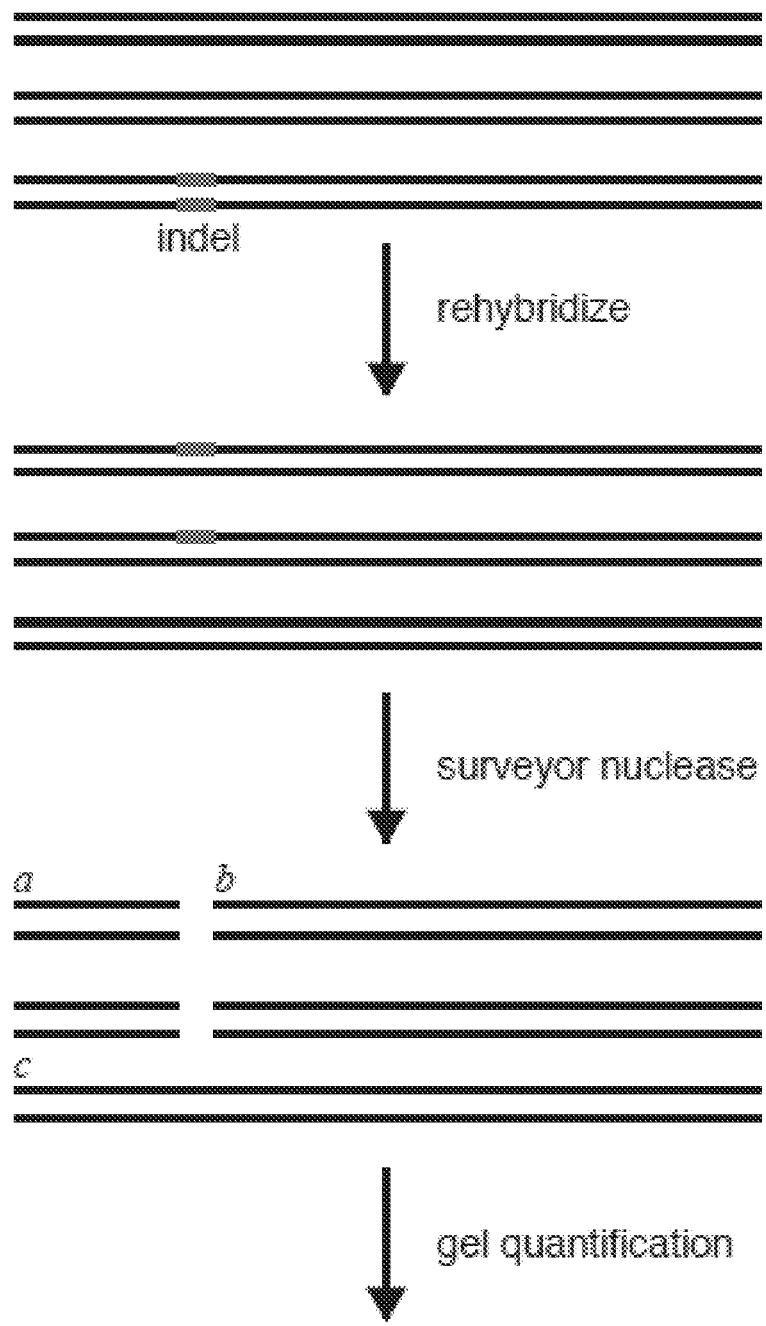
FIG. 29 depicts a SURVEYOR assay for detection of double strand break-induced micro insertions and deletions (D. Y. Guschin et al. Methods Mol Biol 649, 247 (2010)). Schematic of the SURVEYOR assay used to determine Cas9-mediated cleavage efficiency. First, genomic PCR (gPCR) is used to amplify the Cas9 target region from a heterogeneous population of modified and unmodified cells, and the gPCR products are reannealed slowly to generate heteroduplexes. The reannealed heteroduplexes are cleaved by SURVEYOR nuclease, whereas homoduplexes are left intact. Cas9-mediated cleavage efficiency (% indel) is calculated based on the fraction of cleaved DNA.
Figure 39:
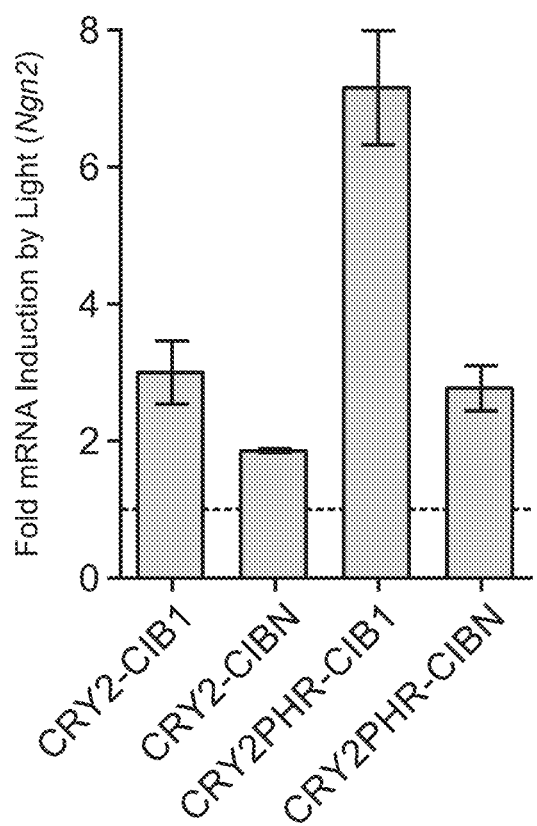
FIG. 39 depicts an activation Ratio of CRY2 and CIB1 truncations. Fold activation of Ngn2 expression by LITEs was calculated as the ratio of mRNA levels in stimulated cells versus unstimulated cells (light/no light; experiment and data corresponding to FIG. 35B), for each CRY2 and CIB1 truncation pair.

The *Streptococcus pyogenes* SF370 type II CRISPR locus consists of four genes, including the Cas9 nuclease, as well as two non-coding RNAs: tracrRNA and a pre-crRNA array containing nuclease guide sequences (spacers) interspaced by identical direct repeats (DRs) (FIG. 27) (19). Applicants sought to harness this prokaryotic RNA-programmable nuclease system to introduce targeted double stranded breaks (DSBs) in mammalian chromosomes through heterologous expression of the key components. It has been previously shown that expression of tracrRNA, pre-crRNA, host factor RNase III, and Cas9 nuclease are necessary and sufficient for cleavage of DNA in vitro (12, 13) and in prokaryotic cells (20, 21). Applicants codon optimized the *S. pyogenes* Cas9 (SpCas9) and RNase III (SpRNase III) and attached nuclear localization signals (NLS) to ensure nuclear compartmentalization in mammalian cells. Expression of these constructs in human 293FT cells revealed that two NLSs are required for targeting SpCas9 to the nucleus (FIG. 23A). To reconstitute the non-coding RNA components of CRISPR, Applicants expressed an 89-nucleotide (nt) tracrRNA (FIG. 28) under the RNA polymerase III U6 promoter (FIG. 23B). Similarly, Applicants used the U6 promoter to drive the expression of a pre-crRNA array comprising a single guide spacer flanked by DRs (FIG. 23B). Applicants designed an initial spacer to target a 30-basepair (bp) site (protospacer) in the human EMX1 locus that precedes an NGG, the requisite protospacer adjacent motif (PAM) (FIG. 23C and FIG. 27) (22, 23).

To test whether heterologous expression of the CRISPR system (SpCas9, SpRNase III, tracrRNA, and pre-crRNA) can achieve targeted cleavage of mammalian chromosomes, Applicants transfected 293FT cells with different combinations of CRISPR components. Since DSBs in mammalian DNA are partially repaired by the indel-forming non-homologous end joining (NHEJ) pathway, Applicants used the SURVEYOR assay to detect endogenous target cleavage (FIG. 23D). Co-transfection of all four required CRISPR components resulted in efficient cleavage of the protospacer (FIG. 23D), which is subsequently verified by Sanger sequencing (FIG. 23E). Removing any of the remaining RNA or Cas9 components abolished the genome cleavage activity of the CRISPR system (FIG. 23D). These results define a minimal three-component system for efficient CRISPR-mediated genome modification in mammalian cells.

Example 6: Optical Control of Endogenous Mammalian Transcription

The ability to directly modulate transcription of the endogenous mammalian genome is critical for elucidating normal gene function and disease mechanisms. Here, Applicants describe the development of Light-Inducible Transcriptional Effectors (LITEs), a two-component system integrating the customizable TALE DNA-binding domain with the light-sensitive cryptochrome 2 protein and its interacting partner CIB1 from *Arabidopsis thaliana*. LITEs can be engineered and delivered to mediate positive and negative regulation of endogenous mammalian gene expression in a reversible manner, and changes in mRNA levels occur within minutes after optical illumination. Applicants have applied this system in cell lines, primary mouse neurons, as well as in the brain of awake, behaving mice in vivo.

An ideal optogenetic approach for controlling endogenous gene transcription would be readily generalizable to target any gene locus, would not require manipulation of the endogenous genomic sequence, would not depend on the addition of exogenous chemical co-factors, and would exhibit fast and reversible kinetics. The DNA-binding domain of transcription activator-like effectors (TALEs) (13, 14) from *Xanthomonas* sp. can be easily customized to bind specific DNA sequences in mammalian cells (15-17). TALE DNA-binding domains are modular and can be fused with a variety of effector domains, including nucleases, transcriptional activators, and transcriptional repressors to edit or modulate endogenous mammalian genomic loci (15-18). Applicants sought to combine TALEs with light-sensitive proteins to create a suite of tools for enabling spatiotemporally precise control of endogenous gene transcription.

Here, Applicants report the development of Light-Inducible Transcriptional Effectors (LITEs), a two-component system integrating the customizable TALE DNA-binding domain with the light-sensitive cryptochrome 2 protein and its interacting partner CIB1 from *Arabidopsis thaliana* (8, 19). LITEs can be engineered to mediate positive and negative regulation of endogenous mammalian gene expression in a reversible manner, and changes in transcript levels occur within minutes after stimulation. Like other optogenetic tools, LITEs can be packaged into viral vectors and genetically targeted to probe gene function within specific cell populations. Applicants demonstrate the application of this system in primary neurons as well as in the mouse brain in vivo.

In the design of the LITE system, Applicants sought to use light-inducible heterodimeric proteins to mediate the recruitment of transcriptional effector domains to a TALE targeted to an endogenous genomic locus. While several plant-based light-sensitive proteins have been developed for mammalian applications, some suffer from slow or irreversible kinetics while others depend on the supplementation of exogenous co-factors that are not present in mammalian cells (5, 6, 9). The *Arabidopsis thaliana* cryptochrome 2 (CRY2) was previously shown to employ flavin adenine dinucleotide—an abundant biomolecule in mammalian cells—as its light-sensing chromophore[19]. The flavin chromophore is reduced upon photoexcitation with blue light (peak ~450 nm), triggering a conformational change in CRY2 that allows dimerization with its interacting protein partner CIB1[19]. The dimerization between CRY2 and CIB1 occurs within seconds and is reversible within a few minutes following withdrawal of light illumination[8]. Based on these properties, Applicants selected CRY2 and CIB1 as light-sensing components for constructing LITEs.

Figure 42:
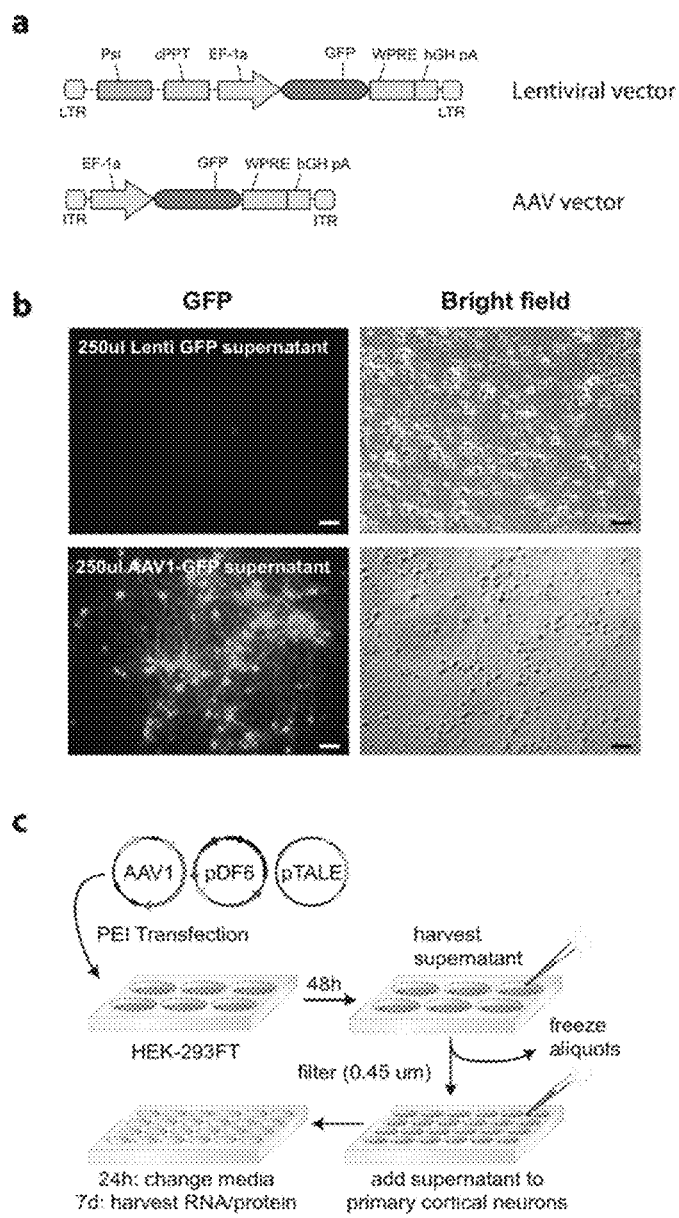
FIGS. 42A-C depict AAV supernatant production. (A) Lentiviral and AAV vectors carrying GFP were used to test transduction efficiency. (B) Primary embryonic cortical neurons were transduced with 250 μL supernatant derived from the same number of AAV or lentivirus-transfected 293FT cells. Representative images of GFP expression were collected at 7 d.p.i. Scale bars=50 (C) The depicted process was developed for the production of AAV supernatant and subsequent transduction of primary neurons. 293FT cells were transfected with an AAV vector carrying the gene of interest, the AAV1 serotype packaging vector (pAAV1), and helper plasmid (pDF6) using PEI. 48 h later, the supernatant was harvested and filtered through a 0.45 μm PVDF membrane. Primary neurons were then transduced with supernatant and remaining aliquots were stored at −80° C. Stable levels of AAV construct expression were reached after 5-6 days.
Figure 46:
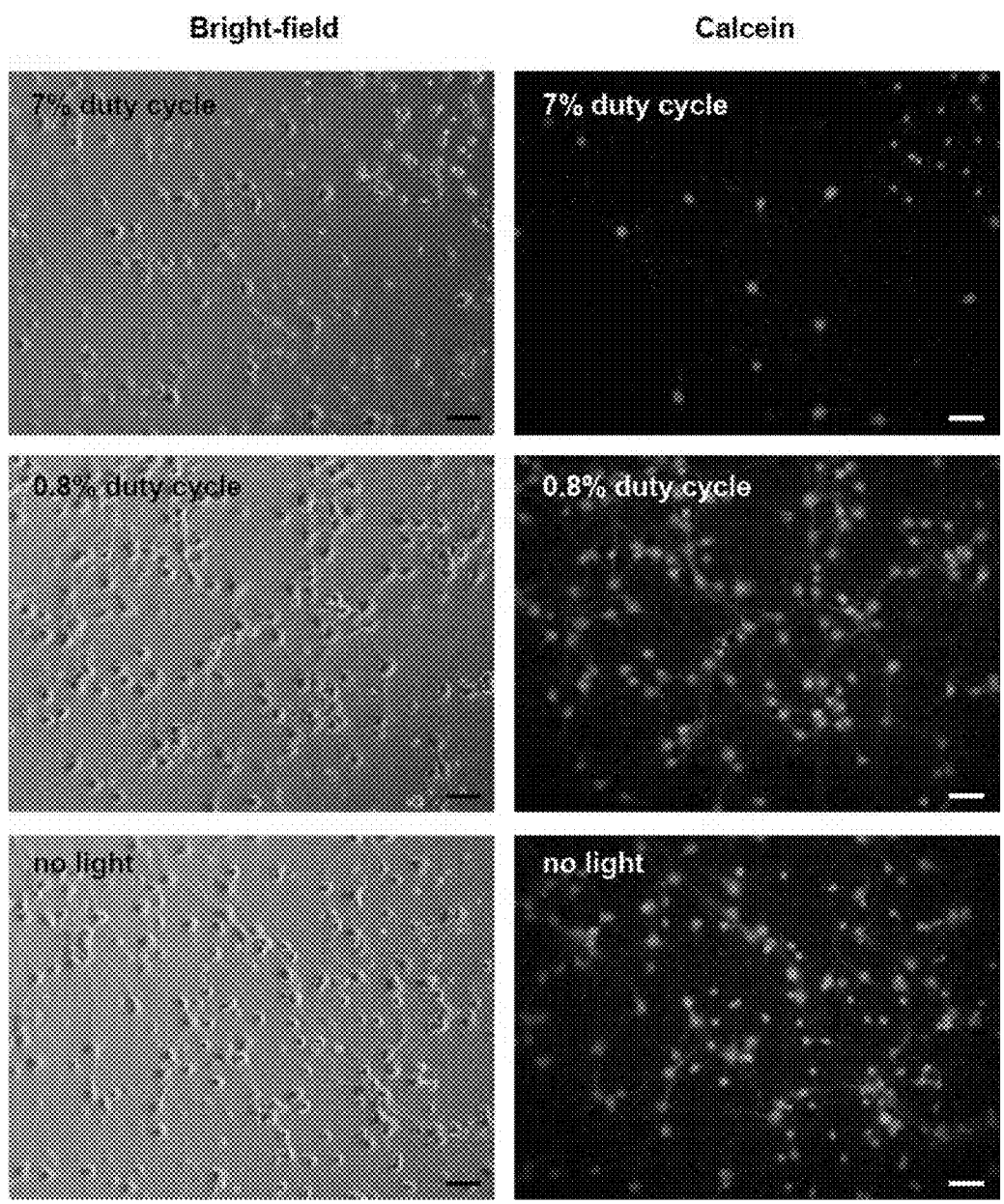
FIG. 46 depicts an impact of light duty cycle on primary neuron health. The effect of light stimulation on primary cortical neuron health was compared for duty cycles of 7%, 0.8%, and no light conditions. Calcein was used to evaluate neuron viability. Bright-field images were captured to show morphology and cell integrity. Primary cortical neurons were stimulated with the indicated duty cycle for 24 h with 5 mW/cm$^2$ of 466 nm light. Representative images, scale bar=50 μm. Pulses were performed in the following manner: 7% duty cycle=1 s pulse at 0.067 Hz, 0.8% duty cycle=0.5 s pulse at 0.0167 Hz.
Figure 49:
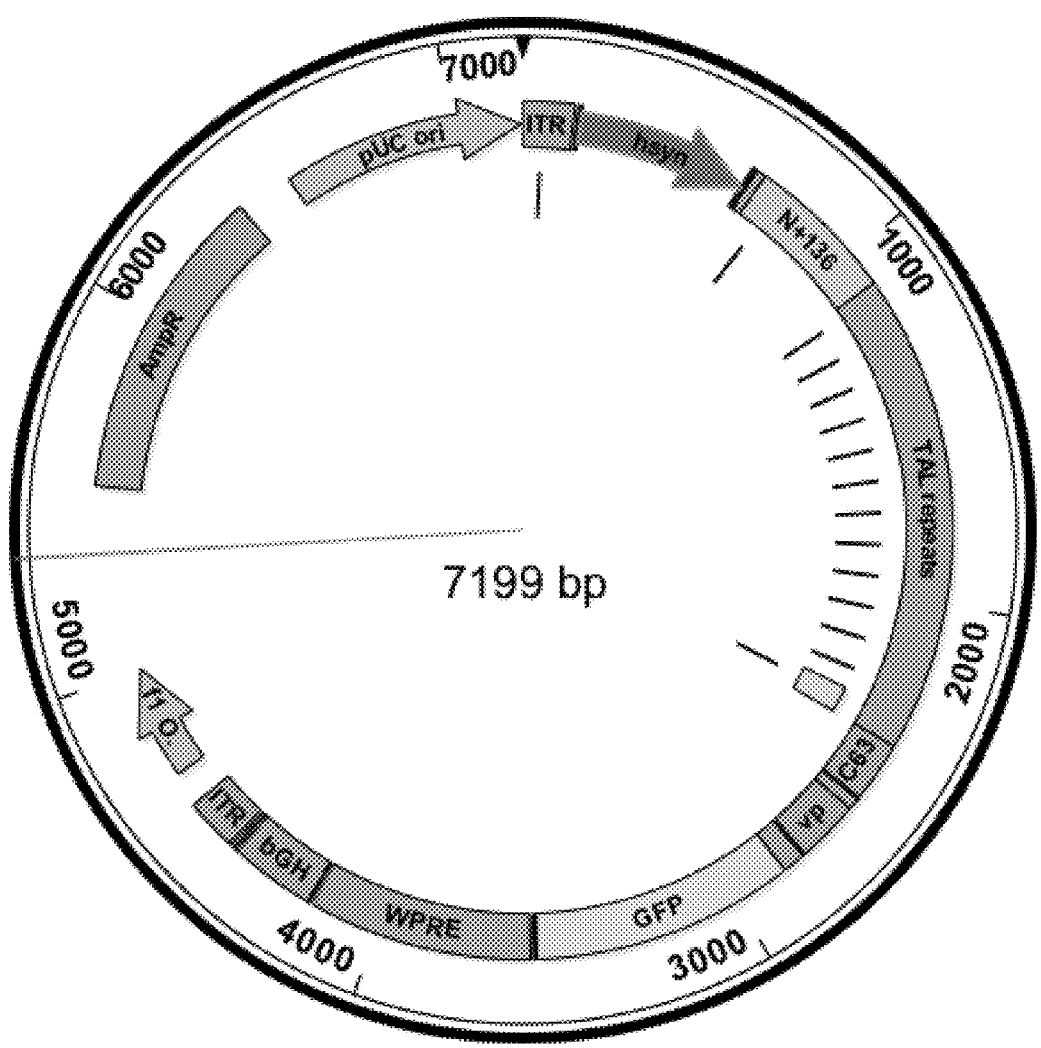
FIG. 49 shows a schematic of an AAV-promotor-TALE-effector construct. In the construct: hSyn=human synapsin 1 promoter; N+136=TALE N-term, AA+136 truncation; C63=TALE C-term, AA+63 truncation; vp=VP64 effector domain; GFP=green fluorescent protein; WPRE=Woodchuck Hepatitis Virus Posttranscriptional Regulatory Element; bGH=bovine growth hormone polyA; ITR=AAV inverted terminal repeat; AmpR=ampicillin resistance gene.

Manipulating endogenous gene expression presents various challenges, as the rate of expression depends on many factors, including regulatory elements, mRNA processing, and transcript stability (22, 23). Applicants sought to investigate the feasibility of using the system to modulate endogenous gene expression in primary neurons and the intact brain. To this end, Applicants pursued viral transduction as an effective method for TALE and LITE gene delivery into neurons. However, lentiviral delivery can compromise TALE integrity due to recombination of the tandem repeat DNA-binding domains during reverse transcription (26). To overcome this challenge, Applicants developed an adeno-associated virus (AAV)-based vector for the delivery of TALE genes and efficient process for AAV production (FIGS. 37A-B, FIG. 42, and Example 7). AAV has an ssDNA-based genome and is therefore less susceptible to recombination (27-29).

AAV1/2 (serotype AAV1/2, i.e., hybrid or mosaic AAV1/AAV2 capsid AAV) heparin purified concentrated virus protocol Media: D10+HEPES
500 ml bottle DMEM high glucose+Glutamax (GIBCO)
50 ml Hyclone FBS (heat-inactivated) (Thermo Fischer)
5.5 ml HEPES solution (1M, GIBCO)
Cells: low passage HEK293FT (passage <10 at time of virus production, thaw new cells of passage 2-4 for virus production, grow up for 3-5 passages)
Transfection Reagent: Polyethylenimine (PEI) "Max"
Dissolve 50 mg PEI "Max" in 50 ml sterile Ultrapure H20
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES
Passage everyday between 1:2 and 1:2.5
Advantageously do not allow cells to reach more than 85% confluency
  For T75
  Warm 10 ml HBSS (—Mg2+, —Ca2+, GIBCO)+1 ml TrypLE Express (GIBCO) per flask to 37° C. (Waterbath)
  Aspirate media fully
  Add 10 ml warm HBSS gently (to wash out media completely)
  Add 1 ml TrypLE per Flask
  Place flask in incubator (37° C.) for 1 min
  Rock flask to detach cells
  Add 9 ml D10+HEPES media (37° C.)
  Pipette up and down 5 times to generate single cell suspension
  Split at 1:2-1:2.5 (12 ml media for T75) ratio (if cells are growing more slowly, discard and thaw a new batch, they are not in optimal growth)
  transfer to T225 as soon as enough cells are present (for ease of handling large amounts of cells)
AAV Production (5*15 cm Dish Scale Per Construct):
Plate 10 million cells in 21.5 ml media into a 15 cm dish
Incubate for 18-22 hours at 37° C.
Transfection is ideal at 80% confluence
  Per Plate
Prewarm 22 ml media (D10+HEPES)
Prepare Tube with DNA Mixture (Use Endofree Maxiprep DNA):
  5.2 ug vector of interest plasmid
  4.35 ug AAV 1 serotype plasmid
  4.35 ug AAV 2 serotype plasmid
  10.4 ug pDF6 plasmid (adenovirus helper genes)
  →Vortex to mix
  Add 434 uL DMEM (no serum!)
  Add 130 ul PEI solution
  Vortex 5-10 seconds
  Add DNA/DMEM/PEI mixture to prewarmed media
  →Vortex briefly to mix
  Replace media in 15 cm dish with DNA/DMEM/PEI mixture
  →Return to 37° C. incubator
  →Incubate 48 h before harvesting (make sure medium isn't turning too acidic)
Virus Harvest:
1. aspirate media carefully from 15 cm dish dishes (advantageously do not dislodge cells)
2. Add 25 ml RT DPBS (Invitrogen) to each plate and gently remove cells with a cell scraper. Collect suspension in 50 ml tubes.
3. Pellet cells at 800×g for 10 minutes.
4. Discard supernatant
→Pause Point: Freeze Cell Pellet at −80 C if Desired
5. resuspend pellet in 150 mM NaCl, 20 mM Tris pH 8.0, use 10 ml per tissue culture plate.
6. Prepare a fresh solution of 10% sodium deoxycholate in dH2O. Add 1.25 ml of this per tissue culture plate for a final concentration of 0.5%. Add benzonase nuclease to a final concentration of 50 units per ml. Mix tube thoroughly.
7. Incubate at 37° C. for 1 hour (Waterbath).
8. Remove cellular debris by centrifuging at 3000×g for 15 mins. Transfer to fresh 50 ml tube and ensure all cell debris has been removed to prevent blocking of heparin columns.
Heparin Column Purification of AAV1/2:
1. Set up HiTrap heparin columns using a peristaltic pump so that solutions flow through the column at 1 ml per minute. It is important to ensure no air bubbles are introduced into the heparin column.
2. Equilibrate the column with 10 ml 150 mM NaCl, 20 mM Tris, pH 8.0 using the peristaltic pump.
3. Binding of virus: Apply 50 ml virus solution to column and allow to flow through.
4. Wash step 1: column with 20 ml 100 mM NaCl, 20 mM Tris, pH 8.0. (using the peristaltic pump)
5. Wash step 2: Using a 3 ml or 5 ml syringe continue to wash the column with 1 ml 200 mM NaCl, 20 mM Tris, pH 8.0, followed by 1 ml 300 mM NaCl, 20 mM Tris, pH 8.0.
→Discard the flow-through.
(prepare the syringes with different buffers during the 50 min flow through of virus solution above)
6. Elution Using 5 ml syringes and gentle pressure (flow rate of <1 ml/min) elute the virus from the column by applying:
  1.5 ml 400 mM NaCl, 20 mM Tris, pH 8.0
  3.0 ml 450 mM NaCl, 20 mM Tris, pH 8.0
  1.5 ml 500 mM NaCl, 20 mM Tris, pH 8.0
Collect these in a 15 ml centrifuge tube.
Concentration of AAV1/2:
1. Concentration step 1: Concentrate the eluted virus using Amicon ultra 15 ml centrifugal filter units with a 100,000 molecular weight cutoff. Load column eluate into the concentrator and centrifuge at 2000×g for 2 minutes (at room temperature. Check concentrated volume—it should be approximately 500 μl. If necessary, centrifuge in 1 min intervals until correct volume is reached.
2. buffer exchange: Add 1 ml sterile DPBS to filter unit, centrifuge in 1 min intervals until correct volume (500 ul) is reached.
3. Concentration step 2: Add 500 ul concentrate to an Amicon Ultra 0.5 ml 100K filter unit. Centrifuge at 6000 g for 2 min. Check concentrated volume—it should be approximately 100 μl. If necessary, centrifuge in 1 min intervals until correct volume is reached.
4. Recovery: Invert filter insert and insert into fresh collection tube. Centrifuge at 1000 g for 2 min.
→Aliquot and freeze at −80° C.
→1 ul is typically required per injection site, small aliquots (e.g. 5 ul) are therefore recommended (avoid freeze-thaw of virus).
→determine DNaseI-resistant GC particle titer using qPCR (see separate protocol)
Materials
Amicon Ultra, 0.5 ml, 100K; MILLIPORE; UFC510024
Amicon Ultra, 15 ml, 100K; MILLIPORE; UFC910024
Benzonase nuclease; Sigma-Aldrich, E1014

HiTrap Heparin cartridge; Sigma-Aldrich; 54836
Sodium deoxycholate; Sigma-Aldrich; D5670

AAV1 Supernatant Production Protocol

Media: D10+HEPES
500 ml bottle DMEM high glucose+Glutamax (Invitrogen)
50 ml Hyclone FBS (heat-inactivated) (Thermo Fischer)
5.5 ml HEPES solution (1M, GIBCO)
Cells: low passage HEK293FT (passage <10 at time of virus production)
Thaw new cells of passage 2-4 for virus production, grow up for 2-5 passages
Transfection reagent: Polyethylenimine (PEI) "Max"
Dissolve 50 mg PEI "Max" in 50 ml sterile Ultrapure H2O
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES Passage everyday between 1:2 and 1:2.5 Advantageously do let cells reach more than 85% confluency
For T75
  Warm 10 ml HBSS (—Mg2+, —Ca2+, GIBCO)+1 ml TrypLE Express (GIBCO) per flask to 37° C. (Waterbath)
  Aspirate media fully
  Add 10 ml warm HBSS gently (to wash out media completely)
  Add 1 ml TrypLE per Flask
  Place flask in incubator (37° C.) for 1 min
  Rock flask to detach cells
  Add 9 ml D10+HEPES media (37° C.)
  Pipette up and down 5 times to generate single cell suspension
  Split at 1:2-1:2.5 (12 ml media for T75) ratio (if cells are growing more slowly, discard and thaw a new batch, they are not in optimal growth)
  transfer to T225 as soon as enough cells are present (for ease of handling large amounts of cells)
AAV production (Single 15 cm Dish Scale)
Plate 10 million cells in 21.5 ml media into a 15 cm dish
Incubate for 18-22 hours at 37° C.
Transfection is ideal at 80% confluence per plate
Prewarm 22 ml media (D10+HEPES)
Prepare tube with DNA mixture (use endofree maxiprep DNA):
  5.2 ug vector of interest plasmid
  8.7 ug AAV 1 serotype plasmid
  10.4 ug DF6 plasmid (adenovirus helper genes)
Vortex to mix
Add 434 uL DMEM (no serum!)
Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48 h before harvesting (advantageously monitor to ensure medium is not turning too acidic)
Virus Harvest:
Remove supernatant from 15 cm dish
Filter with 0.45 um filter (low protein binding) Aliquot and freeze at −80° C.
Transduction (primary neuron cultures in 24-well format, SDIV)
Replace complete neurobasal media in each well of neurons to be transduced with fresh neurobasal (usually 400 ul out of 500 ul per well is replaced)
Thaw AAV supernatant in 37° C. waterbath
Let equilibrate in incubator for 30 min
Add 250 ul AAV supernatant to each well
Incubate 24 h at 37° C.
Remove media/supernatant and replace with fresh complete neurobasal
Expression starts to be visible after 48 h, saturates around 6-7 Days Post Infection
Constructs for pAAV plasmid with GOI should not exceed 4.8 kb including both ITRS
AAV Supernatant Production HEK 293FT cells (Life Technologies) were grown in antibiotic-free D10 media (DMEM high glucose with GlutaMax and Sodium Pyruvate, 10% heat-inactivated Hyclone FBS, and 1% 1M HEPES) and passaged daily at 1:2-2.5. The total number of passages was kept below 10 and cells were never grown beyond 85% confluence. The day before transfection, $1\times10^6$ cells in 21.5 mL of D10 media were plated onto 15 cm dishes and incubated for 18-22 hours or until ~80% confluence. For use as a transfection reagent, 1 mg/mL of PEI "Max" (Polysciences) was dissolved in water and the pH of the solution was adjusted to 7.1. For AAV production, 10.4 μg of pDF6 helper plasmid, 8.7 μg of pAAV1 serotype packaging vector, and 5.2 μg of pAAV vector carrying the gene of interest were added to 434 μL of serum-free DMEM and 1304, of PEI "Max" solution was added to the DMEM-diluted DNA mixture. The DNA/DMEM/PEI cocktail was vortexed and incubated at room temperature for 15 min. After incubation, the transfection mixture was added to 22 mL of complete media, vortexed briefly, and used to replace the media for a 15 cm dish of 293FT cells. For supernatant production, transfection supernatant was harvested at 48 hours, filtered through a 0.45 micron PVDF filter (Millipore), distributed into aliquots, and frozen for storage at −80° C.

To test the efficacy of AAV-mediated TALE delivery for modulating transcription in primary mouse cortical neurons, Applicants constructed six TALE-DNA binding domains targeting the genetic loci of three mouse neurotransmitter receptors: Grm5, Grin2a, and Grm2, which encode mGluR5, NMDA subunit 2A and mGluR2, respectively (FIG. 37C). To increase the likelihood of a target site accessibility, Applicants used mouse cortex DNase I sensitivity data from the UCSC genome browser to identify putative open chromatin regions. DNase I sensitive regions in the promoter of each target gene provided a guide for the selection of TALE binding sequences (FIG. 43). For each TALE, Applicants employed VP64 as a transcriptional activator or a quadruple tandem repeat of the mSin3 interaction domain (SID) (20, 30) as a repressor. Applicants have previously shown that a single SID fused to TALE downregulated a target gene effectively in 293FT cells (18). Hoping to further improve this TALE repressor, Applicants reasoned that four repeats of SID—analogous to the successful quadruple VP16 repeat architecture of VP64 (20)—might augment its repressive activity. This was indeed the case, as TALE-SID4X constructs enhanced repression ~2-fold over TALE-SID in 293FT cells (FIG. 44).

Applicants found that four out of six TALE-VP64 constructs (T1, T2, T5 and T6) efficiently activated their target genes Grm5 and Grm2 in AAV-transduced primary neurons by up to 3- and 8-fold, respectively (FIG. 37C). Similarly, four out of six TALE-SID4X repressors (T9, T10, T11, T12) reduced the expression of their endogenous targets Grin2a and Grm2 by up to 2- and 8-fold, respectively (FIG. 37C). Together, these results indicate that constitutive TALEs can positively or negatively modulate endogenous target gene expression in neurons. Notably, efficient activation or repression by a given TALE did not predict its efficiency at transcriptional modulation in the opposite direction. Therefore, multiple TALEs may need to be screened to identify the most effective TALE for a particular locus.

As a confirmation of TALE expression and activity in vivo, Applicants performed stereotactic injection of concentrated AAV vectors into the mouse prefrontal cortex. Delivery of constitutive TALE-VP64 AAV vectors resulted in robust TALE expression in the mouse prefrontal cortex (FIG. 37D-E). Tissue punches from the AAV-transduced brain regions showed that a TALE-VP64 targeting the Grm2 gene locus is able to activate mRNA levels by up to 2.5-fold (FIG. 37F).

In order to deliver LITEs into neurons using AAV, Applicants had to ensure that the total viral genome size, with the LITE transgenes included, did not exceed 4.8 kb[31, 32]. To that end, Applicants shortened the TALE N- and C-termini (keeping 136 aa in the N-terminus and 63 aa in the C-terminus) and exchanged the CRY2 PHR and CIB1 domains (TALE-CIB1 and CRY2 PHR-VP64; FIG. 38A). This switch allowed each component of LITE to fit into AAV vectors and did not reduce the efficacy of light-mediated transcription modulation (FIG. 45). These LITEs can be efficiently delivered into primary cortical neurons via co-transduction by a combination of two AAV vectors (FIG. 38B; delivery efficiencies of 83-92% for individual components with >80% co-transduction efficiency).

Figure 40:
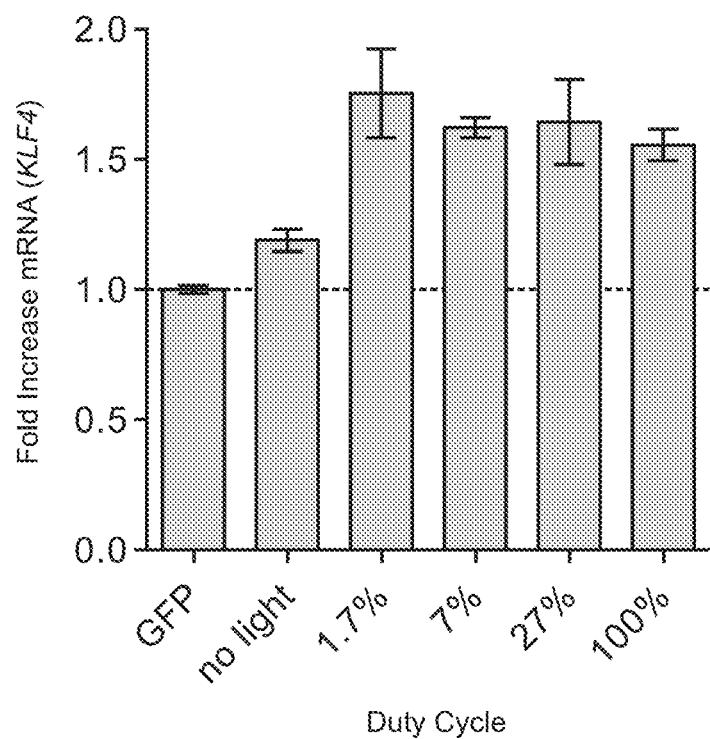
FIG. 40 depicts an impact of illumination duty cycle on LITE-mediated gene expression. Varying duty cycles (illumination as percentage of total time) were used to stimulate HEK293FT cells expressing LITEs targeting the KLF4 gene, in order to investigate the effect of duty cycle on LITE activity. KLF4 expression levels were compared to cells expressing GFP only. Stimulation parameters were: 466 nm, 5 mW/cm$^2$ for 24 h. Pulses were performed at 0.067 Hz with the following durations: 1.7%=0.25 s pulse, 7%=1 s pulse, 27%=4 s pulse, 100%=constant illumination.
Figure 41:
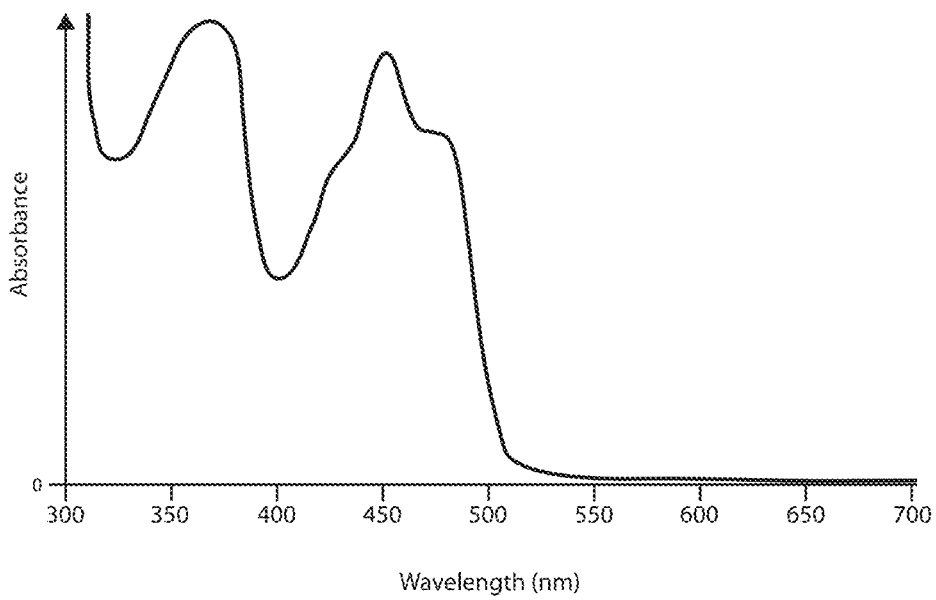
FIG. 41 depicts an illustration of the absorption spectrum of CRY2 in vitro. Cryptochrome 2 was optimally activated by 350-475 nm light[1]. A sharp drop in absorption and activation was seen for wavelengths greater than 480 nm. Spectrum was adapted from Banerjee, R. et al. The Signaling State of *Arabidopsis* Cryptochrome 2 Contains Flavin Semiquinone. *Journal of Biological Chemistry* 282, 14916-14922, doi:10.1074/jbc.M700616200 (2007).

When implementing a neuron specific light-stimulation protocol, cultured neurons proved to be much more sensitive to blue light than Neuro-2a cells. Stimulation parameters that Applicants previously optimized for Neuro 2a cells (466 nm, 5 mW/cm$^2$ intensity, 7% duty cycle with 1 s light pulse at 0.067 Hz for a total of 24 h) caused >50% toxicity in primary neurons. Applicants therefore tested survival with a lower duty cycle, as Applicants had previously observed that a wide range of duty cycles had little effect on LITE-mediated transcriptional activation (FIG. 40).

For a neuronal application of LITEs, Applicants selected the Grm2 TALE (T6), which exhibited the strongest level of target upregulation in primary neurons, based on Applicants' comparison of 6 constitutive TALE activators (FIG. 37C). Applicants investigated its function using 2 light pulsing frequencies with the same duty cycle of 0.8%. Both stimulation conditions achieved a ~7-fold light-dependent increase in Grm2 mRNA levels (FIG. 38C). Further study confirmed that, significant target gene expression increases could be attained quickly (4-fold upregulation within 4 h; FIG. 38D). In addition, Applicants observed significant upregulation of mGluR2 protein after stimulation, demonstrating that changes effected by LITEs at the mRNA level are translated to the protein domain (FIG. 38E). Taken together, these results confirm that LITEs enable temporally precise optical control of endogenous gene expression in neurons.

As a compliment to Applicants' previously implemented LITE activators, Applicants next engineered a LITE repressor based on the TALE-SID4X constructs. Constitutive Grm2 TALEs (T11 and T12, FIG. 38F) mediated the highest level of transcription repression, and were chosen as LITE repressors (FIG. 38F-G). Both light-induced repressors mediated significant downregulation of Grm2 expression, with 1.95-fold and 1.75-fold reductions for T11 and T12, respectively, demonstrating the feasibility of optically controlled repression in neurons (FIG. 38G).

Light-mediated control of gene expression would be particularly desirable in vivo. In contrast to current chemically inducible expression systems, LITEs have the potential for finer anatomical localization. Moreover, the kinetics of the system do not depend on drug diffusion, metabolism, or clearance, and stimulation can be achieved without drug-related side effects. To apply the LITE system in vivo, Applicants stereotactically delivered a 1:1 mixture of high concentration AAV vectors ($10^{12}$ DNAseI resistant particles/mL) carrying the Grm2-targeting T6-CIB1 and CRY2 PHR-VP64 LITE components into the infralimbic cortex (ILC) of wildtype C57BL/6N mice. To provide optical stimulation of LITE-expressing neurons in vivo, Applicants also implanted a fiber optic cannula at the injection site (FIG. 38H)[33]. Neurons in the injection site were efficiently co-transduced by both viruses, with >80% of transduced cells expressing both TALE12-CIB1 and CRY2 PHR-VP64 (FIGS. 38I and 48). 8 days post-surgery, Applicants stimulated the ILC by connecting a solid-state 473 nm laser to the implanted fiber cannula. Following a 12 h stimulation period (5 mW, 0.8% duty cycle using 0.5 s light pulses at 0.0167 Hz), brain tissue from the fiber optic cannula implantation site was analyzed (FIG. 38I) for changes in Grm2 mRNA. Applicants observed a significant increase in Grm2 mRNA after light stimulation compared with unstimulated ILC (2.1-fold, p<0.01 vs. 1.3-fold background FIG. 38J), successfully demonstrating the utility of the LITE system for altering gene expression in vivo. This experiment suggests the potential value of LITEs for probing gene functions in the brain.

The investigation of dynamic transcriptional networks in heterogeneous tissues such as the brain would benefit greatly from spatiotemporally precise in vivo gene regulation. Such a system would allow researchers to ask questions about the role of dynamic gene regulation in processes as diverse as development, learning, memory, and disease progression. LITEs can be used to enable temporally precise, spatially-targeted, and bi-modal control of endogenous gene expression in cell lines, primary neurons, and in the mouse brain in vivo. The TALE DNA binding component of LITEs can be customized to target a wide range of genomic loci. Independently, novel functionalities can be achieved via alteration of the LITE effector domain. This system provides a powerful addition to existing optogenetic platforms, establishing a highly generalizable mode of altering endogenous gene transcription using light. Future work will increase the potency of LITE-mediated transcription modulation, reduce the level of background activity, and expand the range of wavelengths through which LITEs may be controlled. This may be achieved through exploration of other naturally occurring light-sensitive proteins[34-37] or through directed evolution[38-41] of cryptochrome proteins. Finally, the modular design of the LITE system provides the opportunity for the development of a broad array of light-switchable tools for reverse-engineering genetic and epigenetic functions in a variety of biological systems.

LITE constructs were transfected into in Neuro 2A cells using GenJetAAV vectors carrying TALE or LITE constructs were used to transduce mouse primary embryonic cortical neurons as well as the mouse brain in vivo. RNA was extracted and reverse transcribed and mRNA levels were measured using TaqMan-based RT-qPCR. Light emit-

REFERENCES

1. Deisseroth, K. Optogenetics. *Nature methods* 8, 26-29 (2011).
2. Zhang, F. et al. The microbial opsin family of optogenetic tools. *Cell* 147, 1446-1457 (2011).
3. Yizhar, O., Fenno, L. E., Davidson, T. J., Mogri, M. & Deisseroth, K. Optogenetics in neural systems. *Neuron* 71, 9-34 (2011).
4. Airan, R. D., Thompson, K. R., Fenno, L. E., Bernstein, H. & Deisseroth, K. Temporally precise in vivo control of intracellular signalling. *Nature* 458, 1025-1029 (2009).
5. Levskaya, A., Weiner, O.D., Lim, W. A. & Voigt, C. A. Spatiotemporal control of cell signalling using a light-switchable protein interaction. *Nature* 461, 997-1001 (2009).
6. Yazawa, M., Sadaghiani, A. M., Hsueh, B. & Dolmetsch, R. E. Induction of protein-protein interactions in live cells using light. *Nat Biotechnol* 27, 941-945 (2009).
7. Strickland, D. et al. TULIPs: tunable, light-controlled interacting protein tags for cell biology. *Nature methods* 9, 379-384 (2012).
8. Kennedy, M. J. et al. Rapid blue-light-mediated induction of protein interactions in living cells. *Nature methods* 7, 973-975 (2010).
9. Shimizu-Sato, S., Huq, E., Tepperman, J. M. & Quail, P. H. A light-switchable gene promoter system. *Nat Biotechnol* 20, 1041-1044 (2002).
10. Ye, H., Daoud-El Baba, M., Peng, R. W. & Fussenegger, M. A synthetic optogenetic transcription device enhances blood-glucose homeostasis in mice. Science 332, 1565-1568 (2011).
11. Wang, X., Chen, X. & Yang, Y. Spatiotemporal control of gene expression by a light-switchable transgene system. *Nature methods* 9, 266-269 (2012).
12. Polstein, L. R. & Gersbach, C. A. Light-inducible spatiotemporal control of gene activation by customizable zinc finger transcription factors. *J Am Chem Soc* 134, 16480-16483 (2012).
13. Boch, J. et al. Breaking the code of DNA binding specificity of TAL-type III effectors. *Science* 326, 1509-1512 (2009).
14. Moscou, M. J. & Bogdanove, A. J. A simple cipher governs DNA recognition by TAL effectors. *Science* 326, 1501 (2009).
15. Zhang, F. et al. Efficient construction of sequence-specific TAL effectors for modulating mammalian transcription. *Nat Biotechnol* 29, 149-153 (2011).
16. Miller, J. C. et al. A TALE nuclease architecture for efficient genome editing. *Nat Biotechnol* 29, 143-148 (2011).
17. Geissler, R. et al. Transcriptional activators of human genes with programmable DNA-specificity. *PLoS One* 6, e19509 (2011).
18. Cong, L., Zhou, R., Kuo, Y.-c., Cunniff, M. & Zhang, F. Comprehensive interrogation of natural TALE DNA-binding modules and transcriptional repressor domains. *Nat Commun* 3, 968 (2012).
19. Liu, H. et al. Photoexcited CRY2 interacts with CIB1 to regulate transcription and floral initiation in *Arabidopsis*. *Science* 322, 1535-1539 (2008).
20. Beerli, R. R., Segal, D. J., Dreier, B. & Barbas, C. F., 3rd Toward controlling gene expression at will: specific regulation of the erbB-2/HER-2 promoter by using polydactyl zinc finger proteins constructed from modular building blocks. *Proc Natl Acad Sci USA* 95, 14628-14633 (1998).
21. Banerjee, R. et al. The signaling state of *Arabidopsis* cryptochrome 2 contains flavin semiquinone. *J Biol Chem* 282, 14916-14922 (2007).
22. Moore, M. J. & Proudfoot, N.J. Pre-mRNA processing reaches back to transcription and ahead to translation. *Cell* 136, 688-700 (2009).
23. Proudfoot, N.J., Furger, A. & Dye, M. J. Integrating mRNA processing with transcription. *Cell* 108, 501-512 (2002).
24. Kang, H. J. et al. Spatio-temporal transcriptome of the human brain. *Nature* 478, 483-489 (2011).
25. Colantuoni, C. et al. Temporal dynamics and genetic control of transcription in the human prefrontal cortex. *Nature* 478, 519-523 (2011).
26. Holkers, M. et al. Differential integrity of TALE nuclease genes following adenoviral and lentiviral vector gene transfer into human cells. *Nucleic Acids Res* (2012).
27. Fisher, K. J. et al. Recombinant adeno-associated virus for muscle directed gene therapy. *Nat Med* 3, 306-312 (1997).
28. Ledley, F. Pharmaceutical Approach to Somatic Gene Therapy. *Pharm Res* 13, 1595-1614 (1996).
29. Logan, G. J., Wang, L., Zheng, M., Coppel, R. L. & Alexander, I. E. Antigen fusion with C3d3 augments or inhibits humoral immunity to AAV genetic vaccines in a transgene-dependent manner. *Immunol Cell Biol* 88, 228-232 (2009).
30. Ayer, D. E., Laherty, C. D., Lawrence, Q. A., Armstrong, A. P. & Eisenman, R. N. Mad proteins contain a dominant transcription repression domain. *Molecular and Cellular Biology* 16, 5772-5781 (1996).
31. Wu, Z., Yang, H. & Colosi, P. Effect of Genome Size on AAV Vector Packaging. *Mol Ther* 18, 80-86 (2009).
32. Dong JY, F. P., Frizzell RA Quantitative analysis of the packaging capacity of recombinant adeno-associated virus. *Human Gene Therapy* 7, 2101-2112 (1996).
33. Zhang, F. et al. Optogenetic interrogation of neural circuits: technology for probing mammalian brain structures. *Nat Protoc* 5, 439-456 (2010).
34. Zoltowski, B. D. & Crane, B. R. Light Activation of the LOV Protein Vivid Generates a Rapidly Exchanging Dimer†‡. *Biochemistry* 47, 7012-7019 (2008).
35. Zoltowski, B. D. et al. Conformational Switching in the Fungal Light Sensor Vivid. *Science* 316, 1054-1057 (2007).
36. Zhou, X. X., Chung, H. K., Lam, A. J. & Lin, M. Z. Optical Control of Protein Activity by Fluorescent Protein Domains. *Science* 338, 810-814 (2012).
37. Strickland, D. et al. TULIPs: tunable, light-controlled interacting protein tags for cell biology. *Nat Meth* 9, 379-384 (2012).
38. Shaner, N.C. et al. Improved monomeric red, orange and yellow fluorescent proteins derived from Discosoma sp. red fluorescent protein. *Nat Biotech* 22, 1567-1572 (2004).
39. Mukherjee, A., Weyant, K., Walker, J. & Schroeder, C. Directed evolution of bright mutants of an oxygen-independent flavin-binding fluorescent protein from *Pseudomonas putida*. *Journal of Biological Engineering* 6, 20 (2012).
40. Nguyen, A. W. & Daugherty, P. S. Evolutionary optimization of fluorescent proteins for intracellular FRET. *Nat Biotech* 23, 355-360 (2005).

41. Shu, X. et al. Mammalian Expression of Infrared Fluorescent Proteins Engineered from a Bacterial Phytochrome. *Science* 324, 804-807 (2009).
42. McClure, C., Cole, K. L., Wulff, P., Klugmann, M. & Murray, A. J. Production and titering of recombinant adeno-associated viral vectors. *J Vis Exp*, e3348 (2011).

Neuro 2a cells (Sigma-Aldrich) were grown in media containing a 1:1 ratio of OptiMEM (Life Technologies) to high-glucose DMEM with GlutaMax and Sodium Pyruvate (Life Technologies) supplemented with 5% HyClone heat-inactivated FBS (Thermo Scientific), 1% penicillin/streptomycin (Life Technologies), and passaged at 1:5 every 2 days. 120,000 cells were plated in each well of a 24-well plate 18-20 h prior to transfection. 1 h before transfection, media was changed to DMEM supplemented with 5% HyClone heat-inactivated FBS and 1% penicillin/streptomycin. Cells were transfected with 1.0 µg total of construct DNA (at equimolar ratios) per well with 1.5 µL of GenJet (SignaGen Laboratories) transfection reagent according to the manufacturer's instructions. Media was exchanged 24 h and 44 h post-transfection and light stimulation was started at 48 h. Stimulation parameters were: 5 mW/cm2, 466 nm, 7% duty cycle (1 s light pulse 0.067 Hz) for 24 h unless indicated otherwise in figure legends. RNA was extracted using the RNeasy kit (Qiagen) according to manufacturer's instructions and 1 µg of RNA per sample was reverse-transcribed using qScript (Quanta Biosystems). Relative mRNA levels were measured by quantitative real-time PCR (qRT-PCR) using TaqMan probes specific for the targeted gene as well as GAPDH as an endogenous control (Life Technologies, see Table 2 for Taqman probe IDs). ΔΔCt analysis was used to obtain fold-changes relative to negative controls transduced with GFP only and subjected to light stimulation. Toxicity experiments were conducted using the LIVE/DEAD assay kit (Life Technologies) according to instructions.

293FT cells (Life Technologies) were grown in antibiotic-free D10 media (DMEM high glucose with GlutaMax and Sodium Pyruvate, 10% heat-inactivated Hyclone FBS, and 1% 1M HEPES) and passaged daily at 1:2-2.5. The total number of passages was kept below 10 and cells were never grown beyond 85% confluence. The day before transfection, 1×10⁶ cells in 21.5 mL of D10 media were plated onto 15 cm dishes and incubated for 18-22 hours or until ~80% confluence. For use as a transfection reagent, 1 mg/mL of PEI "Max" (Polysciences) was dissolved in water and the pH of the solution was adjusted to 7.1. For AAV production, 10.4 µg of pDF6 helper plasmid, 8.7 µg of pAAV1 serotype packaging vector, and 5.2 µg of pAAV vector carrying the gene of interest were added to 434 µL of serum-free DMEM and 130 µL of PEI "Max" solution was added to the DMEM-diluted DNA mixture. The DNA/DMEM/PEI cocktail was vortexed and incubated at room temperature for 15 min. After incubation, the transfection mixture was added to 22 mL of complete media, vortexed briefly, and used to replace the media for a 15 cm dish of 293FT cells. For supernatant production, transfection supernatant was harvested at 48 h, filtered through a 0.45 µm PVDF filter (Millipore), distributed into aliquots, and frozen for storage at −80° C.

Dissociated cortical neurons were prepared from C57BL/6N mouse embryos on E16 (Charles River Labs). Cortical tissue was dissected in ice-cold HBSS—(50 mL 10×HBSS, 435 mL dH$_2$O, 0.3 M HEPES pH 7.3, and 1% penicillin/streptomycin). Cortical tissue was washed 3× with 20 mL of ice-cold HBSS and then digested at 37° C. for 20 min in 8 mL of HBSS with 240 µL of 2.5% trypsin (Life Technologies). Cortices were then washed 3 times with 20 mL of warm HBSS containing 1 mL FBS. Cortices were gently triturated in 2 ml of HBSS and plated at 150,000 cells/well in poly-D-lysine coated 24-well plates (BD Biosciences). Neurons were maintained in Neurobasal media (Life Technologies), supplemented with 1× B27 (Life Technologies), GlutaMax (Life Technologies) and 1% penicillin/streptomycin.

Primary cortical neurons were transduced with 250 µL of AAV1 supernatant on DIV 5. The media and supernatant were replaced with regular complete neurobasal the following day. Neurobasal was exchanged with Minimal Essential Medium (Life Technologies) containing 1× B27, GlutaMax (Life Technologies) and 1% penicillin/streptomycin 6 days after AAV transduction to prevent formation of phototoxic products from HEPES and riboflavin contained in Neurobasal during light stimulation.

Light stimulation was started 6 days after AAV transduction (DIV 11) with an intensity of 5 mW/cm$^2$, duty cycle of 0.8% (250 ms pulses at 0.033 Hz or 500 ms pulses at 0.016 Hz), 466 nm blue light for 24 h unless indicated otherwise in figure legends. RNA extraction and reverse transcription were performed using the Cells-to-Ct kit according to the manufacturers instructions (Life Technologies). Relative mRNA levels were measured by quantitative real-time PCR (qRT-PCR) using TaqMan probes as described above for Neuro 2a cells.

For immunohistochemistry of primary neurons, cells were plated on poly-D-lysine/laminin coated coverslips (BD Biosciences) after harvesting. AAV1-transductions were performed as described above. Neurons were fixed 7 days post-transduction with 4% paraformaldehyde (Sigma Aldrich) for 15 min at RT. Blocking and permeabilization were performed with 10% normal goat serum (Life Technologies) and 0.5% Triton-X100 (Sigma-Aldrich) in DPBS (Life Technologies) for 1 h at room temperature. Neurons were incubated with primary antibodies overnight at 4° C., washed 3× with DPBS and incubated with secondary antibodies for 90 min at RT. For antibody providers and concentrations used, see Table 3. Coverslips were finally mounted using Prolong Gold Antifade Reagent with DAPI (Life Technologies) and imaged on an Axio Scope A.1 (Zeiss) with an X-Cite 120Q light source (Lumen Dynamics). Image were acquired using an AxioCam MRm camera and AxioVision 4.8.2.

For preparation of total protein lysates, primary cortical neurons were harvested after light stimulation (see above) in ice-cold lysis buffer (RIPA, Cell Signaling; 0.1% SDS, Sigma-Aldrich; and cOmplete ultra protease inhibitor mix, Roche Applied Science). Cell lysates were sonicated for 5 min at 'M' setting in a Bioruptor sonicator (Diagenode) and centrifuged at 21,000×g for 10 min at 4° C. Protein concentration was determined using the RC DC protein assay (Bio-Rad). 30-40 µg of total protein per lane was separated under non-reducing conditions on 4-15% Tris-HCl gels (Bio-Rad) along with Precision Plus Protein Dual Color Standard (Bio-Rad) After wet electrotransfer to polyvinylidene difluoride membranes (Millipore) and membrane blocking for 45 min in 5% BLOT-QuickBlocker (Millipore) in Tris-buffered saline (TBS, Bio-Rad), western blots were probed with anti-mGluR2 (Abcam, 1:1.000) and anti-α-tubulin (Sigma-Aldrich 1:20,000) overnight at 4° C., followed by washing and anti-mouse-IgG HRP antibody incubation (Sigma-Aldrich, 1:5,000-1:10,000). For further antibody details see Table 3. Detection was performed via ECL Western blot substrate (SuperSignal West Femto Kit, Thermo Scientific). Blots were imaged with an AlphaImager (Innotech) system, and quantified using ImageJ software 1.46r.

Production of concentrated and purified AAV for stereotactic injection in-vivo was done using the same initial steps outlined above for production of AAV1 supernatant. However, for transfection, equal ratios of AAV1 and AAV2 serotype plasmids were used instead of AAV1 alone. 5 plates were transfected per construct and cells were harvested with a cell-scraper 48 h post transfection. Purification of AAV1/2 particles was performed using HiTrap heparin affinity columns (GE Healthcare)[42]. Applicants added a second concentration step down to a final volume of 100 µl per construct using an Amicon 500 µl concentration column (100 kDa cutoff, Millipore) to achieve higher viral titers. Titration of AAV was performed by qRT-PCR using a custom Taqman probe for WPRE (Life Technologies). Prior to qRT-PCR, concentrated AAV was treated with DNaseI (New England Biolabs) to achieve a measurement of DNaseI-resistant particles only. Following DNaseI heat-inactivation, the viral envelope was degraded by proteinase K digestion (New England Biolabs). Viral titer was calculated based on a standard curve with known WPRE copy numbers.

Adult (10-14 weeks old) male C57BL/6N mice were anaesthetized by intraperitoneal (i.p.) injection of Ketamine/Xylazine (100 mg/kg Ketamine and 10 mg/kg Xylazine) and pre-emptive analgesia was given (Buprenex, 1 mg/kg, i.p.). Craniotomy was performed according to approved procedures and 1 µl of AAV1/2 was injected into ILC at 0.35/1.94/−2.94 (lateral, anterior and inferior coordinates in mm relative to bregma). During the same surgical procedure, an optical cannula with fiber (Doric Lenses) was implanted into ILC unilaterally with the end of the optical fiber located at 0.35/1.94/−2.64 relative to bregma. The cannula was affixed to the skull using Metabond dental cement (Parkell Inc) and Jet denture repair (Lang dental) to build a stable cone around it. The incision was sutured and proper post-operative analgesics were administered for three days following surgery.

Mice were injected with a lethal dose of Ketamine/Xylazine anaesthetic and transcardially perfused with PBS and 4% paraformaldehyde (PFA). Brains were additionally fixed in 4% PFA at 4° C. overnight and then transferred to 30% sucrose for cryoprotection overnight at room temperature. Brains were then transferred into Tissue-Tek Optimal Cutting Temperature (OCT) Compound (Sakura Finetek) and frozen at −80° C. 18 µm sections were cut on a cryostat (Leica Biosystems) and mounted on Superfrost Plus glass slides (Thermo Fischer). Sections were post-fixed with 4% PFA for 15 min, and immunohistochemistry was performed as described for primary neurons above.

8 days post-surgery, awake and freely moving mice were stimulated using a 473 nm laser source (OEM Laser Systems) connected to the optical implant via fiber patch cables and a rotary joint. Stimulation parameters were the same as used on primary neurons: 5 mW (total output), 0.8% duty cycle (500 ms light pulses at 0.016 Hz) for a total of 12 h. Experimental conditions, including transduced constructs and light stimulation are listed in Table 4.

After the end of light stimulations, mice were euthanized using CO2 and the prefrontal cortices (PFC) were quickly dissected on ice and incubated in RNA later (Qiagen) at 4° C. overnight. 200 µm sections were cut in RNA later at 4° C. on a vibratome (Leica Biosystems). Sections were then frozen on a glass coverslide on dry ice and virally transduced ILC was identified under a fluorescent stereomicroscope (Leica M165 FC). A 0.35 mm diameter punch of ILC, located directly ventrally to the termination of the optical fiber tract, was extracted (Harris uni-core, Ted Pella). The brain punch sample was then homogenized using an RNase-free pellet-pestle grinder (Kimble Chase) in 50 µl Cells-to-Ct RNA lysis buffer and RNA extraction, reverse transcription and qRT-PCR was performed as described for primary neuron samples.

All experiments were performed with a minimum of three independent biological replicates. Statistical analysis was performed with Prism (GraphPad) using student's t-test when comparing two conditions, ANOVA with Tukey's post-hoc analysis when comparing multiple samples with each other, ANOVA with Duncan's post-hoc analysis when comparing multiple samples to the negative control, and two-way ANOVA with Bonferroni post-hoc analysis to compare multiple groups over time.

Example 7

Development of AAV1 supernatant process: Traditional AAV particle generation required laborious production and purification processes, and made testing many constructs in parallel impractical (4). In this study, a simple yet highly effective process of AAV production using filtered supernatant from transfected 293FT cells (FIG. 42). Recent reports indicate that AAV particles produced in 293FT cells could be found not only it the cytoplasm but also at considerable amounts in the culture media (5). The ratio of viral particles between the supernatant and cytosol of host cells varied depending on the AAV serotype, and secretion was enhanced if polyethylenimine (PEI) was used to transfect the viral packaging plasmids (5). In the current study, it was found that $2 \times 10^5$ 293FT cells transfected with AAV vectors carrying TALEs (FIG. 37A) and packaged using AAV1 serotype were capable of producing 250 µl of AAV1 at a concentration of $5.6 \pm 0.24 \times 10^{10}$ DNaseI resistant genome copies (gc) per mL. 250 µl of filtered supernatant was able to transduce 150,000 primary cortical neurons at efficiencies of 80-90% (FIGS. 37B and 42B). This is a dramatic increase over the 1-2% transduction efficiency achieved using lentivirus supernatant produced from the same number of 293FT cells (FIG. 42B).

TABLE 2

Product information for all Taqman probes (Life Technologies)

| Target | Species | Probe # |
| --- | --- | --- |
| Ngn2 | mouse | Mm00437603_g1 |
| Grm5 (mGluR5) | mouse | Mm00690332_m1 |
| Grm2 (mGluR2) | mouse | Mm01235831_m1 |
| Grin2a (NMDAR2A) | mouse | Mm00433802_m1 |
| GAPD (GAPDH) | mouse | 4352932E |
| KLF4 | human | Hs00358836_m1 |
| GAPD (GAPDH) | human | 4352934E |
| WPRE | custom | |

TABLE 3

Clone, product numbers and concentrations for antibodies used in this study

Primary Antibodies

| Target | Host | Clone # | Manufacturer | Product # | IsoType | Concentration |
|---|---|---|---|---|---|---|
| mGluR2 | mouse | mG2Na-s | Abcam | Ab15672 | IgG | 1:1000 |
| α-tubulin | mouse | B-5-1-2 | Sigma-Aldrich | T5168 | IgG1 | 1:20000 |
| NeuN | mouse | A60 | Millipore | MAB377 | IgG1 | 1:200 |
| HA (Alexa Fluor 594 conjugated) | mouse | 6E2 | Cell Signaling | 3444 | IgG1 | 1:100 |
| GFP | chicken | polyclonal | Aves Labs | GFP-1020 | IgY | 1:500 |

Secondary Antibodies

| Target | Host | Conjugate | Manufacturer | Product # | Concentration |
|---|---|---|---|---|---|
| mouse IgG | goat | HRP | Sigma-Aldrich | A9917 | 1:5000-10000 |
| mouse IgG | goat | Alexa Fluor 594 | Life Technologies | A11005 | 1:1000 |
| chicken IgG | Goat | Alexa Fluor 488 | Life Technologies | A11039 | 1:1000 |

TABLE 4

Viral transduction and light stimulation parameters for in vivo LITE-mediated activation of Grm2 in the mouse infralimbic cortex (ILC). Grm2 mRNA levels in the ipsilateral LITE-expressing hemisphere are compared with the contralateral mCherry-expressing control hemisphere for all three experimental conditions shown in FIG. 38J.

| Experimental condition | ILC Hemisphere (ipsilateral) | | | ILC Hemisphere (contralateral) |
|---|---|---|---|---|
| | AAV vector | Light stimulation | | AAV vector |
| GFP | GFP | yes | | mCherry |
| LITEs/no Light | TALE-CIB1::CRY2PHR-VP64 | no | | mCherry |
| LITEs/+Light | TALE-CIB1::CRY2PHR-VP64 | yes | | mCherry |

Sequences of constructs used in Neuro-2A cells (FIGS. 35, 36)

```
>TALE(Ngn2)(underlined) - NLS (in italics)-CRY2 (in bold)
                                              (SEQ ID NO: 168)
MSRTRLPSPPAPSPAFSADSFSDLLRQFDPSLFNTSLFDSLPPFGAHHTEAATGEWDEVQSGLR

AADAPPPTMRVAVTAARPPRAKPAPPRRAAQPSDASPAAQVDLRTLGYSQQQQEKIKPKVRSTV

AQHHEALVGHGFTHAHIVALSQHPAALGTVAVKYQDMIAALPEATHEAIVGVGKQWSGARALEA

LLTVAGELRGPPLQLDTGQLLKIAKRGGVTAVEAVHAWRNALTGAPLNLTPEQVVAIASNNGGK

QALETVQRLLPVLCQAHGLTPEQVVAIASHDGGKQALETVQRLLPVLCQAHGLTPEQVVAIASH

DGGKQALETVQRLLPVLCQAHGLTPEQVVAIASNIGGKQALETVQRLLPVLCQAHGLTPEQVVA

IASNNGGKQALETVQRLLPVLCQAHGLTPEQVVAIASNGGGKQALETVQRLLPVLCQAHGLTPE

QVVAIASHDGGKQALETVQRLLPVLCQAHGLTPEQVVAIASNIGGKQALETVQRLLPVLCQAHG

LTPEQVVAIASHDGGKQALETVQRLLPVLCQAHGLTPEQVVAIASNNGGKQALETVQRLLPVLC

QAHGLTPEQVVAIASNGGGKQALETVQRLLPVLCQAHGLTPEQVVAIASHDGGKQALETVQRLL

PVLCQAHGLTPEQVVAIASHDGGKQALETVQRLLPVLCQAHGLTPEQVVAIASNNGGKQALETV

QRLLPVLCQAHGLTPEQVVAIASHDGGKQALETVQRLLPVLCQAHGLTPEQVVAIASHDGGKQA

LETVQRLLPVLCQAHGLTPEQVVAIASHDGGRPALESIVAQLSRPDPALAALTNDHLVALACLG

GRPALDAVKKGLPHAPALIKRTNRRIPERTSHRVADHAQVVRVLGFFQCHSHPAQAFDDAMTQF

GMSRHGLLQLFRRVGVTELEARSGTLPPASQRWDRILQASGMKRAKPSPTSTQTPDQASLHAFA
```

<u>DSLERDLDAPSPMHEGDQTRAS</u>*SPKKKRKVEAS*KMDKKTIVWFRRDLRIEDNPALAAAAHEGS

VFPVFIWCPEEEGQFYPGRASRWWMKQSLAHLSQSLKALGSDLTLIKTHNTISAILDCIRVTGA

TKVVFNHLYDPVSLVRDHTVKEKLVERGISVQSYNGDLLYEPWEIYCEKGKPFTSFNSYWKKCL

DMSIESVMLPPPWRLMPITAAAEAIWACSIEELGLENEAEKPSNALLTRAWSPGWSNADKLLNE

FIEKQLIDYAKNSKKVVGNSTSLLSPYLHFGEISVRHVFQCARMKQIIWARDKNSEGEESADLF

LRGIGLREYSRYICFNFPFTHEQSLLSHLRFFPWDADVDKFKAWRQGRTGYPLVDAGMRELWAT

GWMHNRIRVIVSSFAVKFLLLPWKWGMKYFWDTLLDADLECDILGWQYISGSIPDGHELDRLDN

PALQGAKYDPEGEYIRQWLPELARLPTEWIHHPWDAPLTVLKASGVELGTNYAKPIVDIDTARE

LLAKAISRTREAQIMIGAAPDEIVADSFEALGANTIKEPGLCPSVSSNDQQVPSAVRYNGSKRV

KPEEEEERDMKKSRGFDERELFSTAESSSSSSVFFVSQSCSLASEGKNLEGIQDSSDQITTSLG

KNG

>TALE(Ngn2)(underlined) -NLS (in italics)-CRY2PHR (in bold)
(SEQ ID NO: 169)

<u>MSRTRLPSPPAPSPAFSADSFSDLLRQFDPSLFNTSLFDSLPPFGAHHTEAATGEWDEVQSGLR</u>

<u>AADAPPPTMRVAVTAARPPRAKPAPRRRAAQPSDASPAAQVDLRTLGYSQQQQEKIKPKVRSTV</u>

<u>AQHHEALVGHGFTHAHIVALSQHPAALGTVAVKYQDMIAALPEATHEAIVGVGKQWSGARALEA</u>

<u>LLTVAGELRGPPLQLDTGQLLKIAKRGGVTAVEAVHAWRNALTGAPLNLTPEQVVAIASNNGGK</u>

<u>QALETVQRLLPVLCQAHGLTPEQVVAIASHDGGKQALETVQRLLPVLCQAHGLTPEQVVAIASH</u>

<u>DGGKQALETVQRLLPVLCQAHGLTPEQVVAIASNIGGKQALETVQRLLPVLCQAHGLTPEQVVA</u>

<u>IASNNGGKQALETVQRLLPVLCQAHGLTPEQVVAIASNGGGKQALETVQRLLPVLCQAHGLTPE</u>

<u>QVVAIASHDGGKQALETVQRLLPVLCQAHGLTPEQVVAIASNIGGKQALETVQRLLPVLCQAHG</u>

<u>LTPEQVVAIASHDGGKQALETVQRLLPVLCQAHGLTPEQVVAIASNNGGKQALETVQRLLPVLC</u>

<u>QAHGLTPEQVVAIASNGGGKQALETVQRLLPVLCQAHGLTPEQVVAIASHDGGKQALETVQRLL</u>

<u>PVLCQAHGLTPEQVVAIASHDGGKQALETVQRLLPVLCQAHGLTPEQVVAIASNNGGKQALETV</u>

<u>QRLLPVLCQAHGLTPEQVVAIASHDGGKQALETVQRLLPVLCQAHGLTPEQVVAIASHDGGKQA</u>

<u>LETVQRLLPVLCQAHGLTPEQVVAIASHDGGRPALESIVAQLSRPDPALAALTNDHLVALACLG</u>

<u>GRPALDAVKKGLPHAPALIKRTNRRIPERTSHRVADHAQVVRVLGFFQCHSHPAQAFDDAMTQF</u>

<u>GMSRHGLLQLFRRVGVTELEARSGTLPPASQRWDRILQASGMKRAKPSPTSTQTPDQASLHAFA</u>

<u>DSLERDLDAPSPMHEGDQTRAS</u>*SPKKKRKVEAS*KMDKKTIVWFRRDLRIEDNPALAAAAHEGS

VFPVFIWCPEEEGQFYPGRASRWWMKQSLAHLSQSLKALGSDLTLIKTHNTISAILDCIRVTGA

TKVVFNHLYDPVSLVRDHTVKEKLVERGISVQSYNGDLLYEPWEIYCEKGKPFTSFNSYWKKCL

DMSIESVMLPPPWRLMPITAAAEAIWACSIEELGLENEAEKPSNALLTRAWSPGWSNADKLLNE

FIEKQLIDYAKNSKKVVGNSTSLLSPYLHFGEISVRHVFQCARMKQIIWARDKNSEGEESADLF

LRGIGLREYSRYICFNFPFTHEQSLLSHLRFFPWDADVDKFKAWRQGRTGYPLVDAGMRELWAT

GWMHNRIRVIVSSFAVKFLLLPWKWGMKYFWDTLLDADLECDILGWQYISGSIPDGHELDRLDN

PALQGAKYDPEGEYIRQWLPELARLPTEWIHHPWDAPLTVLKASGVELGTNYAKPIVDIDTARE

LLAKAISRTREAQIMIGAAP

>CIB1 (in bold) - NLS (in italics)- VP64 (in bold, under-
lined) _2A_ GFP
(underlined)
(SEQ ID NO: 170)

MNGAIGGDLLLNFPDMSVLERQRAHLKYLNPTFDSPLAGFFADSSMITGGEMDSYLSTAGLNLP

MMYGETTVEGDSRLSISPETTLGTGNFKKRKFDTETKDCNEKKKKMTMNRDDLVEEGEEEKSKI

TEQNNGSTKSIKKMKHKAKKEENNFSNDSSKVTKELEKTDYIHVRARRGQATDSHSIAERVRRE

KISERMKFLQDLVPGCDKITGKAGMLDEIINYVQSLQRQIEFLSMKLAIVNPRPDFDMDDIFAK

EVASTPMTVVPSPEMVLSGYSHEMVHSGYSSEMVNSGYLIWNPMQQVNTSSDPLSCFNNGEAPS

MWDSHVQNLYGNLGV*ASPKKKRKVEAS*GSGRADALDDFDLDMLGSDALDDFDLDMLGSDALDDF

DLDMLGSDALDDFDLDMLINSRGSGEGRGSLLTCGDVEENPGPVSKGEELFTGVVPILVELDGD

VNGHKFSVSGEGEGDATYGKLTLKFICTTGKLPVPWPTLVTTLTYGVQCFSRYPDHMKQHDFFK

SAMPEGYVQERTIFFKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNHYLSTQSALSKDPNE

KRDHMVLLEFVTAAGITLGMDELYK

>CIBN (in bold)- NLS (in italics)-VP64 (in bold, underlined) _2A_ GFP (underlined)
(SEQ ID NO: 171)

MNGAIGGDLLLNFPDMSVLERQRAHLKYLNPTFDSPLAGFFADSSMITGGEMDSYLSTAGLNLP

MMYGETTVEGDSRLSISPETTLGTGNFKKRKFDTETKDCNEKKKKMTMNRDDLVEEGEEEKSKI

TEQNNGSTKSIKKMKHKAKKEENNFSNDSSKVTKELEKTDYI*ASPKKERKVEAS*GSGRADALDD

FDLDMLGSDALDDFDLDMLGSDALDDFDLDMLGSDALDDFDLDMLINSRGSGEGRGSLLTCGDV

EENPGPVSKGEELFTGVVPILVELDGDVNGHKFSVSGEGEGDATYGKLTLKFICTTGKLPVPWP

TLVTTLTYGVQCFSRYPDHMKQHDFFKSAMPEGYVQERTIFFKDDGNYKTRAEVKFEGDTLVNR

IELKGIDFKEDGNILGHKLEYNYNSHNVYIMADKQKNGIKVNFKIRHNIEDGSVQLADHYQQNT

PIGDGPVLLPDNHYLSTQSALSKDPNEKRDHMVLLEFVTAAGITLGMDELYK

>CIB1 (in bold) - NLS (in italics)- VP16 in bold, underlined _2A_ GFP (underlined)
(SEQ ID NO: 172)

MNGAIGGDLLLNFPDMSVLERQRAHLKYLNPTFDSPLAGFFADSSMITGGEMDSYLSTAGLNLP

MMYGETTVEGDSRLSISPETTLGTGNFKKRKFDTETKDCNEKKKKMTMNRDDLVEEGEEEKSKI

TEQNNGSTKSIKKMKHKAKKEENNFSNDSSKVTKELEKTDYIHVRARRGQATDSHSIAERVRRE

KISERMKFLQDLVPGCDKITGKAGMLDEIINYVQSLQRQIEFLSMKLAIVNPRPDFDMDDIFAK

EVASTPMTVVPSPEMVLSGYSHEMVHSGYSSEMVNSGYLHVNPMQQVNTSSDPLSCFNNGEAPS

MWDSHVQNLYGNLGV*ASPKKKRKVEAS*APPTDVSLGDELHLDGEDVAMAHADALDDFDLDMLGD

GDSPGPGFTPHDSAPYGALDMADFEFEQMFTDALGIDEYGGEFPGIRRSRGSGEGRGSLLTCGD

VEENPGPVSKGEELFTGVVPILVELDGDVNGHKFSVSGEGEGDATYGKLTLKFICTTGKLPVPW

PTLVTTLTYGVQCFSRYPDHMKQHDFFKSAMPEGYVQERTIFFKDDGNYKTRAEVKFEGDTLVN

RIELKGIDFKEDGNILGHKLEYNYNSHNVYIMADKQKNGIKVNFKIRHNIEDGSVQLADHYQQN

TPIGDGPVLLPDNHYLSTQSALSKDPNEKRDHMVLLEFVTAAGITLGMDELYK

>CIB1(in bold)- NLS(in italics)-p65 (in bold, underlined) _2A_ GFP (underlined)
(SEQ ID NO: 173)

MNGAIGGDLLLNFPDMSVLERQRAHLKYLNPTFDSPLAGFFADSSMITGGEMDSYLSTAGLNLP

MMYGETTVEGDSRLSISPETTLGTGNFKKRKFDTETKDCNEKKKKMTMNRDDLVEEGEEEKSKI

TEQNNGSTKSIKKMKHKAKKEENNFSNDSSKVTKELEKTDYIHVRARRGQATDSHSIAERVRRE

KISERMKFLQDLVPGCDKITGKAGMLDEIINYVQSLQRQIEFLSMKLAIVNPRPDFDMDDIFAK

EVASTPMTVVPSPEMVLSGYSHEMVHSGYSSEMVNSGYLHVNPMQQVNTSSDPLSCFNNGEAPS

MWDSHVQNLYGNLGV*ASPKKKRKVEAS*PSGQISNQALALAPSSAPVLAQTMVPSSAMVPLAQPP

APAPVLTPGPPQSLSAPVPKSTQAGEGTLSEALLHLQFADADEDLGALLGNSTDPGVFTDLASVD

NSEFQQLLNQGVSMSHSTAEPMLMEYPEAITRLVTGSQRPPDPAPTPLGTSGLPNGLSGDEDFS

-continued

SIADMDFSALLSQISSSGQSRGSGEGRGSLLTCGDVEENPGP<u>VSKGEELFTGVVPILVELDGDV</u>

<u>NGHKFSVSGEGEGDATYGKLTLKFICTTGKLPVPWPTLVTTLTYGVQCFSRYPDHMKQHDFFKS</u>

<u>AMPEGYVQERTIFFKDDGNYKTRAEVKFEGDTLVNRIELKGIDFKEDGNILGHKLEYNYNSHNV</u>

<u>YIMADKQKNGIKVNFKIRHNIEDGSVQLADHYQQNTPIGDGPVLLPDNHYLSTQSALSKDPNEK</u>

<u>RDHMVLLEFVTAAGITLGMDELYK</u>

AAV constructs (constructs used in primary neurons and in-vivo, FIGS. 37-38)[10]

>HA-TALE(12 mer)(in bold) - NLS (in italics)- VP64 in bold underlined _2A_ GFP(underlined)

(SEQ ID NO: 174)

MYPYDVPDYAVDLRTLGYSQQQQEKIKPKVRSTVAQHHEALVGHGFTHAHIVALSQHPAALGTV

AVKYQDMIAALPEATHEAIVGVGKQWSGARALEALLTVAGELRGPPLQLDTGQLLKIAKRGGVT

AVEAVHAWRNALTGAPLNLTPEQVVAIASXXGGKQALETVQRLLPVLCQAHGLTPEQVVAIASX

XGGKQALETVQRLLPVLCQAHGLTPEQVVAIASXXGGKQALETVQRLLPVLCQAHGLTPEQVVA

IASXXGGKQALETVQRLLPVLCQAHGLTPEQVVAIASXXGGKQALETVQRLLPVLCQAHGLTPE

QVVAIASXXGGKQALETVQRLLPVLCQAHGLTPEQVVAIASXXGGKQALETVQRLLPVLCQAHG

LTPEQVVAIASXXGGKQALETVQRLLPVLCQAHGLTPEQVVAIASXXGGKQALETVQRLLPVLC

QAHGLTPEQVVAIASXXGGKQALETVQRLLPVLCQAHGLTPEQVVAIASXXGGKQALETVQRLL

PVLCQAHGLTPEQVVAIASXXGGKQALETVQRLLPVLCQAHGLTPEQVVAIASXXGGRPALESI

VAQLSRPDPALAALTNDHLVALACLGGRPALDAVKKGLPHAPALIKRTNRRIPERTSHRVA*ASP*

*KKKRKVEAS*<u>GSGRADALDDFDLDMLGSDALDDFDLDMLGSDALDDFDLDMLGSDALDDFDLDML</u>

<u>IN</u><u>SRGSGEGRGSLLTCGDVEENPGPVSKGEELFTGVVPILVELDGDVNGHKFSVSGEGEGDATY</u>

<u>GKLTLKFICTTGKLPVPWPTLVTTLTYGVQCFSRYPDHMKQHDFFKSAMPEGYVQERTIFFKDD</u>

<u>GNYKTRAEVKFEGDTLVNRIELKGIDFKEDGNILGHKLEYNYNSHNVYIMADKQKNGIKVNFKI</u>

<u>RHNIEDGSVQLADHYQQNTPIGDGPVLLPDNHYLSTQSALSKDPNEKRDHMVLLEFVTAAGITL</u>

<u>GMDELYK</u>

>HA-TALE(12 mer) (in bold)- NLS (in italics)-SID4X in bold, underlined _2A_phiLOV2.1 (underlined)

(SEQ ID NO: 175)

MYPYDVPDYAVDLRTLGYSQQQQEKIKPKVRSTVAQHHEALVGHGFTHAHIVALSQHPAALGTV

AVKYQDMIAALPEATHEAIVGVGKQWSGARALEALLTVAGELRGPPLQLDTGQLLKIAKRGGVT

AVEAVHAWRNALTGAPLNLTPEQVVAIASXXGGKQALETVQRLLPVLCQAHGLTPEQVVAIASX

XGGKQALETVQRLLPVLCQAHGLTPEQVVAIASXXGGKQALETVQRLLPVLCQAHGLTPEQVVA

IASXXGGKQALETVQRLLPVLCQAHGLTPEQVVAIASXXGGKQALETVQRLLPVLCQAHGLTPE

QVVAIASXXGGKQALETVQRLLPVLCQAHGLTPEQVVAIASXXGGKQALETVQRLLPVLCQAHG

LTPEQVVAIASXXGGKQALETVQRLLPVLCQAHGLTPEQVVAIASXXGGKQALETVQRLLPVLC

QAHGLTPEQVVAIASXXGGKQALETVQRLLPVLCQAHGLTPEQVVAIASXXGGKQALETVQRLL

PVLCQAHGLTPEQVVAIASXXGGKQALETVQRLLPVLGQAHGLTPEQVVAIASXXGGRPALESI

VAQLSRPDPALAALTNDHLVALACLGGRPALDAVKKGLPHAPALIKRTNRRIPERTSHRVA*ASP*

*KKKRKVEASPKKKRKVEAS*<u>GSGMNIQMLLEAADYLERREREAEHGYASMLPGSGMNIQMLLEAA</u>

<u>DYLERREREAEHGYASMLPGSGMNIQMLLEAADYLERREREAEHGYASMLPGSGMNIQMLLEAA</u>

-continued

DYLERREREAEHGYASMLPSRSRGSGEGRGSLLTCGDVEENPGPIEKSFVITDPRLPDYPIIFA
SDGFLELTEYSREEIMGRNARFLQGPETDQATVQKIRDAIRDQRETTVQLINYTKSGKKFWNLL
HLQPVRDRKGGLQYFIGVQLVGSDHV

>HA-TALE(12 mer)(in bold)- NLS (in italics)-CIB1(undertined)

(SEQ ID NO: 176)

MYPYDVPDYAVDLRTLGYSQQQQEKIKPKVRSTVAQHHEALVGHGFTHAHIVALSQHPAALGTV
AVKYQDMIAALPEATHEAIVGVGKQWSGARALEALLTVAGELRGPPLQLDTGQLLKIAKRGGVT
AVEAVHAWRNALTGAPLNLTPEQVVAIASXXGGKQALETVQRLLPVLCQAHGLTPEQVVAIASX
XGGKQALETVQRLLPVLCQAHGLTPEQVVAIASXXGGKQALETVQRLLPVLCQAHGLTPEQVVA
IASXXGGKQALETVQRLLPVLCQAHGLTPEQVVAIASXXGGKQALETVQRLLPVLCQAHGLTET
QVVAIASXXGGKQALETVQRLLPVLCQAHGLTPEQVVAIASXXGGKQALETVQRLLPVLCQAHG
LTPEQVVAIASXXGGKQALETVQRLLPVLCQAHGLTPEQVVAIASXXGGKQALETVQRLLPVLC
QAHGLTPEQVVAIASXXGGKQALETVQRLLPVLCQAHGLTPEQVVAIASXXGGKQALETVQRLL
PVLCQAHGLTPEQVVAIASXXGGKQALETVQRLLPVLCQAHGLTPEQVVAIASXXGGRPALESI
VAQLSRPDPALAALTNDHLVALACLGGRPALDAVKKGLPRAPALIKRTNRRIPERTSHRVA_ASP_
_KKKRKVEAS_NGAIGGDLLLNFPDMSVLERQRAHLKYLNPTFDSPLAGFFADSSMITGGEMDSYL
STAGLNLPMMYGETTVEGDSRLSISPETTLGTGNFKKRKFDTETKDCNEKKKKMTMNRDDLVEE
GEEEKSKITEQNNGSTKSIKKMKHKAKKEENNFSNDSSKVTKELEKTDYIHVRARRGQATDSHS
IAERVRREKISERMKFLQDLVPGCDKITGKAGMLDEIINYVQSLQRQIEFLSMKLAIVNPRPDF
DMDDIFAKEVASTPMTVVPSPEMVLSGYSHEMVHSGYSSEMVNSGYLHVNPMQQVNTSSDPLSC
FNNGEAPSMWDSHVQNLYGNLGV

>CRY2PHR(in bold)- NLS (in italics)-VP64 (in bold, underlined) _2A_ GFP
(underlined)

(SEQ ID NO: 177)

MKMDKKTIVWFRRDLRIEDNPALAAAAHEGSVFPVFIWCPEEEGQFYPGRASRWWMKQSLAHLS
QSLKALGSDLTLIKTHNTISAILDCIRVTGATKVVFNHLYDPVSLVRDHTVKEKLVERGISVQS
YNGDLLYEPWEIYCEKGKPFTSFNSYWKKCLDMSIESVMLPPPWRLMPITAAAEAIWACSIEEL
GLENEAEKPSNALLTRAWSPGWSNADKLLNEFIEKQLIDYAKNSKKVVGNSTSLLSPYLHFGEI
SVRHVFQCARMKQIIWARDKNSEGEESADLFLRGIGLREYSRYICFNFPFTHEQSLLSHLRFFP
WDADVDKFKAWRQGRTGYPLVDAGMRELWATGWMHNRIRVIVSSFAVKFLLLPWKWGMKYFWDT
LLDADLECDILGWQYISGSIPDGHELDRLDNPALQGAKYDPEGEYIRQWLPELARLPTEWIHHP
WDAPLTVLKASGVELGTNYAKPIVDIDTARELLAKAISRTREAQIMIGAAP_ASPKKKRKVEAS_G
SGRADALDDFDLDMLGSDALDDFDLDHLGSDALDDFDLDMLGSDALDDFDLDMLINSRGSGEGR
GSLLTCGDVEENPGPVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIFFKDDGNYKTRAEVK
FEGDTLVNRIELKGIDFKEDGNILGHKLEYNYNSHNVYIMADKQKNGIKVNFKIRHNIEDGSVQ
LADHYQQNTPIGDGPVLLPDNHYLSTQSALSKDPNEKRDHMVLLEFVTAAGITLGMDELYKV

>CRY2PHR (in bold)- NLS (in italics)-SID4X (in bold. underlined) _2A_
phiLOV2.1(underlined)

(SEQ ID NO: 178)

MKMDKKTIVWFRRDLRIEDNPALAAAAHEGSVFPVFIWCPEEEGQFYPGRASRWWMKQSLAHLS
QSLKALGSDLTLIKTHNTISAILDCIRVTGATKVVFNHLYDPVSLVRDHTVKEKLVERGISVQS
YNGDLLYEPWEIYCEKGKPFTSFNSYWKKCLDMSIESVMLPPPWRLMPITAAAEAIWACSIEEL
GLENEAEKPSNALLTRAWSPGWSNADKLLNEFIEKQLIDYAKNSKKVVGNSTSLLSPYLHFGEI

-continued

SVRHVFQCARMKQIIWARDKNSEGEESADLFLRGIGLREYSRYICFNFPFTHEQSLLSHLRFFP
WDADVDKFKAWRQGRTGYPLVDAGMRELWATGWMHNRIRVIVSSFAVKFLLLPWKWGMKYFWDT
LLDADLECDILGWQYISGSIPDGHELDRLDNPALQGAKYDPEGEYIRQWLPELARLPTEWIHHP
WDAPLTVLKASGVELGTNYAKPIVDIDTARELLAKAISRTREAQIMIGAAP*ASPKKKRKVEAS*G
SGMNIQMLLEAADYLERREREAEHGYASMLPGSGMNIQMLLEAADYLERREREAEHGYASMLPG
SGMNIQMLLEAADYLERREREAEHGYASMLPGSGMNIQMLLEAADYLERREREAEHGYASMLPS
RSRGSGEGRGSLLTCGDVEENPGPIEKSFVITDPRLPDYPIIFASDGFLELTEYSREEIMGRNA
RFLQGPETDQATVQKIRDAIRDQRETTVQLINYTKSGKKFWNLLHLQPVRDRKGGLQYFIGVQL
VGSDHV

Sequences of FIGS. 39-48

```
>TALE(KLF4)(underlined)- NLS (in italics)-CRY2PHR (in bold)
                                                      (SEQ ID NO: 179)
```
MSRTRLPSPPAPSPAFSADSFSDLLRQFDPSLFNTSLFDSLPPFGAHHTEAATGEWDEVQSGLR
AADAPPPTMRVAVTAARPPRAKPAPRRRAAQPSDASPAAQVDLRTLGYSQQQQEKIKPKVRSTV
AQHHEALVGHGFTHAHIVALSQHPAALGTVAVKYQDMIAALPEATHEAIVGVGKQWSGARALEA
LLTVAGELRGPPLQLDTGQLLKIAKRGGVTAVEAVHAWRNALTGAPLNLTPEQVVAIASNGGGK
QALETVQRLLPVLCQAHGLTPEQVVAIASHDGGKQALETVQRLLPVLCQAHGLTPEQVVAIASN
GGGKQALETVQRLLPVLCQAHGLTPEQVVAIASNGGGKQALETVQRLLPVLCQAHGLTPEQVVA
IASNIGGKQALETVQRLLPVLCQAHGLTPEQVVAIASHDGGKQALETVQRLLPVLCQAHGLTPE
QVVAIASNGGGKQALETVQRLLPVLCQAHGLTPEQVVAIASNGGGKQALETVQRLLPVLCQAHG
LTPEQVVAIASNIGGKQALETVQRLLPVLCQAHGLTPEQVVAIASNGGGKQALETVQRLLPVLC
QAHGLTPEQVVAIASNIGGKQALETVQRLLPVLCQAHGLTPEQVVAIASNGGGKQALETVQRLL
PVLCQAHGLTPEQVVAIASHDGGRPALESIVAQLSRPDPALAALTNDHLVALACLCGRPALDAV
KKGLPHAPAILKRTNRRIPERTSHRVADHAQVVRVLGFFQCHSHPAQAFDDAMTQFGMSRHGLL
QLFRRVGVTELEARSGTLPPASQRWDRILQASGMKRAKPSPTSTQTPDQASLHAFADSLERDLD
APSPMHEGDQTRAS*ASPKKKRKVEAS*KMDKKTIVWFRRDLRIEDNPALAAAAHEGSVFPVFIWC
PEEEGQFYPGRASRWWMKQSLAHLSQSLKALGSDLTLIKTHNTISAILDCIRVTGATKVVFNHL
YDPVSLVRDHTVKEKLVERGISVQSYNGDLLYEPWEIYCEKGKPFTSFNSYWKKCLDMSIESVM
LPPPWRLMPITAAAEAIWACSIEELGLENEAEKPSNALLTRAWSPGWSNADKLLNEFIEKQLID
YAKNSKKVVGNSTSLLSPYLHFGEISVRHVFQCARMKQIIWARDKNSEGEESADLFLRGIGLRE
YSRYICFNFPFTHEQSLLSHLRFFPWDADVDKFKAWRQGRTGYPLVDAGMRELWATGWMHNRIR
VIVSSFAVKFLLLPWKWGMKYFWDTLLDADLECDILGWQYISGSIPDGHELDRLDNPALQGAKY
DPEGEYIRQWLPELARLPTEWIHHPWDAPLTVLKASGVELGTNYAKPIVDIDTARELLAKAISR
TREAQIMIGAAP

```
>HA-NLS (in italics)-TALE(p11, N136)(in bold)-SID(underlined)
                                                      (SEQ ID NO: 180)
```
MYPYDVPDY*ASPKKKRKVEAS*VDLRTLGYSQQQQEKIKPKVRSTVAQHHEALVGHGFTHAHIVA
LSQHPAALGTVAVKYQDMIAALPEATHEAIVGVGKQWSGARALEALLTVAGELRGPPLQLDTGQ
LLKIAKRGGVTAVEAVHAWRNALTGAPLNLTPEQVVAIASNNGGKQALETVQRLLPVLCQAHGL
TPEQVVAIASHDGGKQALETVQRLLPVLCQAHGLTPEQVVAIASHDGGKQALETVQRLLPVLCQ
AHGLTPEQVVAIASNGGGKQALETVQRLLPVLCQAHGLTPEQVVAIASNNGGKQALETVQRLLP
VLCQAHGLTPEQVVAIASHDGGKQALETVQRLLPVLCQAHGLTPEQVVAIASHDGGKQALETVQ

-continued

RLLPVLCQAHGLTPEQVVAIASHDGGKQALETVQRLLPVLCQAHGLTPEQVVAIASNGGGKQAL

ETVQRLLPVLCQAHGLTPEQVVAIASHDGGKQALETVQRLLPVLCQAHGLTPEQVVAIASHDGG

KQALETVQRLLPVLCQAHGLTPEQVVAIASNIGGKQALETVQRLLPVLCQAHGLTPEQVVAIAS

NNGGKQALETVQRLLPVLCQAHGLTPEQVVAIASNNGGKQALETVQRLLPVLCQAHGLTPEQVV

AIASHDGGKQALETVQRLLPVLCQAHGLTPEQVVAIASNGGGKQALETVQRLLPVLCQAHGLTP

EQVVAIASHDGGKQALETVQRLLPVLCQAHGLTPEQVVAIASHDGGKQALETVQRLLPVLCQAH

GLTPEQVVAIASHDGGRPALESIVAQLSRPDPALAALTNDHLVALACLGGRPALDAVKKGLPHA

PALIKRTNRRIPERTSHRVADHAQVVRVLGFFQCHSHPAQAFDDAMTQFGMSRHGLLQLFRRVG

VTELEARSGTLPPASQRWDRILQASGMKRAKPSPTSTQTPDQASLHAFADSLERDLDAPSPMHE

GDQTRASAS<u>GSGMNIQMLLEAADYLERREREAEHGYASMLP</u>.

>HA-NLS(in italics)-TALE(p11, N136)(in bold)-SID4X(underlined)
(SEQ ID NO: 181)
MYPYDVPDY*ASPKKKRKVEAS*VDLRTLGYSQQQQEKIKPKVRSTVAQHHEALVGHGFTHAHIVA

LSQHPAALGTVAVKYQDMIAALPEATHEAIVGVGKQWSGARALEALLTVAGELRGPPLQLDTGQ

LLKIAKRGGVTAVEAVHAWRNALTGAPLNLTPEQVVAIASNNGGKQALETVQRLLPVLCQAHGL

TPEQVVAIASHDGGKQALETVQRLLPVLCQAHGLTPEQVVAIASHDGGKQALETVQRLLPVLCQ

AHGLTPEQVVAIASNGGGKQALETVQRLLPVLCQAHGLTPEQVVAIASNNGGKQALETVQRLLP

VLCQAHGLTPEQVVAIASHDGGKQALETVQRLLPVLCQAHGLTPEQVVAIASHDGGKQALETVQ

RLLPVLCQAHGLTPEQVVAIASHDGGKQALETVQRLLPVLCQAHGLTPEQVVAIASNGGGKQAL

ETVQRLLPVLCQAHGLTPEQVVAIASHDGGKQALETVQRLLPVLCQAHGLTPEQVVAIASHDGG

KQALETVQRLLPVLCQAHGLTPEQVVAIASNIGGKQALETVQRLLPVLCQAHGLTPEQVVAIAS

NNGGKQALETVQRLLPVLCQAHGLTPEQVVAIASNNGGKQALETVQRLLPVLCQAHGLTPEQVV

AIASHDGGKQALETVQRLLPVLCQAHGLTPEQVVAIASNGGGKQALETVQRLLPVLCQAHGLTP

EQVVAIASHDGGKQALETVQRLLPVLCQAHGLTPEQVVAIASHDGGKQALETVQRLLPVLCQAH

GLTPEQVVAIASHDGGRPALESIVAQLSRPDPALAALTNDHLVALACLGGRPALDAVKKGLPHA

PALIKRTNRRIPERTSHRVADHAQVVRVLGFFQCHSHPAQAFDDAMTQFGMSRHGLLQLFRRVG

VTELEARSGTLPPASQRWDRILQASGMKRAKPSPTSTQTPDQASLHAFADSLERDLDAPSPMHE

GDQTRASAS<u>GSGMNIQMLLEAADYLERRERFAEHGYASMLPGSGMNIQMLLEAADYLERREA

EHGYASMLPGSGMNIQMLLEAADYLERREREAEHGYASMLPGSGMNIQMLLEAADYLERREREA

EHGYASMLPSR</u>

The following Arduino script was used to enable the individual control of each 4-well column of a light-stimulated 24-well plate:

```
//Basic control code for LITE LED array using Arduino UNO
//LED column address initialization to PWM-ready Arduino outputs
int led1_pin = 3;
int led2_pin = 5;
int led3_pin = 6;
int led4_pin = 9;
int led5_pin = 10;
int led6_pin = 11;
//Maximum setting for Arduino PWM
int uniform_brightness = 255;
//PWM settings for individual LED columns
int led1_brightness = uniform_brightness/2;
int led2_brightness = uniform_brightness/2;
int led3_brightness = uniform_brightness/2;
int led4_brightness = uniform_brightness/2;
```

-continued

```
int led5_brightness = uniform_brightness/2;
int led6_brightness = uniform_brightness/2;
//'on' time in msec
unsigned long uniform_stim_time = 1000; /
//individual 'on' time settings for LED columns
unsigned long led1_stim_time = uniform_stim_time;
unsigned long led2_stim_time = uniform_stim_time;
unsigned long led3_stim_time = uniform_stim_time;
unsigned long led4_stim_time = uniform_stim_time;
unsigned long led5_stim_time = uniform_stim_time;
unsigned long led6_stim_time = uniform_stim_time;
//'off' time in msec
unsigned long uniform_off_time = 14000;
//individual 'off' time settings for LED columns
unsigned long led1_off_time = uniform_off_time;
unsigned long led2_off_time = uniform_off_time;
unsigned long led3_off_time = uniform_off_time;
unsigned long led4_off_time = uniform_off_time;
```

```
unsigned long led5_off_time = uniform_off_time;
unsigned long led6_off_time = uniform_off_time;
unsigned long currentMillis = 0;
//initialize timing and state variables
unsigned long led1_last_change = 0;
unsigned long led2_last_change = 0;
unsigned long led3_last_change = 0;
unsigned long led4_last_change = 0;
unsigned long led5_last_change = 0;
unsigned long led6_last_change = 0;
int led1_state = HIGH;
int led2_state = HIGH;
int led3_state = HIGH;
int led4_state = HIGH;
int led5_state = HIGH;
int led6_state = HIGH;
unsigned long led1_timer = 0;
unsigned long led2_timer = 0;
unsigned long led3_timer = 0;
unsigned long led4_timer = 0;
unsigned long led5_timer = 0;
unsigned long led6_timer = 0;
void setup( ) {
    // setup PWM pins for output
    pinMode(led1_pin, OUTPUT);
    pinMode(led2_pin, OUTPUT);
    pinMode(led3_pin, OUTPUT);
    pinMode(led4_pin, OUTPUT);
    pinMode(led5_pin, OUTPUT);
    pinMode(led6_pin, OUTPUT);
    //LED starting state
    analogWrite(led1_pin, led1_brightness);
    analogWrite(led2_pin, led2_brightness);
    analogWrite(led3_pin, led3_brightness);
    analogWrite(led4_pin, led4_brightness);
    analogWrite(led5_pin, led5_brightness);
    analogWrite(led6_pin, led6_brightness);
}
void loop( ) {
    currentMillis = millis( );
    //identical timing loops for the 6 PWM output pins
    led1_timer = currentMillis - led1_last_change;
    if (led1_state == HIGH){ //led state is on
        if (led1_timer >= led1_stim_time){ //TRUE if stim
        time is complete
            analogWrite(led1_pin, 0); //turn LED off
            led1_state = LOW;       //change LED state variable
            led1_last_change = currentMillis; //mark time of
                                              most recent change
        }
    }
    else{ //led1 state is off
        if (led1_timer >= led1_off_time){ //TRUE if off
        time is complete
            analogWrite(led1_pin, led1_brightness); //turn LED on
            led1_state = HIGH;          //change LED state variable
            led1_last_change = currentMillis;   //mark time of most
                                                recent change
        }
    }
    led2_timer = currentMillis - led2_last_change;
    if (led2_state = HIGH){
        if (led2_timer >= led2_stim_time){
            analogWrite(led2_pin, 0);
            led2_state = LOW;
            led2_last_change = currentMillis;
        }
    }
    else{ //led2 state is off
        if (led2_timer >= led2_off_time){
            analogWrite(led2_pin, led2_brightness);
            led2_state = HIGH;
            led2_last_change = currentMillis;
        }
    }
    led3_timer = currentMillis - led3_last_change;
    if (led3_state == HIGH){
        if (led3_timer >= led3_stim_time){
            analogWrite(led3_pin, 0);
            led3_state = LOW;
            led3_last_change = currentMillis;
        }
    }
    else{ //led3 state is off
        if (led3_timer >= led3_off_time){
            analogWrite(led3_pin, led3_brightness);
            led3_state = HIGH;
            led3_last_change = currentMillis;
        }
    }
    led4_timer = currentMillis - led4_last_change;
    if (led4_state == HIGH){
        if (led4_timer >= led4_stim_time){
            analogWrite(led4_pin, 0);
            led4_state = LOW;
            led4_last_change = currentMillis;
        }
    }
    else{ //led4 state is off
        if (led4_timer >= led4_off_time){
            analogWrite(led4_pin, led4_brightness);
            led4_state = HIGH;
            led4_last_change = currentMillis;
        }
    }
    led5_timer = currentMillis - led5_last_change;
    if (led5_state == HIGH){
        if (led5_timer >= led5_stim_time){
            analogWrite(led5_pin, 0);
            led5_state = LOW;
            led5_last_change = currentMillis;
        }
    }
    else{ //led5 state is off
        if (led5_timer >= led5_off_time){
            analogWrite(led5_pin, led5_brightness);
            led5_state = HIGH;
            led5_last_change = currentMillis;
        }
    }
    led6_timer = currentMillis - led6_last_change;
    if (led6_state == HIGH){
        if (led6_timer >= led6_stim_time){
            analogWrite(led6_pin, 0);
            led6_state = LOW;
            led6_last_change = currentMillis;
        }
    }
    else { //led6 state is off
        if (led6_timer >= led6_off_time){
            analogWrite(led6_pin, led6_brightness);
            led6_state = HIGH;
            led6_last_change = currentMillis;
        }
    }
}
```

REFERENCES

1 Banerjee, R. et al. The Signaling State of *Arabidopsis* Cryptochrome 2 Contains Flavin Semiquinone. Journal of Biological Chemistry 282, 14916-14922, doi:10.1074/jbc.M700616200 (2007).

2 McClure, C., Cole, K. L., Wulff, P., Klugmann, M. & Murray, A. J. Production and titering of recombinant adeno-associated viral vectors. J Vis Exp, e3348, doi: 10.3791/3348 (2011).

3 Witten, Ilana B. et al. Recombinase-Driver Rat Lines: Tools, Techniques, and Optogenetic Application to Dopamine-Mediated Reinforcement. Neuron 72, 721-733, doi: at the website dx.doi.org/10.1016/j.neuron.2011.10.028 (2011).

4 Grieger, J. C., Choi, V. W. & Samulski, R. J. Production and characterization of adeno-associated viral vectors. Nat Protoc 1, 1412-1428, doi:10.1038/nprot.2006.207 (2006).

5 Lock M, A. M., Vandenberghe L H, Samanta A, Toelen J, Debyser Z, Wilson J M. Rapid, Simple, and Versatile Manufacturing of Recombinant Adeno-Associated Viral Vectors at Scale. Human Gene Therapy 21, 1259-1271, doi:10.1089/hum.2010.055 (2010).

Example 8

Cloning (Construction) of AAV Constructs
Construction of AAV-Promoter-TALE-Effector Backbone
For construction of AAV-promoter-TALE-effector a backbone was cloned by standard subcloning methods. Specifically, the vector contained an antibiotics resistance gene, such as ampicillin resistance and two AAV inverted terminal repeats (itr's) flanking the promoter-TALE-effector insert (sequences, see below). The promoter (hSyn), the effector domain (VP64, SID4X or CIB1 in this example)/the N- and C-terminal portion of the TALE gene containing a spacer with two typeIIS restriction sites (BsaI in this instance) were subcloned into this vector. To achieve subcloning, each DNA component was amplified using polymerase-chain reaction and then digested with specific restriction enzymes to create matching DNA sticky ends. The vector was similarly digested with DNA restriction enzymes. All DNA fragments were subsequently allowed to anneal at matching ends and fused together using a ligase enzyme.

Assembly of Individual TALEs into AAV-Promoter-TALE-Effector Backbone

For incorporating different TALE monomer sequences into the AAV-promoter-TALE-effector backbone described above, a strategy based on restriction of individual monomers with type IIS restriction enzymes and ligation of their unique overhangs to form an assembly of 12 to 16 monomers to form the final TALE and ligate it into the AAV-promoter-TALE-effector backbone by using the type IIS sites present in the spacer between the N- and C-term (termed golden gate assembly). This method of TALE monomer assembly has previously been described by us (NE Sanjana, L Cong, Y Zhou, M M Cunniff, G Feng & F Zhang A transcription activator-like effector toolbox for genome engineering Nature Protocols 7, 171-192 (2012) doi: 10.1038/nprot.2011.431)

By using the general cloning strategy outlined above, AAV vectors containing different promoters, effector domains and TALE monomer sequences can be easily constructed.

Nucleotide Sequences:

```
Left AAV ITR
                                                    (SEQ ID NO: 182)
Cctgcaggcagctgcgcgctcgctcgctcactgaggccgcccgggcaaagcccgggcgtcgggc gacctttggtcgcccggcctcagtgagcgagcgagcgcgcagagagggagtggccaactccatc actagggttcct_

Right AAV ITR
                                                    (SEQ ID NO: 183)
Aggaaccctagtgatggagttggccactccctctctgcgcgctcgctcgctcactgaggccgg gcgaccaaaggtcgcccgacgcccgggctttgcccgggcggcctcagtgagcgagcgagcgcgc agctgcctgcagg_ hSyn promoter
                                                    (SEQ ID NO: 184)
gtgtctagactgcagagggccctgcgtatgagtgcaagtgggttttaggaccaggatgaggcgg ggtgggggtgcctacctgacgaccgaccccgacccactggacaagcacccaaccccattcccc aaattgcgcatccctatcagagaggggagggaaacaggatgcggcgaggcgcgtgcgcact gccagcttcagcaccgcggacagtgccttcgccccgcctggcggcgcgcgccaccgccgcctc agcactgaaggcgcgctgacgtcactcgccggtccccgcaaactccccttcccggccaccttg gtcgcgtccgcgccgccgccggcccagccggaccgcaccacgcgaggcgcgagataggggggca cgggcgcgaccatctgcgctgcggcgccggcgactcagcgctgcctcagtctgcggtgggcagc ggaggagtcgtgtcgtgcctgagagcgcagtcgagaa_

TALE N-term (+136 AA truncation)
                                                    (SEQ ID NO: 185)
GTAGATTTGAGAACTTTGGGATATTCACAGCAGCAGCAGGAAAAGATCAAGCCCAAAGTGAGGT

CGACAGTCGCGCAGCATCACGAAGCGCTGGTGGGTCATGGGTTTACACATGCCCACATCGTAGC

CTTGTCGCAGCACCCTGCAGCCCTTGGCACGGTCGCCGTCAAGTACCAGGACATGATTGCGGCG

TTGCCGGAAGCCACACATGAGGCGATCGTCGGTGTGGGGAAACAGTGGAGCGGAGCCCGAGCGC

TTGAGGCCCTGTTGACGGTCGCGGGAGAGCTGAGAGGGCCTCCCCTTCAGCTGGACACGGGCCA
```

-continued
GTTGCTGAAGATCGCGAAGCGGGGAGGAGTCACGGCGGTCGAGGCGGTGCACGCGIGGCGCAAT

GCGCTCACGGGAGCACCCCTCAAC_

TALE C-term (+63 AA truncation)
(SEQ ID NO: 186)
CGGACCCCGCGCTGGCCGCACICACTAATGATCATCTIGTAGCGCTGGCCTGCCTCGGCGGACG

ACCCGCCTTGGATGCGGTGAAGAAGGGGCTCCCGCACGCGCCTGCATTGATTAAGCGGACCAAC

AGAAGGATTCCCGAGAGGACATCACATCGAGTGGCA_

Ampicillin resistance gene
(SEQ ID NO: 187)
atgagtattcaacatttccgtgtcgcccttattccctttttttgcggcattttgccttcctgttt ttgctcacccagaaacgctggtgaaagtaaaagatgctgaagatcagttgggtgcacgagtggg ttacatcgaactggatctcaacagcggtaagatccttgagagttttcgccccgaagaacgtttt ccaatgatgagcacttttaaagttctgctatgtggcgcggtattatcccgtattgacgccgggc aagagcaactcggtcgccgcatacactattctcagaatgacttggttgagtactcaccagtcac agaaaagcatcttacggatggcatgacagtaagagaattatgcagtgctgccataaccatgagt gataacactgcggccaacttacttctgacaacgatcggaggaccgaaggagctaaccgcttttt tgcacaacatggggatcatgtaactcgccttgatcgttgggaaccggagctgaatgaagccat accaaacgacgagcgtgacaccacgatgcctgtagcaatggcaacaacgttgcgcaaactatta actggcgaactacttactctagcttcccggcaacaattaatagactggatggaggcggataaag ttgcaggaccacttctgcgctcggcccttccggctggctggtttattgctgataaatctggagc cggtgagcgtgggtctcgcggtatcattgcagcactggggccagatggtaagccctcccgtatc gtagttatctacacgacggggagtcaggcaactatggatgaacgaaatagacagatcgctgaga taggtgcctcactgattaagcattgg_

Example 9

DNA Ratios

In this application, Applicants provide for varying plasmid ratios. The ratios of vector of interest plasmid:AAV serotype plasmid:pHelper plasmid may be varied. Specific values used in examples above are: 1:1.7:2 for AAV supernatant production down to 24-well scale. Values that may be used for production in 96-well format are: 1:2:1. Values may be varied in a wider range (e.g. up to fivefold excess of one plasmid) if desired.

Scalability

The present invention also comprehends AAV supernatant production as described herein being easily scaled up into higher throughput formats. The examples listed describe scaling from 15 cm dishes to 96-well plates for production. Through the same principle of scaling it may be possible to produce AAV in more dense well plate formats (e.g. 384-well, 1536-well etc.). The invention further comprehends using this process in even smaller volume units as would be possible with e.g. a microfluidic device capable of maintaining cell cultures in individual chambers. Hence, the present invention allows for an unprecedented throughput of production of different AAV viral particles. Applicants submit that one further important advantage of the invention described is that due to the highly efficient recovery of functional viral particles (due to minimal loss compared to extensive purification procedures traditionally used) AAV supernatant can be produced at the same scale as it will be applied. This is especially relevant for automated processing as it provides not only a simplified production and application process but also reduces the possibility for variability. In a preferred embodiment, the invention comprehends the automated production of 96 different AAV particles in 96-well plate format and application of the harvested supernatant to 3 replicate plates of cells to be transduced. This requires minimal pipetting steps, no necessary rearrangement (entire plates of virus can be applied to cells with a 96-channel pipette head) and minimal chance of pipetting error.

Filtering/Purification

Multiple methods may be used to purify the cell supernatant containing AAV particles after harvest and before application to cells for transduction. For a basic purification which mostly serves to remove any potential 293FT cells and large cell debris from the supernatant, filtration with a 22 micron or 45 micron pore size low protein binding filter or centrifugation for pelleting cells and cell debris may be employed. In the case of filtration, the flow-through will be harvested and used subsequently and in the case of centrifugation (at speeds in a range of e.g. 200 g for 10 min to 6000 g for 1-10 min) the supernatant will be used. In cases where more stringent purification is desired (e.g. for particularly sensitive cell types such as human ES cells or in a clinical application) it may be possible to follow up with subsequent purification steps. In an aspect of the invention, a sequence of molecular weight cutoff filters may be used (e.g. Amicon filters, millipore).

FBS Substitutes

The use of fetal bovine serum in the production of supernatant AAV may prove problematic for certain downstream applications. For example, the application of FBS-containing AAV supernatant to embryonic stem cells would result in uncontrolled differentiation of the pluripotent cultures. Also, the use of undefined FBS is incompatible with human clinical applications. In order to mitigate the issues arising from the use of FBS, the invention comprehends the culture medium used to support the AAV producing 293FT cells being replaced with a chemically-defined serum-free medium. For example, Pro293a from Lanza Biologics is a chemically-defined, serum-free medium designed to support the growth and protein production of adherent 293 lineage cells. With regards to the AAV supernatant production protocol details in the examples herein, all media components would simply be replaced with Pro293a or another suitable medium substitute.

Reasons to Use AAV

Non-integration: A major motivation for the use of AAV in the field of gene therapy is the relative lack of random genomic integration compared to lentivirus, retrovirus, and other integrating viral vectors. The majority of transduced recombinant AAV genetic material exists in the host cell as episomes, rather than at randomly integrated chromosomal locations. In human cells, if the appropriate helper genes are provided, the AAV genome can integrate at the well-characterized safe harbor locus AAVS 1. These characteristics reduce the chance for oncogenic integration, making AAV the current preferred viral system for human gene therapy. The non-integration of AAV also provides advantages for functional genomic studies. By providing trans genes or expression modulation systems via AAV, rather than an integrating virus, one can be assured that the cell population being used maintains an otherwise isogenic background.

Functional Genomics: Cell Type Addressability

The generation of large libraries of RNAi, ORFs, targeted nucleases (ZFNs, TALENs, CRISPR/Cas9), transcriptional modulators (TALE-TFs, CRISPR/dCAS9 effectors), and other gene expression tools has enabled large-scale arrayed functional genomics. These types of experiments, however, are limited to cell types to which such gene expression tools can be delivered in high-throughput. The high-throughput scalability of Applicants' AAV supernatant production protocol allows for the application of functional genomics techniques to cell types for which AAV is the ideal delivery mechanism. For example, AAV may be used to transduce primary cortical neurons with higher efficiency than lentiviral transduction or plasmid transfection, with lower toxicity than lentiviral delivery.

Pooling

The herein described AAV supernatant production method may be used to generate functional, pooled AAV supernatant. In an embodiment of the invention, several genes of interest, encoded on separate AAV backbone plasmids can be pooled at the plasmid stage to produce a final supernatant containing a mixture of the desired AAV vectors. Several types of gene delivery applications may benefit from a pooling approach. First, some experiments in which a large number of viral vectors must be functionally tested could be performed in a hierarchical pooled fashion. For example, groups of multiple RNAi or ORFs could be delivered in pooled AAV format to reduce the size of the initial search space, saving experimental time and cost. Second, complicated multicomponent gene expression systems may be produced via a pooled AAV format. For example, the differentiation of embryonic stem cells or reprogramming of one cell type to another often requires the delivery of numerous transcription factors simultaneously. Methods of the invention encompassing pooled AAV supernatant production could rapidly provide many different transcription factor combinations, simply by altering the mixtures of AAV backbone plasmids, which may be automated by liquid handling robotics. Third, artificial transcription factors, such as TALE-TFs and CRISPR/Cas9 activators, have been shown to have synergistic effects when provided in combination to target cells. Pooled AAV supernatant production could rapidly provide many different TALE-TF, CRISPR/Cas9, or other engineered gene expression modulators, simply by altering the mixtures of AAV backbone plasmids. This approach has been validated for pooled TALE-TFs designed to activate gene expression in mouse primary cortical neurons. Ten separate TALE-VP64 activators designed to target the Drd2 locus were produced by Applicants' standard AAV supernatant production method. Simultaneously, an equimolar mixture of all 10 Drd2 targeting TALE-VP64 plasmids was made, referred to as the "10 TALE mixture". The identical AAV supernatant production protocol was used produce the pooled AAV mixture, with the exception that the gene of interest backbone plasmid was replaced by an equal mass of "10 TALE mixture" plasmids. All AAV supernatants were harvested and applied to mouse primary neuron cultures as previously described. Six days after transduction, cell lysis, reverse transcription and qPCR were performed on the neuron cultures to determine the expression levels of Drd2. Gene expression levels were elevated for several of the TALE-VP64 transduced cultures. The culture transduced with supernatant from the "10 TALE mixture" was found to activate expression from the Drd2 locus at a level equivalent to the most potent individual TALE-VP64.

Multiple Harvests

Multiple supernatant AAV batches may be harvested from a single AAV producing 293FT culture. Specifically, following the 48 hour post-transfection harvested described in Applicants' standard AAV supernatant protocol, the culture medium may be replenished and harvested again 24 hours later (72 hours post-transfection). Both harvests contain functional AAV particles. In this presently described multiple harvest protocol, the value of producing twice as much AAV supernatant as Applicants' standard protocol saves time and resources when producing many AAV cultures in an arrayed format. This approach offers an advantage over current large-scale AAV production methods. In current methods, the amount of AAV that can be produced is limited by the mass of 293 cells producing the viral particles, as these methods typically require lysing the producer cells to harvest the AAV particles. By stably expressing the AAV expression plasmids in a 293 producer cell line, one could continually harvest AAV supernatant batches simply by maintaining the cell cultures, periodically collecting the supernatant, and replenishing the culture medium.

In additional embodiments, the invention comprises a method for obtaining and optionally storing a sample containing a set amount of a Dependovirus-based vector comprising or consisting essentially of: (a) creating infected or transfected cells by a process comprising or consisting essentially of one or more methods selected from: (i) transfecting plasmid(s) containing or consisting essentially of exogenous DNA including DNA for expression into Dependovirus-based vector-infected cells along with another helper plasmid that provides Dependovirus rep and/or cap genes which are obligatory for replication and packaging of the Dependovirus-based vector; or (ii) infecting susceptible cells with a Dependovirus-based vector containing or consisting essentially of exogenous DNA including DNA for expression, and helper virus wherein the Dependovirus-based vector lacks functioning cap and/or rep and the helper virus provides the cap and/or rev function that the Dependovirus-based vector lacks; or (iii) infecting susceptible cells with a Dependovirus-based vector containing or consisting essentially of exogenous DNA including DNA for expression, wherein the recombinant construct lacks functioning cap and/or rep, and transfecting said cells with a plasmid supplying cap and/or rep function that the Dependovirus-based vector lacks; or (iv) infecting susceptible cells with a Dependovirus-based vector containing or consisting essentially of exogenous DNA including DNA for expression, wherein the recombinant construct lacks functioning cap and/or rep, wherein said cells supply cap and/or rep function that the recombinant construct lacks; or (v) transfecting the susceptible cells with a Dependovirus-based vector lacking functioning cap and/or rep and plasmids for inserting exogenous DNA into the recombinant construct so that the exogenous DNA is expressed by the recombinant construct and for supplying rep and/or cap functions whereby transfection results in a Dependovirus-based vector containing or consisting essentially of the exogenous DNA including DNA for expression that lacks functioning cap and/or rep; and (b) incubating the infected or transfected cells, whereby there results infected or transfected cells and supernatant containing the Dependovirus-based vector lacking functioning cap and/or rep; (c) after incubating, extracting an aliquot from the supernatant; (d) filtering the aliquot, whereby the filtered aliquot contains and the method obtains a sample containing set amount of the Dependovirus-based vector relative to the type and amount of susceptible cells infected or transfected; and (e) optionally freezing the filtered aliquot, whereby the method optionally includes storing a sample containing set amount of the Dependovirus-based vector relative to the type and amount of susceptible cells infected or transfected.

In one aspect, the Dependovirus-based vector of the invention is derived from one or more Dependoviruses selected from one or more of: adeno associated virus (AAV), Adenovirus, parvovirus, Erythrovirus, Bocavirus and the like. In one aspect, the Dependovirus-based vector of the invention is derived from a recombinant adeno associated virus (rAAV).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for screening recombinant adeno-associated viruses (rAAVs) containing exogenous DNA, comprising,
   (I) obtaining a first plurality of cells that produce a plurality of rAAVs containing exogenous DNA encoding a CRISPR system, wherein (a) one of the rAAVs encodes a Cas9 and a guide RNA or (b) a first rAAV encodes the Cas9 and a second rAAV encodes the guide RNA;
   (II) harvesting supernatant from the first plurality of cells to collect a pool of rAAVs, wherein the first plurality of cells are intact and can be further used to obtain more rAAVs;
   (III) purifying the pool of rAAVs, wherein the purification consists of filtering the supernatant and collecting flow-through, wherein the flow-through constitutes filtered supernatant and comprises a purified pool of rAAVs;
   (IV) contacting a second plurality of cells with a portion of the purified pool of rAAVs from step (III); and
   (V) determining whether the exogenous DNA is expressed in an amount and/or duration sufficient for an intended use.

2. The method of claim 1 wherein the rAAVs are AAV1, AAV2, AAV5 or an AAV having a hybrid or mosaic AAV1, AAV2 and/or AAV5 capsid.

3. The method of claim 1 wherein the first plurality of cells are 293FT cells.

4. The method of claim 1, further comprising adding a secretion enhancer to the first plurality of cells before the harvesting.

5. The method of claim 4 wherein the secretion enhancer is polyethylenimine (PEI).

6. The method of claim 1, wherein the first plurality of cells that express rAAV are obtained by:
   (i) transfecting the first plurality of cells with one or more plasmid(s) containing the exogenous DNA and a helper plasmid that provides AAV rep and/or cap genes; or
   (ii) infecting the first plurality of cells with a rAAV containing the exogenous DNA and helper virus, wherein the rAAV lacks functioning cap and/or rep and the helper virus provides the cap and/or rep function that the rAAV lacks; or
   (iii) infecting the first plurality of cells with a rAAV containing the exogenous DNA, wherein the rAAV lacks functioning cap and/or rep, and transfecting the first plurality of cells with a plasmid supplying cap and/or rep function that the rAAV lacks; or
   (iv) infecting the first plurality of cells with a rAAV containing the exogenous DNA, wherein the rAAV lacks functioning cap and/or rep, wherein the first plurality of cells supply cap and/or rep function that the recombinant construct lacks; or
   (v) transfecting the first plurality of cells with an rAAV plasmid lacking functioning cap and/or rep, and one or more plasmids containing the exogenous DNA, and a helper plasmid that provides rep and/or cap functions.

7. The method of claim 1, further comprising freezing the filtered supernatant.

8. The method of claim 1, wherein the exogenous DNA further encodes a nuclear localization signal (NLS) linked to the Cas9.

9. The method of claim 1, wherein two or more rAAVs encode different guide RNAs.

10. The method of claim 1, wherein the second plurality of cells comprises neuronal cells.

11. The method of claim 1, wherein obtaining the first plurality of cells comprises obtaining cells transduced with at least one vector of interest plasmid, an AAV serotype plasmid, and a pHelper plasmid, wherein the ratio of the vector of interest plasmid:AAV serotype plasmid:pHelper plasmid is about 1:1.7:2 or 1:2:1, and wherein the at least one vector of interest plasmid(s) encodes the CRISPR system.

12. The method of claim 1, wherein determining whether the exogenous DNA is expressed in an amount and/or duration sufficient for an intended use comprises detecting gene knockdown.

13. A method of transducing cells, comprising:
   (a) collecting supernatant from a first population of cells transfected with recombinant adenoassociated viruses (rAAVs) containing exogenous DNA encoding a CRISPR system, wherein (i) one of the rAAVs encodes a Cas9 and a guide RNA; or (ii) a first rAAV encodes the Cas9 and a second rAAV encodes the guide RNA;
   (b) purifying the rAAVs from the supernatant, wherein the purification consists of (i) filtering the supernatant through a filter having a pore size of 45 microns or less; and (ii) collecting flow-through, wherein the flow-through constitutes filtered supernatant consisting essentially of a purified pool of rAAVs; and
   (c) transducing a second population of cells with at least a portion of the filtered supernatant of (b).

14. The method of claim 13, further comprising adding a secretion enhancer to the first population of cells prior to performing step (a).

15. The method of claim 14, wherein the secretion enhancer is polyethylenimine (PEI).

16. The method of claim 13, wherein the second population of cells are neuronal cells.

* * * * *